United States Patent
Vennemann et al.

(10) Patent No.: US 8,957,064 B2
(45) Date of Patent: Feb. 17, 2015

(54) FUSED PYRIMIDINES

(75) Inventors: Matthias Vennemann, Berlin (DE); Thomas Bär, Reichenau (DE); Thomas Maier, Stockach (DE); Swen Hölder, London (GB); Gerrit Beneke, Allensbach (DE); Florian Dehmel, Aachen (DE); Armin Zülch, Schriesheim (DE); Andreas Strub, Planegg (DE); Thomas Beckers, Constance (DE); Barbara Beckers, legal representative, Constance (DE); Stuart Ince, Berlin (DE); Hartmut Rehwinkel, Berlin (DE); Ningshu Liu, Berlin (DE); Ulf Bömer, Glienicke (DE)

(73) Assignee: Bayer Intellectual Property GmbH, Monheim, DE (US)

( * ) Notice: Subject to any disclaimer, the term of this patent is extended or adjusted under 35 U.S.C. 154(b) by 684 days.

(21) Appl. No.: 13/201,277

(22) PCT Filed: Feb. 2, 2010

(86) PCT No.: PCT/EP2010/000620
§ 371 (c)(1),
(2), (4) Date: Dec. 20, 2011

(87) PCT Pub. No.: WO2010/091808
PCT Pub. Date: Aug. 19, 2010

(65) Prior Publication Data
US 2013/0317002 A1  Nov. 28, 2013

(30) Foreign Application Priority Data

Feb. 13, 2009  (EP) .................................. 09075072
Feb. 16, 2009  (EP) .................................. 09152914

(51) Int. Cl.
| | | |
|---|---|---|
| A61K 31/495 | (2006.01) | |
| A61K 31/519 | (2006.01) | |
| A61K 31/505 | (2006.01) | |
| C07D 401/12 | (2006.01) | |
| C07D 487/04 | (2006.01) | |
| A61K 45/06 | (2006.01) | |
| C07D 471/04 | (2006.01) | |

(52) U.S. Cl.
CPC ............. *A61K 31/519* (2013.01); *A61K 31/495* (2013.01); *A61K 31/505* (2013.01); *C07D 401/12* (2013.01); *C07D 487/04* (2013.01); *A61K 45/06* (2013.01); *C07D 471/04* (2013.01)
USPC ................. 514/210.21; 514/249; 514/255.05; 514/259.1; 514/259.3; 514/259.31

(58) Field of Classification Search
USPC ......... 514/210.21, 249, 255.05, 259.1, 259.3, 514/259.31
See application file for complete search history.

(56) References Cited

U.S. PATENT DOCUMENTS

| | | |
|---|---|---|
| 4,163,856 A | 8/1979 | Edwards, III et al. |
| 2007/0265289 A1 | 11/2007 | Okamoto et al. |
| 2008/0009507 A1 | 1/2008 | Cosford et al. |
| 2008/0287457 A1 | 11/2008 | Arruda et al. |
| 2009/0137607 A1 | 5/2009 | Holder et al. |
| 2010/0022502 A1 | 1/2010 | Jimenez et al. |

FOREIGN PATENT DOCUMENTS

| | | |
|---|---|---|
| EP | 0 992 493 A1 | 4/2000 |
| EP | 1 736 472 A1 | 12/2006 |
| WO | 2004/096131 A2 | 11/2004 |
| WO | 2005/100344 A1 | 10/2005 |
| WO | WO 2005/115985 A1 | 12/2005 |
| WO | 2006/036395 A2 | 4/2006 |
| WO | 2006065601 A2 | 6/2006 |
| WO | WO 2006/065601 A2 | 6/2006 |
| WO | 2006/091395 A2 | 8/2006 |
| WO | WO 2006/091395 A2 | 8/2006 |
| WO | 2006/135627 A2 | 12/2006 |
| WO | 2007/044441 A2 | 4/2007 |
| WO | WO 2008/057940 A1 | 5/2008 |
| WO | WO 2009/021992 A2 | 2/2009 |

OTHER PUBLICATIONS

International Search Report of PCT/EP2010/000620 (Apr. 29, 2010).
Y. Li et al., Bioorg. Med. Chem. Lett. 2009, 19, 834-836.
Garcia-Echeverria et al., Oncogene, 2008, 27, 5511-26.

*Primary Examiner* — Raymond Henley, III

(57) ABSTRACT

Compounds of formula (I)

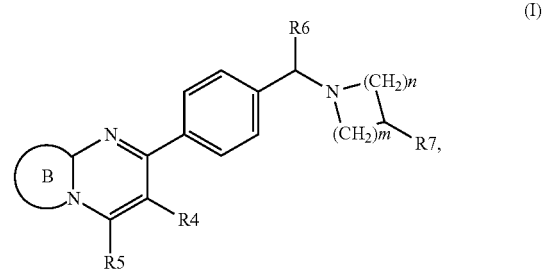

or an N-oxide, a salt, a tautomer or a stereoisomer of said compound, or a salt of said N-oxide, tautomer or stereoisomer,
wherein ring B and the pyrimidine to which it is fused, R4, R5, R6, R7, m and n have the meanings as given in the description and the claims, which are effective inhibitors of the Pi3K/Akt pathway, processes for their production and their use as pharmaceuticals.

13 Claims, No Drawings

FUSED PYRIMIDINES

FIELD OF APPLICATION OF THE INVENTION

The invention relates to fused pyrimidine compounds, which are used in the pharmaceutical industry for the manufacture of pharmaceutical compositions.

KNOWN TECHNICAL BACKGROUND

Cancer is the second most prevalent cause of death in the United States, causing 450,000 deaths per year. While substantial progress has been made in identifying some of the likely environmental and hereditary causes of cancer, there is a need for additional therapeutic modalities that target cancer and related diseases. In particular there is a need for therapeutic methods for treating diseases associated with dysregulated growth/proliferation.

Cancer is a complex disease arising after a selection process for cells with acquired functional capabilities like enhanced survival/resistance towards apoptosis and a limitless proliferative potential. Thus, it is preferred to develop drugs for cancer therapy addressing distinct features of established tumors.

One pathway that has been shown to mediate important survival signals for mammalian cells comprises receptor tyrosine kinases like platelet-derived growth factor receptor (PDGF-R), human epidermal growth factor 2/3 receptor (HER2/3), or the insulin-like growth factor 1 receptor (IGF-1R). After activation the respectives by ligand, these receptors activate the phoshatidylinositol 3-kinase (Pi3K)/Akt pathway. The phoshatidylinositol 3-kinase (Pi3K)/Akt protein kinase pathway is central to the control of cell growth, proliferation and survival, driving progression of tumors. Therefore within the class of serine-threonine specific signalling kinases, Akt (protein kinase B; PKB) with the isoenzmyes Akt1 (PKBα), Akt2 (PKB β) and Akt3 (PKB γ) is of high interest for therapeutic intervention. Akt is mainly activated in a Pi3-kinase dependent manner and the activation is regulated through the tumor suppressor PTEN (phosphatase and tensin homolog), which works essentially as the functional antagonist of Pi3K.

The Pi3K/Akt pathway regulates fundamental cellular functions (e.g. transcription, translation, growth and survival), and is implicated in human diseases including diabetes and cancer. The pathway is frequently overactivated in a wide range of tumor entities like breast and prostate carcinomas. Upregulation can be due to overexpression or constitutively activation of receptor tyrosine kinases (e.g. EGFR, HER2/3), which are upstream and involved in its direct activation, or gain- or loss-of-function mutants of some of the components like loss of PTEN. The pathway is targeted by genomic alterations including mutation, amplification and rearrangement more frequently than any other pathway in human cancer, with the possible exception of the p53 and retinoblastoma pathways. The alterations of the Pi3K/Akt pathway trigger a cascade of biological events, that drive tumor progression, survival, angiogenesis and metastasis.

Activation of Akt kinases promotes increased nutrient uptake, converting cells to a glucose-dependent metabolism that redirects lipid precursors and amino acids to anabolic processes that support cell growth and proliferation. These metabolic phenotype with overactivated Akt lead to malignancies that display a metabolic conversion to aerobic glycolysis (the Warburg effect). In that respect the Pi3K/Akt pathway is discussed to be central for survival despite unfavourable growth conditions such as glucose depletion or hypoxia.

A further aspect of the activated PI3K/Akt pathway is to protect cells from programmed cell death ("apoptosis") and is hence considered to transduce a survival signal. By acting as a modulator of anti-apoptotic signalling in tumor cells, the Pi3K/Akt pathway, particular Akt itself is a target for cancer therapy. Activated Akt phosphorylates and regulates several targets, e.g. BAD, GSK3 or FKHRL1, that affect different signalling pathways like cell survival, protein synthesis or cell movement. This Pi3K/Akt pathway also plays a major part in resistance of tumor cells to conventional anti-cancer therapies. Blocking the Pi3K/Akt pathway could therefore simultaneously inhibit the proliferation of tumor cells (e.g. via the inhibition of the metabolic effect) and sensitize towards pro-apoptotic agents.

Akt inhibition selectively sensitized tumor cells to apoptotic stimuli like Trail, Campthothecin and Doxorubicin. Dependent on the genetic background/molecular apperations of tumors, Akt inhibitors might induce apoptotic cell death in monotherapy as well.

In the International patent applications WO2004096131, WO2005100344, WO2006036395, WO2006065601, WO2006091395 and WO2006135627 Akt inhibitors are described. In a recent disclosure, Y. Li et al (Bioorg. Med. Chem. Lett. 2009, 19, 834-836 and cited references therein) detail the difficulty in finding optimal Akt inhibitors. The potential application of Akt inhibitors in multiple disease settings, such as for example, cancer, makes the provision of new, alternative Akt inhibitors to those currently available highly desirable.

DESCRIPTION OF THE INVENTION

A solution to the above problem is the provision of alternative Akt inhibitors. It has now been found that the new fused pyrimidine compounds, which are described in detail below, have activity as Akt inhibitors.

In accordance with a first aspect, the invention relates to compounds of formula (I)

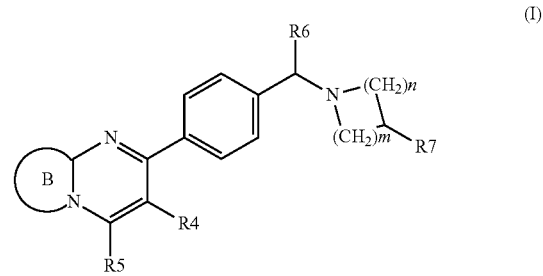

wherein ring B and the pyrimidine to which it is fused form a ring system selected from

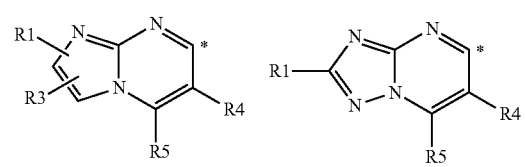

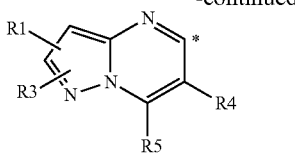

* marks the point of the attachment,
R1 is hydrogen, 1-4C-alkyl (optionally substituted by halogen, hydroxy, amino, mono- or di-1-4C-alkylamino), halogen, amino, —SR2, —SO—R2, SO$_2$—R2, trifluoromethyl, cyano, 3-7C-cycloalkyl, 2-4C-alkenyl, 2-4C-alkynyl, 1-4C-alkoxy (optionally substituted by halogen), 3-7C-cycloalkoxy, NR10R11, —C(O)NR12R13, —C(NH)NH2, —C(O)OR2, or a monocyclic 5- or 6-membered heteroarylene comprising 1 nitrogen atom and optionally 1, 2 or 3 further heteroatoms independently selected from oxygen, nitrogen and sulphur,
R2 is hydrogen, 1-4C-alkyl (optionally substituted by halogen, hydroxy, amino, mono- or di-1-4C-alkylamino) or 3-7C-cycloalkyl,
R3 is hydrogen, 1-4C-alkyl or halogen, 1-4C-alkoxy
R4 is phenyl, thienyl, pyridinyl, thiazolyl or oxazolyl and wherein R4 is optionally independently substituted one or two times by R5A,
R5A is 1-4C-alkyl, halogen or 1-4C-alkoxy or NR10R11,
R5 is hydrogen, 1-4C-alkyl, halogen, 1-4C-alkoxy, NR10R11 or 3-7C-cycloalkyl,
R6 is hydrogen or 1-4C-alkyl,
R7 is —W—Y,
W is a monocyclic 5- or 6-membered heteroarylene comprising 1 nitrogen atom and optionally 1, 2 or 3 further heteroatoms independently selected from oxygen, nitrogen and sulphur or a bicyclic heteroarylene comprising 1 nitrogen atom and optionally 1, 2 or 3 further heteroatoms independently selected from oxygen, nitrogen and sulphur and wherein the monocyclic 5- or 6-membered heteroarylene and the bicyclic heteroarylene are optionally substituted by R8,
R8 is hydrogen, 1-4C-alkyl, 3-7C-cycloalkyl, 1-4C-haloalkyl, NR10R11, 1-4C-alkoxy, cyano, halogen or hydroxy,
Y is hydrogen, aryl or a monocyclic 5- or 6-membered heteroaryl comprising 1 nitrogen atom and optionally 1, 2 or 3 further heteroatoms independently selected from oxygen, nitrogen, sulphur and wherein the aryl or heteroaryl is optionally substituted independently one or more times by R9 and optionally further substituted by R9A
R9 is 1-4C-alkyl, 1-4C-alkoxy, halogen, hydroxy, 1-4C-haloalkyl, NR10R11, cyano, or —C(O)NH2
R9A is 1-4Calkyl or halogen
n is 1 or 2,
m is 1 or 2,
   with the proviso that
   when
   n is 2 and m is 2,
   and
   W is a monocyclic 5-membered heteroarylene
   and
   R4 is phenyl or thienyl
   then
      A:
         R1 must be SR2, SOR2 or SO2R2, or
      B:
         R4 must be substituted by R5A, or
      C:
         R5 must be halogen or
      D:
         R9 must be hydroxy, 1-4C-haloalkyl, NR10R11, cyano, or —C(O)NH2
R10, R11 which can be same or different, is hydrogen, 1-4C-alkyl (optionally substituted by halogen, hydroxy, amino, mono- or di-1-4C-alkylamino) or 3-7C-cycloalkyl,
R12, R13 which can be same or different, is hydrogen, 1-4C-alkyl (optionally substituted by halogen, hydroxy, amino, mono- or di-1-4C-alkylamino) or 3-7C-cycloalkyl,
or an N-oxide, a salt, a tautomer or a stereoisomer of said compound, or a salt of said N-oxide, tautomer or stereoisomer.

Another aspect of the present invention are compounds of formula (I), as described above, wherein
R1 is hydrogen, 1-4C-alkyl (optionally substituted by halogen, hydroxy, amino, mono- or di-1-4C-alkylamino), halogen, amino, —SR2, trifluoromethyl, cyano, 3-7C-cycloalkyl, 2-4C-alkenyl, 2-4C-alkynyl, 1-4C-alkoxy (optionally substituted by halogen), 3-7C-cycloalkoxy, NR10R11, —C(O)NR12R13, —C(NH)NH2, —C(O)OR2, or a monocyclic 5- or 6-membered heteroarylene comprising 1 nitrogen atom and optionally 1, 2 or 3 further heteroatoms independently selected from oxygen, nitrogen and sulphur,
R2 is hydrogen, 1-4C-alkyl (optionally substituted by halogen, hydroxy, amino, mono- or di-1-4C-alkylamino) or 3-7C-cycloalkyl,
R3 is hydrogen, 1-4C-alkyl or halogen,
R4 is phenyl, thienyl, pyridinyl, thiazolyl or oxazolyl and wherein R4 is optionally substituted by R5A,
R5A is 1-4C-alkyl, halogen or 1-4C-alkoxy or NR10R11,
R5 is hydrogen, 1-4C-alkyl, halogen, 1-4C-alkoxy, NR10R11 or 3-7C-cycloalkyl,
R6 is hydrogen or 1-4C-alkyl,
R7 is —W—Y,
W is a monocyclic 5- or 6-membered heteroarylene comprising 1 nitrogen atom and optionally 1, 2 or 3 further heteroatoms independently selected from oxygen, nitrogen and sulphur or a bicyclic heteroarylene comprising 1 nitrogen atom and optionally 1, 2 or 3 further heteroatoms independently selected from oxygen, nitrogen and sulphur and wherein the bicyclic heteroarylene is optionally substituted by R8,
R8 is hydrogen, 1-4C-alkyl, 3-7C-cycloalkyl, 1-4C-haloalkyl, NR10R11, 1-4C-alkoxy, cyano, halogen or hydroxy,
Y is hydrogen, aryl or a monocyclic 5- or 6-membered heteroaryl comprising 1 nitrogen atom and optionally 1, 2 or 3 further heteroatoms independently selected from oxygen, nitrogen, sulphur and wherein the aryl or heteroaryl is optionally substituted by R9,
R9 is 1-4C-alkyl, 1-4C-alkoxy, halogen, hydroxy, 1-4C-haloalkyl, NR10R11, cyano, or —C(O)NH2
n is 1 or 2,
m is 1 or 2, with the proviso that when n is 2 and m is 2, W is not a monocyclic 5-membered heteroarylene,
R10, R11 which can be same or different, is hydrogen, 1-4C-alkyl (optionally substituted by halogen, hydroxy, amino, mono- or di-1-4C-alkylamino) or 3-7C-cycloalkyl,
R12, R13 which can be same or different, is hydrogen, 1-4C-alkyl (optionally substituted by halogen, hydroxy, amino, mono- or di-1-4C-alkylamino) or 3-7C-cycloalkyl, or an N-oxide, a salt, a tautomer or a stereoisomer of said compound, or a salt of said N-oxide, tautomer or stereoisomer Another aspect of the present invention are compounds of formula (I), as described above, wherein R1 is hydrogen, 1-4C-alkyl (optionally substituted by halogen, hydroxy, amino, mono- or di-1-4C-alkylamino), halogen, amino, —SR2, trifluoromethyl, cyano, 3-7C-cycloalkyl, 2-4C-alkenyl, 2-4C-alkynyl, 1-4C-alkoxy (optionally substituted by halogen), 3-7C-cycloalkoxy, NR10R11, —C(O)NR12R13, —C(NH)NH2, —C(O)OR2, or a monocyclic 5- or 6-membered heteroarylene comprising 1 nitrogen atom and optionally 1, 2 or 3 further heteroatoms independently selected from oxygen, nitrogen and sulphur, R2 is hydrogen, 1-4C-alkyl (optionally substituted by halogen, hydroxy, amino, mono- or di-1-4C-alkylamino) or 3-7C-cycloalkyl, R3 is hydrogen, 1-4C-alkyl or halogen, R4 is phenyl, thienyl, pyridinyl, thiazolyl or oxazolyl and wherein phenyl and thienyl are substituted by R5A and pyridinyl, thiazolyl or oxazolyl are optionally substituted by R5A, R5A is 1-4C-alkyl, halogen or 1-4C-alkoxy or NR10R11, R5 is hydrogen, 1-4C-alkyl, halogen, 1-4C-alkoxy, NR10R11 or 3-7C-cycloalkyl, R6 is hydrogen or 1-4C-alkyl, R7 is —W—Y, W is a monocyclic 5- or 6-membered heteroarylene comprising 1 nitrogen atom and optionally 1, 2 or 3 further heteroatoms independently selected from oxygen, nitrogen and sulphur or a bicyclic heteroarylene comprising 1 nitrogen atom and optionally 1, 2 or 3 further heteroatoms independently selected from oxygen, nitrogen and sulphur and wherein the bicyclic heteroarylene is optionally substituted by R8, R8 is hydrogen, 1-4C-alkyl, 3-7C-cycloalkyl, 1-4C-haloalkyl, NR10R11, 1-4C-alkoxy, cyano, halogen or hydroxy, Y is hydrogen, aryl or a monocyclic 5- or 6-membered heteroaryl comprising 1 nitrogen atom and optionally 1, 2 or 3 further heteroatoms independently selected from oxygen, nitrogen, sulphur and wherein the aryl or heteroaryl is optionally substituted by R9, R9 is 1-4C-alkyl, 1-4C-alkoxy, halogen, hydroxy, 1-4C-haloalkyl, NR10R11, cyano, or —C(O)NH2 n is 1 or 2, m is 1 or 2,

R10, R11 which can be same or different, is hydrogen, 1-4C-alkyl (optionally substituted by halogen, hydroxy, amino, mono- or di-1-4C-alkylamino) or 3-7C-cycloalkyl, R12, R13 which can be same or different, is hydrogen, 1-4C-alkyl (optionally substituted by halogen, hydroxy, amino, mono- or di-1-4C-alkylamino) or 3-7C-cycloalkyl, or an N-oxide, a salt, a tautomer or a stereoisomer of said compound, or a salt of said N-oxide, tautomer or stereoisomer A compound of formula (I)

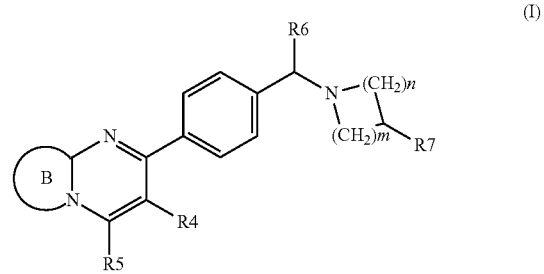

wherein ring B and the pyrimidine to which it is fused form a ring system selected from

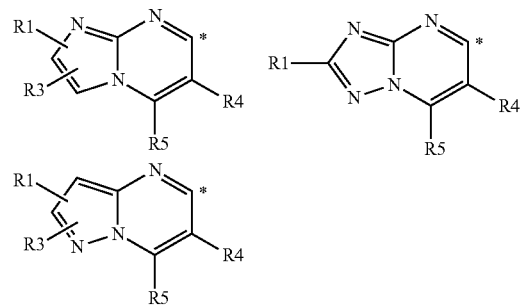

* marks the point of the attachment,

R1 is hydrogen, 1-4C-alkyl (optionally substituted by halogen, hydroxy, amino, mono- or di-1-4C-alkylamino), halogen, amino, —SR2, —SO—R2, SO₂—R2, trifluoromethyl, cyano, 3-7C-cycloalkyl, 1-4C-alkoxy, NR10R11, —C(O)NR12R13, —C(NH)NH2, —C(O)OR2, or a monocyclic 5- or 6-membered heteroarylene comprising 1 nitrogen atom and optionally 1, 2 or 3 further heteroatoms independently selected from oxygen, nitrogen and sulphur, R2 is hydrogen, 1-4C-alkyl (optionally substituted by halogen, hydroxy, amino, mono- or di-1-4C-alkylamino) or 3-7C-cycloalkyl, R3 is hydrogen, 1-4C-alkyl or halogen, 1-4C-alkoxy R4 is phenyl, and wherein R4 is optionally independently substituted one or two times by R5A, R5A halogen, R5 is hydrogen, 1-4C-alkyl, NR10R11

R6 is hydrogen

R7 is —W—Y,

W is a monocyclic 5- or 6-membered heteroarylene comprising 1 nitrogen atom and optionally 1, 2 or 3 further heteroatoms independently selected from oxygen, nitrogen and sulphur or a bicyclic heteroarylene comprising 1 nitrogen atom and optionally 1, 2 or 3 further heteroatoms independently selected from oxygen, nitrogen and sulphur and wherein the bicyclic heteroarylene are optionally substituted by R8, R8 is hydrogen, 1-4C-alkyl, 3-7C-cycloalkyl, 1-4C-haloalkyl, NR10R11, 1-4C-alkoxy, cyano, halogen or hydroxy, Y is hydrogen, aryl or a monocyclic 5- or 6-membered heteroaryl comprising 1 nitrogen atom and optionally 1, 2 or 3 further heteroatoms independently selected from oxygen, nitrogen, sulphur and wherein the aryl or heteroaryl is optionally substituted by R9 and optionally further substituted by R9A R9 is 1-4C-alkyl, halogen,
n is 1 or 2,
m is 1 or 2,
  with the proviso that
  when
  n is 2 and m is 2,
  and
  W is a monocyclic 5-membered heteroarylene
  and
  R4 is phenyl or thienyl
  then
    A:
      R1 must be SR2, SOR2 or SO2R2, or
    B:
      R4 must be substituted by R5A, or
    C:
      R5 must be halogen or
    D:
      R9 must be hydroxy, 1-4C-haloalkyl, NR10R11, cyano, or —C(O)NH2
R10, R11 which can be same or different, is hydrogen, 1-4C-alkyl or 3-7C-cycloalkyl,
R12, R13 which can be same or different, is hydrogen, 1-4C-alkyl (optionally substituted by halogen, hydroxy, amino, mono- or di-1-4C-alkylamino) or 3-7C-cycloalkyl,
or an N-oxide, a salt, a tautomer or a stereoisomer of said compound, or a salt of said N-oxide, tautomer or stereoisomer.

Another aspect of the invention are compounds of formula (I) according to claim 1 wherein ring B and the pyrimidine to which it is fused form a ring system selected from

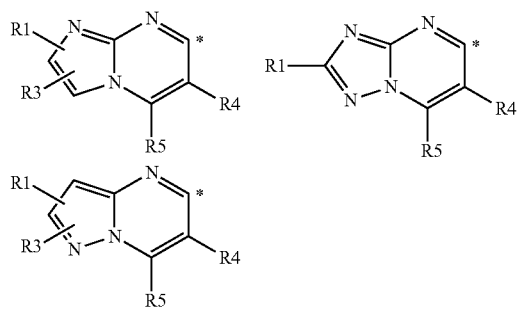

wherein
R1 is hydrogen, halogen, 1-4C-alkyl (optionally substituted by hydroxy), NR10R11, —SR2, 3-7C-cycloalkyl, COOR2, or a monocyclic 6-membered heteroarylene comprising 1 nitrogen atom, 1-4C-alkoxy,
R2 is 1-4C-alkyl
R3 is hydrogen, 1-4C-alkoxy, 1-4C-alkyl, halogen
R4 is phenyl and wherein R4 is optionally substituted one or two times by R5A,
R5A is halogen,
R5 is hydrogen, NR10R11, 1-4C-alkyl,
R6 is hydrogen
R7 W—Y W is 1,2,4-triazolylene or a fused ring system selected from

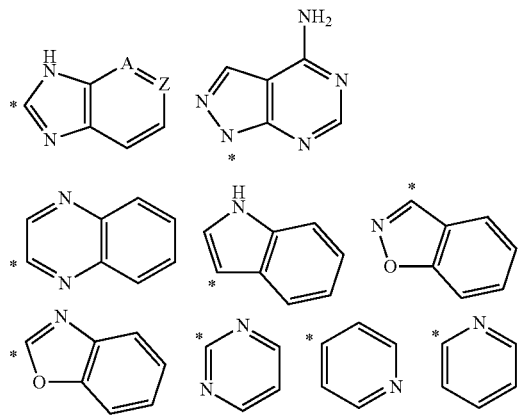

whereby A is —N= or —CH=, and Z is —N= or —CR8=,
  each of which is optionally substituted by R8
R8 is cyano, halogen, trifluoromethyl, amino, 1-4C-alkoxy, 1-4C-alkyl
Y is hydrogen, 2-pyridinyl, 3-pyridinyl, 4-pyridinyl, 2-pyrazinyl, 2-pyrimidinyl,
R9 is 1-4C-alkyl, halogen
n is 1 or 2,
m is 1 or 2,
  with the proviso that
  when
  n is 2 and m is 2,
  and
  W is a monocyclic 5-membered heteroarylene
  and
  R4 is phenyl or thienyl
  then
    A:
      R1 must be SR2, SOR2 or SO2R2, or
    B:
      R4 must be substituted by R5A, or
    C:
      R5 must be halogen or
    D:
      R9 must be hydroxy, 1-4C-haloalkyl, NR10R11, cyano, or —C(O)NH2
R10/R11 are independently hydrogen, 1-4C-alkyl, 3-7C-cycloalkyl,
or an N-oxide, a salt, a tautomer or a stereoisomer of said compound, or a salt of said N-oxide, tautomer or stereoisomer.

Another aspect of the invention are compounds of formula (I) according to claim 1 wherein ring B and the pyrimidine to which it is fused form a ring system selected from

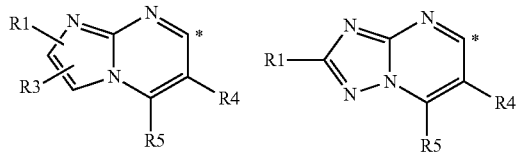

-continued

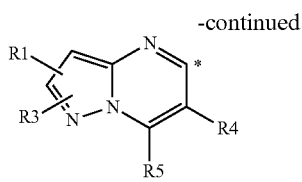

wherein
R1 is hydrogen, halogen, 1-4C-alkyl (optionally substituted by hydroxy), NR10R11, —SR2, 3-7C-cycloalkyl, COOR2, or a monocyclic 6-membered heteroarylene comprising 1 nitrogen atom, 1-4C-alkoxy,
R2 is 1-4C-alkyl
R3 is hydrogen, 1-4C-alkoxy, 1-4C-alkyl, halogen
R4 is phenyl and wherein R4 is optionally substituted one or two times by R5A,
R5A is halogen,
R5 is hydrogen, NR10R11, 1-4C-alkyl,
R6 is hydrogen
R7 W—Y
W is 1,2,4-triazolylene or a fused ring system selected from

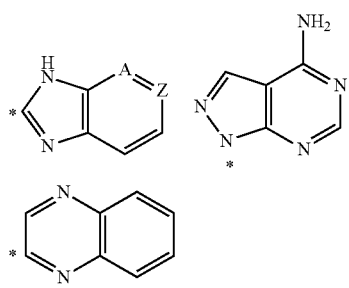

whereby A is —N═ or —CH═, and Z is —N═ or —CR8═,
each of which is optionally substituted by R8
R8 is cyano, halogen, trifluoromethyl, amino, 1-4C-alkoxy, 1-4C-alkyl
Y is hydrogen, 2-pyridinyl, 3-pyridinyl, 4-pyridinyl, 2-pyrazinyl, 2-pyrimidinyl,
R9 is 1-4C-alkyl, halogen
n is 1 or 2,
m is 1 or 2,
with the proviso that
when
n is 2 and m is 2,
and
W is a monocyclic 5-membered heteroarylene
and
R4 is phenyl or thienyl
then
  A:
    R1 must be SR2, SOR2 or SO2R2, or
  B:
    R4 must be substituted by R5A, or
  C:
    R5 must be halogen or
  D:
    R9 must be hydroxy, 1-4C-haloalkyl, NR10R11, cyano, or —C(O)NH2
R10/R11 are independently hydrogen, 1-4C-alkyl, 3-7C-cycloalkyl, or an N-oxide, a salt, a tautomer or a stereoisomer of said compound, or a salt of said N-oxide, tautomer or stereoisomer.

Another aspect of the invention are compounds of formula (I) according to claim 1 wherein ring B and the pyrimidine to which it is fused form a ring system selected from

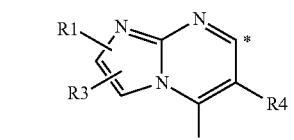 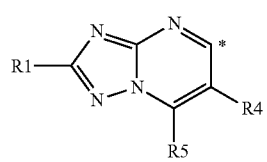

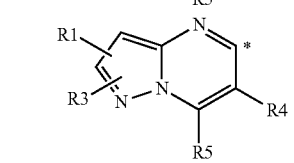

wherein
R1 is hydrogen, bromine, chlorine, fluorine, 1-3C-alkyl, hydroxymethyl, methoxy, NR10R11, —S—R2, —SOR2, SO2R2, 3-4C-cycloalkyl, COOR2, or a monocyclic 6-membered heteroarylene comprising 1 nitrogen atom,
R2 is methyl
R3 is hydrogen, bromine, methoxy
R4 is phenyl and wherein R4 is optionally substituted one or two times by R5A,
R5A is fluorine,
R5 is hydrogen, NR10R11, methyl,
R6 is hydrogen
R7 W—Y
W is 1,2,4-triazolylene or a fused ring system selected from

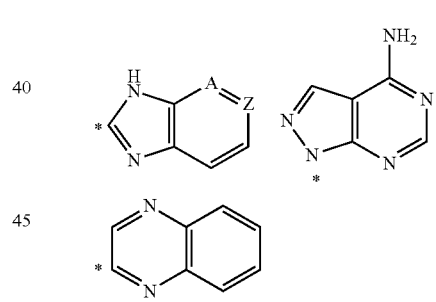

whereby A is —N═ or —CH═, and Z is —N═ or —CR8═, each of which is optionally substituted by R8
R8 is cyano, fluorine, trifluoromethyl, amino,
Y is hydrogen, 2-pyridinyl, 3-pyridinyl, 4-pyridinyl, 2-pyrazinyl, 2-pyrimidinyl,
R9 is methyl, chlorine
n is 1 or 2,
m is 1 or 2,
  with the proviso that
  when
  n is 2 and m is 2,
  and
  W is a monocyclic 5-membered heteroarylene
  and
  R4 is phenyl or thienyl
  then
    A:
      R1 must be SR2, or B:
  R4 must be substituted by R5A,
R10/R11 are independently hydrogen, 1-3C-alkyl, cyclobutyl
or an N-oxide, a salt, a tautomer or a stereoisomer of said compound, or a salt of said N-oxide, tautomer or stereoisomer.

One preferred aspect of the invention is the group of compounds derived from the subcombinations of all definitely disclosed residues of the examples.

As referred to in the priority documents EP 09075072.0 and EP 09152914.9 which are incorporated by reference herein for US purposes, some additional aspects of the present invention are:

A:
compounds of formula (I)

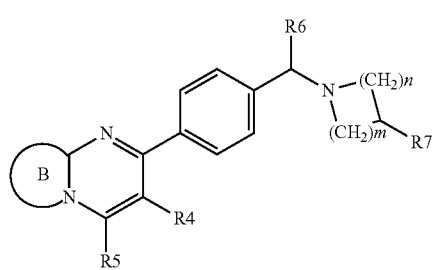

wherein ring B and the pyrimidine to which it is fused form a ring system selected from

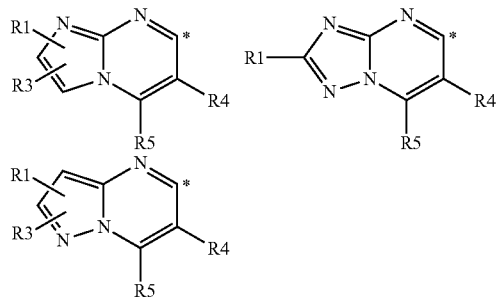

wherein
* marks the point of the attachment,
R1 is hydrogen, 1-4C-alkyl (optionally substituted by halogen, hydroxy, amino, mono- or di-1-4C-alkylamino), halogen, amino, —SR2, trifluoromethyl, cyano, 3-7C-cycloalkyl, 2-4C-alkenyl, 2-4C-alkynyl, 1-4C-alkoxy (optionally substituted by halogen), 3-7C-cycloalkoxy, NR10R11, —C(O)NR12R13, —C(NH)NH2, —C(O)OR2, or a monocyclic 5- or 6-membered heteroarylene comprising 1 nitrogen atom and optionally 1, 2 or 3 further heteroatoms independently selected from oxygen, nitrogen and sulphur,
R2 is hydrogen, 1-4C-alkyl (optionally substituted by halogen, hydroxy, amino, mono- or di-1-4C-alkylamino) or 3-7C-cycloalkyl,
R3 is hydrogen, 1-4C-alkyl or halogen,
R4 is phenyl, thienyl, pyridinyl, thiazolyl or oxazolyl and wherein R4 is optionally substituted by R5A,
R5A is 1-4C-alkyl, halogen or 1-4C-alkoxy or NR10R11,
R5 is hydrogen, 1-4C-alkyl, halogen, 1-4C-alkoxy, NR10R11 or 3-7C-cycloalkyl,
R6 is hydrogen or 1-4C-alkyl,
R7 is —W—Y,
W is a monocyclic 5- or 6-membered heteroarylene comprising 1 nitrogen atom and optionally 1, 2 or 3 further heteroatoms independently selected from oxygen, nitrogen and sulphur or a bicyclic heteroarylene comprising 1 nitrogen atom and optionally 1, 2 or 3 further heteroatoms independently selected from oxygen, nitrogen and sulphur and wherein the bicyclic heteroarylene is optionally substituted by R8,
R8 is hydrogen, 1-4C-alkyl, 3-7C-cycloalkyl, 1-4C-haloalkyl, NR10R11, 1-4C-alkoxy, cyano, halogen or hydroxy,
Y is hydrogen, aryl or a monocyclic 5- or 6-membered heteroaryl comprising 1 nitrogen atom and optionally 1, 2 or 3 further heteroatoms independently selected from oxygen, nitrogen, sulphur and wherein the aryl or heteroaryl is optionally substituted by R9,
R9 is 1-4C-alkyl, 1-4C-alkoxy, halogen, hydroxy, 1-4C-haloalkyl, NR10R11, cyano, or —C(O)NH2
n is 1 or 2,
m is 1 or 2, with the proviso that when n is 2 and m is 2, W is not a monocyclic 5- or 6-membered heteroarylene,
R10, R11 which can be same or different, is hydrogen, 1-4C-alkyl (optionally substituted by halogen, hydroxy, amino, mono- or di-1-4C-alkylamino) or 3-7C-cycloalkyl,
R12, R13 which can be same or different, is hydrogen, 1-4C-alkyl (optionally substituted by halogen, hydroxy, amino, mono- or di-1-4C-alkylamino) or 3-7C-cycloalkyl,
or an N-oxide, a salt, a tautomer or a stereoisomer of said compound, or a salt of said N-oxide, tautomer or stereoisomer, B:
compounds of formula (I) as described above
wherein
R4 is phenyl, thienyl, pyridinyl, thiazolyl or oxazolyl and wherein phenyl and thienyl are substituted by R5A and pyridinyl, thiazolyl or oxazolyl are optionally substituted by R5A,
and
R7 is —W—Y,
W is a monocyclic 5- or 6-membered heteroarylene comprising 1 nitrogen atom and optionally 1, 2 or 3 further heteroatoms independently selected from oxygen, nitrogen and sulphur,
Y is a monocyclic 5- or 6-membered heteroaryl comprising 1 nitrogen atom and optionally 1, 2 or 3 further heteroatoms independently selected from oxygen, nitrogen, sulphur and wherein the heteroaryl is substituted by R9 and optionally further substituted by R9A,
R9A is 1-4C-alkyl or halogen,
n is 2,
m is 2,
and all other residues are defined as in aspect A above.

C:
compounds of formula (I) as described above,
wherein
R1 is hydrogen, 1-4C-alkyl (optionally substituted by halogen, hydroxy, amino, mono- or di-1-4C-alkylamino), halogen, amino, trifluoromethyl, cyano, 3-7C-cycloalkyl, 1-4C-alkoxy (optionally substituted by halogen), NR10R11, —C(O)NR12R13, or —C(O)OR2,
R2 is hydrogen or 1-4C-alkyl,
R3 is hydrogen, 1-4C-alkyl or halogen, R4 is phenyl, thienyl, pyridinyl, thiazolyl or oxazolyl and wherein R4 is optionally substituted by R5A,
R5A is 1-4C-alkyl, halogen, 1-4C-alkoxy or NR10R11,
R5 is hydrogen, 1-4C-alkyl, halogen, 1-4C-alkoxy, NR10R11 or 3-7C-cycloalkyl,
R6 is hydrogen or 1-4C-alkyl,
R7 is —W—Y,
W is a monocyclic 5- or 6-membered heteroarylene comprising 1 nitrogen atom and optionally 1, 2 or 3 further heteroatoms independently selected from oxygen, nitrogen and sulphur or a bicyclic heteroarylene comprising 1 nitrogen atom and optionally 1, 2 or 3 further heteroatoms independently selected from oxygen, nitrogen and sulphur and wherein the bicyclic heteroarylene is optionally substituted by R8,
R8 is hydrogen, 1-4C-alkyl, 1-4C-haloalkyl, NR10R11, 1-4C-alkoxy, cyano, halogen or hydroxy,
Y is hydrogen, aryl or a monocyclic 5- or 6-membered heteroaryl comprising 1 nitrogen atom and optionally 1, 2 or 3 further heteroatoms independently selected from oxygen, nitrogen, sulphur and wherein the aryl or heteroaryl is optionally substituted by R9,
R9 is 1-4C-alkyl, 1-4C-alkoxy, halogen, hydroxy, 1-4C-haloalkyl, NR10R11, cyano or —C(O)NH2,
n is 1 or 2,
m is 1 or 2, with the proviso that when n is 2 and m is 2, W is not a monocyclic 5- or 6-membered heteroarylene,
R10, R11 which can be same or different is hydrogen or 1-4C-alkyl,
R12, R13 which can be same or different is hydrogen or 1-4C-alkyl,
or an N-oxide, a salt, a tautomer or a stereoisomer of said compound, or a salt of said N-oxide, tautomer or stereoisomer.

D:
compounds of formula (I)
wherein
R1 is hydrogen, 1-4C-alkyl (optionally substituted by halogen, hydroxy, amino, mono- or di-1-4C-alkylamino), halogen, amino, trifluoromethyl, cyano, 3-7C-cycloalkyl, 1-4C-alkoxy (optionally substituted by halogen), NR10R11, —C(O)NR12R13, or —C(O)OR2,
R2 is hydrogen or 1-4C-alkyl,
R3 is hydrogen, 1-4C-alkyl or halogen,
R4 is phenyl, thienyl, pyridinyl, thiazolyl or oxazolyl and wherein phenyl and thienyl are substituted by R5A and pyridinyl, thiazolyl or oxazolyl are optionally substituted by R5A,
R5A is 1-4C-alkyl, halogen, 1-4C-alkoxy or NR10R11,
R5 is hydrogen, 1-4C-alkyl, halogen, 1-4C-alkoxy, NR10R11 or 3-7C-cycloalkyl,
R6 is hydrogen or 1-4C-alkyl,
R7 is —W—Y,
W is a monocyclic 5- or 6-membered heteroarylene comprising 1 nitrogen atom and optionally 1, 2 or 3 further heteroatoms independently selected from oxygen, nitrogen and sulphur,
Y is a monocyclic 5- or 6-membered heteroaryl comprising 1 nitrogen atom and optionally 1, 2 or 3 further heteroatoms independently selected from oxygen, nitrogen, sulphur and wherein the heteroaryl is substituted by R9 and optionally further substituted by R9A,
R9 is 1-4Calkly, 1-4C-alkoxy, halogen, hydroxy, 1-4C-haloalkyl, NR10R11, cyano or —C(O)NH2,
R9A is 1-4C-alkyl or halogen,
n is 2,
m is 2,
R10, R11 which can be same or different is hydrogen or 1-4C-alkyl,
R12, R13 which can be same or different is hydrogen or 1-4C-alkyl,
or an N-oxide, a salt, a tautomer or a stereoisomer of said compound, or a salt of said N-oxide, tautomer or stereoisomer, E:
compounds of formula (I) as described above,
wherein
R1 is hydrogen, 1-4C-alkyl (optionally substituted by halogen, hydroxy, amino, mono- or di-1-4C-alkylamino), halogen, amino, trifluoromethyl, cyano, 3-7C-cycloalkyl, 1-4C-alkoxy or NR10R11,
R2 is hydrogen or 1-4C-alkyl,
R3 is hydrogen, 1-4C-alkyl or halogen,
R4 is phenyl, thienyl, pyridinyl, thiazolyl or oxazolyl,
R5 is hydrogen, 1-4C-alkyl, 1-4C-alkoxy or NR10R11,
R6 is hydrogen or 1-4C-alkyl,
R7 is —W—Y,
W is 1,2,4-triazolylene or a bicyclic heteroarylene selected from

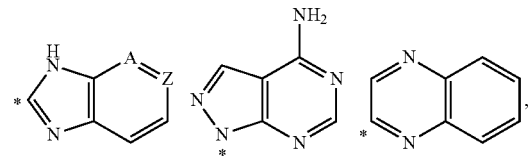

wherein
* marks the point of connection,
A is CH or N,
Z is N or CR8,
R8 is hydrogen, 1-4C-alkyl, 1-4C-haloalkyl, NR10R11, 1-4C-alkoxy, cyano, halogen or hydroxy,
Y is hydrogen, aryl or a monocyclic 5- or 6-membered heteroaryl comprising 1 nitrogen atom and optionally 1, 2 or 3 further heteroatoms independently selected from oxygen, nitrogen, sulphur and wherein the aryl or heteroaryl is optionally substituted by R9,
R9 is 1-4C-alkyl, 1-4C-alkoxy, halogen, hydroxy, 1-4C-haloalkyl, NR10R11, cyano or —C(O)NH2,
n is 1 or 2,
m is 1 or 2, with the proviso that when n is 2 and m is 2, W is not a monocyclic 5- or 6-membered heteroarylene,
R10, R11 which can be same or different is hydrogen or 1-4C-alkyl,
R12, R13 which can be same or different is hydrogen or 1-4C-alkyl,
or an N-oxide, a salt, a tautomer or a stereoisomer of said compound, or a salt of said N-oxide, tautomer or stereoisomer, F:
compounds according to formula (I) as described above,
wherein
R1 is hydrogen, 1-4C-alkyl (optionally substituted by halogen, hydroxy, amino, mono- or di-1-4C-alkylamino), halogen, amino, trifluoromethyl, cyano, 3-7C-cycloalkyl, 1-4C-alkoxy or NR10R11,
R2 is hydrogen or 1-4C-alkyl,
R3 is hydrogen, 1-4C-alkyl or halogen,
R4 is phenyl, thienyl, pyridinyl, thiazolyl or oxazolyl,
R5 is hydrogen, 1-4C-alkyl, 1-4C-alkoxy or NR10R11,
R6 is hydrogen or 1-4C-alkyl, R7 is —W—Y,
W is a monocyclic 5- or 6-membered heteroarylene comprising 1 nitrogen atom and optionally 1, 2 or 3 further heteroatoms independently selected from oxygen, nitrogen and sulphur,
Y is a monocyclic 5- or 6-membered heteroaryl comprising 1 nitrogen atom and optionally 1, 2 or 3 further heteroatoms independently selected from oxygen, nitrogen, sulphur and wherein the heteroaryl is substituted by R9,
R9 is hydroxyl, 1-4C-haloalkyl, NR10R11, cyano or —C(O)NH2,
n is 2,
m is 2,
R10, R1 which can be same or different is hydrogen or 1-4C-alkyl,
R12, R13 which can be same or different is hydrogen or 1-4C-alkyl,
or an N-oxide, a salt, a tautomer or a stereoisomer of said compound, or a salt of said N-oxide, tautomer or stereoisomer,
G:
compounds of formula (I) as described above,
wherein
R1 is hydrogen, 1-4C-alkyl, cyclopropyl, cyclobutyl, halogen
R3 is hydrogen,
R4 is phenyl,
R5 is hydrogen or 1-4C-alkyl,
R6 is hydrogen,
R7 is —W—Y,
W is 1,2,4-triazolylene or a fused ring system selected from

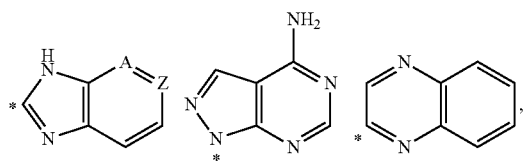

wherein * marks the point of connection,
A is CH or N,
Z is N or CR8,
R8 is hydrogen, halogen, 1-4C-haloalkyl or cyano,
Y is hydrogen or pyridin-2-yl (optionally substituted by R9)
R9 is 1-4C-alkyl,
m, n are both 1 or both 2,
with the proviso that when n is 2 and m is 2, W is not 1,2,4-triazolylene,
or an N-oxide, a salt, a tautomer or a stereoisomer of said compound, or a salt of said N-oxide, tautomer or stereoisomer.
H:
compounds of formula (I) as described above,
wherein
R1 is hydrogen, 1-4C-alkyl, cyclopropyl, cyclobutyl, halogen
R3 is hydrogen,
R4 is phenyl,
R5 is hydrogen or 1-4C-alkyl,
R6 is hydrogen,
R7 is —W—Y,
W is 1,2,4-triazolylene,
Y is pyridinyl and wherein the pyridinyl is substituted by R9,
R9 is hydroxy or 1-4C-haloalkyl,
n is 2,
m is 2,
or an N-oxide, a salt, a tautomer or a stereoisomer of said compound, or a salt of said N-oxide, tautomer or stereoisomer,
I:
compounds of formula (I) as described above, wherein
R1 is hydrogen, methyl, ethyl, cyclopropyl, cyclobutyl, fluoro or chloro,
R3 is hydrogen,
R4 is phenyl,
R5 is hydrogen or methyl,
R6 is hydrogen,
R7 is —W—Y,
W is 1,2,4-triazolylene or a fused ring system selected from

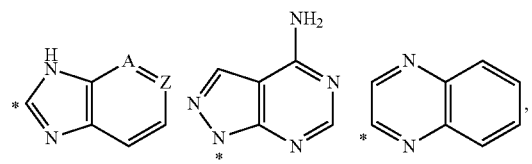

wherein * marks the point of connection,
A is CH or N,
Z is N or CR8,
R8 is hydrogen, fluoro, trifluoromethyl or cyano,
Y is hydrogen or pyridin-2-yl (optionally substituted by R9)
R9 is methyl,
m, n are both 1 or both 2,
with the proviso that when n is 2 and m is 2, W is not 1,2,4-triazolylene,
or an N-oxide, a salt, a tautomer or a stereoisomer of said compound, or a salt of said N-oxide, tautomer or stereoisomer.
J:
compounds of formula (I) as described above, selected from the group consisting of
  6-phenyl-7-(4-{[3-(5-pyridin-2-yl-1,2,4-triazol-3-yl)azetidin-1-yl]methyl}phenyl)imidazo[1,2-a]pyrimidine,
  2-methyl-6-phenyl-5-(4-{[3-(5-pyridin-2-yl-1,2,4-triazol-3-yl)azetidin-1-yl]methyl}phenyl)[1,2,4]triazolo[1,5-a]pyrimidine,
  2-cyclobutyl-6-phenyl-5-(4-{[3-(5-pyridin-2-yl-1,2,4-triazol-3-yl)azetidin-1-yl]methyl}phenyl)[1,2,4]triazolo[1,5-a]pyrimidine,
  3-fluoro-6-phenyl-7-(4-{[3-(5-pyridin-2-yl-1,2,4-triazol-3-yl)azetidin-1-yl]methyl}phenyl)imidazo[1,2-a]pyrimidine,
  3-Chloro-6-phenyl-7-(4-{[3-(5-pyridin-2-yl-1,2,4-triazol-3-yl)azetidin-1-yl]methyl}phenyl)imidazo[1,2-a]pyrimidine,
  2-{1-[4-(6-phenyl-imidazo[1,2-a]pyrimidin-7-yl)-benzyl]-piperidin-4-yl}-3H-imidazo[4,5-c]pyridine,
  2-{1-[4-(6-phenyl-imidazo[1,2-a]pyrimidin-7-yl)-benzyl]-piperidin-4-yl}-3H-imidazo[4,5-b]pyridine,
  7-{4-[4-(6-fluoro-1H-benzimidazol-2-yl)-piperidin-1-ylmethyl]-phenyl}-6-phenylimidazo[1,2-a]pyrimidine,
  2-{1-[4-(6-Phenyl-imidazo[1,2-a]pyrimidin-7-yl)-benzyl]-piperidin-4-yl}-3H-benzimidazole-5-carbonitrile,
  2-{1-[4-(6-phenyl-imidazo[1,2-a]pyrimidin-7-yl)-benzyl]-piperidin-4-yl}-quinoxaline,
  1-{1-[4-(6-phenyl-imidazo[1,2-a]pyrimidin-7-yl)-benzyl]-piperidin-4-yl}-1H-pyrazolo[3,4-d]pyrimidin-4-ylamine,
  2-{1-[4-(6-phenyl-pyrazolo[1,5-a]pyrimidin-5-yl)-benzyl]-piperidin-4-yl}-3H-benzimidazole-5-carbonitrile, 5-{4-[4-(6-fluoro-1H-benzimidazol-2-yl)-piperidin-1-yl-methyl]-phenyl}-2-methyl-6-phenyl-[1,2,4]triazolo[1,5-a]pyrimidine,
5-{4-[4-(3H-imidazo[4,5-c]pyridin-2-yl)-piperidin-1-yl-methyl]-phenyl}-2-methyl-6-phenyl-[1,2,4]triazolo[1,5-a]pyrimidine,
2-{1-[4-(6-phenyl-pyrazolo[1,5-a]pyrimidin-5-yl)-benzyl]-piperidin-4-yl}-3H-imidazo[4,5-c]pyridine,
2-{1-[4-(6-phenyl-pyrazolo[1,5-a]pyrimidin-5-yl)-benzyl]-piperidin-4-yl}-3H-imidazo[4,5-b]pyridine,
6-phenyl-5-{4-[4-(6-trifluoromethyl-1H-benzimidazol-2-yl)-piperidin-1-ylmethyl]-phenyl}-pyrazolo[1,5-a]pyrimidine,
5-{4-[4-(6-fluoro-1H-benzimidazol-2-yl)-piperidin-1-yl-methyl]-phenyl}-6-phenyl-pyrazolo[1,5-a]pyrimidine,
1-{1-[4-(6-phenyl-pyrazolo[1,5-a]pyrimidin-5-yl)-benzyl]-piperidin-4-yl}-1H-pyrazolo[3,4-d]pyrimidin-4-ylamine,
2-{1-[4-(2-methyl-6-phenyl-[1,2,4]triazolo[1,5-a]pyrimidin-5-yl)-benzyl]-piperidin-4-yl}-3H-benzimidazol-5-carbonitrile,
2-methyl-6-phenyl-5-{4-[4-(6-trifluoromethyl-1H-benzimidazol-2-yl)-piperidin-1-ylmethyl]-phenyl}-[1,2,4]triazolo[1,5-a]pyrimidine,
1-{1-[4-(2-methyl-6-phenyl-[1,2,4]-triazolo[1,5-a]pyrimidin-5-yl)-benzyl]-piperidin-4-yl}-1H-pyrazolo[3,4-d]pyrimidine-4-ylamine,
5-{4-[4-(3H-imidazo[4,5-b]pyridin-2-yl)-piperidin-1-yl-methyl]-phenyl}-2-methyl-6-phenyl-[1,2,4]triazolo[1,5-a]pyrimidine,
or an N-oxide, a salt, a tautomer or a stereoisomer of said compound, or a salt of said N-oxide, tautomer or stereoisomer,
compounds according to claim 1 selected from the group consisting of
2-methyl-6-phenyl-5-(4-{4-[5-(6-trifluoromethyl-pyridin-2-yl)-1H-[1,2,4]triazol-3-yl]-piperidin-1-ylmethyl}-phenyl)-[1,2,4]triazolo[1,5-a]pyrimidine,
2-methyl-6-phenyl-5-(4-{4-[5-(4-trifluoromethyl-pyridin-2-yl)-1H-[1,2,4]triazol-3-yl]-piperidin-1-ylmethyl}-phenyl)-[1,2,4]triazolo[1,5-a]pyrimidine,
2,7-dimethyl-6-phenyl-5-(4-{4-[5-(4-trifluoromethyl-pyridin-2-yl)-1H-[1,2,4]triazol-3-yl]-piperidin-1-ylmethyl}-phenyl)-[1,2,4]triazolo[1,5-a]pyrimidine,
5-(5-{1-[4-(2-methyl-6-phenyl-[1,2,4]triazolo[1,5-a]pyrimidin-5-yl)-benzyl]-piperidin-4-yl}-2H-[1,2,4]triazol-3-yl)-pyridin-2-ol,
or an N-oxide, a salt, a tautomer or a stereoisomer of said compound, or a salt of said N-oxide, tautomer or stereoisomer.
Another aspect of the invention are the aspects A-I above in combination with the following disclaimer:
"when
n is 2 and m is 2,
and
W is a monocyclic 5-membered heteroarylene
and
R4 is phenyl or thienyl
then
A:
R1 must be SR2, SOR2 or SO2R2, or
B:
R4 must be substituted by R5A, or
C:
R5 must be halogen or
D:
R9 must be hydroxy, 1-4C-haloalkyl, NR10R11, cyano, or —C(O)NH2"
Another aspect of the invention are the aspects A, C and E in combination with the proviso that when n is 2 and m is 2, W is not a monocyclic 5-membered heteroarylene.
The application PCT/EP2008/060690 filed on Aug. 14, 2008, published on Feb. 19, 2009 (WO2009/021992) leads to the disclaimer used in this document.
One aspect of the present invention are the compounds disclosed in the examples as well as the intermediates as used for their synthesis.
One most preferred aspect are the compounds listed below:
6-phenyl-7-(4-{[3-(5-pyridin-2-yl-1,2,4-triazol-3-yl)azetidin-1-yl]methyl}phenyl)imidazo[1,2-a]pyrimidine,
2-methyl-6-phenyl-5-(4-{[3-(5-pyridin-2-yl-1,2,4-triazol-3-yl)azetidin-1-yl]methyl}phenyl)[1,2,4]triazolo[1,5-a]pyrimidine,
2-cyclobutyl-6-phenyl-5-(4-{[3-(5-pyridin-2-yl-1,2,4-triazol-3-yl)azetidin-1-yl]methyl}phenyl)[1,2,4]triazolo[1,5-a]pyrimidine,
3-fluoro-6-phenyl-7-(4-{[3-(5-pyridin-2-yl-1,2,4-triazol-3-yl)azetidin-1-yl]methyl}phenyl)imidazo[1,2-a]pyrimidine,
3-Chloro-6-phenyl-7-(4-{[3-(5-pyridin-2-yl-1,2,4-triazol-3-yl)azetidin-1-yl]methyl}phenyl)imidazo[1,2-a]pyrimidine,
2-{1-[4-(6-phenyl-imidazo[1,2-a]pyrimidin-7-yl)-benzyl]-piperidin-4-yl}-3H-imidazo[4,5-c]pyridine,
2-{1-[4-(6-phenyl-imidazo[1,2-a]pyrimidin-7-yl)-benzyl]-piperidin-4-yl}-3H-imidazo[4,5-b]pyridine,
7-{4-[4-(6-fluoro-1H-benzimidazol-2-yl)-piperidin-1-ylmethyl]-phenyl}-6-phenylimidazo[1,2-a]pyrimidine,
2-{1-[4-(6-Phenyl-imidazo[1,2-a]pyrimidin-7-yl)-benzyl]-piperidin-4-yl}-3H-benzimidazole-5-carbonitrile,
2-{1-[4-(6-phenyl-imidazo[1,2-a]pyrimidin-7-yl)-benzyl]-piperidin-4-yl}-quinoxaline,
1-{1-[4-(6-phenyl-imidazo[1,2-a]pyrimidin-7-yl)-benzyl]-piperidin-4-yl}-1H-pyrazolo[3,4-d]pyrimidin-4-ylamine,
2-{1-[4-(6-phenyl-pyrazolo[1,5-a]pyrimidin-5-yl)-benzyl]-piperidin-4-yl}-3H-benzimidazole-5-carbonitrile,
5-{4-[4-(6-fluoro-1H-benzimidazol-2-yl)-piperidin-1-ylmethyl]-phenyl}-2-methyl-6-phenyl-[1,2,4]triazolo[1,5-a]pyrimidine,
5-{4-[4-(3H-imidazo[4,5-c]pyridin-2-yl)-piperidin-1-ylmethyl]-phenyl}-2-methyl-6-phenyl-[1,2,4]triazolo[1,5-a]pyrimidine,
2-{1-[4-(6-phenyl-pyrazolo[1,5-a]pyrimidin-5-yl)-benzyl]-piperidin-4-yl}-3H-imidazo[4,5-c]pyridine,
2-{1-[4-(6-phenyl-pyrazolo[1,5-a]pyrimidin-5-yl)-benzyl]-piperidin-4-yl}-3H-imidazo[4,5-b]pyridine,
6-phenyl-5-{4-[4-(6-trifluoromethyl-1H-benzimidazol-2-yl)-piperidin-1-ylmethyl]-phenyl}-pyrazolo[1,5-a]pyrimidine,
5-{4-[4-(6-fluoro-1H-benzimidazol-2-yl)-piperidin-1-ylmethyl]-phenyl}-6-phenyl-pyrazolo[1,5-a]pyrimidine,
1-{1-[4-(6-phenyl-pyrazolo[1,5-a]pyrimidin-5-yl)-benzyl]-piperidin-4-yl}-1H-pyrazolo[3,4-d]pyrimidin-4-ylamine,
2-{1-[4-(2-methyl-6-phenyl-[1,2,4]triazolo[1,5-a]pyrimidin-5-yl)-benzyl]-piperidin-4-yl}-3H-benzimidazol-5-carbonitrile,
2-methyl-6-phenyl-5-{4-[4-(6-trifluoromethyl-1H-benzimidazol-2-yl)-piperidin-1-ylmethyl]-phenyl}-[1,2,4]triazolo[1,5-a]pyrimidine, 1-{1-[4-(2-methyl-6-phenyl-[1,2,4]-triazolo[1,5-a]pyrimidin-5-yl)-benzyl]-piperidin-4-yl}-1H-pyrazolo[3,4-d]pyrimidin-4-ylamine,
5-{4-[4-(3H-imidazo[4,5-b]pyridin-2-yl)-piperidin-1-ylmethyl]-phenyl}-2-methyl-6-phenyl-[1,2,4]triazolo[1,5-a]pyrimidine,
(±)-2-methyl-6-phenyl-5-{4-[3-(5-pyridin-2-yl-1H-[1,2,4]triazol-3-yl)-pyrrolidin-1-ylmethyl]-phenyl}-[1,2,4]triazolo[1,5-a]pyrimidine,
2-{1-[4-(2-methyl-6-phenyl-[1,2,4]triazolo[1,5-a]pyrimidin-5-yl)-benzyl]-piperidin-4-yl}-quinoxaline,
3-methyl-7-(4-{3-[5-(6-methylpyridine-2-yl)-1H-[1,2,4]triazole-3-yl]-azetidine-1-ylmethyl}-phenyl)-6-phenyl-imidazo[1,2-a]pyrimidine,
3-bromo-2-methyl-6-phenyl-7-{4-[3-(5-pyridine-2-yl-1H-[1,2,4]triazole-3-yl]-azetidine-1-ylmethyl]-phenyl}-imidazo[1,2-a]pyrimidine,
6-(2,6-difluorophenyl)-5-(4-{3-[5-(6-methylpyridine-2-yl)-1H-[1,2,4]triazole-3-yl]-azetidine-1-ylmethyl}-phenyl)-pyrazolo[1,5-a]pyrimidine-3-carboxylic acid methyl ester,
6-(2,6-difluorophenyl)-5-(4-{3-[5-(pyridine-2-yl)-1H-[1,2,4]triazole-3-yl]-azetidine-1-ylmethyl}-phenyl)-pyrazolo[1,5-a]pyrimidine-3-carboxylic acid methyl ester,
2-isopropyl-6-phenyl-5-{4-[3-[5-pyridine-2-yl)-1H-[1,2,4]triazole-3-yl]-azetidine-1-ylmethyl}-phenyl}-[1,2,4]triazolo[1,5-a]pyrimidine,
2-{1-[4-(2-isopropyl-6-phenyl-[1,2,4]triazolo[1,5-a]pyrimidin-5-yl)benzyl]-piperidine-4-yl}-quinoxaline,
2-isopropyl-5-(4-{3-[5-(6-methyl-pyridine-2-yl)-1H-[1,2,4]triazolo-3-yl]-azetidine-1-ylmethyl}-phenyl)-6-phenyl-[1,2,4]triazolo[1,5-a]pyrimidine,
6-(2,4-difluorophenyl)-5-(4-{3-[5-(pyridine-2-yl)-1H-[1,2,4]triazole-3-yl]-azetidine-1-ylmethyl}-phenyl)-pyrazolo[1,5-a]pyrimidine-3-carboxylic acid methyl ester,
6-(4-fluorophenyl)-7-{4-[3-(5-pyridine-2-yl-1H-[1,2,4]triazole-3-yl]-azetidine-1-ylmethyl]-phenyl}-imidazo[1,2-a]pyrimidine,
2-(1-{4-[6-(4-fluorophenyl)-imidazo[1,2-a]pyrimidin-7-yl]-benzyl}-piperidine-4-yl)-quinoxaline,
6-(2,4-difluorophenyl)-2-methyl-5-(4-{3-[5-(6-methylpyridine-2-yl)-1H-[1,2,4]triazole-3-yl]-azetidine-1-ylmethyl}-phenyl)-[1,2,4]triazolo[1,5-a]pyrimidine,
2-{1-[4-(6-phenyl-imidazo[1,2-a]pyrimidin-7-yl)-benzyl]-piperidine-4-yl}-quinoxaline, 2-{1-[4-(2-methyl-6-phenyl-imidazo[1,2-a]pyrimidin-7-yl)-benzyl]-piperidine-4-yl}-quinoxaline,
2-methyl-7-(4-{3-[5-(6-methylpyridine-2-yl)-1H-[1,2,4]triazole-3-yl]-azetidine-1-ylmethyl}-phenyl)-6-phenyl-imidazo[1,2-a]pyrimidine,
2-cyclopropyl-6-(4-fluorophenyl)-5-(4-{3-[5-(6-methylpyridine-2-yl)-1H-[1,2,4]triazole-3-yl]-azetidine-1-ylmethyl}-phenyl)-[1,2,4]triazolo[1,5-a]pyrimidine,
2-{1-[4-(2-cyclopropyl-6-phenyl-[1,2,4]triazolo[1,5-a]pyrimidin-5-yl)-benzyl]-piperidine-4-yl}-quinoxaline,
2-cyclopropyl-5-(4-{3-[5-(6-methylpyridine-2-yl)-1H-[1,2,4]triazole-3-yl]-azetidine-1-ylmethyl}-phenyl)-6-phenyl-[1,2,4]triazolo[1,5-a]pyrimidine,
3-ethyl-5-(4-{3-[5-(6-methyl-pyridin-2-yl)-1H-[1,2,4]triazol-3-yl]-azetidin-1-ylmethyl}-phenyl)-6-phenyl-pyrazolo[1,5-a]pyrimidine,
2-{1-[4-(3-ethyl-6-phenyl-pyrazolo[1,5-a]pyrimidin-5-yl)-benzyl]-piperidin-4-yl}-quinoxaline,
methyl-(6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidin-2-yl)-amine,
isopropyl-(6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidin-2-yl)-amine,
2,7-dimethyl-6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidine,
2,7-Dimethyl-5-(4-{3-[5-(6-methyl-pyridin-2-yl)-1H-[1,2,4]triazol-3-yl]-azetidin-1-ylmethyl}-phenyl)-6-phenyl-[1,2,4]triazolo[1,5-a]pyrimidine,
cyclobutyl-(2-methyl-6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidin-7-yl)-amine,
methyl-[2-methyl-5-(4-{3-[5-(6-methyl-pyridin-2-yl)-1H-[1,2,4]triazol-3-yl]-azetidin-1-ylmethyl}-phenyl)-6-phenyl-[1,2,4]triazolo[1,5-a]pyrimidin-7-yl]-amine,
isopropyl-(2-methyl-6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidin-7-yl)-amine,
(2-cyclopropyl-6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidin-7-yl)-methyl-amine,
2-methyl-6-phenyl-5-(4-{4-[5-(6-trifluoromethyl-pyridin-2-yl)-1H-[1,2,4]triazol-3-yl]-piperidin-1-ylmethyl}-phenyl)-[1,2,4]triazolo[1,5-a]pyrimidine,
2-methyl-6-phenyl-5-(4-{4-[5-(4-trifluoromethyl-pyridin-2-yl)-1H-[1,2,4]triazol-3-yl]-piperidin-1-ylmethyl}-phenyl)-[1,2,4]triazolo[1,5-a]pyrimidine,
2,7-dimethyl-6-phenyl-5-(4-{4-[5-(4-trifluoromethyl-pyridin-2-yl)-1H-[1,2,4]triazol-3-yl]-piperidin-1-ylmethyl}-phenyl)-[1,2,4]triazolo[1,5-a]pyrimidine,
5-(5-{1-[4-(2-methyl-6-phenyl-[1,2,4]triazolo[1,5-a]pyrimidin-5-yl)-benzyl]-piperidin-4-yl}-2H-[1,2,4]triazol-3-yl)-pyridin-2-ol,
6-(2,6-difluorophenyl)-5-(4-{4-[5-(6-methylpyridine-2-yl)-1H-[1,2,4]triazole-3-yl]-piperidine-1-ylmethyl}-phenyl)-pyrazolo[1,5-a]pyrimidine-3-carboxylic acid methyl ester,
6-(2,6-difluorophenyl)-5-(4-{4-[5-(pyridine-2-yl)-1H-[1,2,4]triazole-3-yl]-piperidine-1-ylmethyl}-phenyl)-pyrazolo[1,5-a]pyrimidine-3-carboxylic acid methyl ester,
6-(3-fluorophenyl)-2-methyl-5-(4-{4-[5-(6-methylpyridine-2-yl)-1H-[1,2,4]triazole-3-yl]-piperidine-1-ylmethyl}-phenyl)-[1,2,4]triazolo[1,5-a]pyrimidine,
6-(3-fluorophenyl)-2-methyl-5-{4-[4-(5-pyridine-2-yl)-1H-[1,2,4]triazole-3-yl)-piperidine-1-ylmethyl]-phenyl}-[1,2,4]triazolo[1,5-a]pyrimidine formiate,
5-(4-{4-[5-(4-chloropyridine-2-yl)-1H-[1,2,4]triazole-3-yl]-piperidine-1-ylmethyl}-phenyl) 6-(2,4-difluorophenyl)-2-methyl-[1,2,4]triazolo[1,5-a]pyrimidine,
6-(2,4-difluorophenyl)-2-methyl-5-(4-{4-[5-(6-methylpyridine-2-yl)-1H-[1,2,4]triazole-3-yl]-piperidine-1-ylmethyl}-phenyl)-[1,2,4]triazolo[1,5-a]pyrimidine,
6-(2,4-difluorophenyl)-2-methyl-5-[4-{4-(5-pyrazine-2-yl-1H-[1,2,4]triazole-3-yl)-piperidine-1-ylmethyl]-phenyl}-[1,2,4]triazolo[1,5-a]pyrimidine,
2-cyclopropyl-6-(4-fluorophenyl)-5-(4-{4-[5-(6-methylpyridine-2-yl)-1H-[1,2,4]triazole-3-yl]-piperidine-1-ylmethyl}-phenyl)-[1,2,4]triazolo[1,5-a]pyrimidine,
2-cyclopropyl-6-(4-fluorophenyl)-5-{4-[4-(5-pyridine-2-yl-1H-[1,2,4]triazole-3-yl)-piperidine-1-ylmethyl]-phenyl}-[1,2,4]triazolo[1,5-a]pyrimidine,
5-(4-{4-[5-(4-chloropyridine-2-yl)-1H-[1,2,4]triazole-3-yl]-piperidine-1-ylmethyl}-phenyl)-2-cyclopropyl-6-(4-fluorophenyl)-[1,2,4]triazolo[1,5-a]pyrimidine, 6-(4-fluorophenyl)-7-(4-{4-[5-(6-methylpyridine-2-yl)-1H-[1,2,4]triazole-3-yl]-piperidine-1-ylmethyl}-phenyl)-imidazo[1,2-a]pyrimidine formiate, 6-(4-fluorophenyl)-7-{4-[4-(5-pyridine-2-yl)-1H-[1,2,4]triazole-3-yl]-piperidine-1-ylmethyl)-phenyl}-imidazo[1,2-a]pyrimidine formiate, 6-(4-fluorophenyl)-7-{4-[4-(5-pyrazine-2-yl-1H-[1,2,4]triazole-3-yl]-piperidine-1-ylmethyl]-phenyl}-imidazo[1,2-a]pyrimidine, 3-bromo-6-(4-fluorophenyl)-7-(4-{4-[5-(6-methylpyridine-2-yl)-1H-[1,2,4]triazole-3-yl]-piperidine-1-ylmethyl}-phenyl)-imidazo[1,2-a]pyrimidine, 3-chloro-6-(4-fluorophenyl)-7-{4-[4-(5-pyridine-2-yl-1H-[1,2,4]triazole-3-yl]-piperidine-1-ylmethyl]-phenyl}-imidazo[1,2-a]pyrimidine, 6-(2-fluorophenyl)-7-(4-{4-[5-(6-methylpyridine-2-yl)-1H-[1,2,4]triazole-3-yl]-piperidine-1-ylmethyl}-phenyl)-imidazo[1,2-a]pyrimidine, 3-bromo-6-phenyl-7-{4-{3-[5-(pyridine-2-yl)-1H-[1,2,4]triazole-3-yl)-azetidine-1-ylmethyl]-phenyl}-imidazo[1,2-a]pyrimidine, 2-methyl-6-phenyl-7-{4-{3-[5-(pyridine-2-yl)-1H-[1,2,4]triazole-3-yl)-azetidine-1-ylmethyl]-phenyl}-imidazo[1,2-a]pyrimidine, 3-bromo-2-methyl-7-{4-{3-[5-(6-methylpyridine-2-yl)-1H-[1,2,4]triazole-3-yl)-azetidine-1-ylmethyl]-phenyl}-6-phenyl-imidazo[1,2-a]pyrimidine, methyl-(6-phenyl-7-{4-{3-[5-(pyridine-2-yl)-1H-[1,2,4]triazole-3-yl)-azetidine-1-ylmethyl]-phenyl}-imidazo[1,2-a]pyrimidin-5-yl)-amine, (3-bromo-6-phenyl-7-{4-{3-[5-(pyridine-2-yl)-1H-[1,2,4]triazole-3-yl)-azetidine-1-ylmethyl]-phenyl}-imidazo[1,2-a]pyrimidin-5-yl)-methylamine, methyl-(2-methyl-6-phenyl-7-{4-{3-[5-(pyridine-2-yl)-1H-[1,2,4]triazole-3-yl)-azetidine-1-ylmethyl]-phenyl}-imidazo[1,2-a]pyrimidin-5-yl)-amine, methyl-(2-methyl-7-{4-{3-[5-(6-methylpyridine-2-yl)-1H-[1,2,4]triazole-3-yl)-azetidine-1-ylmethyl]-phenyl}-6-phenyl-imidazo[1,2-a]pyrimidin-5-yl)-amine, (6-(2,6-difluorophenyl)-5-{4-[3-[5-pyridine-2-yl-1H-[1,2,4]triazole-3-yl)-azetidine-1-ylmethyl]-phenyl}-pyrazolo[1,5-a]pyrimidin-3-yl)-methanol, (6-(2,6-difluorophenyl)-2-methoxy-5-{4-[3-[5-pyridine-2-yl-1H-[1,2,4]triazole-3-yl)-azetidine-1-ylmethyl]-phenyl}-pyrazolo[1,5-a]pyrimidin-3-yl)-methanol,

[6-(2,6-difluorophenyl)-2-methoxy-5-(4-{3-[5-(6-methylpyridine-2-yl-1H-[1,2,4]triazole-3-yl)-azetidine-1-ylmethyl}-phenyl)-pyrazolo[1,5-a]pyrimidin-3-yl)-methanol,

[6-(2,6-difluorophenyl)-2-methoxy-5-(4-{4-[5-(6-methylpyridine-2-yl-1H-[1,2,4]triazole-3-yl)-piperidine-1-ylmethyl}-phenyl)-pyrazolo[1,5-a]pyrimidin-3-yl)-methanol, (6-(2,6-difluorophenyl)-2-methoxy-5-{4-[4-(5-pyridine-2-yl-1H-[1,2,4]triazole-3-yl)-piperidine-1-ylmethyl]-phenyl}-pyrazolo[1,5-a]pyrimidin-3-yl)-methanol, isopropyl-(2-methyl-6-phenyl-7-{4-{3-[5-(pyridine-2-yl)-1H-[1,2,4]triazole-3-yl)-azetidine-1-ylmethyl]-phenyl}-imidazo[1,2-a]pyrimidin-5-yl)-amine, isopropyl-(2-methyl-6-phenyl-7-{4-{3-[5-(6-methylpyridine-2-yl)-1H-[1,2,4]triazole-3-yl)-azetidine-1-ylmethyl]-phenyl}-imidazo[1,2-a]pyrimidin-5-yl)-amine, isopropyl-(6-phenyl-7-{4-{3-[5-(pyridine-2-yl)-1H-[1,2,4]triazole-3-yl)-azetidine-1-ylmethyl]-phenyl}-imidazo[1,2-a]pyrimidin-5-yl)-amine, methyl-(6-phenyl-2-pyridine-2-yl-5-{4-[3-[5-pyridine-2-yl)-1H-[1,2,4]triazole-3-yl)-azetidine-1-ylmethyl]-phenyl}-[1,2,4]triazolo[1,5-a]pyrimidin-7-yl)-amine, isopropyl-(6-phenyl-2-pyridine-2-yl-5-{4-[3-[5-pyridine-2-yl)-1H-[1,2,4]triazole-3-yl)-azetidine-1-ylmethyl]-phenyl}-[1,2,4]triazolo[1,5-a]pyrimidin-7-yl)-amine, isopropyl-(6-phenyl-2-pyridine-2-yl-5-{4-[3-[5-(6-methylpyridine-2-yl)-1H-[1,2,4]triazole-3-yl)-azetidine-1-ylmethyl]-phenyl}-[1,2,4]triazolo[1,5-a]pyrimidin-7-yl)-amine, 2-cyclopropyl-6-phenyl-5-{4-[3-(5-pyridine-2-yl)-1H-[1,2,4]triazole-3-yl)-azetidine-1-ylmethyl]-phenyl}-[1,2,4]triazolo[1,5-a]pyrimidine, 5-(4-{3-[5-(6-methyl-pyridin-2-yl)-1H-[1,2,4]triazol-3-yl]-azetidin-1-ylmethyl}-phenyl)-2-methylsulfanyl-6-phenyl-[1,2,4]triazolo[1,5-a]pyrimidine, 2-methylsulfanyl-6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidine, 2-methylsulfanyl-6-phenyl-5-{4-[4-(5-pyridin-2-yl-1H-[1,2,4]triazol-3-yl)-piperidin-1-ylmethyl]-phenyl}-[1,2,4]triazolo[1,5-a]pyrimidine, 2-methylsulfanyl-6-phenyl-5-{4-[4-(5-pyrimidin-2-yl-1H-[1,2,4]triazol-3-yl)-piperidin-1-ylmethyl]-phenyl}-[1,2,4]triazolo[1,5-a]pyrimidine, 2-methylsulfanyl-6-phenyl-5-{4-[4-(5-pyrazin-2-yl-1H-[1,2,4]triazol-3-yl)-piperidin-1-ylmethyl]-phenyl}-[1,2,4]triazolo[1,5-a]pyrimidine, 5-(4-{4-[5-(6-methyl-pyridin-2-yl)-1H-[1,2,4]triazol-3-yl]-piperidin-1-ylmethyl}-phenyl)-2-methylsulfanyl-6-phenyl-[1,2,4]triazolo[1,5-a]pyrimidine, 2-methanesulfonyl-6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidine, 2-methanesulfonyl-6-phenyl-5-{4-[4-(5-pyridin-2-yl-1H-[1,2,4]triazol-3-yl)-piperidin-1-ylmethyl]-phenyl}-[1,2,4]triazolo[1,5-a]pyrimidine, 7-(4-{3-[5-(6-methylpyridine-2-yl)-1H-[1,2,4]triazole-3-yl]-azetidine-1-ylmethyl}-phenyl)-6-phenyl-imidazo[1,2-a]pyrimidine-2-carboxylic acid methyl ester, 6-phenyl-7-{4-[3-[5-pyridine-2-yl-1H-[1,2,4]triazole-3-yl)-azetidine-1-ylmethyl]-phenyl}-imidazo[1,2-a]pyrimidine-2-carboxylic acid methyl ester, 6-phenyl-7-{4-[3-[5-pyridine-2-yl-1H-[1,2,4]triazole-3-yl)-azetidine-1-ylmethyl]-phenyl}-imidazo[1,2-a]pyrimidin-2-yl)-methanol, 6-(2,5-difluorophenyl)-2-methyl-5-{4-[4-(5-pyridine-2-yl-1H-[1,2,4]triazole-3-yl)-piperidine-1-ylmethyl]-phenyl}-[1,2,4]triazolo[1,5-a]pyrimidine, or an N-oxide, a salt, a tautomer or a stereoisomer of said compound, or a salt of said N-oxide, tautomer or stereoisomer.

In a further embodiment of the above-mentioned aspects, the invention relates to compounds of formula (I), wherein ring B and the pyrimidine to which it is fused form the following ring system

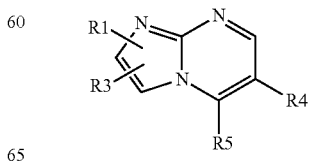

and R3 is hydrogen, or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein ring B and the pyrimidine to which it is fused form the following ring system

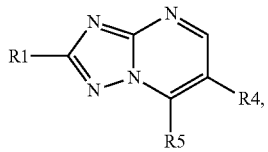

or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein ring B and the pyrimidine to which it is fused form the following ring system

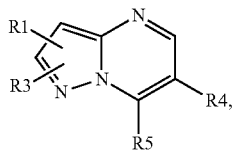

and R3 is hydrogen, or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein ring B and the pyrimidine to which it is fused form the following ring system

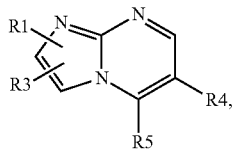

R3 is hydrogen, R6 is hydrogen and R4 is phenyl, or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein ring B and the pyrimidine to which it is fused form the following ring system

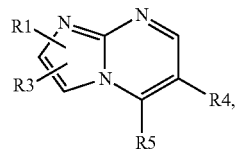

R3 is hydrogen, R6 is hydrogen, m=n=2 and R4 is unsubstituted phenyl and W is not a 5-membered heteroarylene.

or an N-oxide, a salt, a tautomer or a stereoisomer of said compound, or a salt of said N-oxide, tautomer or stereoisomer In a further embodiment of the above-mentioned aspects, the invention relates to compounds of formula (I), wherein ring B and the pyrimidine to which it is fused form the following ring system

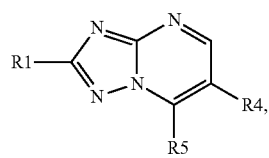

R6 is hydrogen, and R4 is phenyl, or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein ring B and the pyrimidine to which it is fused form the following ring system

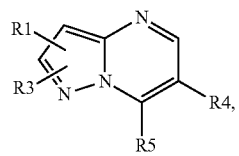

R3 is hydrogen, R6 is hydrogen and R4 is phenyl, or an N-oxide, a salt, a tautomer or a stereoisomer of said compound, or a salt of said N-oxide, tautomer or stereoisomer and the other residues are defined as is done in all aspects including aspects A-I or as in the claims.

In a further embodiment of the above-mentioned aspects, the invention relates to compounds of formula (I), wherein ring B and the pyrimidine to which it is fused form the following ring system

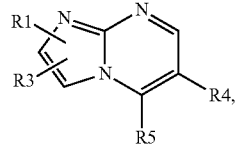

R3 is hydrogen, R6 is hydrogen, m=n=2 and R4 is a mono- or disubstituted phenyl and W is a 5-membered heteroarylene.

or an N-oxide, a salt, a tautomer or a stereoisomer of said compound, or a salt of said N-oxide, tautomer or stereoisomer and the other residues are defined as done in the claims.

In a further embodiment of the above-mentioned aspects, the invention relates to compounds of formula (I), wherein ring B and the pyrimidine to which it is fused form the following ring system

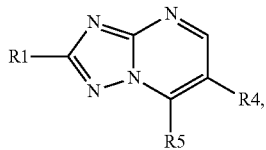

R6 is hydrogen, m=n=2 and R4 is a mono- or disubstituted phenyl and W is a 5-membered heteroarylene.
or an N-oxide, a salt, a tautomer or a stereoisomer of said compound, or a salt of said N-oxide, tautomer or stereoisomer the other residues are defined as done in the claims or in the embodiments related to one specific residue below.

In a further embodiment of the above-mentioned aspects, the invention relates to compounds of formula (I), wherein ring B and the pyrimidine to which it is fused form the following ring system

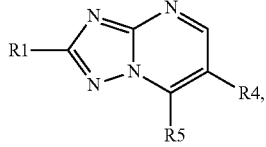

R6 is hydrogen, m=n=2 and R4 is a disubstituted phenyl and W is a 5-membered heteroarylene.
or an N-oxide, a salt, a tautomer or a stereoisomer of said compound, or a salt of said N-oxide, tautomer or stereoisomer the other residues are defined as done in the claims or in the embodiments related to one specific residue below.

In a further embodiment of the above-mentioned aspects, the invention relates to compounds of formula (I), wherein ring B and the pyrimidine to which it is fused form the following ring system

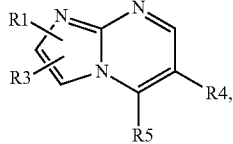

R3 is hydrogen, R6 is methyl, and R4 is phenyl,
or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein ring B and the pyrimidine to which it is fused form the following ring system

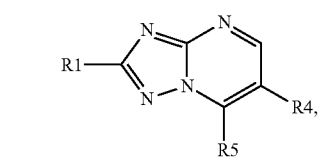

R6 is methyl, and R4 is phenyl,
or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein ring B and the pyrimidine to which it is fused form the following ring system

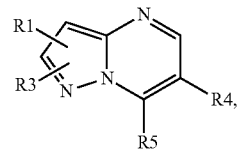

R3 is hydrogen, R6 is methyl, and R4 is phenyl,
or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein ring B and the pyrimidine to which it is fused is

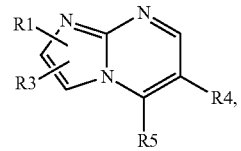

R3 is hydrogen, R6 is hydrogen, R4 is phenyl, R7 is —W—Y, W is 1,2,4-triazolylene, and Y is pyridin-2-yl (optionally substituted by R9),
or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein ring B and the pyrimidine to which it is fused is

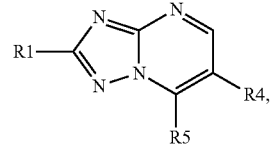

R6 is hydrogen, R4 is phenyl, R7 is —W—Y, W is 1,2,4-triazolylene, and Y is pyridin-2-yl (optionally substituted by R9),
or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein ring B and the pyrimidine to which it is fused is

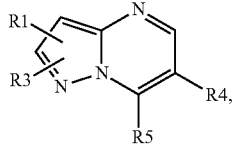

R3 is hydrogen, R6 is hydrogen, R4 is phenyl, R7 is —W—Y, W is 1,2,4-triazolylene, and Y is pyridin-2-yl (optionally substituted by R9),
or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein ring B and the pyrimidine to which it is fused is

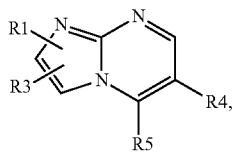

R3 is hydrogen or halogen, R6 is hydrogen, R4 is phenyl, R7 is —W—Y, W is 1,2,4-triazolylene and Y is pyridin-2-yl or Y is hydrogen and W is a bicyclic heteroarylen comprising 1 nitrogen atom and optionally 1, 2 or 3 further nitrogen atoms optionally substituted by R8,
or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein ring B and the pyrimidine to which it is fused is

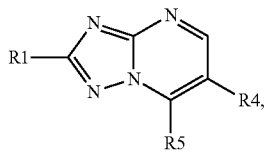

R1 is 1-4Calkyl optionally substituted by hydroxy, SR2, R6 is hydrogen, R4 is phenyl or phenyl substituted one or two time by R5A, R5 is 1-4Calkyl, NR10R11, R7 is —W—Y, W is 1,2,4-triazolylene, and Y is pyridin-2-yl optionally substituted by methyl,
or an N-oxide, a salt, a tautomer or a stereoisomer of said compound, or a salt of said N-oxide, tautomer or stereoisomer and the other residues are defined as done in all aspects including aspects A-I or as in the claims.

In one embodiment of the above-mentioned aspects, the invention relates to compounds of formula (I), wherein ring B and the pyrimidine to which it is fused is

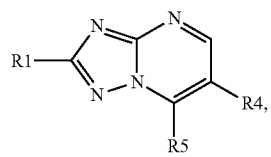

R1 is 1-4Calkyl optionally substituted by hydroxy, SR2, R6 is hydrogen, R4 is phenyl or phenyl substituted one or two time by R5A, R5 is 1-4Calkyl, NR10R11, R7 is —W—Y, W is 1,2,4-triazolylene, and Y is pyridin-2-yl which is substituted by methyl,
or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein ring B and the pyrimidine to which it is fused is

R3 is hydrogen, R6 is hydrogen, R4 is phenyl, R7 is —W—Y, W is 1,2,4-triazolylene, chinoxalinylene, and Y is pyridin-2-yl optionally substituted by methyl,
or an N-oxide, a salt, a tautomer or a stereoisomer of said compound, or a salt of said N-oxide, tautomer or stereoisomer and the other residues are defined as done in all aspects including aspects A-I or as in the claims.

In a further embodiment of the above-mentioned aspects, the invention relates to compounds of formula (I), wherein m is 1 and n is 1.

In a further embodiment of the above-mentioned aspects, the invention relates to compounds of formula (I), wherein m is 1 and n is 1 and Y is 2-pyridinyl optionally substituted by R9.

In a further embodiment of the above-mentioned aspects, the invention relates to compounds of formula (I), wherein m is 1 and n is 2.

In a further embodiment of the above-mentioned aspects, the invention relates to compounds of formula (I), wherein m is 2 and n is 2.

Another embodiment of the above-mentioned aspects are compounds of formula (I) wherein W is 5-membered heteroarylene which is substituted by R8.

A further embodiment of the above-mentioned aspects are compounds of formula (I) wherein W is a 6-membered heteroarylene which is optionally substituted by R8.

Another embodiment of the above-mentioned aspects are compounds of formula (I) wherein R1 is —S—R2. For those compounds no disclaimer applies.

Another embodiment of the above-mentioned aspects are compounds of formula (I) wherein R1 is 1-4C-alkyl, 3-5C-cycloalkyl, preferably 3-4C-cycloalkyl.

Another embodiment of the above-mentioned aspects are compounds of formula (I) wherein R1 and R5 are not hydrogen.

Another embodiment of the above-mentioned aspects are compounds of formula (I) wherein R4 is phenyl.

In a further embodiment of the above-mentioned aspects, the invention relates to compounds of formula (I), wherein R4 is phenyl which is substituted twice by R5A.

In a further embodiment of the above-mentioned aspects, the invention relates to compounds of formula (I), wherein ring B and the pyrimidine to which it is fused form a ring system selected from

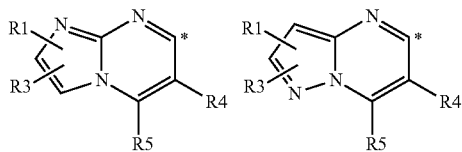

and the residues R1 and R3 are not hydrogen.

In a further embodiment of the above-mentioned aspects, the invention relates to compounds of formula (I), wherein R5 is NR10R11.

In a further embodiment of the above-mentioned aspects, the invention relates to compounds of formula (I), wherein Y is hydrogen.

In another embodiment of the above-mentioned aspects, the invention relates to compounds of formula (I) as an N-oxide of said compound.

In another embodiment of the above-mentioned aspects, the invention relates to compounds of formula (I) as a tautomer of said compound.

In another embodiment of the above-mentioned aspects, the invention relates to compounds of formula (I) as a stereoisomer of said compound.

In another embodiment the invention relates to compounds of formula (I), wherein R1 is hydrogen, 1-4C-alkyl (optionally substituted by halogen, hydroxy, amino, mono- or di-1-4C-alkylamino), halogen, amino, —SR2, —SOR2, —SO2R2, trifluoromethyl, cyano, 3-7C-cycloalkyl, 2-4C-alkenyl, 2-4C-alkynyl, 1-4C-alkoxy (optionally substituted by halogen), 3-7C-cycloalkoxy, NR10R11, C(O)NR12R13, —C(NH)NH2, —C(O)OR2.

In a further embodiment of the above-mentioned aspects, the invention relates to compounds of formula (I), wherein R1 is hydrogen, 1-4C-alkyl (optionally substituted by halogen, hydroxy, amino, mono- or di-1-4C-alkylamino), halogen, trifluoromethyl, cyano, 3-7C-cycloalkyl, 1-4C-alkoxy (optionally substituted by halogen) or NR10R11.

In a further embodiment of the above-mentioned aspects, the invention relates to compounds of formula (I), wherein R1 is hydrogen, 1-4C-alkyl, halogen, trifluoromethyl, cyano, 3-7C-cycloalkyl, 1-4C-alkoxy or NR10R11.

In a further embodiment of the above-mentioned aspects, the invention relates to compounds of formula (I), wherein R1 is hydrogen, methyl, ethyl, fluoro, chloro, trifluoromethyl, cyano, 3-4C-cycloalkyl, methoxy, amino, or mono- or di-1-4C-alkylamino.

In a further embodiment of the above-mentioned aspects, the invention relates to compounds of formula (I), wherein R3 is hydrogen.

In a further embodiment of the above-mentioned aspects, the invention relates to compounds of formula (I), wherein R4 is phenyl or thienyl.

In a further embodiment of the above-mentioned aspects, the invention relates to compounds of formula (I), wherein R5A is halogen.

In a further embodiment of the above-mentioned aspects, the invention relates to compounds of formula (I), wherein R5A is fluorine.

In a further embodiment of the above-mentioned aspects, the invention relates to compounds of formula (I), wherein R5 is hydrogen, 1-4C-alkyl, halogen, 1-4C-alkoxy or NR10R11.

In a further embodiment of the above-mentioned aspects, the invention relates to compounds of formula (I), wherein R5 is hydrogen, 1-4C-alkyl, 1-4C-alkoxy, amino or mono- or di-1-4C-alkylamino.

In a further embodiment of the above-mentioned aspects, the invention relates to compounds of formula (I), wherein R5 is hydrogen or 1-4C-alkyl.

In a further embodiment of the above-mentioned aspects, the invention relates to compounds of formula (I), wherein R5 is hydrogen or methyl.

In a further embodiment of the above-mentioned aspects, the invention relates to compounds of formula (I), wherein R6 is hydrogen.

In a further embodiment of the above-mentioned aspects, the invention relates to compounds of formula (I), wherein R8 is hydrogen, fluoro, trifluoromethyl or cyano.

In a further embodiment of the above-mentioned aspects, the invention relates to compounds of formula (I), wherein W is a monocyclic 5- or -6-membered heteroarylene.

In a further embodiment of the above-mentioned aspects, the invention relates to compounds of formula (I), wherein W is 1,2,4-triazolylene.

In a further embodiment of the above-mentioned aspects, the invention relates to compounds of formula (I), wherein Y is pyridin-2-yl optionally substituted by R9 and R9 is 1-4C-alkyl, 1-4C-alkoxy, halogen, hydroxy, 1-4C-haloalkyl, NR10R11, cyano or —C(O)NH2.

In a further embodiment of the above-mentioned aspects, the invention relates to compounds of formula (I), wherein Y is pyridin-2-yl optionally substituted by R9 and R9 is 1-4C-alkyl, 1-4C-alkoxy, halogen, hydroxy, 1-4C-haloalkyl, amino, mono- or di-1-4C-alkylamino, cyano or —C(O)NH2.

In a further embodiment of the above-mentioned aspects, the invention relates to compounds of formula (I), wherein R9 is 1-4C-alkyl, 1-4C-alkoxy or halogen.

In a further embodiment of the above-mentioned aspects, the invention relates to compounds of formula (I), wherein R10, R11, which can be same or different, is hydrogen, 1-4C-alkyl (optionally substituted by halogen, hydroxy, amino, mono- or di-1-4C-alkylamino) or 3-7C-cycloalkyl.

In a further embodiment of the above-mentioned aspects, the invention relates to compounds of formula (I), wherein R10, R11, which can be same or different, is hydrogen, 1-4C-alkyl.

Definitions 1-4C-Alkyl is a straight-chain or branched alkyl group having 1 to 4 carbon atoms. Examples are methyl, ethyl, n propyl, iso-propyl, n butyl, iso-butyl, sec-butyl and tert-butyl.

Mono- or di-1-4C-alkylamino radicals contain in addition to the nitrogen atom, one or two of the abovementioned 1-4C-alkyl radicals. Examples are the methyamino, the ethylamino, the isopropylamino, the dimethylamino, the diethylamino and the diisopropylamino radical.

Mono- or di-1-4C-alkylaminocarbonyl radicals contain in addition to the carbonyl group one of the abovementioned mono- or di-1-4C-alkylamino radicals. Examples are the N-methylaminocarbonyl, the N,N-dimethylaminocarbonyl, the N-ethylaminocarbonyl, the N-propylaminocarbonyl, the N,N-diethylaminocarbonyl and the N-isopropylaminocarbonyl.

Halogen within the meaning of the present invention is iodine, bromine, chlorine or fluorine.

1-4C-Haloalkyl is a straight-chain or branched alkyl group having 1 to 4 carbon atoms in which at least one hydrogen is substituted by a halogen atom. Examples are chloromethyl or 2-bromoethyl. For a partially or completely fluorinated C1-C4-alkyl group, the following partially or completely fluorinated groups are considered, for example: fluoromethyl, difluoromethyl, trifluoromethyl, fluoroethyl, 1,1-difluoroethyl, 1,2-difluoroethyl, 1,1,1-trifluoroethyl, tetrafluoroethyl, and pentafluoroethyl. Partially or completely fluorinated C1-C4-alkyl groups are considered to be encompassed by the term 1-4C-haloalkyl.

1-4C-Alkoxy represents radicals, which in addition to the oxygen atom, contain a straight-chain or branched alkyl radical having 1 to 4 carbon atoms. Examples which may be mentioned are the butoxy, iso-butoxy, sec-butoxy, tert-butoxy, propoxy, isopropoxy, ethoxy and methoxy radicals.

3-7C-Cycloalkyl stands for cyclopropyl, cyclobutyl, cyclopentyl, cyclohexyl or cycloheptyl.

3-7C-Cycloalkyloxy stands for cyclopropyloxy, cyclobutyloxy, cyclopentyloxy, cyclohexyloxy or cycloheptyloxy.

2-4C-Alkenyl is a straight chain or branched alkenyl radical having 2 to 4 carbon atoms. Examples are the but-2-enyl, but-3-enyl (homoallyl), prop-1-enyl, prop-2-enyl (allyl) and the ethenyl (vinyl) radicals.

2-4C-Alkynyl is a straight chain or branched alkynyl radical having 2 to 4 carbon atoms. Examples are the but-2-ynyl, but-3-ynyl (homopropargyl), prop-1-ynyl, 1-methylprop-2-ynyl (1-methylpropargyl), prop-2-ynyl (propargyl) and the ethinyl radicals.

The term "monocyclic 5- or 6-membered heteroaryl" comprised without being restricted thereto, the 5-membered heteroaryl radicals furyl, thienyl, pyrrolyl, oxazolyl, isoxazolyl, thiazolyl, isothiazolyl, imidazolyl, pyrazolyl, triazolyl (1,2,4-triazolyl, 1,3,4-triazolyl or 1,2,3-triazolyl), thiadiazolyl (1,3,4-thiadiazolyl, 1,2,5-thiadiazolyl, 1,2,3-thiadiazolyl or 1,2,4-thiadiazolyl) and oxadiazolyl (1,3,4-oxadiazolyl, 1,2,5-oxadiazolyl, 1,2,3-oxadiazolyl or 1,2,4-oxadiazolyl), as well as the 6-membered heteroaryl radicals pyridinyl, pyrimidinyl, pyrazinyl and pyridazinyl. Preferred 5- or 6-membered heteroaryl radicals are furanyl, thienyl, pyrrolyl, thiazolyl, oxazolyl, thiadiazolyl, oxadiazolyl, pyridinyl, pyrimidinyl, pyrazinyl or pyridazinyl. More preferred 5- or 6-membered heteroaryl radicals are furan-2-yl, thien-2-yl, pyrrol-2-yl, thiazolyl, oxazolyl, 1,3,4-thiadiazolyl, 1,3,4-oxadiazolyl, pyridin-2-yl, pyridin-4-yl, pyrimidin-2-yl, pyrimidin-4-yl, pyrazin-2-yl or pyridazin-3-yl.

The term "monocyclic 5-membered heteroarylene" is a divalent radical in which arbitrary one hydrogen atom is eliminated from the above described "heteroaryl" and may include, without being restricted thereto, the 5-membered heteroaryl radicals furylene, thienylene, pyrrolylene, oxazolylene, isoxazolylene, thiazolylene, isothiazolylene, imidazolylene, pyrazolylene, triazolylene (1,2,4-triazolylene, 1,3,4-triazolylene or 1,2,3-triazolylene), thiadiazolylene (1,3,4-thiadiazolylene, 1,2,5-thiadiazolylene, 1,2,3-thiadiazolylene or 1,2,4-thiadiazolylene) and oxadiazolylene (1,3,4-oxadiazolylene, 1,2,5-oxadiazolylene, 1,2,3-oxadiazolylene or 1,2,4-oxadiazolylene). Preferred 5-membered heteroaryl radicals are triazolylene, pyrazolyleneor imidazolylene. More preferred 5-membered heteroaryl radicals are 1,2,4-triazolylene, pyrazolylene or imidazolylene.

The NR10R11 group includes, for example, NH2, N(H)CH3, N(CH3)2, N(H)CH2CH3 and N(CH3)CH2CH3.

The C(O)NR12R13 group includes, for example, C(O)NH2, C(O)N(H)CH3, C(O)N(CH3)2, C(O)N(H)CH2CH3, C(O)N(CH3)CH2CH3 or C(O)N(CH2CH3)2.

In general and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

Constituents which are optionally substituted as stated herein, may be substituted, unless otherwise noted, one or more times, independently from one another at any possible position. Analogously it is being understood that it is possible for any heteroaryl group if chemically suitable that said heteroaryl group may be attached to the rest of the molecule via any suitable atom.

The heteroarylic or heteroarylenic groups mentioned herein may be substituted by their given substituents or parent molecular groups, unless otherwise noted, at any possible position, such as e.g. at any substitutable ring carbon or ring nitrogen atom.

Unless otherwise noted, rings containing quaternizable amino- or imino-type ring nitrogen atoms (—N=) may be preferably not quaternized on these amino- or imino-type ring nitrogen atoms by the mentioned substituents or parent molecular groups.

Unless otherwise noted, any heteroatom of a heteroarylic or heteroarylenic ring with unsatisfied valences mentioned herein is assumed to have the hydrogen atom(s) to satisfy the valences.

When any variable occurs more than one time in any constituent, each definition is independent.

In general and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

Salts of the compounds according to the invention include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

One aspect of the invention are salts of the compounds according to the invention including all inorganic and organic acid addition salts, especially all pharmaceutically acceptable inorganic and organic acid addition salts, particularly all pharmaceutically acceptable inorganic and organic acid addition salts customarily used in pharmacy. Another aspect of the invention are the salts with di- and tricarboxylic acids.

Examples of acid addition salts include, but are not limited to, hydrochlorides, hydrobromides, phosphates, nitrates, sulfates, salts of sulfamic acid, formates, acetates, propionates, citrates, D-gluconates, benzoates, 2-(4-hydroxybenzoyl)-benzoates, butyrates, salicylates, sulfosalicylates, lactates, maleates, laurates, malates, fumarates, succinates, oxalates, malonates, pyruvates, acetoacetates, tartarates, stearates, benzensulfonates, toluenesulfonates, methanesulfonates, trifluoromethansulfonates, 3-hydroxy-2-naphthoates, benzenesulfonates, naphthalinedisulfonates and trifluoroacetates.

Examples of salts with bases include, but are not limited to, lithium, sodium, potassium, calcium, aluminum, magnesium, titanium, meglumine, ammonium, salts optionally derived from NH3 or organic amines having from 1 to 16 C-atoms such as e.g. ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylendiamine, N-methylpiperindine and guanidinium salts.

The salts include water-insoluble and, particularly, water-soluble salts.

According to the person skilled in the art the compounds of formula (I) according to this invention as well as their salts may contain, e.g. when isolated in crystalline form, varying amounts of solvents. Included within the scope of the invention are therefore all solvates and in particular all hydrates of the compounds of formula (I) according to this invention as well as all solvates and in particular all hydrates of the salts of the compounds of formula (I) according to this invention.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The term "(chemotherapeutic) anti-cancer agents", includes but is not limited to (i) alkylating/carbamylating agents such as Cyclophosphamid (Endoxan®), Ifosfamid (Holoxan®), Thiotepa (Thiotepa Lederle®), Melphalan (Alkeran®), or chloroethyl-nitrosourea (BCNU); (ii) platinum derivatives like cis-platin (Platinex® BMS), oxaliplatin (Eloxatin®), satraplatin or carboplatin (Cabroplat® BMS); (iii) antimitotic agents/tubulin inhibitors such as vinca alkaloids (vincristine, vinblastine, vinorelbine), taxanes such as Paclitaxel (Taxol®), Docetaxel (Taxotere®) and analogs as well as new formulations and conjugates thereof (like the nanoparticle formulation Abraxane® with paclitaxel bound to albumin), epothilones such as Epothilone B (Patupilone®), Azaepothilone (Ixabepilone®) or ZK-EPO, a fully synthetic epothilone B analog; (iv) topoisomerase inhibitors such as anthracyclines (exemplified by Doxorubicin/Adriblastin®), epipodophyllotoxines (exemplified by Etoposide/Etopophos®) and camptothecin and camptothecin analogs (exemplified by Irinotecan/Camptosar® or Topotecan/Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (Puri-Nethol®), 6-thioguanine or fludarabine (Fludara®) and (vii) folic acid antagonists such as methotrexate (Farmitrexat®) or premetrexed (Alimta®).

The term "target specific anti-cancer agent", includes but is not limited to (i) kinase inhibitors such as e.g. Imatinib (Glivec®), ZD-1839/Gefitinib (Iressa®), Bay43-9006 (Sorafenib, Nexavar®), SU11248/Sunitinib (Sutent®), OSI-774/Erlotinib (Tarceva®), Dasatinib (Sprycel®), Lapatinib (Tykerb®), or, see also below, Vatalanib, Vandetanib (Zactima®) or Pazopanib; (ii) proteasome inhibitors such as PS-341/Bortezumib (Velcade®); (iii) histone deacetylase inhibitors like SAHA (Zolinza®), PXD101, MS275, MGCD0103, Depsipeptide/FK228, NVP-LBH589, Valproic acid (VPA), CRA/PCI 24781, ITF2357, SB939 and butyrates (iv) heat shock protein 90 inhibitors like 17-allylaminogeldanamycin (17-AAG) or 17-dimethylaminogeldanamycin (17-DMAG); (v) vascular targeting agents (VTAs) like combretastin A4 phosphate or AVE8062/AC7700 and anti-angiogenic drugs like the VEGF antibodies, such as Bevacizumab (Avastin®), or KDR tyrosine kinase inhibitors such as PTK787/ZK222584 (Vatalanib®) or Vandetanib (Zactima®) or Pazopanib; (vi) monoclonal antibodies such as Trastuzumab (Herceptin®), Rituximab (MabThera/Rituxan®), Alemtuzumab (Campath®), Tositumomab (Bexxar®), C225/Cetuximab (Erbitux®), Avastin (see above) or Panitumumab (Vectibix®) as well as mutants and conjugates of monoclonal antibodies, e.g. Gemtuzumab ozogamicin (Mylotarg®) or Ibritumomab tiuxetan (Zevalin®), and antibody fragments; (vii) oligonucleotide based therapeutics like G-3139/Oblimersen (Genasense®) or the DNMT1 inhibitor MG98; (viii) Toll-like receptor/TLR 9 agonists like Promune®, TLR 7 agonists like Imiquimod (Aldara®) or Isatoribine and analogues thereof, or TLR 7/8 agonists like Resiquimod as well as immunostimulatory RNA as TLR 7/8 agonists; (ix) protease inhibitors; (x) hormonal therapeutics such as anti-estrogens (e.g. Tamoxifen or Raloxifen), anti-androgens (e.g. Flutamide or Casodex), LHRH analogs (e.g. Leuprolide, Goserelin or Triptorelin) and aromatase inhibitors (e.g. Femara, Arimedex or Aromasin).

Other "target specific anti-cancer agents" include bleomycin, retinoids such as all-trans retinoic acid (ATRA), DNA methyltransferase inhibitors such as 5-Aza-2'-deoxycytidine (Decitabine, Dacogen®) and 5-azacytidine (Vidaza®), alanosine, cytokines such as interleukin-2, interferons such as interferon α2 or interferon-γ, bcl2 antagonists (e.g. ABT-737 or analogs), death receptor agonists, such as TRAIL, DR4/5 agonistic antibodies, FasL and TNF-R agonists (e.g. TRAIL receptor agonists like mapatumumab or lexatumumab).

Specific examples include, but are not limited to 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEVACIZUMAB, BEXXAR, BICALUTAMIDE, BLEOMYCIN, BORTEZOMIB, BROXURIDINE, BUSULFAN, CAMPATH, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DASATINIB, DAUNORUBICIN, DECITABINE, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ERLOTINIB, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GENASENSE, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, IXABEPILONE, LANREOTIDE, LAPATINIB, LETROZOLE, LEUPRORELIN, LOBAPLATIN, LOMUSTINE, LUPROLIDE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, MYLOTARG, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PANITUMUMAB, PATUPILONE, PAZOPANIB, PEGASPARGASE, PEGFILGRASTIM, PEMETREXED, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALOXIFEN, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SORAFENIB, SPIROMUSTINE, STREPTOZOCIN, SUNITINIB, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRAIL, TRASTUZUMAB, TREOSULFAN, TRIAZIQUONE, TRIMETREXATE, TRIPTORELIN, TROFOSFAMIDE, UREDEPA, VALRUBICIN, VATALANIB, VANDETANIB, VERTEPORFIN, VINBLASTINE, VINCRISTINE, VINDESINE, VINORELBINE, VOROZOLE, ZEVALIN and ZOLINZA.

The compounds according to the invention and their salts can exist in the form of tautomers which are included in the embodiments of the invention. In particular, those compounds of the invention which contain a pyrazole moiety for example can exist as a 1H tautomer, or a 2H tautomer, or even a mixture in any amount of the two tautomers, or a 1,2,4-triazole moiety for example can exist as a 1H tautomer, a 2H tautomer, or a 4H tautomer, or even a mixture in any amount of said 1H, 2H and 4H tautomers:

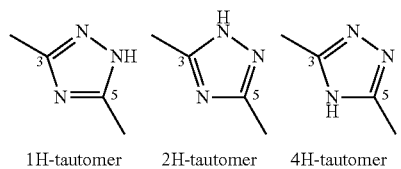

1H-tautomer    2H-tautomer    4H-tautomer

The compounds according to the invention and the salts thereof include stereoisomers. Each of the stereogenic centers present in said stereoisomers may have the absolute configuration R or the absolute configuration S (according to the rules of Cahn, Ingold and Prelog). Accordingly, the stereoisomers (1S) and (1R) in case of a compound of formula (Ia*)

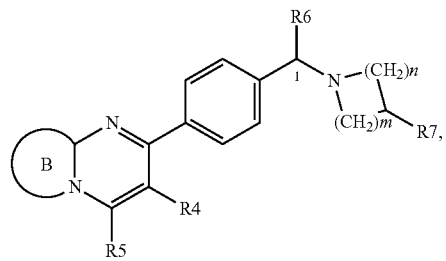

wherein ring B and the pyrimidine to which it is fused, R4, R5, R6, R7, m and n are defined as above,
or an N-oxide, a salt, a tautomer or a stereoisomer of said compound, or a salt of said N-oxide, tautomer or stereoisomer.

The invention further includes all mixtures of the stereoisomers mentioned above independent of the ratio, including the racemates.

Some of the compounds and salts according to the invention may exist in different crystalline forms (polymorphs) which are within the scope of the invention.

Furthermore, derivatives of the compounds of formula (I) and the salts thereof which are converted into a compound of formula (I) or a salt thereof in a biological system (biopre-cursors or pro-drugs) are covered by the invention. Said biological system is e.g. a mammalian organism, particularly a human subject. The bioprecursor is, for example, converted into the compound of formula (I) or a salt thereof by metabolic processes.

The intermediates used for the synthesis of the compounds of claims 1-4 as described below, as well as their use for the synthesis of the compounds of claims 1-4, are one further aspect of the present invention. Preferred intermediates are the Intermediate Examples as disclosed below.

The compounds according to the invention can be prepared as follows.

As shown in reaction scheme 1, the compounds of formula (I), wherein ring B and the pyrimidine to which it is fused, R4, R5, R7, m and n have the above mentioned meanings and R6 is hydrogen or 1-4C-alkyl, can be obtained by a reductive amination reaction of a corresponding compound of formula (III), wherein R has the meaning —C(O)R6, with a piperidine derivative of formula (II), wherein R7 has the above-mentioned meanings. The reductive amination can be carried out according to standard procedures, for example by the use of NaBH(OAc)3 or NaBH3CN in a suitable solvent such as, for example, DMF, MeOH, THF, or NMP, or mixtures of the same.

Reaction scheme 1:

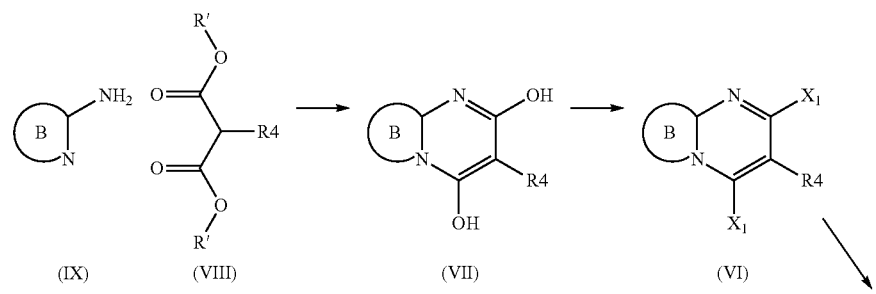

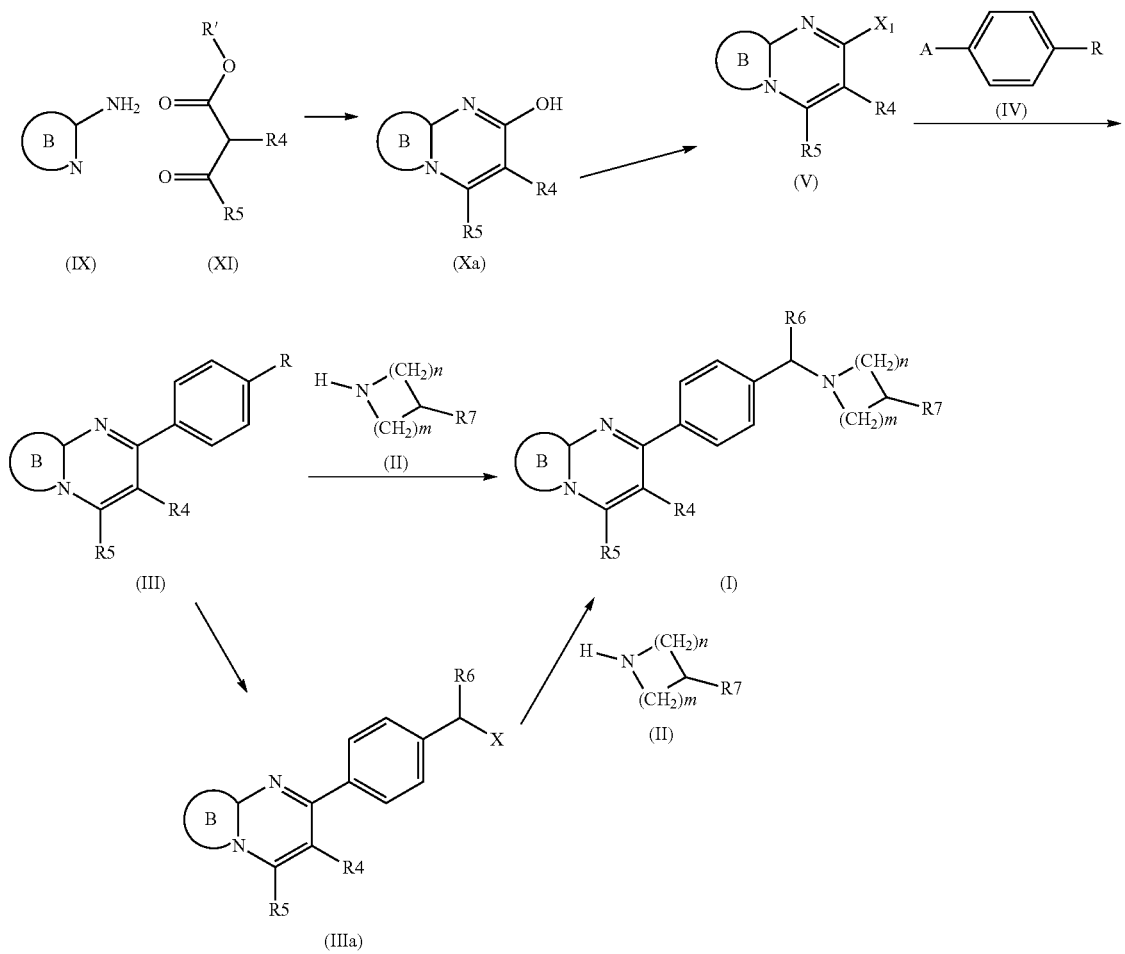

The amine derivatives of formula (II), wherein R7, m and n have the above-mentioned meanings are known or can be prepared according to known procedures (they may contain protecting group(s) in certain cases to protect other functionalities such as but not limited to NH functions). The amine derivatives of formula (II) may be prepared as as a suitable salt, such as, for example a hydrochloride salt, whereby the hydrochloride salt may be a monohydrochloride, or a dihydrochloride. Reactions using salts of amine derivatives of formula (II) require the addition of a suitable base, such as, for example triethylamine. Unless otherwise stated, for the purposes of calculating the amounts of base necessary for reactions with the salts of amine derivatives of formula (II), it is assumed that the salt of the amine derivative of formula (II) is a divalent salt, such as, for example the dihydrochloride salt.

The use of the compounds of formula (II), or the salts thereof, for the synthesis of the compounds of claims 1-4 is one aspect of the present invention.

Compounds of formula (III), wherein R has the meaning —C(O)H can be obtained from corresponding compounds of formula (III), wherein R has the meaning —C(O)O(1-4C-alkyl), in a one or two step procedure. The ester group is selectively reduced to the aldehyde group by methods known to the skilled person, for example by the use of diisobutylaluminium hydride (DIBAL) under low temperature for example −80 to −60° C. in the one step procedure. Alternatively, the ester group is reduced to the alcohol group (—CH2OH) according to known procedures, for example by the use of LiAlH4 or NaBH4, and then, the resulting alcohol is selectively oxidized to the —C(O)H group by methods known to the skilled person, for example with SO3-pyridine complex or Dess-Martin Periodinane, in the two step procedure.

Alternatively to the reaction sequence described above, the compounds of formula (I), wherein ring B and the pyrimidine to which it is fused, R4, R5, R7, m and n have the above mentioned meanings and R6 is hydrogen or 1-4C-alkyl, can be obtained by reaction of a corresponding compound of formula (IIIa), wherein X is a suitable leaving group, such as for example a halogen atom or a sulfonester, with amine derivatives of formula (II), wherein R7, m and n have the above-mentioned meanings. The reaction is preferably carried out in an inert solvent, such as for example DMF, at a temperature of from 60 to 100° C. in presence of a base, such as for example triethylamine.

Compounds of formula (IIIa), wherein X is a suitable leaving group, for example a halogen atom can be obtained from corresponding compounds of formula (III), wherein R is —CH(R6)OH and R6 is hydrogen or 1-4C-alkyl, by a halogenation reaction. Such a halogenation reaction can be accomplished, for example, by the use of PBr3 in dichloromethane.

Alternatively, compounds of formula (IIIa), wherein X is a suitable leaving group, for example a halogen atom can be obtained by benzylic halogenation from corresponding compounds of formula (III), wherein R is —CH2R6 and R6 is hydrogen or 1-4C-alkyl. Benzylic halogenation can, for example, be achieved by the use of N-bromosuccinimide (NBS).

Compounds of formula (III), wherein R is —CH(R6)OH and R6 is hydrogen or 1-4C-alkyl, can, for example, be obtained from corresponding compounds of formula (III), wherein R is —C(O)R6, by methods known to the person skilled in the art, for example by reduction with NaBH4 or LiAlH4.

Alternatively, compounds of formula (III), wherein R is —CH(R6)OH and R6 is hydrogen or 1-4C-alkyl, can be obtained from corresponding compounds of formula (III), wherein R is —CH2R6, by means of benzylic oxidation, which can be achieved, for example, by the use of catalytic or equimolar amounts of SeO2.

In a further alternative, compounds of formula (III), wherein R is —CH(1-4C-alkyl)OH can be obtained from corresponding compounds of formula (III), wherein R is —C(O)H by the addition of a suitable metal organic reagent, such as, but not limited to Grignard or Lithium reagents.

If necessary for the reactions in reaction scheme 1, for the synthesis of compounds of formula (III), wherein ring B and the pyrimidine to which it is fused, R4 and R5 have the above mentioned meanings and R is —C(O)R6 or —CH(R6)OH, these groups can be protected in some or all of the precursors by suitable protecting groups known to the person skilled in the art. Compounds of formula (III), wherein ring B and the pyrimidine to which it is fused, R4 and R5 have the above mentioned meanings and R is a protected ketone, aldehyde or alcohol group, can be deprotected by art-known removal of the protecting groups to generate the corresponding deprotected compounds.

Compounds of formula (III), wherein ring B and the pyrimidine to which it is fused and R4 and R5 have the above mentioned meanings and R is —C(O)O(1-4C-alkyl), —C(O)R6, —CH(R6)OH or —CH2R6 and R6 is hydrogen or 1-4C-alkyl, can be obtained by a transition metal catalysed C—C bond formation of a corresponding compound of formula (V), wherein X1 is Cl, Br, I, or —OS(O)2CF3, with a corresponding compound of formula (IV), wherein A, for example, is —B(OH)2, —Sn(1-4C-alkyl)3, —ZnCl, —ZnBr, —ZnI, or,

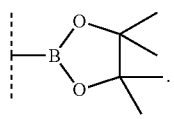

This transition metal catalysed C—C bond formation reaction can, for example, be achieved if A has the meaning of —B(OH)2 in a mixture of 1,2-dimethoxyethane and Na2CO3 solution at a temperature between 60-100° C. and by employing a Pd catalyst such as but not limited to 1,1'-bis(diphenylphosphino)ferrocene]palladium or Pd(PPh3)4.

Compounds of formula (IV) are either commercially available or can be prepared from commercially available compounds by methods known to the person skilled in the art.

Compounds of formula (V), wherein ring B and the pyrimidine to which it is fused and R4 have the above mentioned meanings and X1 is a halogen or —OS(O)2CF3 and R5 is hydrogen, can be obtained by reaction of a corresponding compound of formula (VI). This reaction can for example be achieved by reaction with a Zinc/Copper pair in a mixture of glacial acetic acid, methanol and tetrahydrofuran (THF) at elevated temperatures of from 70 to 130° C. Alternative this reaction can for example be achieved by reaction with zinc in a mixture of ammonia solution, dichloromethane and brine at elevated temperatures of from 0 to 80° C.

Alternatively, compounds of formula (V), wherein R5 is a amino or mono- or di-1-4C-alkylamino, can be obtained by reaction of a corresponding compound of formula (VI) with the respective corresponding amino compound, for example NH2CH3.

Alternatively, compounds of formula (V), wherein R5 is a 1-4C-alkyl or 3-7C-cycloalkyl, can be obtained by reaction of a corresponding compound of formula (VI) with reagents suitable for catalyzed or uncatalyzed C—C bond formation such as but not limited to boronic acids, zinc reagents, tin reagents, cyanide salts and Gringnard reagents. Catalysts suitable for these conversions are for example certain Pd or Cu complexes such as Pd(PPh3)4.

Alternatively, compounds of formula (V), wherein R5 is a 1-4C-alkoxy, can be obtained by reaction of a corresponding compound of formula (VI) with the respective compounds of formula NaO(1-4C-alkyl) in the respective solvents of formula HO(1-4C-alkyl).

A further alternatively, compound of formula (V), wherein ring B and the pyrimidine to which it is fused and R4 have the meanings described above and X1 is a halogen or —OS(O)2CF3 and R5 has the meaning of 1-4C-alkyl or 3-7-cycloalkyl, can for example be prepared from corresponding compounds of formula (Xa) by treatment with POCl3 in the case that X1 has the meaning of Cl, PBr3 or POBr3 in the case that X1 has the meaning of Br and or treatment with trifluoromethanesulfonic acid anhydride if X1 has the meaning of —OS(O)2CF3.

Compounds of formula (VI), wherein ring B and the pyrimidine to which it is fused and R4 have the meanings described above and X1 is halogen or —OS(O)2CF3, can be synthesized from corresponding compounds of formula (VII) with, for example, POCl3, PBr3, POBr3 or trifluoromethanesulfonic acid anhydride.

Compounds of formula (VII), wherein ring B and the pyrimidine to which it is fused and R4 have the above mentioned meanings, can be prepared with a condensation of the corresponding amino heterocycle of formula (IX) and the malonate esters of formula (VIII), wherein R' has the meaning of 1-4C alkyl. This reaction can, for example, be accomplished in DMF at elevated temperatures of from 80 to 200° C. and by employing a base such diaza(1,3)bicyclo[5.4.0]undecane (DBU) or tributylamine.

Compounds of formula (Xa), wherein ring B and the pyrimidine to which it is fused and R4 have the above mentioned meanings and R5 is 1-4C-alkyl or 3-7-cycloalkyl can, for example, be prepared from corresponding compounds of formula (XI) with corresponding compounds of formula (IX). This reaction can, for example, be accomplished in DMF at elevated temperatures of from 80 to 200° C. and by employing a base such DBU or tributylamine.

Compounds of formulae (VIII), (IX) and (XI) are either commercially available or can be prepared from commercially available compounds by methods known to the person skilled in the art.

Reaction scheme 2

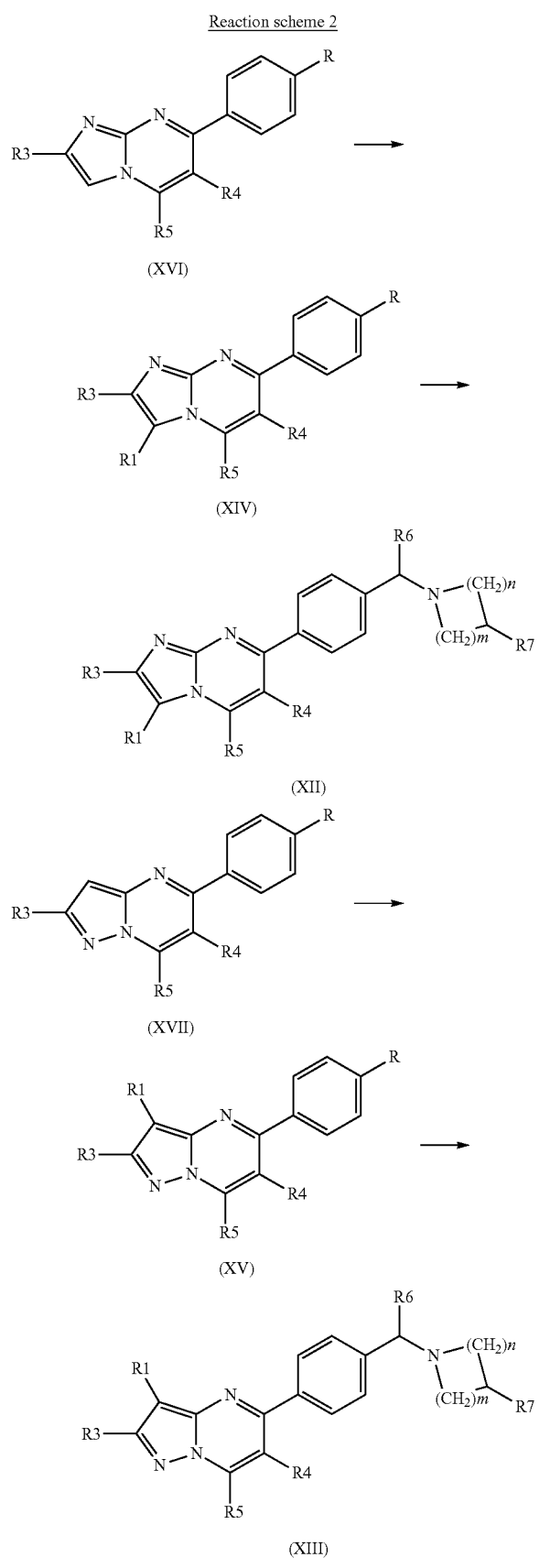

(XVI)

(XIV)

(XII)

(XVII)

(XV)

(XIII)

Compounds of formula (XII) and (XIII) in reaction scheme 2, wherein R1, R3, R4, R5, R6, R7, m and n have the meanings described above, can be prepared from corresponding compounds of formula (XIV) and (XV), wherein R is —C(O)O(1-4C-alkyl), —C(O)R6, —CH(R6)OH or —CH2R6 and R6 is hydrogen or 1-4C-alkyl, by a reductive amination reaction analogously as described above for the conversion of compounds of formula (III) to compounds of formula (I) in reaction scheme 1.

Compounds of formula (XIV) and (XV) wherein R3, R4 and R5 have the above mentioned meanings and R is —C(O)O(1-4C-alkyl), —C(O)R6, —CH(R6)OH or —CH2R6 and R6 is hydrogen or 1-4C-alkyl and R1 is halogen, can be directly synthesized by a halogenation reaction of the corresponding compounds of formula (XVI) and (XVII). For example by treatment with N-bromosuccinimide if R1 has the meaning of Br or N-chlorosuccinimide if R1 has the meaning of Cl or N-iodosuccinimide if R1 has the meaning of I. If R1 has the meaning of F in compounds of formula (XIV) and (XV), this conversion can for example be achieved by treatment of compounds of formula (XVI) and (XVI) respectively with 1-chloromethyl-4-fluoro-1,4-diazoniabicyclo[2.2.2]octane bis(tetrafluoroborate), for example in chloroform at temperatures such as 80-130° C.

Compounds of formula (XIV) and (XV), wherein R1 has the meaning of 1-3C-alkyl, 3-7C-cycloalkyl, —CN, 2-4C-alkenyl and 2-4C-alkynyl can be obtained from corresponding compounds of formula (XIV) and (XV), wherein R1 has the meaning of a halogen, by reaction with a metal organic reagent, such as, but not limited to 1-3C-alkyl-B(OH)2, 1-3C-alkyl-ZnCl, 1-3C-alkyl-ZnBr, 1-3C-alkyl-ZnI, 3-7C-cycloalkyl-B(OH)2, 3-7C-cycloalkyl-ZnCl, 3-7C-cycloalkyl-ZnBr, 3-7C-cycloalkyl-ZnI, 2-4C-alkenyl-B(OH)2, 2-4C-alkenyl-ZnCl, 2-4C-alkenyl-ZnBr, 2-4C-alkenyl-ZnI, 2-4C-alkynyl-B(OH)2, 2-4C-alkynyl-ZnCl, 2-4C-alkynyl-ZnBr, 2-4C-alkynyl-ZnI, Zn(CN)2 and 2-4C-alkynyls with a terminal triple bond, for example by employing Pd catalysts know to the person skilled in the art, for example Pd(PPh3)4 or 1,1'-bis(diphenylphosphino)ferrocene]palladium.

Compounds of formula (XIV) and (XV) wherein R1 has the meaning 1-4C-alkyl can be synthesized from respective compounds formula (XIV) and (XV) wherein R1 has the meaning of 1-4C-alkenyl or 1-4C-alkynyl for example by means of hydrogenation.

Compounds of formula (XVI) and (XVII) in reaction scheme 2, wherein R3, R4 and R5 have the meaning described above and R is —C(O)O(1-4C-alkyl), —C(O)R6, —CH(R6)OH or —CH2R6 and R6 is hydrogen or 1-4C-alkyl can prepared as described in reaction scheme 1 for compounds of formula (III).

If necessary for the reactions in reaction scheme 2, for the synthesis of compounds of formula (XII) and (XIII), wherein R is —C(O)R6 or —CH(R6)OH and R6 is hydrogen or 1-4C-alkyl, these groups can be protected in some or all of the precursors by suitable protecting groups known to the person skilled in the art. Compounds of formula (XII) and (XIII), in which R is a protected ketone, aldehyde or alcohol group, can be deprotected by art-known removal of the protecting groups to generate the corresponding deprotected compounds.

Reaction scheme 3

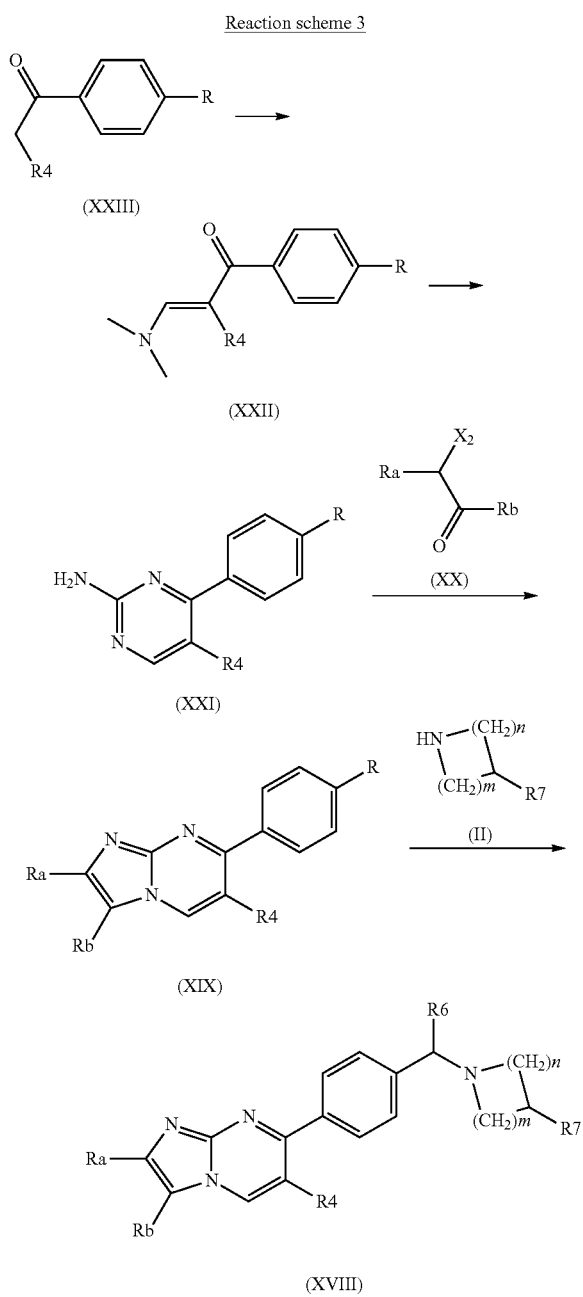

As shown in reaction scheme 3, compounds of formula (XVIII), wherein one of Ra and Rb has the meaning of R1 and the other of R3 and wherein R1, R3, R4, R6, R7, m and n have the meanings described above, can be prepared by a reductive amination reaction from corresponding compounds of formula (XIX), wherein R is —C(O)O(1-4C-alkyl), —C(O)R6, —CH(R6)OH or —CH2R6 and R6 is hydrogen or 1-4C-alkyl, with a compound of formula (II). This reductive amination reaction can be achieved analogously as described above in reaction scheme 1 for the conversion of compounds of formula (III) to compounds of formula (I).

Compounds of formula (XIX), wherein one of Ra and Rb has the meaning of R1 and the other of R3 and wherein R1, R3, R4 have the meanings described above and wherein R is —C(O)O(1-4C-alkyl), —C(O)R6, —CH(R6)OH or —CH2R6 and R6 is hydrogen or 1-4C-alkyl, can be prepared by reaction of a compound of formula (XX), wherein X2 has the meaning of a halogen or a sulfonester, with a corresponding compound of formula (XXI). This reaction can for example be achieved in refluxing ethanol.

Compounds of formula (XX) are either commercially available or can be prepared from commercially available compounds by methods known to the person skilled in the art.

Compounds of formula (XXI), wherein R4 has the meaning described above and R has the meanings of —C(O)O(1-4C-alkyl), —C(O)R6, —CH(R6)OH or —CH2R6 and R6 is hydrogen or 1-4C-alkyl, can for example be prepared from corresponding compounds of formula (XXII) by reaction with guanidine hydrochloride and NaOCH3 in methanol.

Compounds of formula (XXII), wherein R4 has the meaning described above and R has the meaning of —C(O)O(1-4C-alkyl), —C(O)R6, —CH(R6)OH or —CH2R6 and R6 is hydrogen or 1-4C-alkyl, can be prepared from corresponding compounds of formula (XXIII). This can for example be achieved by reaction with N,N-dimethylformamide dimethylacetal in DMF at elevated temperature of from 80 to 120° C.

Compounds of formula (XXIII) are either commercially available or can be prepared from commercially available compounds by methods known to the person skilled in the art.

If necessary for the reactions in reaction scheme 3, for the synthesis of compounds of formula (XIX), wherein R is —C(O)O(1-4C-alkyl), —C(O)R6 or —CH(R6)OH and R6 is hydrogen or 1-4C-alkyl these groups can be protected in some or all of the precursors by suitable protecting groups known to the person skilled in the art. Compounds of formula (XIX), in which R is a protected ketone, aldehyde or alcohol group, can be deprotected by art-known removal of the protecting groups to generate the corresponding deprotected compounds.

One preferred aspect of the invention is the process for the preparation of the compounds of claims 1-4 according to the examples.

Optionally, compounds of the formula (I) can be converted into their salts, or, optionally, salts of the compounds of the formula (I) can be converted into the free compounds. Corresponding processes are customary for the skilled person.

Optionally, compounds of the formula (I) can be converted into their N-oxides. The N-oxide may also be introduced by way of an intermediate. N-oxides may be prepared by treating an appropriate precursor with an oxidizing agent, such as metachloroperbenzoic acid, in an appropriate solvent, such as dichloromethane, at suitable temperatures, such as from 0° C. to 40° C., whereby room temperature is generally preferred. Further corresponding processes for forming N-oxides are customary for the skilled person.

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids such as e.g. mandelic acid can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

Commercial Utility

The compounds of formula (I) and the stereoisomers of the compounds of formula (I) according to the invention are hereinafter referred to as the compounds of the invention. In particular, the compounds of the invention are pharmaceutically acceptable. The compounds according to the invention have valuable pharmaceutical properties, which make them commercially utilizable. In particular, they inhibit the Pi3K/Akt pathway and exhibit cellular activity. They are expected to be commercially applicable in the therapy of diseases (e.g. diseases dependent on overactivated Pi3K/Akt). An abnormal activation of the PI3K/AKT pathway is an essential step towards the initiation and maintenance of human tumors and thus its inhibition, for example with AKT inhibitors, is understood to be a valid approach for treatment of human tumors. For a recent review see Garcia-Echeverria et al (Oncogene, 2008, 27, 551-5526).

Cellular activity and analogous terms in the present invention is used as known to persons skilled in the art, as an example, inhibition of phosphorylation, inhibition of cellular proliferation, induction of apoptosis or chemosensitization.

Chemosensitization and analogous terms in the present invention is used as known to persons skilled in the art. These stimuli include, for example, effectors of death receptor and survival pathways as well as cytotoxic/chemotherapeutic and targeted agents and finally radiation therapy. Induction of apoptosis and analogous terms according to the present invention are used to identify a compound which excecutes programmed cell death in cells contacted with that compound or in combination with other compounds routinely used for therapy.

Apoptosis in the present invention is used as known to persons skilled in the art. Induction of apoptosis in cells contacted with the compound of this invention might not necessarily be coupled with inhibition of cell proliferation. Preferably, the inhibition of proliferation and/or induction of apoptosis are specific to cells with aberrant cell growth.

Further on, the compounds according to the present invention inhibit protein kinase activity in cells and tissues, causing a shift towards dephosphorylated substrate proteins and as functional consequence, for example the induction of apoptosis, cell cycle arrest and/or sensitization towards chemotherapeutic and target-specific cancer drugs. In a preferred embodiment, inhibition of Pi3K/Akt pathway induces cellular effects as mentioned herein alone or in combination with standard cytotoxic or targeted cancer drugs.

Compounds according to the present invention exhibit anti-proliferative and/or pro-apoptotic and/or chemosensitizing properties. Accordingly, the compounds of the present invention are useful for treatment of hyperproliferative disorders, in particular cancer. Therefore the compounds of the present invention are used in the production of an anti-proliferative and/or pro-apoptotic and/or chemosensitizing effect in mammals such as human being suffering from a hyperproliferative disorders, like cancer.

Compounds according to the present invention exhibit anti-proliferative and/or pro-apoptotic properties in mammals such as humans due to inhibition of metabolic activity of cancer cells which are able to survive despite of unfavourable growth conditions such as glucose depletion, hypoxia or other chemo stress.

Thus, the compounds according to the present invention are useful for treating, ameliorating or preventing diseases of benign or malignant behaviour as described herein, such as e.g. for inhibiting cellular neoplasia.

Neoplasia in the present invention is used as known to persons skilled in the art. A benign neoplasia is described by hyperproliferation of cells, incapable of forming an aggressive, metastasizing tumor in-vivo. In contrast, a malignant neoplasia is described by cells with multiple cellular and biochemical abnormalities, capable of forming a systemic disease, for example forming tumor metastasis in distant organs.

The compounds according to the present invention can be preferably used for the treatment of malignant neoplasia. Examples of malignant neoplasia treatable with the compounds according to the present invention include solid and hematological tumors. Solid tumors can be exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). Hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

It is noted that a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function and death.

Drug resistance is of particular importance for the frequent failure of standard cancer therapeutics. This drug resistance is caused by various cellular and molecular mechanisms. One aspect of drug resistance is caused by constitutive activation of anti-apoptotic survival signals with PKB/Akt as a key signalling kinase. Inhibition of the Pi3K/Akt pathway leads to a resensitization towards standard chemotherapeutic or target specific cancer therapeutics. As a consequence, the commercial applicability of the compounds according to the present invention is not limited to $1^{st}$ line treatment of cancer patients. In a preferred embodiment, cancer patients with resistance to cancer chemotherapeutics or target specific anti-cancer drugs are also amenable for treatment with these compounds for e.g. $2^{nd}$ or $3^{rd}$ line treatment cycles. In particular, the compounds according to the present invention might be used in combination with standard chemotherapeutic or targeted drugs to resensitize tumors towards these agents.

In the context of their properties, functions and utilities mentioned herein, the compounds according to the present invention are distinguished by unexpected valuable and desirable effects related therewith, such as e.g. superior therapeutic window, superior bioavailability (such as e.g. good oral absorption), low toxicity and/or further beneficial effects related with their therapeutic and pharmaceutical qualities.

Compounds according to the present invention are for treatment, prevention or amelioration of the diseases of benign and malignant behavior as described before, such as e.g. benign or malignant neoplasia, particularly cancer, especially a cancer that is sensitive to Pi3K/Akt pathway inhibition.

The present invention further includes a method for treating, prevention or amelioration mammals, including humans, which are suffering from one of the above-mentioned conditions, illnesses, disorders or diseases. The method is characterized in that a pharmacologically active and therapeutically effective and tolerable amount of one or more of compounds according to the present invention is administered to the subject in need of such treatment.

The present invention further includes a method for treating, preventing or ameliorating diseases responsive to inhibition of the Pi3K/Akt pathway, in a mammal, including human, comprising administering a pharmacologically active and therapeutically effective and tolerable amount of one or more of the compounds according to the present invention to said mammal.

The present invention further includes a method for treating hyperproliferative diseases of benign or malignant behaviour and/or disorders responsive to induction of apoptosis, such as e.g. cancer, particularly any of those cancer diseases described above, in a mammal, comprising administering a pharmacologically active and therapeutically effective and tolerable amount of one or more of the compounds according to the present invention to said mammal.

The present invention further includes a method for inhibiting cellular hyperproliferation or arresting aberrant cell growth in a mammal, comprising administering a pharmacologically active and therapeutically effective and tolerable amount of one or more of the compounds according to the present invention to said mammal.

The present invention further includes a method for inducing apoptosis in the therapy of beningn or malignant neoplasia, particularly cancer, comprising administering a pharmacologically active and therapeutically effective and tolerable amount of one or more of the compounds according to the present invention to a subject in need of such therapy.

The present invention further includes a method for inhibiting protein kinase activity in cells comprising administering a pharmacologically active and therapeutically effective and tolerable amount of one or more of the compounds according to the present invention to a patient in need of such therapy.

The present invention further includes a method for sensitizing towards chemotherapeutic or target-specific anti-cancer agents in a mammal, comprising administering a pharmacologically active and therapeutically effective and tolerable amount of one or more of the compounds according to the present invention to said mammal.

The present invention further includes a method for treating benign and/or malignant neoplasia, particularly cancer, in a mammal, including human, comprising administering a pharmacologically active and therapeutically effective and tolerable amount of one or more of the compounds according to the present invention to said mammal.

The present invention further relates to the use of the compounds for the production of pharmaceutical compositions, which are employed for the treatment, prophylaxis, and/or amelioration of one or more of the illnesses mentioned.

The present invention further relates to the use of the compounds for the manufacture of pharmaceutical compositions for treating, preventing or ameliorating hyperproliferative diseases and/or disorders responsive to the induction of apoptosis, such as e.g. beningn or malignant neoplasia, in particular cancer.

The present invention further relates to the use of the compounds according to this invention for the production of pharmaceutical compositions for treating, preventing or ameliorating benign or malignant neoplasia, particularly cancer, such as e.g. any of those cancer diseases described above.

The invention further relates to a compound according to the invention or a pharmaceutically acceptable salt thereof, for the treatment and/or prophylaxis of (hyper)proliferative diseases and/or disorders responsive to induction of apoptosis, which include benign neoplasia and malignant neoplasia, including cancer.

The invention further related to the use of a compound according to the invention or a pharmaceutically acceptable salt thereof, for the production of a pharmaceutical composition for the treatment, prevention or amelioration of a disease mediated by a dysregulated function of a single protein kinase or multiple protein kinases and/or disorders responsive to the induction of apoptosis.

The invention further relates to a pharmaceutical composition, comprising a compound according to the invention or a pharmaceutically acceptable salt thereof, for the treatment and/or prophylaxis of (hyper)proliferative diseases and/or disorders responsive to induction of apoptosis, which include benign neoplasia and malignant neoplasia, including cancer.

The present invention further relates to the use of compounds and pharmaceutically acceptable salts according to the present invention for the manufacture of pharmaceutical compositions, which can be used for sensitizing towards chemotherapeutic and/or target specific anti-cancer agents.

The present invention further relates to the use of compounds according to the present invention for the manufacture of pharmaceutical compositions, which can be used for sensitizing towards radiation therapy of those diseases mentioned herein, particularly cancer.

The present invention further relates to the use of the compounds according to the present invention for the manufacture of pharmaceutical compositions, which can be used in the treatment of diseases sensitive to protein kinase inhibitor therapy and different to cellular neoplasia. These non-malignant diseases include, but are not limited to benign prostate hyperplasia, neurofibromatosis, dermatoses, and myelodysplastic syndromes.

The present invention further relates to pharmaceutical compositions comprising one or more of the compounds according to this invention and a pharmaceutically acceptable carrier or diluent.

The present invention further relates to pharmaceutical compositions comprising one or more of the compounds according to this invention and pharmaceutically acceptable auxiliaries and/or excipients.

The pharmaceutical compositions according to this invention are prepared by processes, which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, dragees, pills, cachets, granules, capsules, caplets, suppositories, patches (e.g. as TTS), emulsions (such as e.g. micro-emulsions or lipid emulsions), suspensions (such as e.g. nano suspensions), gels, solubilisates or solutions (e.g. sterile solutions), or encapsuled in liposomes or as beta-cyclodextrine or beta-cyclodextrin derivative inclusion complexes or the like, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers (such as e.g. polyoxyethylenglyceroltriricinoleat 35, PEG 400, Tween 80, Captisol, Solutol HS15 or the like), colorants, complexing agents, permeation promoters, stabilizers, fillers, binders, thickeners, disintegrating agents, buffers, pH regulators (e.g. to obtain neutral, alkaline or acidic formulations), polymers, lubricants, coating agents, propellants, tonicity adjusting agents, surfactants, flavorings, sweeteners or dyes, can be used.

In particular, auxiliaries and/or excipients of a type appropriate to the desired formulation and the desired mode of administration are used.

The administration of the compounds, pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous deliveries are preferred.

Generally, the pharmaceutical compositions according to the invention can be administered such that the dose of the active compound is in the range customary for Pi3K/Akt pathway inhibitors. In particular, a dose in the range of from 0.01 to 4000 mg of the active compound per day is preferred for an average adult patient having a body weight of 70 kg. In this respect, it is to be noted that the dose is dependent, for example, on the specific compound used, the species treated, age, body weight, general health, sex and diet of the subject treated, mode and time of administration, rate of excretion, severity of the disease to be treated and drug combination.

The pharmaceutical composition can be administered in a single dose per day or in multiple subdoses, for example, 2 to 4 doses per day. A single dose unit of the pharmaceutical composition can contain e.g. from 0.01 mg to 4000 mg, preferably 0.1 mg to 2000 mg, more preferably 0.5 to 1000 mg, most preferably 1 to 500 mg, of the active compound. Furthermore, the pharmaceutical composition can be adapted to weekly, monthly or even more infrequent administration, for example by using an implant, e.g. a subcutaneous or intramuscular implant, by using the active compound in form of a sparingly soluble salt or by using the active compound coupled to a polymer.

The choice of the optimal dosage regime and duration of medication, particularly the optimal dose and manner of administration of the active compounds necessary in each case can be determined by a person skilled in the art.

The present invention further relates to combinations comprising one or more first active ingredients selected from the compounds of the invention and one or more second active ingredients selected from chemotherapeutic anti-cancer agents and target-specific anti-cancer agents e.g. for treating, preventing or ameliorating diseases responsive or sensitive to inhibition of the Pi3K/Akt pathway, such as hyperproliferative diseases of benign or malignant behaviour and/or disorders responsive to the induction of apoptosis, particularly cancer, such as e.g. any of those cancer diseases described above.

The invention further relates to the use of a pharmaceutical composition comprising one or more of the compounds according to this invention as sole active ingredient(s) and a pharmaceutically acceptable carrier or diluent in the manufacture of pharmaceutical products for the treatment and/or prophylaxis of the illnesses mentioned above.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

The anti-cancer agents mentioned herein above as combination partners of the compounds according to this invention are meant to include pharmaceutically acceptable derivatives thereof, such as e.g. their pharmaceutically acceptable salts.

The person skilled in the art is aware of the total daily dosage(s) and administration form(s) of the additional therapeutic agent(s) coadministered. Said total daily dosage(s) can vary within a wide range.

In practicing the present invention, the compounds according to this invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics (chemotherapeutic and/or target specific anti-cancer agents), in particular art-known anti-cancer agents, such as any of e.g. those mentioned above.

In this context, the present invention further relates to a combination comprising a first active ingredient, which is at least one compound according to this invention, and a second active ingredient, which is at least one art-known anti-cancer agent, such as e.g. one or more of those mentioned herein above, for separate, sequential, simultaneous, concurrent or chronologically staggered use in therapy, such as e.g. in therapy of any of those diseases mentioned herein.

The present invention further relates to a pharmaceutical composition comprising a first active ingredient, which is at least one compound according to this invention, and a second active ingredient, which is at least one art-known anti-cancer agent, such as e.g. one or more of those mentioned herein above, and, optionally, a pharmaceutically acceptable carrier or diluent, for separate, sequential, simultaneous, concurrent or chronologically staggered use in therapy.

The present invention further relates to a combination product comprising
a.) at least one compound according to this invention formulated with a pharmaceutically acceptable carrier or diluent, and
b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat hyperproliferative diseases and diseases responsive or sensitive to inhibition of the Pi3K/Akt pathway, such as e.g. beningn or malignant neoplasia, particularly cancer, more precisely, any of those cancer diseases described above.

The present invention further relates to a combined preparation comprising at least one compound according to this invention and at least one art-known anti-cancer agent for simultaneous, concurrent, sequential or separate administration.

The present invention further relates to combinations, compositions, formulations, preparations or kits according to the present invention having Pi3K/Akt pathway inhibitory activity.

In addition, the present invention further relates to a method for treating in combination therapy hyperproliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating hyperproliferative diseases of benign or malignant behaviour and/or disorders responsive to the induction of apoptosis, such as e.g. cancer, in a patient comprising administering in combination therapy separately, simultaneously, concurrently, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In further addition, the present invention relates to a method for treating, preventing or ameliorating hyperproliferative diseases and/or disorders responsive to induction of apoptosis, such as e.g. benign or malignant neoplasia, e.g. cancer, particularly any of those cancer diseases mentioned herein, in a patient comprising administering separately, simultaneously, concurrently, sequentially or chronologically staggered to said patient in need thereof an amount of a first active compound, which is a compound according to the present invention, and an amount of at least one second active compound, said at least one second active compound being a standard therapeutic agent, particularly at least one art-known anti-cancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, preventing or ameliorating hyperproliferative diseases and/or disorders responsive to induction of apoptosis, such as e.g. benign or malignant neoplasia, e.g. cancer, particularly any of those cancer diseases mentioned herein, in a patient comprising administering a combination according to the present invention.

In addition, the present invention further relates to the use of a composition, combination, formulation, preparation or kit according to this invention in the manufacture of a pharmaceutical product, such as e.g. a commercial package or a medicament, for treating, preventing or ameliorating hyperproliferative diseases, such as e.g. cancer, and/or disorders responsive to the induction of apoptosis, particularly those diseases mentioned herein, such as e.g. malignant or benign neoplasia.

The present invention further relates to a commercial package comprising one or more compounds of the present invention together with instructions for simultaneous, concurrent, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, concurrent, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, concurrent, sequential or separate use with one or more compounds according to the present invention.

The compositions, combinations, preparations, formulations, kits or packages mentioned in the context of the combination therapy according to this invention may also include more than one of the compounds according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be according, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a hyperproliferative diseases and/or a disorder responsive to the induction of apoptosis, particularly one of those diseases mentioned herein, such as e.g. malignant or benign neoplasia, especially cancer, like any of those cancer diseases mentioned herein.

In addition, compounds according to the present invention can be used in the pre- or post-surgical treatment of cancer.

In further addition, compounds of the present invention can be used in combination with radiation therapy.

A combination according to this invention can refer to a composition comprising both the compound(s) according to this invention and the other active anti-cancer agent(s) in a fixed combination (fixed unit dosage form), or a medicament pack comprising the two or more active ingredients as discrete separate dosage forms (non-fixed combination). In case of a medicament pack comprising the two or more active ingredients, the active ingredients are preferably packed into blister cards, which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

EXPERIMENTAL PART

The following table lists the abbreviations used in this paragraph and in the Examples section as far as they are not explained within the text body. NMR peak forms are stated as they appear in the spectra, possible higher order effects have not been considered. Chemical names were generated using AutoNom2000 as implemented in MDL ISIS Draw. In some cases generally accepted names of commercially available reagents were used in place of AutoNom2000 generated names. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography. In some cases, the compounds may be purified by preparative HPLC. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the persion skilled in the art, or be used as salts in subsequent biological assays. It is to be understood that the specific form (e.g. salt, free base . . . ) of a compound of the present invention as isolated as described herein is not necessarily the only form in which said compound can be applied to a biological assay in order to quantify the specific biological activity.

| Abbreviation | meaning |
| --- | --- |
| Ac | acetyl |
| ACN | acetonitrile |
| br | broad |
| d | doublet |
| DBU | diaza(1,3)bicyclo[5.4.0]undecane |
| dd | doublet of doublet |
| DCM | dichloromethane |
| DIBAL | diisobutylaluminiumhydride |
| DMAP | 4-dimethylaminopyridine |
| DMF | N,N-dimethylformamide |
| DMSO | dimethyl sulfoxide |
| Eq. | equivalent |
| ESI | electrospray ionisation |
| EtOAc | ethylacetate |
| HBTU | 2-(1H-benzotriazol-1-yl)-1,1,3,3-tetramethyluroniumhexafluorophosphate |
| HPLC | high performance liquid chromatography |
| LC-MS | liquid chromatography mass spectrometry |
| m | Multiplet |
| MS | mass spectrometry |
| NBS | N-bromosuccinimide |
| NIS | N-iodosuccinimide |
| NMP | N-methylpyrrolidinone |
| NMR | nuclear magnetic resonance spectroscopy: |

-continued

| Abbreviation | meaning |
|---|---|
| | chemical shifts (δ) are given in ppm. |
| q | quartet |
| qn | quintet |
| rf | at reflux |
| r.t. or rt | room temperature |
| RT | retention time (in minutes), measured by UPLC with a standard procedure, unless stated |
| s | singlet |
| t | triplet |
| TLC | thin layer chromatography |
| THF | Tetrahydrofuran |

Other abbreviations have their meanings customary per se to the skilled person. The various aspects of the invention described in this application are illustrated by the following examples which are not meant to limit the invention in any way.

EXAMPLES

UPLC-MS Standard Procedure

Analytical UPLC-MS was performed under the following conditions unless otherwise stated.

Instrument: Waters Acquity UPLC-MS ZQ4000; Column: Acquity UPLC BEH C18 1.7 50×2.1 mm; Eluent A: water+0.05% formic acid, Eluent B: acetonitrile+0.05% formic acid; Gradient: 0-1.6 min 1-99% B, 1.6-2.0 min 99% B; Flow rate 0.8 ml/min; Temperature: 60° C.; Injection: 2 µl; DAD scan: 210-400 nm. The masses (m/z) are reported from the positive mode electrospray ionisation unless the negative mode is indicated (ES−)

INTERMEDIATE EXAMPLES

Intermediate Example 1.0

4-(6-phenylimidazo[1,2-a]pyrimidin-7-yl)benzaldehyde

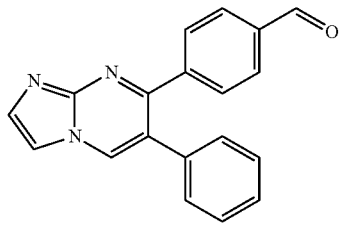

Step 1: 6-phenylimidazo[1,2-a]pyrimidine-5,7-diol 18.3 g (0.0776 mol) diethylphenylmalonate and 20.5 g (0.0776 mol) 2-aminoimidazole sulfate were dissolved in 93 mL DMF and 35 mL DBU and the mixture was heated to 100° C. for 15 h. The solvent was removed, the residue dissolved in water and re-precipitated by adjusting the pH to 1 with 2 mol/l HCl. The precipitate was collected by filtration to obtain the desired product.

MS (M+1): 228

Step 2: 5,7-dichloro-6-phenylimidazo[1,2-a]pyrimidine 8 g 6-phenylimidazo[1,2-a]pyrimidine-5,7-diol was dissolved in 40 mL $POCl_3$ and 6.7 mL (52.8 mmol) dimethylaniline. The mixture was heated to 100° C. for 2 h. The solvent was removed, the residue was dissolved in a mixture of dichloromethane, water and ice, the organic phase separated and the water-phase extracted with dichloromethane. The combined dichloromethane phase was washed with sodium chloride-solution, dried over $Na_2SO_4$ and evaporated. The residue was purified by silica gel chromatography (dichloromethane/ethyl acetate) yielding the desired product.

MS (M+1) 264

Characteristic 1H NMR signals (200 MHz, d6-DMSO): 8.1 (d, 1H); 7.9 (d, 1H)

Step 3: 7-chloro-6-phenylimidazo[1,2-a]pyrimidine 10 g 5,7-dichloro-6-phenylimidazo[1,2-a]pyrimidine and 7.3 g Zinc/Copper pair were suspended in 5 mL glacial acetic acid, 10 mL methanol and 60 mL THF and the mixture was heated to 50° C. for 1 h. The mixture was filtered over celite, diluted with dichloromethane and washed with water. The organic phase was dried over sodium sulfate and evaporated to obtain the crude product, a mixture of the desired product and 6-phenylimidazo[1,2-a]pyrimidine. This mixture was used for the next reaction without further purification.

MS (M+1): 230/232

Characteristic 1H NMR signals (200 MHz, d6-DMSO): 9.1 ppm (s, 1H); 7.8 (d, 1H); 7.9 (d, 1H)

Step 4: 4-(6-phenylimidazo[1,2-a]pyrimidin-7-yl)benzaldehyde

To a mixture of 6 g of the crude product obtained in step 3 and 5.1 g 4-formylphenylboronic acid in 210 mL 1,2-dimethoxyethane were added 0.96 g dichloro[1,1'-bis(diphenylphosphino)ferrocene]palladium (II) dichloromethane adduct and 42 mL of a 10% w/w sodium carbonate solution. The resulting mixture was heated to 80° C. under an inert gas atmosphere for 15 h. The work up was performed by diluting the reaction mixture with water and dichloromethane, separating the phases and extraction of the aqueous phase with dichloromethane. The combined organic layers were dried over sodium sulphate and evaporated. The residue was suspended in ethyl acetate and the resulting mixture stirred for 2 h at room temperature. The product was collected by filtration and used without further purification.

MS (M+1): 300

Characteristic 1H NMR (300 MHz, d6-DMSO) signals: 10 ppm (s, 1H), 9.1 ppm (s, 1H), 8.0 ppm (d, 1H)

Intermediate Example 1.1

4-[6-(4-fluorophenyl)-imidazo[1,2-a]pyrimidine-7-yl]-benzaldehyde

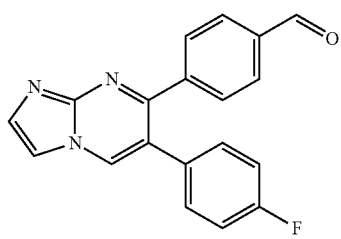 [SMILES: O=Cc1ccc(-c2nc3nccn3cc2-c2ccc(F)cc2)cc1]

Step 1: 6-(4-fluorophenyl)-imidazo[1,2-a]pyrimidine-5,7-diol 7.2 g (39.3 mmol) 1H-Imidazol-2-ylamine sulfate are dissolved in 45 mL DMF. 10 g (39.3 mmol) diethyl (4-fluorophenyl)malonate is added. After dropwise addition of 17.6 mL (118 mmol) 1,8-diazabicyclo[5.4.0]undec-7-ene the reaction mixture is stirred at 100° C. over night. The DMF has been removed and the darkbrown oily residue treated with 150 mL water (complete dissolution). 2M HCl (60 mL) is added at room temperature until a pH of 1. After stirring for 1 h at ice bath cooling the formed crystals are collected by filtration to yield the product (5.78 g=53.9%), which is used without further purification. Another crop of 0.48 g (4.5%) is obtained by treating the solid residue in the flask with water and 2M HCl. After stirring for one hour the crystals are collected.

MS (Cl, M+1): 246
$^1$H-NMR (300 MHz, d6-DMSO): 10.90-12.70 (br., 2H), 7.40-7.50 (m, 3H), 7.35 (d, 1H), 7.02-7.12 (m, 2H).

Step 2: 5,7-dichloro-6-(4-fluorophenyl)imidazo[1,2-a]pyrimidine 6.2 g (25.3 mmol) 6-(4-Fluorophenyl)-imidazo[1,2-a]pyrimidine-5,7-diol are dissolved in 28.7 mL (308 mmol) POCl$_3$ and 5.1 mL (40.5 mmol) N,N-dimethylaniline. The mixture is heated at 100° C. for 2 h. POCl$_3$ is evaporated and the oily residue treated with ice-water (caution: stirring and cooling necessary due to strong development of heat). A precipitate forms. After addition of 30 mL dichloromethane the precipitate has been collected by filtration via a glass microfibre filter and washed with dichloromethane/water. The precipitate is collected by filtration, washed with water and dried. 5.78 g (77%) of the desired product are obtained. The filtrate is extracted twice with dichloromethane (150 mL each). The combined organic phases are washed with water and brine and dried (Na$_2$SO$_4$). After evaporation of the solvent the residue is purified by chromatography (silicagel, eluents: dichloromethane/methanol) yielding another 0.43 g (6%) of the dichloro derivate.

MS (Cl, M+1): 282
$^1$H-NMR (400 MHz, d6-DMSO): 8.22 (s, 1H), 8.07 (s, 1H), 7.45-7.52 (m, 2H), 7.35-7.45 (m, 2H).

Step 3: 7-chloro-6-(4-fluorophenyl)-imidazo[1,2-a]pyrimidine 5.3 g (18.9 mmol) 5,7-Dichloro-6-(4-fluorophenyl)-imidazo[1,2-a]pyrimidine are given in 480 mL ethanol, 184 mL THF and 342 mL water. After addition of 4.7 g (89.5 mmol) NH$_4$Cl and 7.9 g (120 mmol) zinc the mixture is vigorously stirred at rt for two and a half hours. The reaction mixture is filtered via a glass microfibre filter and washed with plenty of methanol. The solvent has been removed and the residue redissolved in ethyl acetate (1 L). After washing twice with brine the solvent is evaporated (without prior drying due to solid material in the solvent). 3.83 g (81.8%) of the desired product containing 11% of the bisdeschloro compound are obtained which is used without further purification.

MS (Cl, M+1): 248
$^1$H-NMR (300 MHz, d6-DMSO): 9.09 (s, 1H), 7.91 (d, 1H), 7.74 (d, 1H), 7.52-7.62 (m, 2H), 7.29-7.40 (m, 2H).

Step 4: 4-[6-(4-fluorophenyl)-imidazo[1,2-a]pyrimidine-7-yl]-benzaldehyde 2.8 g (11.3 mmol) 7-Chloro-6-(4-fluorophenyl)-imidazo[1,2-a]pyrimidine are given in 39 mL dimethoxyethane (not completely dissolved). 1.86 g (12.4 mmol) 4-formylphenylboronic acid and 22 mL Na$_2$CO$_3$ solution (10%) are added. After addition of 0.42 g (0.51 mmol) 1,1'-bis(diphenylphosphino)ferrocenedichloropalladium(II) the reaction mixture is purged 3× with argon and heated to 90° C. After 22 h stirring at 90° C. complete dissolution has taken place. The reaction mixture is cooled down and treated with 100 mL water and 150 mL dichloromethane. After vigorous stirring at rt for one hour the organic phase is separated. The aqueous phase is extracted twice with dichloromethane (100 mL each). The combined organic phases are washed twice with water (50 mL each), dried (Na$_2$SO$_4$) and the solvent is removed. The crude product is purified via chromatography (silicagel, dichloromethane/methanol). 1.52 g (42.4%) of the pure compound and two other fractions (224.6 mg=6.3% and 456.9 mg=12.7%) with contaminated product are obtained.

MS (Cl, M+1): 318
$^1$H-NMR (300 MHz, d6-DMSO): 9.98 (s, 1H), 9.10 (s, 1H), 7.96 (d, 1H), 7.76-7.88 (m, 3H), 7.48-7.59 (m, 2H), 7.12-7.34 (m, 4).

Intermediate Example 1.2

4-(6-phenylimidazo[1,2-a]pyrimidine-7-yl)phenyl]-methanol

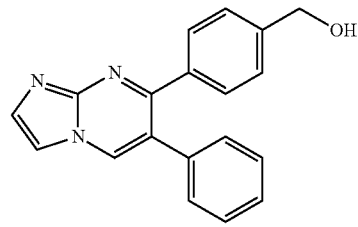 [SMILES: OCc1ccc(-c2nc3nccn3cc2-c2ccccc2)cc1]

2.2 g (7.35 mmol) 4-(6-phenylimidazo[1,2-a]pyrimidine-7-yl)benzaldehyde (intermediate example 1.0) is suspended in 44 mL ethanol and 11 mL dichloromethane. 0.56 g (14.7 mmol) NaBH$_4$ are added in portions at −10° C., whereupon the suspension dissolves, and the reaction mixture is stirred for 90 minutes at this temperature. The reaction is quenched with 50 mL water, the cooling bath is removed and stirring is continued for 30 minutes. The solvents are evaporated and the residue (water phase) is extracted three times with dichloromethane (50 mL each). The combined organic extracts are washed with water and brine and dried (Na$_2$SO$_4$). After filtration and evaporation of the solvent the residue is purified by chromatography (silicagel, eluents: dichloromethane/methanol). 1.41 g (62.1%) of the desired alcohol are obtained.

MS (Cl, M+1): 302
$^1$H-NMR (400 MHz, CDCl$_3$): 8.40 (s, 1H), 7.83 (s, 1H), 7.58 (s, 1H), 7.39-7.49 (m, 2H), 7.18-7.39 (m, 7H), 4.70 (s, 2H).

Intermediate Example 1.3

4-[6-(2-fluorophenyl)-imidazo[1,2-a]pyrimidine-7-yl]-benzaldehyde

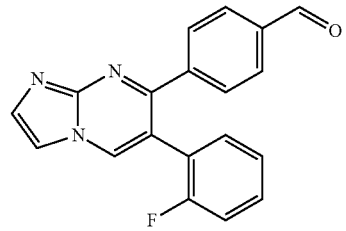 [SMILES: O=Cc1ccc(-c2nc3nccn3cc2-c2ccccc2F)cc1]

Step 1: 6-(2-fluorophenyl)-imidazo[1,2-a]pyrimidine-5,7-diol 5 g (27.5 mmol) 1H-Imidazol-2-ylamine sulfate are dissolved in 31.7 mL DMF. 7 g (27.5 mmol) diethyl (2-fluorophenyl)malonate are added. After dropwise addition of 12.3 mL (82.6 mmol) 1,8-diazabicyclo[5.4.0]undec-7-ene the reaction mixture is stirred at 100° C. over night. The DMF is evaporated and the darkbrown oily residue treated with 150 mL water (complete dissolution). 2M HCl (60 mL) is added at room temperature until a pH of 1. After stirring for 1 h at ice bath cooling the formed crystals are collected by filtration to yield the product (3.43 g=48.3%), which is used without further purification. Another crop of 0.41 g (6.1%) is obtained by evaporating the solvent, treating the oily residue with water and 2M HCl. After stirring for five hours the crystals are collected and washed with water.

MS (Cl, M+1): 246

$^1$H-NMR (400 MHz, d6-DMSO): 12.52 (br., 1H), 11.12 (br., 1H), 7.49 (d, 1H), 7.40 (d, 1H), 7.20-7.32 (m, 2H), 7.05-7.18 (m, 2H).

Step 2: 5,7-dichloro-6-(2-fluorophenyl)-imidazo[1,2-a]pyrimidine 3.63 g (14.8 mmol) 6-(2-Fluorophenyl)-imidazo[1,2-a]pyrimidine-5,7-diol are dissolved in 16.8 mL (180 mmol) POCl$_3$ and 2.9 mL (23.7 mmol) N,N-dimethylaniline. The mixture is heated at 100° C. for 6 h. Additional 18.4 mL POCl$_3$ and 1.5 mL N,N-dimethylaniline are added and the mixture is heated at 100° C. for two days. Heating is continued for another two days at 120° C. The POCl$_3$ is evaporated and the oily residue treated with ice-water (caution: stirring and cooling necessary due to strong development of heat). A precipitate forms. After addition of 30 mL dichloromethane and stirring for ten minutes the precipitate is collected by filtration, washed with dichloromethane/water and dried. The crude product (1.4 g, strongly contaminated) is treated with 30 mL 2N NaOH and vigorously stirred for one hour. The precipitate is filtered off, washed with plenty of water and dried. 0.96 g (23.1%) of the desired product (contaminated) are obtained. The filtrate is discarded.

MS (Cl, M+1): 282

$^1$H-NMR (300 MHz, d6-DMSO): 8.10 (d, 1H), 7.91 (d, 1H), 7.48-7.67 (m, 2H), 7.32-7.48 (m, 2H).

Step 3: 7-chloro-6-(2-fluorophenyl)-imidazo[1,2-a]pyrimidine 0.86 g (3.05 mmol) 5,7-Dichloro-6-(2-fluorophenyl)-imidazo[1,2-a]pyrimidine are given in 1.5 mL methanol and 8.6 mL THF. After addition of 0.589 g (4.6 mmol) zinc/copper pair the mixture is stirred at rt for 18 hours. The reaction mixture is filtered via a glass microfibre filter and washed with plenty of methanol. The solvent is evaporated and the residue is treated and evaporated three times with toluene. After chromatography on silicagel (eluents dichloromethane/methanol) 672.4 mg (89%) of the desired product containing bisdeschloro compound are obtained which is used without further purification.

MS (Cl, M+1): 248

Step 4: 4-[6-(2-fluorophenyl)-imidazo[1,2-a]pyrimidine-7-yl]-benzaldehyde 665 mg (2.68 mmol) 7-Chloro-6-(2-fluorophenyl)-imidazo[1,2-a]pyrimidine are given in 9.2 mL dimethoxyethane (not completely dissolved). 442.9 mg (2.95 mmol) 4-formylphenylboronic acid and 5.3 mL Na$_2$CO$_3$ solution (10%) are added. After addition of 98.6 mg (0.12 mmol) 1,1'-bis(diphenylphosphino)ferrocenedichloropalladium(II) the reaction mixture is purged 3× with argon and heated to 90° C. for 20 hours. The reaction mixture is cooled down and treated with 30 mL water and 150 mL dichloromethane. After vigorous stirring at rt for 90 minutes the organic phase is separated. The aqueous phase is extracted with dichloromethane (100 mL). The combined organic phases are washed with water (50 mL) and brine (50 mL) and dried (Na$_2$SO$_4$). The solvent is removed and the crude product purified via chromatography (silicagel, dichloromethane/methanol). 404.8 mg (47.5%) of the desired product (contaminated) are obtained.

MS (Cl, M+1): 318

Intermediate Example 2.0

4-(6-phenyl[1,2,4]triazolo[1,5-a]pyrimidin-5-yl)benzaldehyde

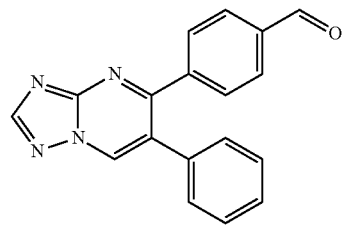

Step 1: 6-phenyl[1,2,4]triazolo[1,5-a]pyrimidine-5,7-diol

A solution of 10 g 1,2,4-triazol-3-amine and 33.7 g diethyl phenylmalonate in N,N-dibutylbutan-1-amine was stirred at 185° C. over night. The solution was diluted with 10% w/w NaOH solution, the resulting mixture was stirred for 30 min and the organic phase was separated. The aqueous layer was extracted with diethylether, acidified with concentrated HCl until precipitation of the product was complete and the precipitate collected by filtration to yield the product, which was used without further purification.

MS (M+1): 229

Characteristic 1H NMR (200 MHz, d6-DMSO) signals: 8.7 ppm (s, 1H)

Step 2: 5,7-dichloro-6-phenyl[1,2,4]triazolo[1,5-a]pyrimidine 2.45 g 6-phenyl[1,2,4]triazolo[1,5-a]pyrimidine-5,7-diol was suspended in 4.1 mL POCl$_3$ and the mixture was stirred for 4 h at 100° C. The solvent was removed, the residue dissolved in a mixture of dichloromethane, water and ice, the organic phase was separated and water-phase was extracted with dichloromethane. The combined dichloromethane phase was dried over Na$_2$SO$_4$ and evaporated. The crude product was used without further purification.

MS (M+1): 265

Characteristic 1H NMR (200 MHz, d6-DMSO) signals: 8.8 ppm (s, 1H)

Step 3:
5-chloro-6-phenyl[1,2,4]triazolo[1,5-a]pyrimidine

A mixture of 0.5 g 5,7-dichloro-6-phenyl[1,2,4]triazolo[1,5-a]pyrimidine, 0.22 mL glacial acetic acid, 0.5 mL methanol, 3 mL THF and 366 mg of Zn/Cu pair were stirred for 3 h at ambient temperature. The mixture was filtered through celite, evaporated to dryness and the residue was purified on silica gel (dichloromethane/ethyl acetate) to yield the desired product.
MS (M+1): 231/233
Characteristic 1H NMR (400 MHz, d6-DMSO) signals: 9.6 ppm (s, 1H); 8.8 ppm (s, 1H)

Step 4: 4-(6-phenyl[1,2,4]triazolo[1,5-a]pyrimidin-5-yl)benzaldehyde

To a mixture of 130 mg 5-chloro-6-phenyl[1,2,4]triazolo[1,5-a]pyrimidine and 93 mg 4-formylphenylboronic acid in 5 mL 1,2-dimethoxyethane was added 1.2 mL of a 10% w/w sodium carbonate solution and 65 mg tetrakis (triphenylphosphine) palladium(0) and the resulting mixture was heated to 90° C. under an inert gas atmosphere for 18 h. The work up was performed by diluting the reaction mixture with water and dichloromethane, separating the phases and extraction of the aqueous phase with dichloromethane. The combined organic layers were dried over sodium sulphate, evaporated and the residue suspended in methanol. The crystalline product was isolated by filtration yielding the desired product. The filtrate was evaporated to dryness, dissolved in ethyl acetate and additional product precipitated by the addition of petrolether.
MS (M+1): 301
Characteristic 1H NMR (400 MHz, d6-DMSO) signals: 10 ppm (s, 1H), 9.6 ppm (s, 1H); 8.8 ppm (d, 1H)

Intermediate Example 3.0

4-(2-Methyl-6-phenyl-[1,2,4]triazolo[1,5-a]pyrimidin-5-yl)-benzaldehyde

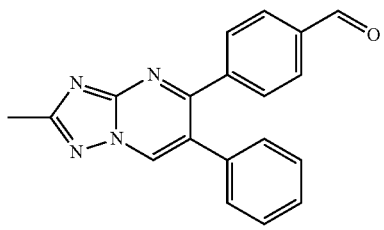

Step 1: 2-methyl-6-phenyl[1,2,4]triazolo[1,5-a]pyrimidine-5,7-diol

A solution of 25.0 g 3-amino-5-methyltriazole and 66.0 mL diethyl phenylmalonate in 100 mL N,N-dibutylbutan-1-amine was stirred at 18500 for 20 h. The reaction mixture consisted of two layers after cooling to room temperature. The top layer was removed and the lower layer was diluted with 10% w/w NaOH solution and water. The aqueous layer was extracted with diethyl ether and acidified with concentrated HCl until precipitation of the product was complete. The precipitate was collected by filtration to yield the product, which was used without further purification.
MS (M+1): 243

Characteristic 1H NMR (200 MHz, d6-DMSO) signals: 7.4 ppm (m, 2H); 7.3 ppm (m, 2H); 7.2 ppm (m, 1H); 2.4 ppm (s, 3H)

Step 2: 5,7-dichloro-2-methyl-6-phenyl[1,2,4]triazolo[1,5-a]pyrimidine 35.0 g 2-methyl-6-phenyl[1,2,4]triazolo[1,5-a]pyrimidine-5,7-diol was suspended in 80 mL $POCl_3$, and 27.47 mL N,N-dimethylaniline were added. The mixture was stirred at 100° C. for 1 h. The excess of $POCl_3$ was removed and the residue was dissolved in a mixture of dichloromethane, water and ice. The organic phase was separated and the water-phase was extracted with dichloromethane. The combined organic layers were dried over $Na_2SO_4$ and the solvent was evaporated.
The crude product was used without further purification.
MS (M+1): 279

Step 3: 5-chloro-2-methyl-6-phenyl[1,2,4]triazolo[1,5-a]pyrimidine 34.5 g 5,7-dichloro-2-methyl-6-phenyl[1,2,4]triazolo[1,5-a]pyrimidine was dissolved in 500 mL dichloromethane. 500 mL brine, 250 mL 25% aqueous ammonia solution and 34.0 g zinc powder were added and the mixture was stirred at room temperature for 1 h. The reaction mixture was filtered through Celite and was washed with dichloromethane and water. The organic phase was separated and the water phase was extracted with dichloromethane. The combined dichloromethane phase was dried over $Na_2SO_4$ and the solvent was evaporated. The crude product was purified by chromatography on silica gel (dichloromethane/ethyl acetate) to yield the desired compound.
MS (M+1): 245
Characteristic 1H NMR (300 MHz, d6-DMSO) signals: 9.45 ppm (s, 1H); 2.6 ppm (s, 3H)

Step 4: 4-(2-methyl-6-phenyl[1,2,4]triazolo[1,5-a]pyrimidin-5-yl)benzaldehyde

To a mixture of 6.90 g 5-chloro-2-methyl-6-phenyl[1,2,4]triazolo[1,5-a]pyrimidine and 4.65 g 4-formylphenylboronic acid in 100 mL 1,2-dimethoxyethane were added 55 mL of a 10% w/w sodium carbonate solution and 1.03 g dichloro[1,1'-bis(diphenylphosphino)ferrocene]palladium (II). The resulting mixture was heated to 90° C. under an inert gas atmosphere for 18 h. The work up was performed by diluting the reaction mixture with water and dichloromethane, separating the phases and extraction of the aqueous phase with dichloromethane. The combined organic layers were dried over sodium sulphate and the solvent was evaporated. The residue was purified by chromatography on silica gel (dichloromethane/methanol) to yield the desired product.
MS (M+1): 315
Characteristic 1H NMR (300 MHz, d6-DMSO) signals: 10.0 ppm (s, 1H); 9.4 ppm (s, 1H); 7.8 ppm (m, 2H); 7.6 ppm (m, 2H); 2.6 ppm (s, 3H)

Intermediate Example 3.1

4-[6-(2,4-difluorophenyl)-2-methyl-[1,2,4]triazolo[1,5-a]pyrimidine-5-yl]-benzaldehyde

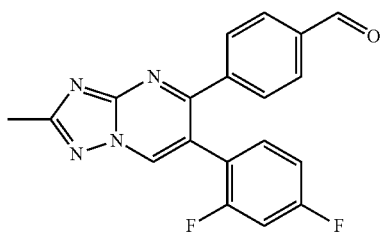 [SMILES: Cc1nc2nc(-c3ccc(C=O)cc3)c(-c3ccc(F)cc3F)cn2n1]

Step 1: 6-(2,4-difluorophenyl)-2-methyl-[1,2,4]triazolo[1,5-a]pyrimidine-5,7-diol 4 g (40.95 mmol) 3-Amino-5-methyl-1,2,4-triazole, 10 g diethyl (2,4-difluorophenyl)malonate and 9 g tributylamine are stirred at 180° C. over night. The solution is diluted with 2N NaOH solution and water and the resulting mixture is extracted three times with methyl-tert. butylether. These organic extracts are discarded. The aqueous phase is acidified at 0° C. with concentrated HCl. The precipitate is collected by filtration, washed with water and dried. This product (4.47 g=33.4%) is used without further purification.

MS (Cl, M+1): 279
$^1$H-NMR (300 MHz, d6-DMSO): 7.25-7.61 (m, 1H), 7.09-7.22 (m, 1H), 6.95-7.09 (m, 1H), 2.40 (s, 3H).

Step 2: 5,7-dichloro-6-(2,4-difluorophenyl)-2-methyl-[1,2,4]triazolo[1,5-a]pyrimidine 4.45 g (16 mmol)-(2,4-Difluorophenyl)-2-methyl-[1,2,4]triazolo[1,5-a]pyrimidine-5,7-diol, 8.9 mL (95.96 mmol) POCl$_3$ and 3 mL (23.8 mmol) N,N-dimethylaniline are stirred at 100° C. over night. The mixture is poured slowly and cautiously (strong development of heat) to a large amount of ice water. After vigorous stirring for one hour the precipitate is collected by filtration and purified by chromatography (2.85 g=48%)

MS (Cl, M+1): 315
$^1$H-NMR (300 MHz, d6-DMSO): 7.48-7.68 (m, 2H), 7.25-7.42 (m, 1H), 2.57 (s, 3H).

Step 3: 5-chloro-6-(2,4-difluorophenyl)-2-methyl-[1,2,4]triazolo[1,5-a]pyrimidine 2.35 g (7.5 mmol) 5,7-Dichloro-6-(2,4-difluorophenyl)-2-methyl-[1,2,4]triazolo[1,5-a]pyrimidine are given in 189 mL ethanol, 135 mL water and 73 mL THF. 1.89 g (35.3 mmol) NH$_4$Cl and 3.1 g (47.7 mmol) zinc powder are added and the mixture is stirred at room temperature for 3 h. The reaction mixture is filtered and the organic solvents are removed. The residue is diluted with water and extracted three times with ethyl acetate. The combined organic layers are washed with brine and dried over Na$_2$SO$_4$. After evaporation of the solvent, the residue is purified by chromatography. 1.2 g (51.6%) of the desired product are obtained.

MS (Cl, M+1): 280;
$^1$H-NMR (300 MHz, d6-DMSO): 9.58 (s, 1H), 7.53-7.65 (m, 1H), 7.40-7.53 (m, 1H), 7.22-7.32 (m, 1H), 2.52 (s, 3H).

Step 4: 4-[6-(2,4-difluorophenyl)-2-methyl-[1,2,4]triazolo[1,5-a]pyrimidine-5-yl]-benzaldehyde To a mixture of 1 g (3.56 mmol) of the 5-chloro-6-(2,4-difluorophenyl)-2-methyl-[1,2,4]triazolo[1,5-a]pyrimidine described in step 3 and 587.6 mg (3.9 mmol) 4-formylphenylboronic acid in 12 mL 1,2-dimethoxyethane are added 131 mg (0.16 mmol) dichloro[1,1'-bis(diphenylphosphino)ferrocene]palladium (II) and 6.9 mL of a sodium carbonate solution (10%). The resulting mixture is heated to 90° C. under an inert gas atmosphere for 2 h. The reaction mixture is diluted with water and extracted three times with dichloromethane. The combined organic layers are washed with brine and dried over sodium sulphate; the solvent is evaporated and the residue is purified by chromatography on silica gel (dichloromethane/methanol) to yield 1.01 g (77%) of the desired aldehyde.

MS (Cl, M+1): 351
$^1$H-NMR (300 MHz, d6-DMSO): 9.90 (s, 1H), 9.53 (s, 1H), 7.82-7.89 (m, 2H), 7.50-7.65 (m, 3H), 7.16-7.27 (m, 2H), 2.55 (s, 3H).

Intermediate Example 3.2

4-[6-(3-fluorophenyl)-2-methyl-[1,2,4]triazolo[1,5-a]pyrimidine-5-yl]-benzaldehyde

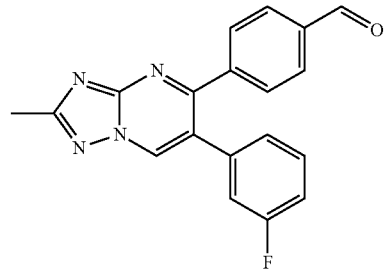 [SMILES: Cc1nc2nc(-c3ccc(C=O)cc3)c(-c3cccc(F)c3)cn2n1]

Step 1: 6-(3-fluorophenyl)-2-methyl-[1,2,4]triazolo[1,5-a]pyrimidine-5,7-diol 5 g (51.87 mmol) 3-Amino-5-methyl-1,2,4-triazole, 16.2 g (67.4 mmol) diethyl (3-fluorophenyl)malonate and 20.4 mL tributylamine are stirred at 180° C. over night. The mixture is diluted with 2N NaOH solution and water and extracted three times with methyl-tert. butylether. These organic extracts are discarded. The aqueous phase is acidified at 0° C. with concentrated HCl until pH 3. The white precipitate is collected by filtration, washed with water (4 L) and dried in vacuo at 50° C. 11.97 g (88.7%) of the product are obtained and are used without further purification.

MS (Cl, ES+): 261
$^1$H-NMR (300 MHz, d6-DMSO): 6.88-7.39 (m, 4H), 2.39 (s, 3H).

Step 2: 5,7-dichloro-6-(3-fluorophenyl)-2-methyl-[1,2,4]triazolo[1,5-a]pyrimidine 11.97 g (46 mmol) (3-Fluorophenyl)-2-methyl-[1,2,4]triazolo[1,5-a]pyrimidine-5,7-diol are given in 8.76 mL (69 mmol) N,N-dimethylaniline. 25.7 mL (276 mmol) POCl$_3$ are added slowly keeping the temperature at 20° C. (ice bath). After removal of the ice bath the reaction mixture is heated at 100° C. for two hours. The mixture has changed its colour to greygreen. It is poured slowly and cautiously (strong development of heat) to a large amount of ice water and stirred over night. The precipitate is collected by filtration and dried. 10.4 g (76.1%) of the desired product are obtained.

MS (Cl, ES+): 297

$^1$H-NMR (300 MHz, d6-DMSO): 7.52-7.68 (m, 1H), 7.23-7.44 (m, 3H), 2.56 (s, 3H).

Step 3: 5-chloro-6-(3-fluorophenyl)-2-methyl-[1,2,4]triazolo[1,5-a]pyrimidine 10.4 g (35 mmol) 5,7-Dichloro-6-(3-fluorophenyl)-2-methyl-[1,2,4]triazolo[1,5-a]pyrimidine are given in 898 mL ethanol. 8.8 g (164.5 mmol) NH$_4$Cl, 630 mL water, 340 mL THF and 14.6 g (224 mmol) zinc powder are added. The mixture is stirred at room temperature for 3.5 hours. The reaction mixture is filtered and the organic solvents are removed. The residue is diluted with water and extracted three times with ethyl acetate. The combined organic layers are washed with brine and dried over Na$_2$SO$_4$. After evaporation of the solvent the residue is purified by chromatography giving 0.73 g (7.9%) of the desired product. Due to this low yield the zinc- and the Na$_2$SO$_4$ filter cakes are extracted with methanol delivering 2.3 g starting material.

$^1$H-NMR (300 MHz, d6-DMSO): 9.50 (s, 1H), 7.50-7.61 (m, 1H), 7.28-7.48 (m, 3H), 2.50 (s, 3H).

Step 4: 4-[6-(3-fluorophenyl)-2-methyl-[1,2,4]triazolo[1,5-a]pyrimidine-5-yl]-benzaldehyde To a mixture of 0.73 g (2.8 mmol) 5-chloro-6-(3-fluorophenyl)-2-methyl-[1,2,4]triazolo[1,5-a]pyrimidine and 458.3 mg (3.1 mmol) 4-formylphenylboronic acid in 14 mL 1,2-dimethoxyethane are added 5.2 mL of a sodium carbonate solution (10%) and 102 mg (0.13 mmol) dichloro[1,1'-bis(diphenylphosphino)ferrocene]palladium (II). The resulting mixture is heated to 90° C. under an inert gas atmosphere over night. The reaction mixture is diluted with water and extracted three times with dichloromethane. The combined organic layers are washed with brine and dried over sodium sulphate. After evaporation of the solvent the residue is purified by chromatography on silica gel (dichloromethane/methanol) to yield 0.85 g (87.3%) of the desired aldehyde.

Intermediate Example 4.0

4-(2-cyclopropyl-6-phenyl-[1,2,4]triazolo[1,5-a]pyrimidin-5-yl)-benzaldehyde

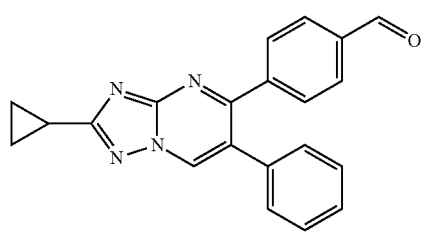 [SMILES: O=Cc1ccc(-c2nc3nc(C4CC4)nn3cc2-c2ccccc2)cc1]

This compound was prepared in a manner according to 4-(2-methyl-6-phenyl-[1,2,4]triazolo[1,5-a]pyrimidin-5-yl)-benzaldehyde by using 5-cyclopropyl-1,2,4-triazol-3-amine in the first step.

MS (M+1): 341

1H NMR (300 MHz, d6-DMSO): 9.96 (s, 1H), 9.37 (s, 1H), 7.80 (d, 2H), 7.50 (d, 1H), 7.30-7.34 (m, 3H), 7.21-7.27 (m, 2H), 2.19 (m, 1H), 0.99-1.13 (m, 4H)

Intermediate Example 4.1

2-cyclopropyl-4-[6-(4-fluorophenyl)-[1,2,4]triazolo[1,5-a]pyrimidine-5-yl]-benzaldehyde

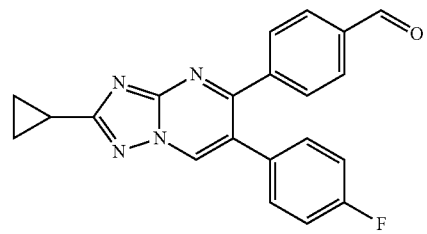 [SMILES: O=Cc1ccc(-c2nc3nc(C4CC4)nn3cc2-c2ccc(F)cc2)cc1]

Step 1: 2-cyclopropyl-6-(4-fluorophenyl)-[1,2,4]triazolo[1,5-a]pyrimidine-5,7-diol 10.2 g (81.9 mmol) 5-Cyclopropyl-1,2,4-triazole-3-ylamine, 25 g (98.3 mmol) diethyl (4-fluorophenyl)malonate and 32.2 mL (135.2 mmol) tributylamine are stirred at 180° C. for 18 hours. The solution is diluted with 120 mL 2N NaOH solution and 120 mL water and the resulting mixture is extracted three times with methyl-tert. butylether. These organic extracts are discarded. The aqueous phase is acidified to pH 1 with 2N HCl. The precipitate is collected by filtration, washed with plenty of water and dried. This material (13.5 g=57.6%) is used without further purification.

MS (Cl, M+1): 287

$^1$H-NMR (300 MHz, d6-DMSO): 7.35-7.52 (m, 2H), 6.98-7.18 (m, 2H), 1.95-2.10 (m, 1H), 0.90-1.18 (m, 4H).

Step 2: 5,7-dichloro-2-cyclopropyl-6-(4-fluorophenyl)-[1,2,4]triazolo[1,5-a]pyrimidine 13.5 g (47.2 mmol) 2-Cyclopropyl-6-(4-fluorophenyl)-[1,2,4]triazolo[1,5-a]pyrimidine-5,7-diol, 53.5 mL (574.3 mmol) POCl$_3$ and 9.6 mL (74.5 mmol) N,N-dimethylaniline are stirred at 100° C. for 21 hours. Additional 26.7 mL POCl$_3$ and 4.8 mL N,N-dimethylaniline are added and the reaction mixture is heated (100° C.) for another 18 hours. The mixture is poured slowly and cautiously (strong development of heat) on a large amount of ice water. After vigorous stirring for one hour the precipitate is collected by filtration. Further precipitated material is collected and dried as well. The combined precipitates yield 7.81 g=50.7% of the product.

MS (Cl, M+1): 323

$^1$H-NMR (300 MHz, d6-DMSO): 7.32-7.58 (m, 4H), 2.18-2.30 (m, 1H), 0.95-1.20 (m, 4H).

Step 3: 5-chloro-2-cyclopropyl-6-(4-fluorophenyl)-[1,2,4]triazolo[1,5-a]pyrimidine 7.78 g (24.1 mmol) 5,7-Dichloro-2-cyclopropyl-6-(4-fluorophenyl)-[1,2,4]triazolo[1,5-a]pyrimidine are given in 612 mL ethanol, 435 mL water and 234 mL THF. After addition of 6.1 g (114 mmol) NH$_4$Cl, 10.1 g (154 mmol) zinc powder are added and the mixture is stirred at room temperature for 3 h. Stirring is continued over night. The reaction mixture is filtered via a glass microfibre filter and the filter is washed with plenty of methanol. The zinc slurry is stirred twice with ethylacetate/methanol (250 mL each) and the combined organic filtrates are evaporated. The residue is extracted with ethyl acetate (1 L). The organic phase is washed twice with brine and dried over Na$_2$SO$_4$. After evaporation of the solvent, the residue is purified by chromatography on silicagel (eluents dichloromethane/methanol) yielding 0.76 g (10.4%) of the desired product. Additionally 3.57 g are obtained which are a mixture of the desired product and the bis deschloro derivate (ratio 6:4).

MS (Cl, M+1): 289

$^1$H-NMR (300 MHz, d6-DMSO) of the pure product: 9.40 (s, 1H), 7.52-7.62 (m, 2H), 7.29-7.42 (m, 2H), 2.10-2.28 (m, 1H), 0.92-1.18 (m, 4H).

Step 4: 2-cyclopropyl-4-[6-(4-fluorophenyl)-[1,2,4]triazolo[1,5-a]pyrimidine-5-yl]-benzaldehyde To a mixture of 3.57 g of the 5-chloro-2-cyclopropyl-6-(4-fluorophenyl)-[1,2,4]triazolo[1,5-a]pyrimidine (60% pure) described in step 3 and 1.22 g (8.1 mmol) 4-formylphenyl-boronic acid in 25 mL 1,2-dimethoxyethane are added 273 mg (0.33 mmol) dichloro[1,1'-bis(diphenylphosphino)ferrocene]palladium (II) and 14.5 mL of a sodium carbonate solution (10%). The resulting mixture was heated to 90° C. under an inert gas atmosphere for 20 h. The reaction mixture is diluted with 100 mL water and 250 mL dichloromethane. After vigorous stirring for one hour, the organic phase is separated and the aqueous phase extracted twice with dichloromethane. The combined organic layers are washed with water and dried over sodium sulphate. The solvent is evaporated and the residue is purified by chromatography on silica gel (dichloromethane/methanol) to yield 1.68 g (31.6%) of the desired aldehyde contaminated with 2-cyclopropyl-6-(4-fluorophenyl)-[1,2,4]triazolo[1,5-a]pyrimidine. Despite the impurity the aldehyde is used in the next reaction.

Intermediate Example 5.0

4-(2-cyclobutyl-6-phenyl-[1,2,4]triazolo[1,5-a]pyrimidin-5-yl)-benzaldehyde

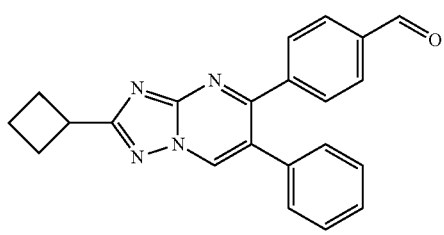 [SMILES: O=Cc1ccc(-c2nc3nc(C4CCC4)nn3cc2-c2ccccc2)cc1]

This compound was prepared in a manner according to 4-(2-methyl-6-phenyl-[1,2,4]triazolo[1,5-a]pyrimidin-5-yl)-benzaldehyde by using 5-cyclobutyl-1,2,4-triazol-3-amine in the first step.

MS (M+1): 355

1H NMR (300 MHz, d6-DMSO): 9.97 (s, 1H), 9.41 (s, 1H), 7.81 (d, 2H), 7.53 (d, 2H), 7.31-7.33 (m, 3H), 7.22-7.25 (m, 2H), 3.77 (qn, 1H), 2.35-2.42 (m, 4H), 1.90-2.12 (m, 2H)

Intermediate Example 6.0

7-(4-formylphenyl)-6-phenylimidazo[1,2-a]pyrimidine-3-carbonitrile

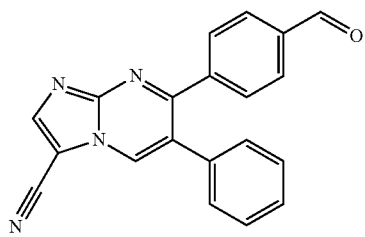 [SMILES: N#Cc1cnc2nc(-c3ccc(C=O)cc3)c(-c3ccccc3)cn12]

350 mg 4-(3-bromo-6-phenylimidazo[1,2-a]pyrimidin-7-yl)benzaldehyde, 5.6 mg Zn, 63.7 mg Zn(CN)$_2$ and dichloro [1,1'-bis(diphenylphosphino)ferrocene]palladium (II) dichloromethane adduct were suspended in dimethylacetamide and the mixture was heated for 45 min under microwave irradiation to 160° C. The workup was performed by diluting the mixture with water and dichlormethane, extracting the aqueous layer twice and drying the combined organic layers over Na$_2$SO$_4$. The compound was isolated by evaporation of the solvent and chromatography on silica gel (dichloromethane/methanol).

MS (M+1): 325

Characteristic 1H NMR (300 MHz, d6-DMSO) signals: 10.0 ppm (s, 1H), 9.1 ppm (s, 1H), 8.7 ppm (s, 1H);

Intermediate Example 7.0

4-(3-fluoro-6-phenylimidazo[1,2-a]pyrimidin-7-yl)benzaldehyde

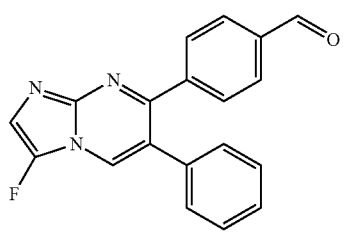

500 mg 4-(6-phenylimidazo[1,2-a]pyrimidin-7-yl)benzaldehyde and 880 mg 1-chloromethyl-4-fluoro-1,4-diazoniabicyclo[2.2.2]octane bis(tetrafluoroborate were dissolved in 25 mL chloroform and heated under microwave irradiation to 120° C. After for 45 min and 4 h additional portions of 200 mg of 1-chloromethyl-4-fluoro-1,4-diazoniabicyclo[2.2.2]octane bis(tetrafluoroborate were added and heating continued at 120° C. The reaction was worked up after 5 h by diluting with water and extraction with dichloromethane. The combined organic layers were dried over Na$_2$SO$_4$ and the solvent evaporated. The crude material was purified on silica gel (dichloromethane/ethyl acetate.

MS (M+1): 318

Characteristic 1H NMR (300 MHz, d6-DMSO) signals: 10.0 ppm (s, 1H); 8.9 ppm (s, 1H); 7.6 ppm (d, 1H);

Intermediate Example 8.0

4-(5-methylamino-6-phenyl-imidazo[1,2-a]pyrimidin-7-yl)-benzaldehyde

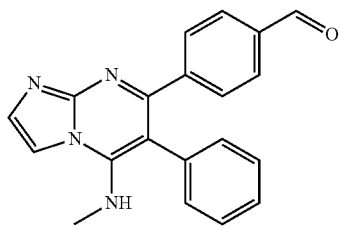 [SMILES: CNc1c(-c2ccccc2)c(-c2ccc(C=O)cc2)nc2nccn12]

Step 1: 7-chloro-N-methyl-6-phenylimidazo[1,2-a]pyrimidin-5-amine 850 mg 5,7-dichloro-6-phenylimidazo[1,2-a]pyrimidine (prepared as described for example 1) was dissolved in 18 mL of a 8M Solution of MeNH$_2$ in methanol and stirred at room temperature for 1.5 h. The product precipitated upon dilution with water and cooling to 0° C. The solid material was collected by filtration and washed twice with water to yield the desired material.
MS (M+1): 259
Characteristic 1H NMR (300 MHz, d6-DMSO) signals: 8.0 ppm (d, 1H); 2.3 ppm (d, 3H)

Step 2: 4-[5-(methylamino)-6-phenylimidazo[1,2-a]pyrimidin-7-yl]benzaldehyde

To a mixture of 550 mg of the product of step 1 and 350 mg 4-formylphenylboronic acid in 10 mL 1,2-dimethoxyethane, 55 mg tetrakis (triphenylphosphine) palladium(0) and 4 mL of a 10% w/w sodium carbonate solution were added and the resulting mixture was heated by microwave for 2 h. The work up was performed by diluting the reaction mixture with water and dichloromethane, separating the phases and extraction of the aqueous phase with dichloromethane. The combined organic layers were dried over sodium sulphate and evaporated. The residue was suspended in ethyl acetate and the resulting mixture was stirred for 2 h at room temperature. The product was collected by filtration and used without further purification.
MS (M+1): 329
Characteristic 1H NMR (300 MHz, d6-DMSO) signals: 9.9. ppm (s, 1H), 2.4 ppm (d, 3H)

Intermediate Example 9.0

4-(3-bromo-6-phenylimidazo[1,2-a]pyrimidin-7-yl)benzaldehyde

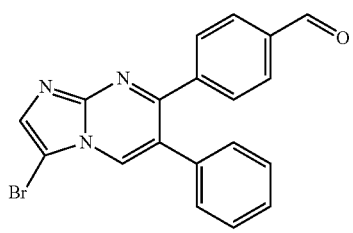 [SMILES: O=Cc1ccc(-c2nc3ncc(Cl)n3cc2-c2ccccc2)cc1]

1.5 g 4-(6-phenylimidazo[1,2-a]pyrimidin-7-yl)benzaldehyde and 0.9 g NBS were refluxed in 30 mL chloroform for 1 h. The solvent was removed by distillation and the crude product was purified by column chromatography (dichloromethane/methanol).
MS (M+1): 378/380
Characteristic 1H NMR (300 MHz, d6-DMSO) signals: 10 ppm (s, 1H), 9.7 ppm (s, 1H); 8.0 (s, 1H)

Intermediate Example 10.0

4-(3-chloro-6-phenylimidazo[1,2-a]pyrimidin-7-yl)benzaldehyde

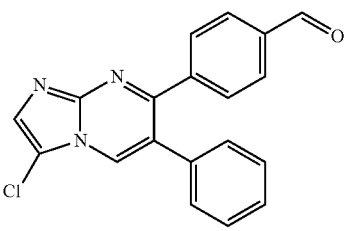

The compound was synthesized in a manner according to 4-(3-bromo-6-phenylimidazo[1,2-a]pyrimidin-7-yl)benzaldehyde by using NCS instead of NBS.

Intermediate Example 11.0

4-{6-phenyl-3-[(trimethylsilyl)ethynyl]imidazo[1,2-a]pyrimidin-7-yl}benzaldehyde

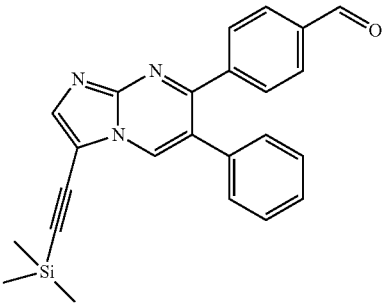 [SMILES: C[Si](C)(C)C#Cc1cnc2nc(-c3ccc(C=O)cc3)c(-c3ccccc3)cn12]

400 mg 4-(3-bromo-6-phenylimidazo[1,2-a]pyrimidin-7-yl)benzaldehyde, 820 mg trimethyl[(tributylstannyl)ethynyl]silane and 60 mg Pd(PPh$_3$)$_4$ were suspended in 8 mL toluene under a nitrogen atmosphere. The mixture was heated (microwave) to 130 for 1 h. The solvent was evaporated and the crude product was purified by column chromatography (dichloromethane/methanol)
MS (M+1): 396
Characteristic 1H NMR (300 MHz, d6-DMSO) signals: 10 ppm (s, 1H), 8.7 ppm (s, 1H); 8.2 ppm (s, 1H); 0.3 ppm (s, 9H)

Intermediate Example 12.0

4-(3-methyl-6-phenyl-imidazo[1,2-a]pyrimidin-7-yl)-benzaldehyde

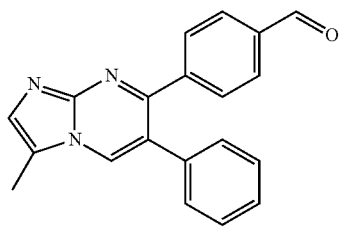 [SMILES: Cc1cnc2nc(-c3ccc(C=O)cc3)c(-c3ccccc3)cn12]

The compound was synthesized in a manner according to 7-(4-formylphenyl)-6-phenylimidazo[1,2-a]pyrimidine-3-carbonitrile by using MeZnCl instead of Zn and $ZnCN_2$.

Intermediate Example 13.0

4-(6-phenyl-3-vinylimidazo[1,2-a]pyrimidin-7-yl)benzaldehyde

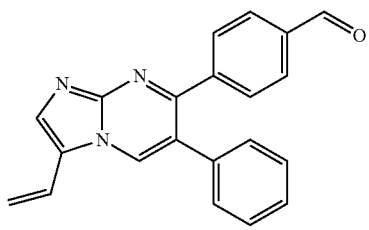 [SMILES: C=Cc1cnc2nc(-c3ccc(C=O)cc3)c(-c3ccccc3)cn12]

500 mg 4-(3-bromo-6-phenylimidazo[1,2-a]pyrimidin-7-yl)benzaldehyde, 180 mg $K_2CO_3$, 215 mg $Et_4NCl$, 25 mg PdCl2(PPh3)2 and 620 mg tributyl(vinyl)stannane were suspended in 10 mL THF. The mixture was heated to 110° C. for 45 min. This mixture was worked up by diluting with water and extraction with dichloromethane. The organic layers were dried over Na2SO4 and concentrated to yield the crude product, which was purified by chromatography on silica gel (ethyl acetate/dichloromethane).

MS (M+1): 326

Characteristic 1H NMR (300 MHz, d6-DMSO) signals: 10.0 ppm (s, 1H); 9.1 ppm (s, 1H); 8.2 ppm (s, 1H), 6.0 ppm (d, 1H) 5.4 ppm (d, 1H),

Intermediate Example 14.0

Ethyl 7-(4-formylphenyl)-6-phenylimidazo[1,2-a]pyrimidine-2-carboxylate

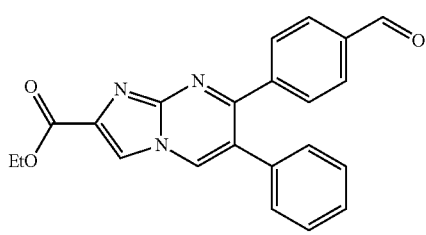 [SMILES: CCOC(=O)c1cn2cc(-c3ccccc3)c(-c3ccc(C=O)cc3)nc2n1]

Step 1:
1-[4-(dimethoxymethyl)phenyl]-2-phenylethanol

A mixture of Mg turnings 2.4 g (0.1 mol) and 2 mL 1-bromo-4-(dimethoxymethyl)benzene (0.012 mol) in THF (100 mL) was heated under nitrogen atmosphere until the reaction starts. Subsequently additional 1-bromo-4-(dimethoxymethyl)benzene 14.71 mL (0.088 mol) dissolved in 30 mL THF was added slowly and the reaction refluxed for 1 h mixture to complete formation of the Gringnard reagent. A solution of 11.70 mL phenylacetaldehyde (0.1 mol) in 100 mL THF was added at to 0° C. and the reaction refluxed for 2 h upon completion of the addition. The mixture was worked up by pouring into saturated aqueous NH4Cl and extraction with ethyl acetate. The combined organic layers were washed with brine, dried over $MgSO_4$ and the solvents were evaporated under reduced pressure. The brown-black oily product was used for the next step without purification.

Step 2:
1-[4-(dimethoxymethyl)phenyl]-2-phenylethanone 29.16 g (0.183 mol) sulfur trioxide pyridine complex was added in portions to a solution of 33 g 1-[4-(dimethoxymethyl)phenyl]-2-phenylethanol in dichlormethane (540 mL), DMSO (140 mL) and triethylamine (25.5 mL) at 10° C. The mixture was slowly warmed to room temperature and stirred for 2 h. Water was added and the organic phase was separated, washed with 1 mol/l HCl, 3 times with 5% w/w sodium thiosulfate solution and saturated NaCl solution. The combined organic phases were dried over sodium sulfate and the solvents was evaporated. The residue was purified on a silica gel column chromatography (n-Hexane/EtOAc) to yield the desired product.

MS (M+1): 271

Characteristic 1H NMR (300 MHz, d6-DMSO) signals: 8.1 ppm (d, 2H); 7.6 ppm (d, 2H); 5.4 ppm (s, 1H), 4.3 ppm (s, 2H)

Step 3: 1-[4-(dimethoxymethyl)phenyl]-3-(dimethylamino)-2-phenylprop-2-en-1-one 5 g 1-[4-(dimethoxymethyl)phenyl]-2-phenylethanone and 4.43 g N,N-dimethylformamide dimethylacetal were stirred for 18 h at 100° C. in DMF. The solvent was removed and the crude product used without further purification.

MS (M+1): 326.

Step 4: 4-[4-(dimethoxymethyl)phenyl]-5-phenylpyrimidin-2-amine 5 g of the product of step 3 and 3 g guanidine hydrochloride were dissolved in 100 mL methanol and 2.7 g of NaOMe was added. The mixture was heated to reflux for 17 h. The product was precipitated upon dilution of the mixture with water and was collected by filtration and washed twice with water.

MS (M+1): 322

Step 5: Ethyl 7-(4-formylphenyl)-6-phenylimidazo[1,2-a]pyrimidine-2-carboxylate 200 mg of the product of step 2 were suspended in 5 mL EtOH and 183 mg of ethyl 3-bromo-2-oxopropanoate was added and the solution stirred under reflux for 5 h.

The solvent was evaporated, the residue was suspended in a mixture of water and isopropanol, stirred for 24 h and finally collected by filtration.

MS (M+1): 372

Intermediate Example 15.0

4-(2-ethyl-6-phenyl-imidazo[1,2-a]pyrimidin-7-yl) benzaldehyde

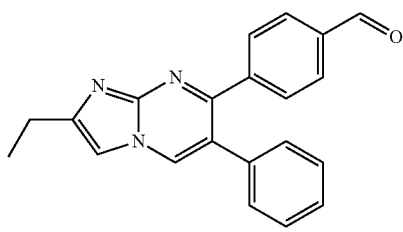 [SMILES: CCc1cn2cc(-c3ccccc3)c(-c3ccc(C=O)cc3)nc2n1]

This compound was prepared in a manner according to ethyl 7-(4-formylphenyl)-6-phenylimidazo[1,2-a]pyrimidine-2-carboxylate by using 1-bromobutan-2-one instead of ethyl 3-bromo-2-oxopropanoate in step 5.

Intermediate Example 15.1

4-(2-methyl-6-phenyl-imidazo[1,2-a]pyrimidin-7-yl)-benzaldehyde

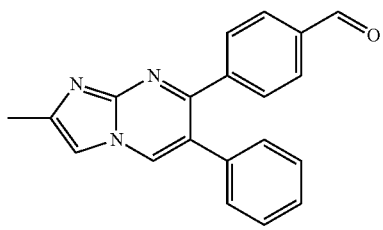 [SMILES: Cc1cn2cc(-c3ccccc3)c(-c3ccc(C=O)cc3)nc2n1]

Step 1: 2-methyl-6-phenyl-imidazo[1,2-a]pyrimidine-5,7-diol 18 g (135 mmol) 5-Methyl-1H-imidazol-2-ylamine are dissolved in 155 mL DMF and 31.8 g (135 mmol) diethyl phenylmalonate are added. After dropwise addition of 61.5 g (404 mmol) 1,8-diazabicyclo[5.4.0]undec-7-ene the reaction mixture is stirred at 100° C. for 16 h. The DMF has been removed and the darkbrown oily residue treated with 150 mL water (complete dissolution). 2M HCl (250 mL) is added at room temperature until a pH of 1. After stirring for 1 h at ice bath cooling the formed crystals are collected by filtration to yield the product (10.2 g=31%), which is used without further purification.

MS (Cl, M+1): 242
$^1$H-NMR (300 MHz, d6-DMSO): 12.25 (br., 1H), 10.97 (br., 1H), 7.33-7.48 (m, 2H), 7.18-7.30 (m, 3H), 7.05-7.18 (m, 1H), 2.21 (s, 3H).

Step 2: 5,7-dichloro-2-methyl-6-phenyl-imidazo[1,2-a]pyrimidine 10.2 g (42.3 mmol) 2-Methyl-6-phenyl-imidazo[1,2-a]pyrimidine-5,7-diol are dissolved in 48 mL (515 mmol) POCl$_3$ and 8.6 mL (67.6 mmol) N,N-dimethylaniline. The mixture is heated at 100° C. for 16 h. Due to the presence of starting material additional 18.4 mL POCl$_3$ and 1.5 mL N,N-dimethylaniline are added. The heating has been continued for two days. POCl$_3$ is evaporated and the oily residue treated with ice-water (caution: stirring and cooling necessary due to strong development of heat). A precipitate forms. After addition of 30 mL dichloromethane the precipitate has been collected by filtration and washed with dichloromethane/water. The crude precipitate is stirred with 2N NaOH (200 mL) for one hour and collected by filtration, washed with water and dried. 10.54 g (89.6%) of the desired product are obtained.

MS (Cl, M+1): 278
$^1$H-NMR (300 MHz, d6-DMSO): 7.82 (s, 1H), 7.38-7.58 (m, 5H), 2.40 (s, 3H).

Step 3: 7-chloro-2-methyl-6-phenyl-imidazo[1,2-a]pyrimidine 8.3 g (30 mmol) 5,7-Dichloro-2-methyl-6-phenyl-imidazo[1,2-a]pyrimidine are dissolved in 14.5 mL methanol and 85 mL THF. After addition of 3.4 mL acetic acid 5.8 g (45 mmol) zinc/copper pair are added in portions and the mixture is stirred at rt for four and a half hours. The reaction mixture is filtered via a glass microfibre filter and washed with plenty of methanol. The solvent has been removed and the residue redissolved in ethyl acetate. After washing twice with brine and drying over Na$_2$SO$_4$, the solvent is evaporated and the residue purified by chromatography on silica gel (dichloromethane/methanol) yielding only 260 mg of the desired compound. 2N NaOH is added to the zinc/copper slurry of the reaction until a pH of 8. Afterwards the slurry is treated four times with 300 mL ethyl acetate/methanol (1%) each. The solvent mixture is decanted each time and the extracts are combined. After evaporation of the solvents 3.1 g of the desired product are obtained. Repetition of this process yields additional 2.32 g product. Altogether 74.4% of the desired material have been obtained.

MS (Cl, M+1): 244
$^1$H-NMR (300 MHz, d6-DMSO): 8.99 (s, 1H), 7.64 (s, 1H), 7.40-7.58 (m, 5H), 2.35 (s, 3H).

Step 4: 4-(2-methyl-6-phenyl-imidazo[1,2-a]pyrimidin-7-yl)-benzaldehyde 2.3 g (9.4 mmol) 7-Chloro-2-methyl 6-phenyl-imidazo[1,2-a]pyrimidine is given in 32 mL dimethoxyethane (not completely dissolved). 18.5 mL Na$_2$CO$_3$ solution (10%) and 1.56 g (10.4 mmol) 4-formylphenylboronic acid are added. After addition of 0.35 g (0.43 mmol) 1,1'-bis(diphenylphosphino)ferrocenedichloropalladium(II) the reaction mixture is purged 3× with argon and heated to 90° C. After 18 h stirring at 90° C. complete dissolution has taken place. The reaction mixture is cooled down and treated with 100 mL water and 150 mL dichloromethane. After vigorous stirring at rt for one hour the organic phase is separated, washed twice with water (100 mL each) and dried (Na$_2$SO$_4$). After removal of the solvent the crude product is purified via chromatography (Isolute, dichloromethane/methanol). 1.82 g (61.5%) of the pure compound and 0.82 g (27.7%) of the product containing traces of the starting material have been obtained.

MS (Cl, M+1): 314

$^1$H-NMR (300 MHz, d6-DMSO): 9.98 (s, 1H), 9.00 (s, 1H), 7.75-7.82 (m, 2H), 7.70 (s, 1H), 7.47-7.53 (m, 2H), 7.29-7.35 (m, 3H), 7.18-7.28 (m, 2H), 2.39 (s, 3H).

Intermediate Example 15.2

4-(3-bromo-2-methyl-6-phenyl-imidazo[1,2-a]pyrimidin-7-yl)-benzaldehyde

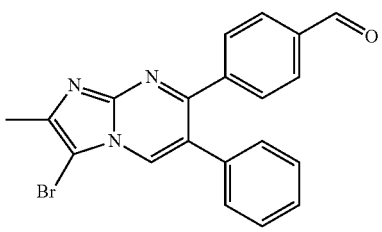 [SMILES: Cc1nc2nc(-c3ccc(C=O)cc3)c(-c3ccccc3)cn2c1Br]

0.2 g (0.64 mmol) 4-(2-Methyl-6-phenyl-imidazo[1,2-a]pyrimidin-7-yl)benzaldehyde, described in intermediate example 15.1, are dissolved in 2.8 mL chloroform and treated with 170 mg (0.96 mmol) N-bromosuccinimide. The mixture is heated for 2.5 hours at reflux. The solvent is removed and the residue purified by chromatography (silicagel, dichloromethane/methanol). 198.4 mg (75.3%) of the desired compound are obtained.

MS (CI, M+1): 392

$^1$H-NMR (400 MHz, d6-DMSO): 9.97 (s, 1H), 8.59 (s, 1H), 7.75-7.86 (m, 2H), 7.47-7.55 (m, 2H), 7.21-7.39 (m, 5H). 2.40 (s, 3H).

Intermediate Example 16.0

4-(6-phenylpyrazolo[1,5-a]pyrimidin-5-yl)benzaldehyde

N0

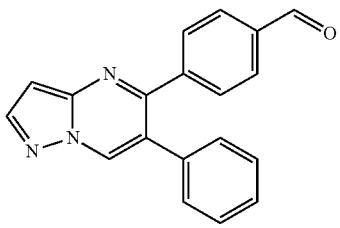 [SMILES: O=Cc1ccc(-c2nc3ccnn3cc2-c2ccccc2)cc1]

Step 1: 6-phenylpyrazolo[1,5-a]pyrimidine-5,7-diol

A solution of 9 g 3-amino pyrazole and 25.6 g diethyl phenylmalonate in N,N-dibutylbutan-1-amine was stirred at 185° C. over night. The reaction mixture consisted of two layers after cooling to room temperature. The top layer was removed and the lower layer was diluted with dichloromethane and methanol. The resulting solution was concentrated and extracted with a mixture of diethyl ether and 10% w/w NaOH solution. The organic layer was discarded and aqueous layer acidified with concentrated HCl. The precipitated product was collected by filtration.

MS (M+1): 228

Characteristic 1H NMR (d6-DMSO, 400 MHz) signals: 7.9 ppm (d, 1H),

Step 2:
5,7-dichloro-6-phenylpyrazolo[1,5-a]pyrimidine 3 g 6-phenylpyrazolo[1,5-a]pyrimidine-5,7-diol was suspended in 6 mL POCl$_3$ and the mixture was stirred for 20 h at 100° C. for 2 h. The solvent was removed, the residue was dissolved in a mixture of dichloromethane, water and ice, the organic phase was separated and water-phase was extracted with dichloromethane. The combined dichloromethane phases were dried over Na$_2$SO$_4$ and evaporated yielding the crude product, which was purified by column chromatography on silica gel (dichloromethane/methanol).

MS (M+1): 264

Characteristic 1H NMR (d6-DMSO, 300 MHz) signals: 8.4 ppm (d, 1H), 6.9 ppm (d, 1H), Step 3: 5-chloro-6-phenylpyrazolo[1,5-a]pyrimidine A mixture of 1 g 5,7-dichloro-6-phenylpyrazolo[1,5-a]pyrimidine, 0.5 mL glacial acetic acid, 1 mL methanol, 6 mL THF and 730 mg of Zn/Cu pair were stirred for 3 h at 50° C. The mixture was filtered through celite, evaporated to dryness and the residue was purified on silica gel (hexanes/ethyl acetate) to yield 550 mg of a 1:1 mixture of the desired product and the starting material, which was used without further purification.

MS (M+1): 230

Step 4: 4-(6-phenylpyrazolo[1,5-a]pyrimidin-5-yl)benzaldehyde

To a mixture of 300 mg of the mixture from step 3 and 360 mg 4-formylphenylboronic acid in 9 mL 1,2-dimethoxyethane were added 1.8 mL of a 10% w/w sodium carbonate solution and 36 mg dichloro[1,1'-bis(diphenylphosphino)ferrocene]palladium (II) and the resulting mixture was heated to 80° C. under an inert gas atmosphere for 18 h. The work up was performed by diluting the reaction mixture with water and dichloromethane, separating the phases and extraction of the aqueous phase with dichloromethane. The combined organic layers were dried over sodium sulphate, evaporated and the residue was purified by chromatography on silica gel (dichloromethane/methanol). The product was crystallized from ethyl acetate.

MS (M+1): 300

Characteristic 1H NMR (300 MHz, d6-DMSO) signals: 10 ppm (s, 1H), 9.2 ppm (s, 1H); 8.3 ppm (m, 1H)

Intermediate Example 17.0

4-(3-ethyl-6-phenylimidazo[1,2-a]pyrimidin-7-yl)benzaldehyde

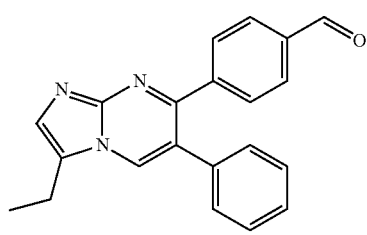 [SMILES: CCc1cnc2nc(-c3ccc(C=O)cc3)c(-c3ccccc3)cn12]

100 mg 4-(6-phenyl-3-vinylimidazo[1,2-a]pyrimidin-7-yl)benzaldehyde (prepared as described under intermediate example 13) were dissolved in a mixture of 5 mL THF and 5 mL EtOH. 10 mg 10% Pd/C were added and the mixture stirred under an atmosphere of hydrogen for 2 h. The mixture was filtered through Celite, the solvent was evaporated and the crude product was purified by chromatography on silica gel (dichloromethane/methanol).

MS (M+1): 328

Characteristic 1H NMR (d6-DMSO, 400 MHz) signals: 10.0 ppm (s, 1H); 8.8 ppm (s, 1H); 7.7 ppm (s, 1H); 3.0 ppm (qu, 2H); 1.3 ppm (t, 3H)

Intermediate Example 18.0

4-(6-Phenyl-2-trifluoromethyl-imidazo[1,2-a]pyrimidin-7-yl)-benzaldehyde

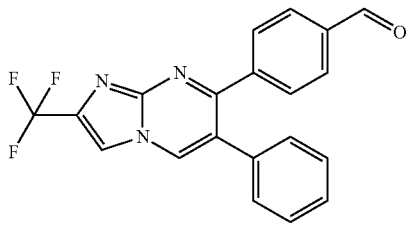

This compound was prepared in a manner according to ethyl 7-(4-formylphenyl)-6-phenylimidazo[1,2-a]pyrimidine-2-carboxylate by using 3-bromo-1,1,1-trifluoroacetone instead of ethyl 3-bromo-2-oxopropanoate in step 5.

Intermediate Example 19.0

4-(5-methyl-6-phenylimidazo[1,2-a]pyrimidin-7-yl)benzaldehyde

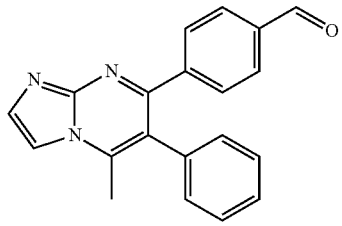 [SMILES: Cc1c(-c2ccccc2)c(-c2ccc(C=O)cc2)nc2nccn12]

Step 1:
5-methyl-6-phenylimidazo[1,2-a]pyrimidin-7-ol

A solution of 3.8 g 1H-imidazol-2-ylamine and 6 g ethyl 3-oxo-2-phenylbutanoate was suspended in a mixture of 32 mL DMF and 32 mL N,N-dibutylbutan-1-amine and heated by microwave irradiation to 180° C. for 10 h. The reaction mixture was diluted with water and dichloromethane, the phases separated, the aqueous layer extracted twice with dichloromethane, the combined organic layers were dried over Na2SO4 and concentrated to give the crude product. The crude product was purified by column chromatography (silica gel, dichloromethane/methanol).

MS (M+1): 226

Characteristic 1H NMR (d6-DMSO, 400 MHz) signals: 7.1 ppm (d, 1H); 2.3 ppm (s, 3H)

Step 2:
7-chloro-5-methyl-6-phenylimidazo[1,2-a]pyrimidine 250 mg of the product of step 1 and 10 mL POCl3 were heated to 100° C. for 1 h. The excess POCl3 was removed by distillation and the residue was treated with ice and diluted with dichloromethane. The phases were separated, the aqueous layer was extracted twice with dichloromethane, the combined organic layers were dried over Na2SO4 and concentrated to give the crude product.

MS (M+1): 244

Characteristic 1H NMR (d6-DMSO, 300 MHz) signals: 8.4 ppm (d, 1H); 8.3 ppm (d, 1H); 2.6 ppm (s, 3H)

Step 3: 4-(5-methyl-6-phenylimidazo[1,2-a]pyrimidin-7-yl)benzaldehyde

To a mixture of 220 mg of the product obtained in step 2 and 131 mg 4-formylphenylboronic acid in 10 mL 1,2-dimethoxyethane were added 25 mg dichloro[1,1'-bis(diphenylphosphino)ferrocene]palladium (II) dichloromethane adduct and 7 mL of a 10% w/w sodium carbonate solution and the resulting mixture was heated to 120° C. by microwave irradiation under an inert gas atmosphere for 1 h. The work up was performed by diluting the reaction mixture with water and dichloromethane, separating the phases and extraction of the aqueous phase with dichloromethane. The combined organic layers were dried over sodium sulphate and evaporated. The crude product was purified by silica gel chromatography (dichloromethane/methanol).

MS (M+1): 314

Characteristic 1H NMR (d6-DMSO, 300 MHz) signals: 10.0 ppm (s, 1H); 8.1 ppm (d, 1H); 7.8 ppm (d, 2H); 7.5 ppm (d, 2H); 2.6 ppm (s, 3H)

Intermediate Example 20.0

4-(2-Isopropyl-6-phenyl[1,2,4]triazolo[1,5-a]pyrimidin-5-yl)benzaldehyde

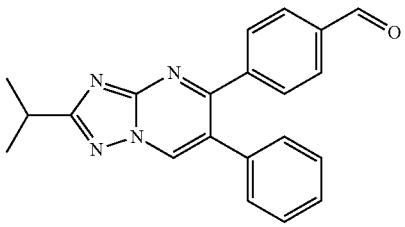 [SMILES: CC(C)c1nc2nc(-c3ccc(C=O)cc3)c(-c3ccccc3)cn2n1]

Step 1: 2-Isopropyl-6-phenyl[1,2,4]triazolo[1,5-a]pyrimidine-5,7-diol

A solution of 5.00 g 3-amino-5-isopropyl-1,2,4-triazol and 11.24 g diethyl phenylmalonate in 18 mL N,N-dibutylbutan-1-amine was stirred at 185° C. over night. The solution was diluted with 20% w/w NaOH solution, the resulting mixture was stirred for 30 min. The aqueous layer was washed with diethylether, acidified at 0° C. with concentrated HCl until precipitation of the product was complete. The precipitate was collected by filtration to yield the product, which was used without further purification.

MS (M+1): 271

Characteristic 1H NMR (300 MHz, d6-DMSO) signals: 3.1 (s, 1H); 1.3 (d, 6H)

Step 2: 5,7-Dichloro-2-isopropyl-6-phenyl[1,2,4]triazolo[1,5-a]pyrimidine 6.1 g 2-isopropyl-6-phenyl[1,2,4]triazolo[1,5-a]pyrimidine-5,7-diol was suspended in 13 mL POCl₃. 4.20 g N,N-dimethylaniline was added and the mixture was stirred at 100° C. for 2 h. The solvent was removed and the residue was treated with ice and water until precipitation of the product. The precipitate was collected by filtration to yield the product, which was used without further purification

MS (M+1): 307

Characteristic 1H NMR (200 MHz, d6-DMSO) signals: 7.6 ppm (m, 3H); 7.4 ppm (m, 2H); 1.4 ppm (d, 6H)

Step 3: 5-Chloro-2-isopropyl-6-phenyl[1,2,4]triazolo[1,5-a]pyrimidine 6.00 g 5,7-dichloro-2-isopropyl-6-phenyl[1,2,4]triazolo[1,5-a]pyrimidine was dissolved in 360 mL dichloromethane. 360 mL brine, 120 mL ammonia solution 25% w/w and 6.00 g zinc powder were added and the mixture was stirred at room temperature for 3 h. The reaction mixture was filtered through Celite and was washed with dichloromethane and water. The organic phase was separated and the water phase was extracted with dichloromethane. The combined dichloromethane phases were dried over Na₂SO₄ and evaporated. The crude product contained 5,7-dichloro-2-isopropyl-6-phenyl[1,2,4]triazolo[1,5-a]pyrimidine. The crude product was dissolved again in dichloromethane. 360 mL brine, 120 mL ammonia solution 25% w/w and 6.00 g zinc powder were added and the mixture was stirred at room temperature for 2 h. The reaction mixture was filtered through Celite and washed with dichloromethane and water. The organic phase was separated and the water phase was extracted with dichloromethane. The combined organic layers were dried over sodium sulphate and the solvent was evaporated. The product was used without further purification.

MS (M+1): 273

Characteristic 1H NMR (300 MHz, d6-DMSO) signals: 9.5 ppm (s, 1H); 1.4 ppm (d, 6H)

Step 4: 4-(2-Isopropyl-6-phenyl[1,2,4]triazolo[1,5-a]pyrimidin-5-yl)benzaldehyde To a mixture of 5.30 g 5-chloro-2-isopropyl-6-phenyl[1,2,4]triazolo[1,5-a]pyrimidine and 3.80 g 4-formylphenylboronic acid in 160 mL 1,2-dimethoxyethane were added 33 mL of a 10% w/w sodium carbonate solution and 0.71 g dichloro[1,1'-bis(diphenylphosphino)ferrocene]palladium (II) and the resulting mixture was heated to 90° C. under an inert gas atmosphere for 18 h. The work up was performed by diluting the reaction mixture with water and dichloromethane, separating the phases and extraction of the aqueous phase with dichloromethane. The combined organic layers were dried over sodium sulphate, the solvent was evaporated and the residue suspended in ethyl acetate. The insoluble solid was filtered and the filtrate was evaporated. The residue was purified by chromatography on silica gel (dichloromethane/ethyl acetate) to yield the product.

MS (M+1): 343

Characteristic 1H NMR (300 MHz, d6-DMSO) signals: 10 ppm (s, 1H); 9.5 ppm (s, 1H); 1.4 ppm (d, 6H)

Intermediate Example 21.0

4-(7-methoxy-6-phenylpyrazolo[1,5-a]pyrimidin-5-yl)benzaldehyde

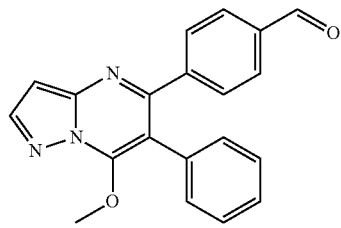

Step 1: 5-Chloro-7-methoxy-6-phenylpyrazolo[1,5-a]pyrimidine 1.00 g 5,7-dichloro-6-phenylpyrazolo[1,5-a]pyrimidine (prepared as described above) were dissolved in 20 mL methanol and 20 mL dichlormethane. 1.2 g sodium methylate was added at 0° C. and stirred at room temperature for 2 h. The solution was diluted with water and dichloromethane. The organic phase was separated and the water phase was extracted with dichloromethane. The combined organic layers were dried over Na₂SO₄ and the solvent was evaporated. The crude product was used without further purification.

MS (M+1): 260

Characteristic 1H NMR (d6-DMSO, 400 MHz) signals: 8.3 ppm (d, 1H); 6.7 ppm (d, 1H); 4.1 ppm (s, 3H)

Step 2: 4-(7-Methoxy-6-phenylpyrazolo[1,5-a]pyrimidin-5-yl)benzaldehyde

To a solution of 1.00 g 5-chloro-7-methoxy-6-phenylpyrazolo[1,5-a]pyrimidine and 0.69 g 4-formylphenylboronic acid in 20 mL 1,2-dimethoxyethane were added 7.3 mL of a 10% w/w sodium carbonate solution and 0.14 g dichloro[1,1'-bis(diphenylphosphino)ferrocene]palladium (II). The mixture was heated for 45 min under microwave irradiation to 120° C. This mixture was worked up by diluting with water and extraction with dichloromethane. The organic layers were dried over Na₂SO₄ and concentrated to yield the crude product, which was purified by chromatography on silica gel (methanol/dichloromethane).

MS (M+1): 330

Characteristic 1H NMR (300 MHz, d6-DMSO) signals: 10.0 ppm (s, 1H); 8.3 ppm (d, 1H); 6.7 ppm (d, 1H)

Intermediate Example 22.0

4-(3-Chloro-6-phenylpyrazolo[1,5-a]pyrimidin-5-yl)benzaldehyde

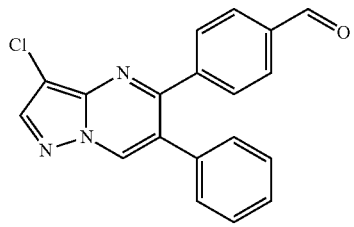

0.4 g 6-phenylpyrazolo[1,5-a]pyrimidin-5-yl)benzaldehyde (prepared as described above) and 0.19 g N-chlorosuccinimide were refluxed in 10 mL chloroform for 5 d. The solvent was removed by distillation and the crude product was purified by chromatography on silica gel (dichloromethane/ethyl acetate).

MS (M+1): 334

Characteristic 1H NMR (400 MHz, d6-DMSO) signals: 10.0 ppm (s, 1H); 9.3 ppm (s, 1H); 8.5 ppm (s, 1H); 7.9 ppm (m, 2H); 7.6 ppm (m, 2H)

Intermediate Example 23.0

4-(3-Bromo-6-phenylpyrazolo[1,5-a]pyrimidin-5-yl)benzaldehyde

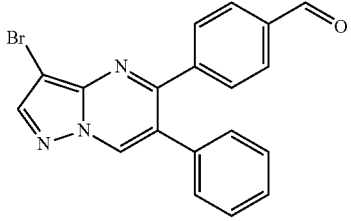 [SMILES: O=Cc1ccc(-c2nc3c(Cl)cnn3cc2-c2ccccc2)cc1]

1.0 g 6-phenylpyrazolo[1,5-a]pyrimidin-5-yl)benzaldehyde (prepared as described above) and 0.65 g N-bromosuccinimide were refluxed in 30 mL Chloroform for 5 h. This mixture was worked up by diluting with water and extraction with dichloromethane. The organic layers were dried over $Na_2SO_4$ and concentrated to yield the crude product, which was suspended in ethyl acetate/petrol ether. The solid desired product was isolated by filtration.

MS (M+1): 378/380

Characteristic 1H NMR (400 MHz, d6-DMSO) signals: 10.0 ppm (s, 1H); 9.3 ppm (s, 1H); 8.5 ppm (s, 1H); 7.9 ppm (m, 2H); 7.6 ppm (m, 2H)

Intermediate Example 24.0

5-(4-Formylphenyl)-6-phenylpyrazolo[1,5-a]pyrimidine-3-carbonitrile

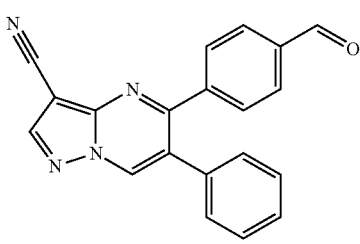 [SMILES: N#Cc1cnn2cc(-c3ccccc3)c(-c3ccc(C=O)cc3)nc12]

400 mg 4-(3-bromo-6-phenylpyrazolo[1,5-a]pyrimidin-5-yl)benzaldehyde (prepared as described above), 7.0 mg zinc powder, 75.0 mg $Zn(CN)_2$ and 39.0 mg dichloride[1,1'-bis(diphenylphosphino)ferrocene]palladium (II) dichloromethane adduct were suspended in 10 mL dimethylacetamide and the mixture was heated for 45 min under microwave irradiation to 160° C. The workup was performed by diluting the mixture with water and dichloromethane, extracting the aqueous layer twice and drying the combined organic layers over $Na_2SO_4$. The compound was isolated by evaporation of the solvent and chromatography on silica gel (dichloromethane/ethyl acetate).

MS (M+1): 325

Characteristic 1H NMR (300 MHz, d6-DMSO) signals: 10.0 ppm (s, 1H); 9.5 ppm (s, 1H); 8.9 ppm (s, 1H); 7.9 ppm (m, 2H); 7.6 ppm (m, 2H)

Intermediate Example 25.0

4-{6-Phenyl-3-[(trimethylsilyl)ethynyl]pyrazolo[1,5-a]pyrimidin-5-yl}benzaldehyde

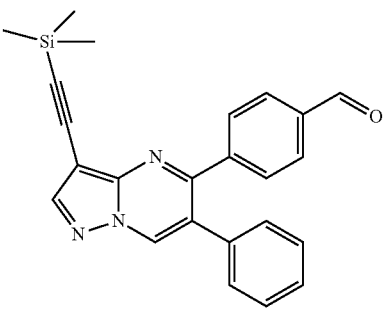 [SMILES: C[Si](C)(C)C#Cc1cnn2cc(-c3ccccc3)c(-c3ccc(C=O)cc3)nc12]

400 mg 4-(3-bromo-6-phenylpyrazolo[1,5-a]pyrimidin-5-yl)benzaldehyde (prepared as described above), 820 mg trimethyl[(tributylstannyl)ethynyl]silane and 60 mg $Pd(PPh_3)_4$ were suspended in 8 mL toluene under a nitrogen atmosphere. The mixture was heated (microwave irradiation) to 1300 for 1 h. This mixture was worked up by diluting with water and extraction with dichloromethane. The combined organic layers were dried over $Na_2SO_4$ and concentrated to yield the crude product, which was purified by chromatography on silica gel (ethyl acetate/dichloromethane).

MS (M+1): 396 and 428 [$MH^+$+32 (MeOH)]

Characteristic 1H NMR (300 MHz, d6-DMSO) signals: 10.0 ppm (s, 1H); 9.3 ppm (s, 1H); 8.5 ppm (s, 1H); 7.9 ppm (m, 2H); 7.6 ppm (m, 2H); 0.3 ppm (s, 9H)

Intermediate Example 26.0

4-(6-Phenyl-3-vinylpyrazolo[1,5-a]pyrimidin-5-yl)benzaldehyde

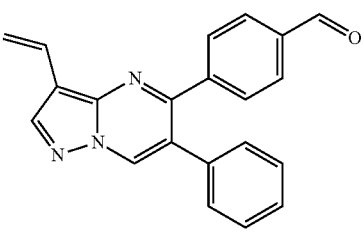 [SMILES: C=Cc1cnn2cc(-c3ccccc3)c(-c3ccc(C=O)cc3)nc12]

400 mg 4-(3-bromo-6-phenylpyrazolo[1,5-a]pyrimidin-5-yl)benzaldehyde (prepared as described above), 504 mg tributyl(vinyl)stannane, 176 mg tetraethylammonium chloride, 147 mg $K_2CO_3$ and 19 mg $Pd(PPh_3)_2Cl_2$ were suspended in 10 mL THF under a nitrogen atmosphere. The mixture was heated (microwave irradiation) to 110° C. for 45 min. This mixture was worked up by diluting with water and extraction with dichloromethane. The combined organic layers were dried over Na$_2$SO$_4$ and concentrated to yield the crude product, which was purified by chromatography on silica gel (ethyl acetate/dichloromethane).

MS (M+1): 326

Characteristic 1H NMR (300 MHz, d6-DMSO) signals: 10.0 ppm (s, 1H); 9.2 ppm (s, 1H); 8.5 ppm (s, 1H); 7.8 ppm (m, 2H); 7.6 ppm (m, 2H); 6.9 ppm (q, 1H); 6.1 ppm (d, 1H), 5.3 ppm (d, 1H)

Intermediate Example 27.0

4-(3-Ethyl-6-phenylpyrazolo[1,5-a]pyrimidin-5-yl)benzaldehyde

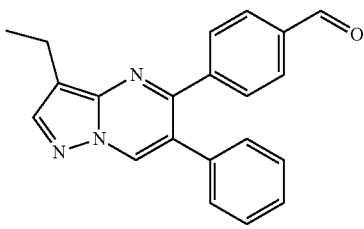 [SMILES: CCc1cnn2cc(-c3ccccc3)c(-c3ccc(C=O)cc3)nc12]

275 mg 4-(6-phenyl-3-vinylpyrazolo[1,5-a]pyrimidin-5-yl)benzaldehyde was dissolved in 10 mL THF and 10 mL ethanol. Pd/C (10% w/w) was added and stirred under H$_2$-atmosphere at room temperature for 1.5 h. The mixture was filtered through Celite. The filtrate was concentrated and the residue was purified by chromatography on silica gel (dichloromethane/ethyl acetate) to yield the desired compound.

MS (M+1): 328

Characteristic 1H NMR (400 MHz, d6-DMSO) signals: 10.0 ppm (s, 1H); 9.1 ppm (s, 1H); 8.2 ppm (s, 1H); 7.8 ppm (m, 2H); 7.6 ppm (m, 2H); 2.8 ppm (q, 2H); 1.3 ppm (t, 3H)

Intermediate Example 28.0

4-(3-Methyl-6-phenylpyrazolo[1,5-a]pyrimidin-5-yl)benzaldehyde

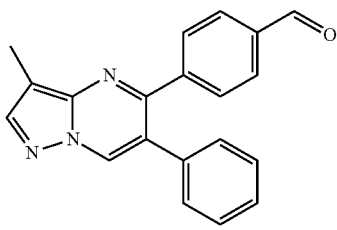

To a mixture of 0.50 g 4-(3-bromo-6-phenylpyrazolo[1,5-a]pyrimidin-5-yl)benzaldehyde (prepared as described under intermediate example 23) and 0.12 g methylboronic acid in 17 mL toluene were added 0.83 g potassium phosphate tribasic, 0.029 g palladium acetate and 0.11 g S-PHOS. The reaction mixture was heated for 1 h under microwave irradiation to 120° C. This mixture was worked up by diluting with water and extraction with dichloromethane. The organic layers were dried over Na$_2$SO$_4$ and concentrated to yield the crude product, which was purified by chromatography on silica gel (ethyl acetate/dichloromethane).

MS (M+1): 314

Characteristic 1H NMR (300 MHz, d6-DMSO) signals: 10.0 ppm (s, 1H); 9.1 ppm (s, 1H); 7.8 ppm (m, 2H); 7.6 ppm (m, 2H); 2.4 ppm (s, 3H)

Intermediate Example 29.0

4-(2,7-Dimethyl-6-phenyl[1,2,4]triazolo[1,5-a]pyrimidin-5-yl)benzaldehyde

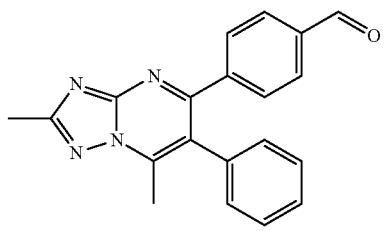 [SMILES: Cc1nc2nc(-c3ccc(C=O)cc3)c(-c3ccccc3)c(C)n2n1]

Step 1: 2,7-Dimethyl-6-phenyl[1,2,4]triazolo[1,5-a]pyrimidin-5-ol

A solution of 1.5 g 3-amino-5-methyltriazole and 3.3 g ethyl 3-oxo-2-phenylbutanoate was dissolved in a mixture of 21 mL DMF and 21 mL N,N-dibutylbutan-1-amine and heated by microwave irradiation to 180° C. for 6 h. The reaction mixture formed two phases. The DMF phase was separated and concentrated. The crude product was purified by column chromatography on silica gel (dichloromethane/methanol).

MS (M+1): 241

Characteristic 1H NMR (d6-DMSO, 300 MHz) signals: 13.0 ppm (m, 1H); 2.3 ppm (m, 6H)

Step 2: 5-Chloro-2,7-dimethyl-6-phenyl[1,2,4]triazolo[1,5-a]pyrimidine 1.34 g of the product of step 1 were suspended in 20 mL POCl$_3$. 1.06 mL N,N-dimethylaniline was added and the mixture was heated to 100° C. for 45 min. The excess of POCl$_3$ was removed by distillation and the residue was treated with ice. The desired product precipitates and was collected by filtration.

MS (M+1): 259

Characteristic 1H NMR (d6-DMSO, 300 MHz) signals: 7.6 ppm (m, 3H); 7.4 ppm (m, 2H); 2.6 ppm (s, 3H); 2.6 ppm (s, 3H)

Step 3: 4-(2,7-Dimethyl-6-phenyl[1,2,4]triazolo[1,5-a]pyrimidin-5-yl)benzaldehyde To a mixture of 1.25 g 5-chloro-2,7-dimethyl-6-phenyl[1,2,4]triazolo[1,5-a]pyrimidine and 0.87 g 4-formylphenylboronic acid in 25 mL 1,2-dimethoxyethane were added 0.18 g dichloro[1,1'-bis(diphenylphosphino)ferrocene]palladium (II) dichloromethane adduct and 9.30 mL of a 10% w/w sodium carbonate solution. The resulting mixture was heated to 110° C. by microwave irradiation under an inert gas atmosphere for 45 min. The work up was performed by diluting the reaction mixture with water and dichloromethane, separating the phases and extraction of the aqueous phase with dichloromethane. The combined organic layers were dried over sodium sulphate and the solvent was evaporated. The residue was purified by chromatography on silica gel (dichloromethane/methanol). The desired product was suspended in ethyl acetate/petrolether and isolated by filtration.

MS (M+1): 329

Characteristic 1H NMR (d6-DMSO, 300 MHz) signals: 10.0 ppm (s, 1H); 7.8 ppm (m, 2H); 7.5 ppm (m, 2H); 2.6 ppm (s, 3H); 2.6 ppm (s, 3H)

Intermediate Example 30.0

4-(2-Ethyl-6-phenyl[1,2,4]triazolo[1,5-a]pyrimidin-5-yl)benzaldehyde

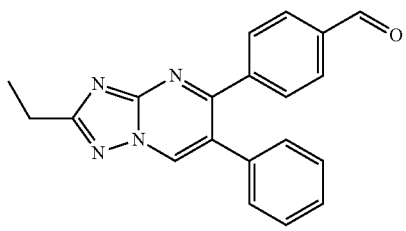 [SMILES: CCc1nc2nc(-c3ccc(C=O)cc3)c(-c3ccccc3)cn2n1]

Step 1: 2-Ethyl-6-phenyl[1,2,4]triazolo[1,5-a]pyrimidine-5,7-diol

A solution of 5.00 g 3-amino-5-ethyl-1,2,4-triazole and 15.00 g diethyl phenylmalonate in 18 mL N,N-dibutylbutan-1-amine was stirred at 185° C. over night. The solution was diluted with 5N NaOH solution, the resulting mixture was stirred for 30 min. The aqueous layer was washed with diethylether, acidified at 0° C. with concentrated HCl until precipitation of the product was complete. The precipitate was collected by filtration to yield the product, which was used without further purification.

MS (M+1): 257

Characteristic 1H NMR (300 MHz, d6-DMSO) signals: 7.4 ppm (m, 2H); 7.3 ppm (m, 2H); 7.1 ppm (m, 1H); 2.8 ppm (q, 2H); 1.3 ppm (t, 3H)

Step 2: 5,7-Dichloro-2-ethyl-6-phenyl[1,2,4]triazolo[1,5-a]pyrimidine 5.7 g 2-ethyl-6-phenyl[1,2,4]triazolo[1,5-a]pyrimidine-5,7-diol was suspended in 12 mL POCl₃. 4.30 mL N,N-dimethylaniline was added and the mixture was stirred at 100° C. for 20 h. The solvent was removed, the residue was treated with ice and water until precipitation of the product. The precipitate was collected by filtration to yield the product, which was used without further purification

MS (M+1): 293

Characteristic 1H NMR (300 MHz, d6-DMSO) signals: 2.9 ppm (q, 2H); 1.4 ppm (t, 3H)

Step 3: 5-Chloro-2-ethyl-6-phenyl[1,2,4]triazolo[1,5-a]pyrimidine 6.00 g 5,7-dichloro-2-ethyl-6-phenyl[1,2,4]triazolo[1,5-a]pyrimidine was dissolved in 180 mL dichloromethane. 180 mL saturated brine, 120 mL ammonia solution 25% w/w and 6.00 g zinc powder were added and the mixture was stirred at room temperature for 3 h. The reaction mixture was filtered through Celite and was washed with dichloromethane and water. The organic phase was separated and the water phase was extracted with dichloromethane. The combined organic layers were dried over Na₂SO₄ and the solvent was evaporated. The residue contained 2-ethyl-6-phenyl[1,2,4]triazolo[1,5-a]pyrimidine. This mixture was used without further purification for the next reaction.

MS (M+1): 259

Characteristic 1H NMR (300 MHz, d6-DMSO) signals: 9.5 ppm (s, 1H); 2.9 ppm (q, 2H); 1.4 ppm (t, 3H)

Step 4: 4-(2-Ethyl-6-phenyl[1,2,4]triazolo[1,5-a]pyrimidin-5-yl)benzaldehyde

To a mixture of 3.90 g of the crude product obtained in step 3 and 3.00 g 4-formylphenylboronic acid in 180 mL 1,2-dimethoxyethane were added 0.55 g dichloro[1,1'-bis(diphenylphosphino)ferrocene]palladium (II) and 25 mL of a 10% w/w sodium carbonate solution. The resulting mixture was heated to 90° C. under an inert gas atmosphere for 20 h. The work up was performed by diluting the reaction mixture with water and dichloromethane, separating the phases and extraction of the aqueous phase with dichloromethane. The combined organic layers were dried over sodium sulphate, the solvent was evaporated and the residue was suspended in ethyl acetate. The crude product was isolated by filtration, which was purified on silica gel (dichloromethane/methanol).

MS (M+1): 329

Characteristic 1H NMR (300 MHz, d6-DMSO) signals: 10.0 ppm (s, 1H); 9.5 ppm (s, 1H); 2.9 ppm (q, 2H); 1.4 ppm (t, 3H)

Intermediate Example 31.0

4-(2-Methyl-6-phenylpyrazolo[1,5-a]pyrimidin-5-yl)benzaldehyde

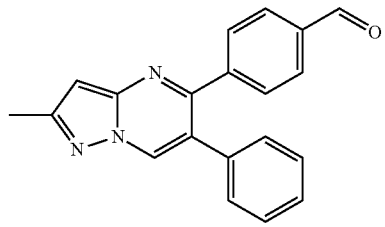 [SMILES: Cc1cc2nc(-c3ccc(C=O)cc3)c(-c3ccccc3)cn2n1]

Step 1: 2-Methyl-6-phenylpyrazolo[1,5-a]pyrimidine-5,7-diol

A solution of 4.5 g 5-amino-3-methylpyrazole and 12.2 mL diethyl phenylmalonate in N,N-dibutylbutan-1-amine was stirred at 185° C. over night. After cooling to room temperature the reaction mixture forms two layers. The top layer was removed and the lower layer was diluted with dichloromethane and methanol. The resulting solution was concentrated and extracted with a mixture of diethyl ether and 10% w/w NaOH solution. The organic layer was discarded and aqueous layer acidified with concentrated HCl. The precipitated product was collected by filtration.

MS (M−1): 240

Characteristic 1H NMR (d6-DMSO, 300 MHz) signals: 5.9 ppm (s, 1H); 2.3 ppm (s, 3H)

Step 2: 5,7-Dichloro-2-methyl-6-phenylpyrazolo[1,5-a]pyrimidine 6.1 g 2-methyl-6-phenylpyrazolo[1,5-a]pyrimidine-5,7-diol was suspended in 15 mL POCl₃. 5.00 mL N,N-dimethylaniline was added and the mixture was stirred at 100° C. for 3 h. The excess of POCl₃ was removed and the residue was treated with ice and water until precipitation of the product. The precipitate was collected by filtration and purified on silica gel (dichloromethane/ethyl acetate) to yield the desired product.

MS (M+1): 278

Characteristic 1H NMR (300 MHz, d6-DMSO) signals: 7.5 ppm (m, 5H); 6.7 ppm (s, 1H)

Step 3: 5-Chloro-2-methyl-6-phenylpyrazolo[1,5-a]pyrimidine 2.47 g 5,7-dichloro-2-methyl-6-phenylpyrazolo[1,5-a]pyrimidine was dissolved in 80 mL dichloromethane. 80 mL brine, 40 mL ammonia solution 25% w/w and 2.47 g zinc powder were added and the mixture was stirred at room temperature for 2 d. Four additional portions of 4.2 equivalents zinc powder were added over 4 days. The reaction mixture was filtered through Celite and washed with dichloromethane and water. The organic phase was separated and the water phase extracted with dichloromethane. The combined dichloromethane phase was dried over Na₂SO₄ and the solvent was evaporated. The residue was purified on silica gel (dichloromethane/ethyl acetate) to yield the desired product.

MS (M+1): 244

Characteristic 1H NMR (300 MHz, d6-DMSO) signals: 9.1 ppm (s, 1H); 6.6 ppm (s, 1H); 2.4 ppm (s, 3H)

Step 4: 4-(2-Methyl-6-phenylpyrazolo[1,5-a]pyrimidin-5-yl)benzaldehyde

To a mixture of 1.35 g of 5-chloro-2-methyl-6-phenylpyrazolo[1,5-a]pyrimidine and 1.04 g 4-formylphenylboronic acid in 20 mL 1,2-dimethoxyethane were added 10.8 mL of a 10% w/w sodium carbonate solution and 120 mg dichloro[1,1'-bis(diphenylphosphino)ferrocene]palladium (II). The resulting mixture was heated to 100° C. by microwave irradiation under an inert gas atmosphere for 75 min. The work up was performed by diluting the reaction mixture with water and dichloromethane, separating the phases and extraction of the aqueous phase with dichloromethane. The combined organic layers were dried over sodium sulphate and evaporated. The crude product was purified by chromatography on silica gel (dichloromethane/methanol) to yield the desired product.

MS (M+1): 314

Characteristic 1H NMR (300 MHz, d6-DMSO) signals: 10.0 ppm (s, 1H); 9.1 ppm (s, 1H); 7.8 ppm (m, 2H); 7.5 ppm (m, 2H)

Intermediate Example 32.0

4-(2-Cyclopropyl-6-phenyl-pyrazolo[1,5-a]pyrimidin-5-yl)-benzaldehyde

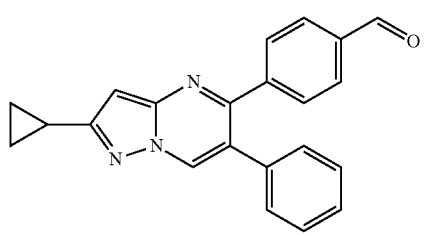 [SMILES: O=Cc1ccc(-c2nc3cc(C4CC4)nn3cc2-c2ccccc2)cc1]

This compound was prepared in a manner according to 4-(2-methyl-6-phenylpyrazolo[1,5-a]pyrimidin-5-yl)benzaldehyde by using 3-cyclopropyl-1H-pyrazol-5 amine in the first step.

Intermediate Example 33.0

2,7-Dimethyl-6-phenyl-5-(4-{[4-(5-pyridin-2-yl-1H-1,2,4-triazol-3-yl)piperidin-1-yl]methyl}phenyl)pyrazolo[1,5-a]pyrimidine

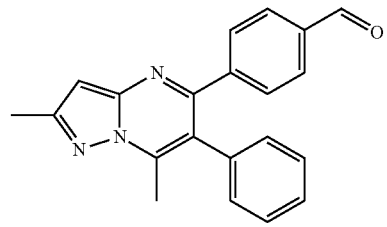 [SMILES: Cc1cc2nc(-c3ccc(C=O)cc3)c(-c3ccccc3)c(C)n2n1]

This compound was prepared in a manner according to 4-(2,7-dimethyl-6-phenyl[1,2,4]triazolo[1,5-a]pyrimidin-5-yl)benzaldehyde by using 3-amino-5-methyl pyrazole in the first step.

Intermediate Example 34.0

4-(6-Thiophen-3-yl-pyrazolo[1,5-a]pyrimidin-5-yl)benzaldehyde

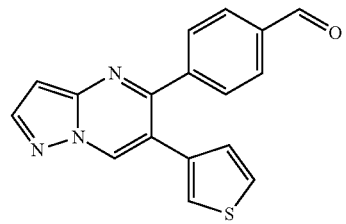 [SMILES: O=Cc1ccc(-c2nc3ccnn3cc2-c2ccsc2)cc1]

Step 1: 5,7-Dichloro-6-thiophen-3-yl-pyrazolo[1,5-a]pyrimidine

To 3.80 g 3-aminopyrazole and 8.50 g 3-thienyl malonic acid were added dropwise over 2 minutes 106 mL POCl₃ and stirred at 90° C. for 48 hours. The mixture was poured on ice and stirred for 1 hour. The precipitate was collected by filtration, washed with water and dissolved in warm ethanol. The mother liquor was added with sodium hydroxide and ethyl acetate. The organic phase was separated and the water phase was extracted with ethyl acetate. The organic layers were dried over Na₂SO₄ and the solvent was evaporated.

Step 2: 5-Chloro-6-thiophen-3-yl-pyrazolo[1,5-a]pyrimidine 2.450 g 5,7-dichloro-2-methyl-6-phenylpyrazolo[1,5-a]pyrimidine were dissolved in 79 mL dichloromethane. 79 mL brine, 40 mL ammonia solution 25% w/w and 2.54 g zinc powder were added and the mixture was stirred at 60° C. for 1.5 h. The reaction mixture was filtered through sand and washed with dichloromethane and water. The organic phase was separated and the aqueous phase was extracted with dichloromethane. The combined dichloromethane phase was dried over Na$_2$SO$_4$ and the solvent was evaporated. The residue was purified on silica gel (dichloromethane/ethyl acetate) to yield the desired product.

Step 3: 4-(6-Thiophen-3-yl-pyrazolo[1,5-a]pyrimidin-5-yl)-benzaldehyde

To a mixture of 276 mg 5-chloro-6-thiophen-3-yl-pyrazolo[1,5-a]pyrimidine and 228 mg 4-formylphenylboronic acid in 13 mL 1,2-dimethoxyethane were added 1.8 mL of a 10% w/w sodium carbonate solution and 48 mg dichloro[1,1'-bis(diphenylphosphino)ferrocene]palladium (II). The resulting mixture was heated to 80° C. under an inert gas atmosphere for 7 h. An additional portion of 228 mg 4-formylphenylboronic acid and 48 mg dichloro[1,1'-bis(diphenylphosphino)ferrocene]palladium (II) was added and the mixture was heated to 80° C. for 2 h. The work up was performed by diluting the reaction mixture with water and dichloromethane, separating the phases and extraction of the aqueous phase with dichloromethane. The combined organic layers were dried over sodium sulphate and the solvent was evaporated. The solid residue was stirred in diethylether, filtered and dried to yield the desired product.

Intermediate Example 35.0

4-(6-Thiophen-3-yl-imidazo[1,2-a]pyrimidin-7-yl)benzaldehyde

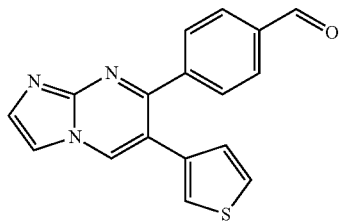 [SMILES: O=Cc1ccc(-c2nc3nccn3cc2-c2ccsc2)cc1]

This compound was prepared in a manner according to 4-(6-thiophen-3-yl-pyrazolo[1,5-a]pyrimidin-5-yl)-benzaldehyde by using 2-aminoimidazole in the first step.

Intermediate Example 36.0

4-(2-Bromo-6-phenyl[1,2,4]triazolo[1,5-a]pyrimidin-5-yl)benzaldehyde

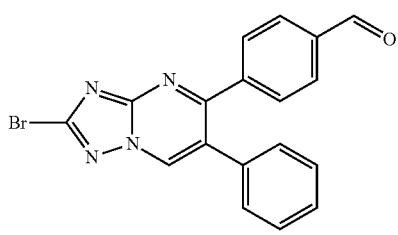 [SMILES: O=Cc1ccc(-c2nc3nc(Br)nn3cc2-c2ccccc2)cc1]

Step 1: 2-Amino-6-phenyl[1,2,4]triazolo[1,5-a]pyrimidine-5,7-diol

A solution of 9.0 g 3,5-diamino-1,2,4-triazole and 22.4 mL diethyl phenylmalonate in N,N-dibutylbutan-1-amine was heated under microwave irradiation to 180° C. for 8 h. The reaction mixture formed two layers after cooling to room temperature. The top layer was removed and the solvent of the lower layer was evaporated. The residue was treated with water and acidified with 5N HCl. The precipitated product was collected by filtration and dried. The crude product was used without further purification.

MS (M+1): 244

Step 2: 5,7-Dichloro-6-phenyl[1,2,4]triazolo[1,5-a]pyrimidin-2-amine 29 g 2-amino-6-phenyl[1,2,4]triazolo[1,5-a]pyrimidine-5,7-diol was suspended in 150 mL POCl$_3$. 17.14 mL N,N-dimethylaniline were added and the mixture was stirred at 100° C. for 2 h. The excess of POCl$_3$ was removed by evaporation and the residue was treated with ice and a mixture of water/ethanol (9:1) until precipitation of the product. The precipitate was collected by filtration and dried to yield the desired product.

MS (M+1): 280

Characteristic 1H NMR (200 MHz, d6-DMSO) signals: 7.6 ppm (m, 3H); 7.4 ppm (m, 2H)

Step 3: 2,7-Dibromo-5-chloro-6-phenyl[1,2,4]triazolo[1,5-a]pyrimidine 25.0 g 5,7-dichloro-6-phenyl[1,2,4]triazolo[1,5-a]pyrimidin-2-amine were suspended in 250 mL hydrobromic acid (48% w/w). A solution of 18.4 g sodium nitrite in 60 mL water was added dropwise over 20 min. The resulting mixture was heated to 65° C. After 1 and 2.5 h additional portions of 3.1 g sodium nitrite dissolved in 10 mL water were added. The reaction mixture was diluted with 500 mL water and 1 l ethyl acetate after 3 h. The organic phase was separated and the water phase was extracted with ethyl acetate. The combined organic layers were washed with 1N NaOH solution, with saturated Na$_2$CO$_3$ solution and brine. The combined organic layers were dried over Na$_2$SO$_4$ and the solvent was evaporated. The solid residue was stirred in ethanol for 2 h. The crude product was filtered, dried and was used without further purification.

MS (M+1): 389

Characteristic 1H NMR (300 MHz, d6-DMSO) signals: 7.6 ppm (m, 3H); 7.4 ppm (m, 2H)

Step 4: 2-Bromo-5-chloro-6-phenyl[1,2,4]triazolo[1,5-a]pyrimidine

A mixture of 29.4 g 2,7-dibromo-5-chloro-6-phenyl[1,2,4]triazolo[1,5-a]pyrimidine, 125 mL methanol, 500 mL THF, 12.9 mL glacial acetic acid and 14.7 g of Zn/Cu pair were stirred at 45° C. After 3 and 5 hours additional portions of 7.3 g Zn/Cu pair were added. The mixture was filtered through celite and the filtrate was diluted with water and ethyl acetate. The phases were separated and the water layer was extracted with ethyl acetate. The combined organic layers were washed with saturated Na$_2$CO$_3$ solution, dried over Na$_2$SO$_4$ and the solvent was evaporated. The solid residue was stirred in a mixture of 2-propanol/ethanol (3:1) for 2 h. The crude product was filtered and dried and was used without further purification.

MS (M+1): 355

Characteristic 1H NMR (300 MHz, d6-DMSO) signals: 9.6 ppm (s, 1H); 7.6 ppm (m, 1H)

Step 5: 4-(2-Bromo-6-phenyl[1,2,4]triazolo[1,5-a]pyrimidin-5-yl)benzaldehyde

To a mixture of 1.0 g 2-bromo-5-chloro-6-phenyl[1,2,4]triazolo[1,5-a]pyrimidine and 0.48 g 4-formylphenylboronic acid in 10 mL 1,2-dimethoxyethane were added 6.2 mL of a 10% w/w sodium carbonate solution and 118 mg dichloro[1,1'-bis(diphenylphosphino)ferrocene]palladium (II) and the resulting mixture was heated to 100° C. by microwave irradiation under a inert gas atmosphere for 50 min. The work up was performed by diluting the reaction mixture with water and dichloromethane, separating the phases and extraction of the aqueous phase with dichloromethane. The combined organic layers were dried over Na$_2$SO$_4$ and the solvent was evaporated. The crude product was purified by chromatography on silica gel (dichloromethane/ethyl acetate) to yield the desired product.

MS (M+1): 379/380

Characteristic 1H NMR (300 MHz, d6-DMSO) signals: 10.0 ppm (s, 1H); 9.6 ppm (s; 1H); 7.9 ppm (m, 2H); 7.6 ppm (m, 2H)

Intermediate Example 37.0

4-{6-Phenyl-2-[(trimethylsilyl)ethynyl][1,2,4]triazolo[1,5-a]pyrimidin-5-yl}benzaldehyde

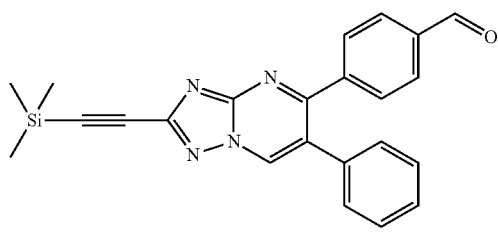 [SMILES: C[Si](C)(C)C#Cc1nc2nc(-c3ccc(C=O)cc3)c(-c3ccccc3)cn2n1]

300 mg 4-(2-bromo-6-phenyl[1,2,4]triazolo[1,5-a]pyrimidin-5-yl)benzaldehyde (prepared as described above), 613 mg trimethyl[(tributylstannyl)ethynyl]silane and 46 mg Pd(PPh$_3$)$_4$ were suspended in 12 mL toluene under a nitrogen atmosphere. The mixture was heated (microwave irradiation) to 120° C. for 1 h. This mixture was worked up by diluting with water and extraction with dichloromethane. The organic layers were dried over Na$_2$SO$_4$ and concentrated to yield the crude product, which was purified by chromatography on silica gel (ethyl acetate/dichloromethane).

MS (M+1): 397

Characteristic 1H NMR (300 MHz, d6-DMSO) signals: 10.0 ppm (s, 1H); 9.5 ppm (s, 1H); 7.9 ppm (m, 2H); 7.6 ppm (m, 2H); 0.3 ppm (s, 9H)

Intermediate Example 38.0

4-(2-methyl-6-thiophen-3-yl-[1,2,4]triazolo[1,5-a]pyrimidin-5-yl)-benzaldehyde

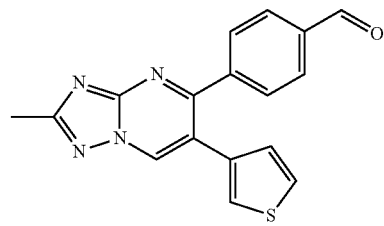 [SMILES: Cc1nc2nc(-c3ccc(C=O)cc3)c(-c3ccsc3)cn2n1]

This compound was prepared in a manner according to 4-(6-thiophen-3-yl-pyrazolo[1,5-a]pyrimidin-5-yl)-benzaldehyde by using 5-methyl-1,2,4-triazol-3-amine in the first step.

Intermediate Example 39.0

4-(2-Dimethylamino-6-phenyl-[1,2,4]triazolo[1,5-a]pyrimidin-5-yl)-benzaldehyde

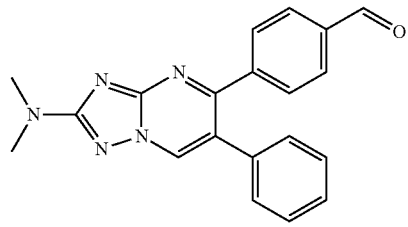 [SMILES: CN(C)c1nc2nc(-c3ccc(C=O)cc3)c(-c3ccccc3)cn2n1]

To 200 mg 4-(2-bromo-6-phenyl[1,2,4]triazolo[1,5-a]pyrimidin-5-yl)benzaldehyde (prepared as described above) in 6 mL DMF were added 0.24 mL of a dimethylamine solution (60% in water). The mixture was heated under microwave irradiation to 100° C. for 2.5 hours. The solvent was removed and the solid residue is was treated with ethyl acetate/petrolether (1:1) and stirred for 2 hours. The desired product was filtered, dried and was used without further purification.

MS (M+1): 344

Intermediate Example 39.1

4-(2-ethylamino-6-phenyl-[1,2,4]triazolo[1,5-a]pyrimidin-5-yl)-benzaldehyde

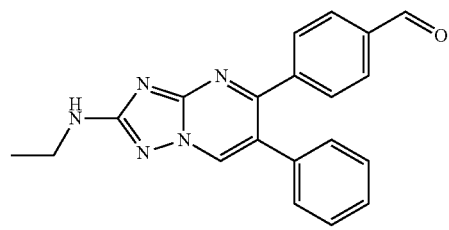 [SMILES: CCNc1nc2nc(-c3ccc(C=O)cc3)c(-c3ccccc3)cn2n1]

To 90 mg 4-(2-bromo-6-phenyl[1,2,4]triazolo[1,5-a]pyrimidin-5-yl)benzaldehyde (prepared as described above) in 2 mL NMP were added 0.71 mL ethylamine. The mixture was heated under microwave irradiation to 100° C. for 80 min and then overnight at 100° C. under conventional heating. On cooling the reaction was diluted with water and extracted with EtOAc. The organic phase was washed with brine, dried and concentrated in vacuo to give the crude title compound as an orange oil which was used in the next step without further purification.

UPLC-MS: RT=1.11 min; m/z=344.51

Intermediate Example 39.2

4-(2-methylamino-6-phenyl-[1,2,4]triazolo[1,5-a]pyrimidin-5-yl)-benzaldehyde

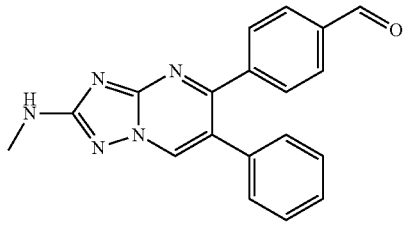

4-(2-Methylamino-6-phenyl-[1,2,4]triazolo[1,5-a]pyrimidin-5-yl)-benzaldehyde was prepared in analogy to Intermediate Example 3.0 Steps 1-4, except that in Step 1 3-amino-5-methyltriazole was replaced with N*3*-methyl-1H-[1,2,4]triazole-3,5-diamine (prepared using the procedure below).

UPLC-MS: RT=1.02 min; m/z=330.1

1H NMR (400 MHz, d6-DMSO): δ 9.95 (s, 1H), 9.12 (s, 1H), 7.79 (d, 2H), 7.49 (d, 2H), 7.29-7.30 (m, 3H), 7.19-7.21 (m, 3H), 7.00 (q, 1H), 2.84 (d, 3H) ppm Preparation of N*3*-methyl-1H-[1,2,4]triazole-3,5-diamine A suspension of N-cyano-N,S-dimethylisothiourea (14.22 g, 0.108 mol) and 80% hydrazine hydrate (13.1 mL) in ethanol (54 mL) was heated at reflux for 2 hours, whereupon the suspension dissolved. On cooling the mixture was concentrated in vacuo to a colourless oil which was triturated with petroleum ether at 0° C. until precipitation was observed. The solid was filtered, washed with petroleum ether and dried to give the title compound as a violet solid (12.75 g) which was used completely in the next step without further purification.

MS (ESI, M+1): 114

Intermediate Example 39.3

4-(2-isopropylamino-6-phenyl-[1,2,4]triazolo[1,5-a]pyrimidin-5-yl)-benzaldehyde

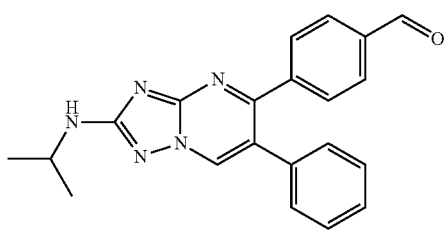 [SMILES: CC(C)Nc1nc2nc(-c3ccc(C=O)cc3)c(-c3ccccc3)cn2n1]

4-(2-isopropylamino-6-phenyl-[1,2,4]triazolo[1,5-a]pyrimidin-5-yl)-benzaldehyde was prepared in analogy to Intermediate Example 39.2 from the appropriate isothiourea.

UPLC-MS: RT=1.20 min; m/z=358.54

1H NMR (300 MHz, d6-DMSO): δ 9.95 (s, 1H), 9.10 (s, 1H), 7.78 (d, 2H), 7.48 (d, 2H), 7.28-7.30 (m, 3H), 7.18-7.21 (m, 2H), 6.99 (d, 1H), 3.80-3.91 (m, 1H), 1.18 (d, 6H) ppm Intermediate Example 39.4

4-(2-methylsulfanyl-6-phenyl-[1,2,4]triazolo[1,5-a]pyrimidin-5-yl)-benzaldehyde

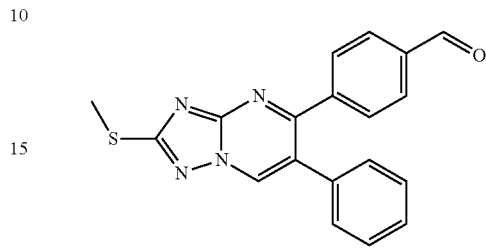

4-(2-Methylsulfanyl-6-phenyl-[1,2,4]triazolo[1,5-a]pyrimidin-5-yl)-benzaldehyde was prepared in analogy to Intermediate Example 3.0 Steps 1-4, except that in Step 1 3-amino-5-methyltriazole was replaced with 5-methylsulfanyl-2H-[1,2,4]triazol-3-ylamine.

UPLC-MS: RT=1.30 min; m/z=347.25

1H NMR (300 MHz, d6-DMSO): δ 9.96 (s, 1H), 9.42 (s, 1H), 7.81 (d, 2H), 7.52 (d, 1H), 7.30-7.33 (m, 3H), 7.22-7.25 (m, 2H), 2.66 (s, 3H) ppm Intermediate Example 40.0

4-(6-Phenyl-2-trifluoromethyl-[1,2,4]triazolo[1,5-a]pyrimidin-5-yl)-benzaldehyde

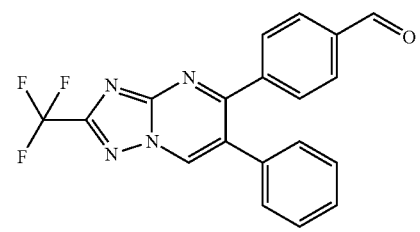 [SMILES: O=Cc1ccc(-c2nc3nc(C(F)(F)F)nn3cc2-c2ccccc2)cc1]

This compound was prepared in a manner according to 4-(6-phenyl[1,2,4]triazolo[1,5-a]pyrimidin-5-yl)benzaldehyde by using 5-trifluoromethyl-2H-[1,2,4]triazol-3-ylamine in the first step.

Intermediate Example 41.0

4-[7-(Dimethylamino)-2-methyl-6-phenyl[1,2,4]triazolo[1,5-a]pyrimidin-5-yl]benzaldehyde

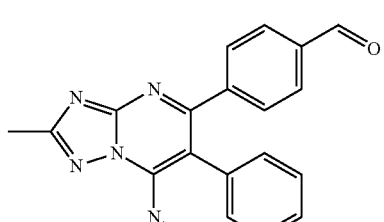

Step 1: 5-Chloro-N,N,2-trimethyl-6-phenyl[1,2,4]triazolo[1,5-a]pyrimidin-7-amine To 500 mg 5,7-dichloro-2-methyl-6-phenyl[1,2,4]triazolo[1,5-a]pyrimidine (prepared as described above) in 25 mL DMF were added 0.8 mL of a dimethylamine solution (60% in water). The mixture was stirred at room temperature for 45 minutes. The reaction mixture was diluted with water and dichloromethane. The phases were separated and the water layer was extracted with dichloromethane. The combined organic layers were dried over $Na_2SO_4$ and the solvent was removed by evaporation. The residue was suspended in diethylether and stirred for 5 hours. The desired product was filtered, dried and was used without further purification for the next step.

MS (M+1): 288
Characteristic 1H NMR (d6-DMSO, 300 MHz) signals: 2.8 ppm (s, 6H); 2.4 ppm (s, 3H)

Step 2: 4-[7-(Dimethylamino)-2-methyl-6-phenyl[1,2,4]triazolo[1,5-a]pyrimidin-5-yl]benzaldehyde To a mixture of 370 mg 5-chloro-N,N,2-trimethyl-6-phenyl[1,2,4]triazolo[1,5-a]pyrimidin-7-amine and 231 mg 4-formylphenylboronic acid in 7 mL 1,2-dimethoxyethane were added 2.5 mL of a 10% w/w sodium carbonate solution and 47 mg dichloro[1,1'-bis(diphenylphosphino)ferrocene]palladium (II). The resulting mixture was heated to 130° C. by microwave irradiation under a inert gas atmosphere for 1 hour. The work up was performed by diluting the reaction mixture with water and dichloromethane, separating the phases and extraction of the aqueous phase with dichloromethane. The combined organic layers were dried over sodium sulphate and the solvent was evaporated. The crude product was purified by chromatography on silica gel (dichloromethane/methanol) to yield the desired product.

MS (M+1): 358
Characteristic 1H NMR (300 MHz, d6-DMSO) signals: 10.0 ppm (s, 1H); 7.7 ppm (m, 2H); 7.4 ppm (m, 2H); 2.8 ppm (s, 6H)

Starting Material for Intermediate Example 41.11

5-chloro-6-phenyl-2-pyridine-2-yl-[1,2,4]triazolo[1,5-a]pyrimidin-7-yl-methylamine

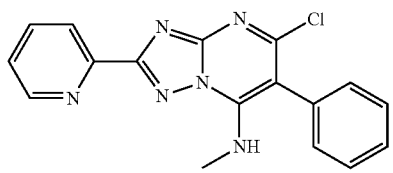 [SMILES: CNc1c(-c2ccccc2)c(Cl)nc2nc(-c3ccccn3)nn12]

Step 1: 6-phenyl-2-pyridine-2-yl-[1,2,4]triazolo[1,5-a]pyrimidine-5,7-diol 20 g (124.1 mmol) 5-Pyridine-2-yl-4H-[1,2,4]triazole-3-ylamine and 52.8 g (223.4 mmol) diethyl phenylmalonate are heated in 48.8 mL (204.8 mmol) tributylamine at 180° C. overnight. After addition of additional 27 mL diethyl phenylmalonate the reaction mixture is heated for another night at 180° C. The reaction mixture is diluted with water and 2N NaOH and extracted three times with methyl-tert.butylether. The organic extracts are discarded after TLC check. The aqueous phase is acidified with 2M HCl until a pH of 1. The formed precipitate is collected by filtration, washed with plenty of water and dried. 18.96 g (45%) of the desired product are obtained which are used in the next step without further purification.

MS (ES+, M+1): 306
$^1$H-NMR (400 MHz, d6-DMSO): 8.79 (d, 1H), 8.28 (d, 1H), 8.05-8.13 (m, 1H), 7.62-7.70 (m, 1H), 7.39-7.48 (m, 2H), 7.23-7.39 (m, 2H), 7.15-7.20 (m, 1H).

Step 2: 5,7-dichloro-6-phenyl-2-pyridine-2-yl-[1,2,4]triazolo[1,5-a]pyrimidine 11.34 g (37.1 mmol) 6-phenyl-2-pyridine-2-yl-[1,2,4]triazolo[1,5-a]pyrimidine-5,7-diol are dissolved in 42.2 mL (452.4 mmol) $POCl_3$ and 7.5 mL (59.4 mmol) N,N-dimethylaniline. The mixture is heated at 100° C. for 3 hours. The reaction mixture is poured on plenty of ice and icewater (caution: strong development of heat). After stirring for 1 hour the formed precipitate is filtered off and washed with water. The filtrate is extracted three times with dichloromethane. The combined organic extracts are dried over $Na_2SO_4$ and the solvent is evaporated. The precipitate and the residue from the extraction are handled separately. After drying at 50° C. the precipitate yields 1.06 g (8.3%) and the residue from the extract 6.84 g (53.8%).

MS (ES+, M+1): 342
$^1$H-NMR (300 MHz, d6-DMSO): 8.79 (d, 1H), 8.32 (d, 1H), 8.05 (dd, 1H), 7.40-7.65 (m, 6H).

Step 3: 5-chloro-6-phenyl-2-pyridine-2-yl-[1,2,4]triazolo[1,5-a]pyrimidin-7-yl-methylamine 1 g (2.9 mmol) 5,7-dichloro-6-phenyl-2-pyridine-2-yl-[1,2,4]triazolo[1,5-a]pyrimidine are given in 8.2 mL DMF (no complete dissolution). After addition of 3.65 mL of a 2M (7.3 mmol) solution of methylamine in THF the reaction mixture is heated in a microwave oven at 100° C. for 20 minutes. From the clear brown solution the DMF is evaporated, the residue is diluted with brine and extracted three times with dichloromethane. The combined organic extracts are dried over $Na_2SO_4$ and the solvent is evaporated and the residue purified by chromatography (silicagel, eluents: dichloromethane, methanol). 265 mg (26.9%) of the desired product are obtained.

MS (ES+, M+1): 337
$^1$H-NMR (400 MHz, $CDCl_3$): 8.79 (d, 1H), 8.48 (d, 1H), 7.90 (dd, 1H), 7.35-7.55 (m, 6H), 6.80 (br., 1H), 2.52 (d, 3H).

Starting Material for Intermediate Example 41.12

5-chloro-6-phenyl-2-pyridine-2-yl-[1,2,4]triazolo[1,5-a]pyrimidin-7-yl-isopropylamine

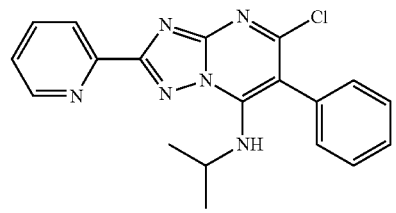 [SMILES: CC(C)Nc1c(-c2ccccc2)c(Cl)nc2nc(-c3ccccn3)nn12]

5-chloro-6-phenyl-2-pyridine-2-yl-[1,2,4]triazolo[1,5-a]pyrimidin-7-yl-isopropylamine 1 g (2.9 mmol) 5,7-dichloro-6-phenyl-2-pyridine-2-yl-[1,2,4]triazolo[1,5-a]pyrimidine described in the former example are given in 10 mL DMF (no complete dissolution). After addition of 0.62 mL (7.3 mmol) isopropylamine the reaction mixture is heated in a microwave oven at 100° C. for 20 minutes. From the clear brown solution the DMF is evaporated, the residue is diluted with brine and water and extracted three times with dichloromethane. The combined organic extracts are dried over $Na_2SO_4$ and the solvent is evaporated. The reaction is repeated twice with 1 g starting material resp. 200 mg. The crude residues after the work-up are combined and purified jointly by chromatography (silicagel, eluents: dichloromethane, methanol) yielding 856.1 mg (36.5%) of the desired product.

$^1$H-NMR (300 MHz, d6-DMSO): 8.72 (d, 1H), 8.28 (d, 1H), 8.00 (dd, 1H), 7.38-7.56 (m, 7H), 3.38 (br., 1H), 1.00 (d, 6H).

The following intermediates were prepared in analogy to Intermediate Example 41.0 by using the appropriate intermediate and amine in Step 1.

| Intermediate Example | Structure/Name | Analytical Data |
|---|---|---|
| 41.1 | 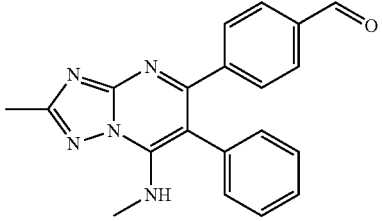<br>4-(2-methyl-7-methylamino-6-phenyl-[1,2,4]triazolo[1,5-a]pyrimidin-5-yl)-benzaldehyde | UPLC-MS: RT = 0.99 min; m/z = 344.1 |
| 41.2 | 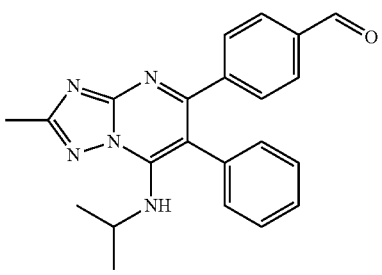<br>4-(7-isopropylamino-2-methyl-6-phenyl-[1,2,4]triazolo[1,5-a]pyrimidin-5-yl)-benzaldehyde | UPLC-MS: RT = 1.21 min; m/z = 372.56<br>1H NMR (300 MHz, d6-DMSO): δ 9.88 (s, 1H), 7.66 (d, 2H), 7.33 (d, 2H), 7.26 (m, 5H), 6.89 (d, 1H), 3.50 (m, 1H), 0.96 (d, 6H) ppm (methyl singlet obscured by solvent) |
| 41.3 | 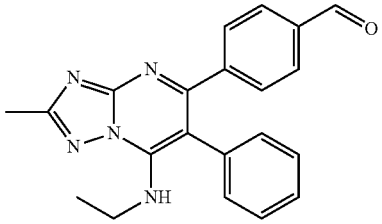<br>4-(7-ethylamino-2-methyl-6-phenyl-[1,2,4]triazolo[1,5-a]pyrimidin-5-yl)-benzaldehyde | UPLC-MS: RT = 1.13 min; m/z = 358.29<br>1H NMR (300 MHz, d6-DMSO): δ 9.89 (s, 1H), 7.66 (d, 2H), 7.52 (t, 1H), 7.34 (d, 2H), 7.25 (m, 5H), 2.99 (m, 2H), 0.87 (t, 3H) ppm (methyl singlet obscured by solvent) |

| Intermediate Example | Structure/Name | Analytical Data |
|---|---|---|
| 41.4 | 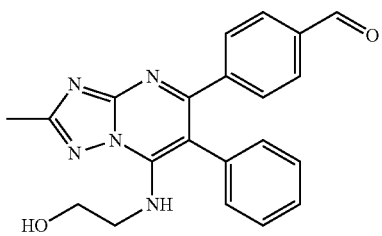<br>4-(7-ethylamino-2-methyl-6-phenyl-[1,2,4]triazolo[1,5-a]pyrimidin-5-yl)-benzaldehyde | UPLC-MS: RT = 0.90 min; m/z = 374.29 |
| 41.5 | 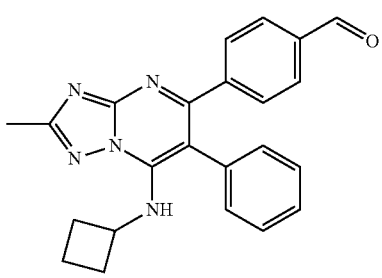<br>4-(7-cyclobutylamino-2-methyl-6-phenyl-[1,2,4]triazolo[1,5-a]pyrimidin-5-yl)-benzaldehyde | UPLC-MS: RT = 1.27 min; m/z = 384.55<br>1H NMR (300 MHz, d6-DMSO): δ 9.88 (s, 1H), 7.66 (d, 2H), 7.48 (d, 1H), 7.32 (d, 2H), 7.20-7.27 (m, 5H), 3.59-3.73 (m, 1H), 1.95-2.06 (m, 2H), 1.66-1.74 (m, 2H), 1.38-1.48 (m, 1H), 1.03-1.17 (m, 1H) ppm (methyl singlet obscured by solvent) |
| 41.6 | 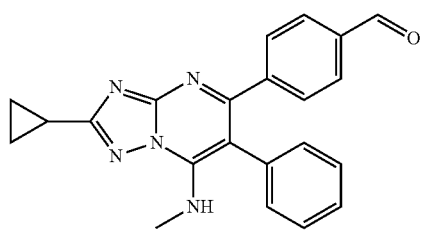<br>4-(2-cyclopropyl-7-methylamino-6-phenyl-[1,2,4]triazolo[1,5-a]pyrimidin-5-yl)-benzaldehyde | UPLC-MS: RT = 1.12 min; m/z = 370.19 |
| 41.7 | 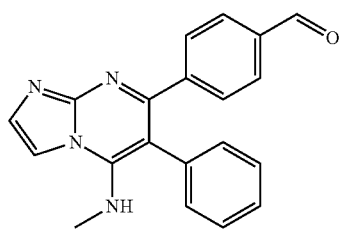<br>4-(5-methylamino-6-phenyl-imidazo[1,2-a]pyrimidin-7-yl)-benzaldehyde | $^1$H-NMR (300 MHz, d6-DMSO): 9.89 (s, 1H), 8.00 (d, 1H), 7.58-7.71 (m, 3H), 7.13-7.38 (m, 7H), 2.39 (d, 3H). |

| Intermediate Example | Structure/Name | Analytical Data |
|---|---|---|
| 41.8 | 4-(2-methyl-5-methylamino-6-phenyl-imidazo[1,2-a]pyrimidin-7-yl)-benzaldehyde | MS (ES+): 343<br>$^1$H-NMR (400 MHz, d6-DMSO): 9.89 (s, 1H), 7.71 (s, 1H), 7.65 (d, 2H), 7.31 (d, 2H), 7.21 ("s", 5H), 2.31 (s and d, 6H). |
| 41.9 | 4-(2-methyl-5-isopropylamino-6-phenyl-imidazo[1,2-a]pyrimidin-7-yl)-benzaldehyde | MS (ES+): 371<br>$^1$H-NMR (300 MHz, CDCl$_3$): 9.92 (s, 1H), 7.63 (d, 2H), 7.52 (d, 2H), 7.31-7.42 (m, 3H), 7.28 (s, 1H, under the signal of the solvent), 7.09-7.21 (m, 2H), 4.27 (d, 1H), 3.90-4.06 (m, 1H), 2.55 (s, 3H), 1.07 (d, 6H). |
| 41.10 | 4-(5-isopropylamino-6-phenyl-imidazo[1,2-a]pyrimidin-7-yl)-benzaldehyde | $^1$H-NMR (400 MHz, d6-DMSO): 9.90 (s, 1H), 8.21 (d, 1H), 7.68 (d and d, 3H), 7.33 (d, 2H), 7.19-7.29 (m, 5H), 6.35 (d, 1H), 3.00-3.12 (m, 1H), 0.92 (d, 6H). |
| 41.11 | 4-(7-methylamino-6-phenyl-2-pyridine-2-yl-[1,2,4]triazolo[1,5-a]pyrimidin-5-yl)-benzaldehyde | MS (Cl, M + 1): 407<br>$^1$H-NMR (300 MHz, d6-DMSO): 9.90 (s, 1H), 8.72 (d, 1H), 8.29 (d, 1H), 7.95-8.06 (m, 2H), 7.72 (d, 2H), 7.49-7.57 (m, 1H), 7.40 (d, 2H), 7.20-7.35 (m, 5H), 2.55 (d, 3H). |

| Intermediate Example | Structure/Name | Analytical Data |
|---|---|---|
| 41.12 | 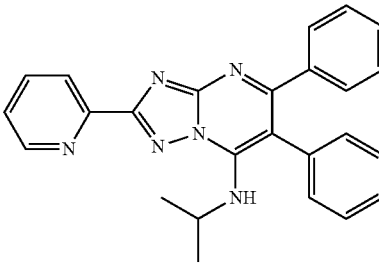<br>4-(7-isopropylamino-6-phenyl-2-pyridine-2-yl-[1,2,4]triazolo[1,5-a]pyrimidin-5-yl)-benzaldehyde | MS (Cl, M + 1): 435<br>$^1$H-NMR (300 MHz, d6-DMSO): 9.90 (s, 1H), 8.75 (d, 1H), 8.31 (d, 1H), 8.00 (dd, 1H), 7.70 (d, 2H), 7.50-7.59 (m, 1H), 7.40 (d, 2H), 7.21-7.37 (m, 5H), 6.99 (d, 1H), 3.59-3.73 (m, 1H), 1.08 (d, 6H). |

Intermediate Example 42.0 and 42.1

Methyl 5-(4-formylphenyl)-6-phenylpyrazolo[1,5-a]pyrimidine-2-carboxylate and 5-(4-formylphenyl)-6-phenyl-pyrazolo[1,5-a]pyrimidine-2-carboxylic acid

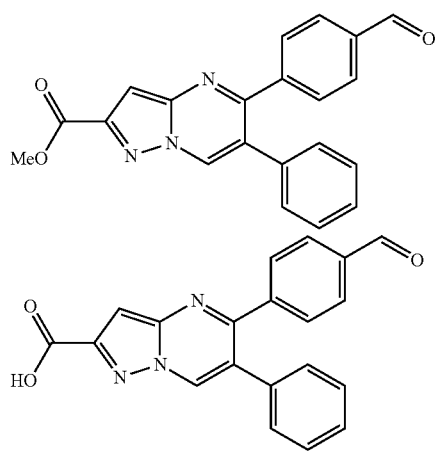

Step 1: Methyl 3-nitro-1H-pyrazole-5-carboxylate 9.0 g 5-nitro-3-pyrazolo carboxylic acid were dissolved in abs. methanol and 7.6 mL thionylchloride were added dropwise at −10° C. The reaction mixture was stirred at room temperature and refluxed for 4 h. The solvent was evaporated and the crude product was used without further purification for the next step.

MS (M+1): 171
Characteristic 1H NMR (300 MHz, d6-DMSO) signals: 7.5 ppm (s, 1H); 3.9 ppm (s, 3H)

Step 2: Methyl 3-amino-1H-pyrazole-5-carboxylate

To 14.0 g methyl 3-nitro-1H-pyrazole-5-carboxylate in 200 mL methanol were added 1.2 g Pd/C (10% w/w). The mixture was stirred under $H_2$-atmosphere at room temperature for 18 h. The mixture was filtered through Celite. The filtrate was concentrated and the crude product was used without further purification.

MS (M+1): 141
Characteristic 1H NMR (300 MHz, d6-DMSO) signals: 5.7 ppm (s, 1H); 3.8 ppm (s, 3H)

Step 3: Methyl 5,7-dihydroxy-6-phenylpyrazolo[1,5-a]pyrimidine-2-carboxylate A solution of 5.0 g Methyl 3-amino-1H-pyrazole-5-carboxylate, 8.3 mL diethylphenylmalonate and 50 mL diisopropylethylamine in 50 mL DMF was heated to 150° C. for 40 h. The solvent was removed, the solid residue was dissolved in 2-propanol the mixture was stirred for 3 hours. The desired product was filtered, dried and was used without further purification.

MS (M+1): 286
Characteristic 1H NMR (300 MHz, d6-DMSO) signals: 6.0 (s, 1H); 3.8 (s, 3H)

Step 4: Methyl 5,7-dichloro-6-phenylpyrazolo[1,5-a]pyrimidine-2-carboxylate 6.4 g methyl 5,7-dihydroxy-6-phenylpyrazolo[1,5-a]pyrimidine-2-carboxylate was suspended in 60 mL $POCl_3$. The mixture was heated to 100° C. for 30 min. The solvent was removed, the residue was treated with ice and water until precipitation of the product. The precipitate was collected by filtration, which was purified by recrystallization from ethanol.

MS (M+1) 322
Characteristic 1H NMR signals (300 MHz, d6-DMSO): 7.4 ppm (s, 1H); 3.9 ppm (s, 3H)

Step 5: Methyl 5-chloro-6-phenylpyrazolo[1,5-a]pyrimidine-2-carboxylate 2.00 g methyl 5,7-dichloro-6-phenylpyrazolo[1,5-a]pyrimidine-2-carboxylate were dissolved in 40 mL dichloromethane. 40 mL brine, 20 mL ammonia solution 25% w/w and 1.22 g zinc powder were added and the mixture was stirred at 60° C. for 3 h. The reaction mixture was filtered through Celite and was washed with dichloromethane and water. The organic phase was separated and the water phase was extracted with dichloromethane. The combined dichloromethane phase was dried over $Na_2SO_4$ and evaporated. The crude product contained methyl 5,7-dichloro-6-phenylpyrazolo[1,5-a]pyrimidine-2-carboxylate. The crude product was dissolved again in 20 mL dichloromethane. 20 mL brine, 10 mL ammonia solution 25% w/w and 0.60 g zinc powder were added and the mixture was stirred at 60° C. for 45 min. The reaction mixture was filtered through Celite and washed with dichloromethane and water. The organic phase was separated and the water phase was extracted with dichloromethane. The combined dichloromethane phase was dried over $Na_2SO_4$, the solvent was evaporated and the residue was purified by chromatography on silica gel (dichloromethane/ethyl acetate) to yield the desired compound.

MS (M+1): 287
Characteristic 1H NMR (300 MHz, d6-DMSO) signals: 9.4 ppm (s, 1H); 7.2 ppm (s, 1H); 3.9 ppm (s, 3H)

Step 6: Methyl 5-(4-formylphenyl)-6-phenylpyrazolo[1,5-a]pyrimidine-2-carboxylate and 5-(4-formylphenyl)-6-phenylpyrazolo[1,5-a]pyrimidine-2-carboxylic acid To a mixture of 1.0 g methyl 5-chloro-6-phenylpyrazolo[1,5-a]pyrimidine-2-carboxylate and 670 mg 4-formylphenyl-boronic acid in 14 mL 1,2-dimethoxyethane were added 6.7 mL of a 10% w/w sodium carbonate solution and 130 mg dichloro[1,1'-bis(diphenylphosphino)ferrocene]-palladium (II). The resulting mixture was heated to 110° C. by microwave irradiation under an inert gas atmosphere for 1 hour. The work up was performed by diluting the reaction mixture with water and dichloromethane, separating the phases and extraction of the aqueous phase with dichloromethane. The combined organic layers were dried over sodium sulphate and the solvent was evaporated. The crude product was purified by chromatography on silica gel (dichloromethane/ethyl acetate) to yield the desired product (methyl 5-(4-formylphenyl)-6-phenylpyrazolo[1,5-a]pyrimidine-2-carboxylate). The water phase contained the free acid of the desired product (5-(4-formylphenyl)-6-phenylpyrazolo[1,5-a]pyrimidine-2-carboxylic acid), which was isolated by acidification of the water layer and extraction with dichloromethane. The combined organic layers were dried over $Na_2SO_4$ and the solvent was evaporated. The residue was suspended in ethyl acetate and petrol ether (1:1) for 2 hours. The product was collected by filtration and used without further purification.

Methyl 5-(4-formylphenyl)-6-phenylpyrazolo[1,5-a]pyrimidine-2-carboxylate

MS (M+1): 358
Characteristic 1H NMR (300 MHz, d6-DMSO) signals: 10.0 ppm (s, 1H); 9.4 ppm (s, 1H); 7.9 ppm (m, 2H); 7.6 ppm (m, 2H); 3.9 ppm (s, 3H)

5-(4-formylphenyl)-6-phenylpyrazolo[1,5-a]pyrimidine-2-carboxylic acid

MS (M+1): 344
Characteristic 1H NMR (300 MHz, d6-DMSO) signals: 10.0 ppm (s, 1H); 9.3 ppm (s, 1H); 7.9 ppm (m, 2H); 7.6 ppm (m, 2H)

Intermediate Example 42.2

6-(2,6-difluoro-phenyl)-5-(4-formyl-phenyl)pyrazolo[1,5-a]pyrimidine-3-carboxylic acid methyl ester

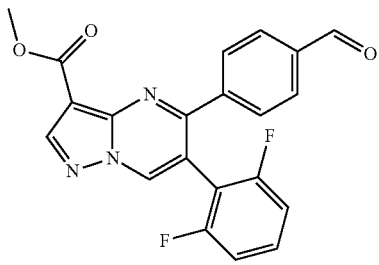 [SMILES: COC(=O)c1cnn2cc(-c3c(F)cccc3F)c(-c3ccc(C=O)cc3)nc12]

Step 1: 5-chloro-6-(2,6-difluorophenyl)pyrazolo[1,5-a]pyrimidine-3-carboxylic acid methyl ester 5 g (13.96 mmol) 5,7-Dichloro-6-(2,6-difluorophenyl)pyrazolo[1,5-a]pyrimidine-3-carboxylic acid methyl ester are dissolved in a mixture of 355 mL ethanol, 253 mL water and 136 mL THF. After addition of 5.8 g (89 mmol) zinc in portions, the mixture is vigorously stirred at rt for three hours. Stirring is continued over night. The reaction mixture is filtered via a glass microfibre filter and washed with plenty of ethanol. The solvent has been removed and the residue redissolved in ethyl acetate. After washing twice with brine and drying over $Na_2SO_4$, the solvent is evaporated and the residue is used in the next step as the crude contaminated product (2.3 g=51%).

Step 2: 6-(2,6-difluorophenyl)-5-(4-formylphenyl)-pyrazolo[1,5-a]pyrimidine-3-carboxylic acid methyl ester 2.3 g (7.1 mmol) 5-Chloro-6-(2,6-difluorophenyl)pyrazolo[1,5-a]pyrimidine-3-carboxylic acid methyl ester are given in 24 mL dimethoxyethane. 13.9 mL $Na_2CO_3$ solution (10%) and 1.18 g (7.8 mmol) 4-formylboronic acid are added. After addition of 0.26 g (0.32 mmol) 1,1'-bis(diphenylphosphino)ferrocenedichloropalladium(II) the reaction mixture is purged 3× with argon and heated at 90° C. for 2 hours. The reaction mixture is cooled down, treated with water and extracted 3 times with dichloromethane. The organic phase is washed with brine and dried ($Na_2SO_4$). The solvent is removed and the crude product purified via chromatography (silicagel, dichloromethane/methanol). 2.57 g (64.4%) of the slightly contaminated compound are obtained.

MS (Cl, M+1): 394
$^1$H-NMR (300 MHz, d6-DMSO): 9.98 (s, 1H), 9.72 (s, 1H), 8.78 (s, 1H), 7.80-7.90 (m, 2H), 7.43-7.60 (m, 3H), 7.09-7.21 (m, 2H), 3.80 (s, 3H).

Intermediate Example 42.3

6-(2,4-difluorophenyl)-5-(4-formyl-phenyl)pyrazolo[1,5-a]pyrimidine-3-carboxylic acid methyl ester

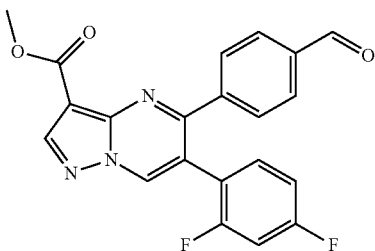 [SMILES: COC(=O)c1cnn2cc(-c3ccc(F)cc3F)c(-c3ccc(C=O)cc3)nc12]

Step 1: 5-chloro-6-(2,4-difluorophenyl)pyrazolo[1,5-a]pyrimidine-3-carboxylic acid methyl ester 500 mg (1.4 mmol) 5,7-Dichloro-6-(2,4-difluorophenyl)pyrazolo[1,5-a]pyrimidine-3-carboxylic acid methyl ester are dissolved in a mixture of 0.68 mL methanol and 3.9 mL THF. After addition of 0.16 mL acetic acid and 264 mg (2 mmol) zinc/copper pair, the mixture is vigorously stirred at rt over night. The reaction mixture is filtered via a glass microfibre filter and washed with plenty of methanol. The solvent has been removed and the residue purified by chromatography (silicagel, ethyl acetate/hexane). 134 mg (29.7%) of the desired product are obtained.

MS (Cl, M+1): 290

$^1$H-NMR (300 MHz, d6-DMSO): 9.54 (s, 1H), 8.73 (s, 1H), 7.58-7.70 (m, 1H), 7.41-7.55 (m, 1H), 7.21-7.34 (m, 1H), 3.82 (s, 3H).

Step 2: 6-(2,4-difluorophenyl)-5-(4-formylphenyl)-pyrazolo[1,5-a]pyrimidine-3-carboxylic acid methyl ester 130 mg (0.4 mmol) 5-Chloro-6-(2,4-difluorophenyl)pyrazolo[1,5-a]pyrimidine-3-carboxylic acid methyl ester are given in 1.4 mL dimethoxyethane (no complete dissolution). 0.8 mL Na$_2$CO$_3$ solution (10%) and 66 mg (0.44 mmol) 4-formylphenylboronic acid are added. After addition of 15 mg (0.02 mmol) 1,1'-bis(diphenylphosphino)ferrocene-dichloropalladium(II) the reaction mixture is purged 3× with argon and heated at 90° C. for 18 hours (complete dissolution). The reaction mixture is cooled down, treated with water and diluted with dichloromethane. The water phase is extracted once more with dichloromethane and the combined organic phases are washed with brine and dried (Na$_2$SO$_4$). The solvent is removed and the crude product purified via chromatography (silicagel, dichloromethane/methanol). 69.4 mg (41.7%) of the desired aldehyde are obtained.

MS (Cl, M+1): 394

$^1$H-NMR (300 MHz, CDCl$_3$): 10.03 (s, 1H), 8.80 (s, 1H), 8.68 (s, 1H), 7.78-7.87 (m, 2H), 7.61-7.69 (m, 2H), 7.21-7.30 (m, 1H), 6.90-7.02 (m, 1H), 6.78-6.89 (m, 1H), 4.00 (s, 3H).

Intermediate Example 43.0

7-[4-(1-bromoethyl)phenyl]-6-phenylimidazo[1,2-a]pyrimidine (Racemic Mixture)

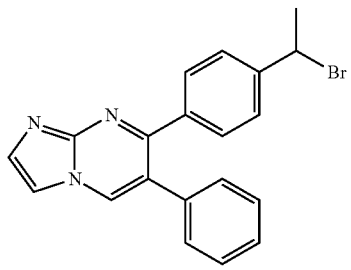 [SMILES: CC(Br)c1ccc(-c2nc3nccn3cc2-c2ccccc2)cc1]

Step 1: 1-[4-(6-phenylimidazo[1,2-a]pyrimidin-7-yl)phenyl]ethanol (Racemic Mixture)

100 mg 4-(6-phenylimidazo[1,2-a]pyrimidin-7-yl)benzaldehyde (prepared as described for example 1) were dissolved in 2 mL THF and 1 mL of a 2M solution of MeZnCl was added. The mixture was heated (100° C., microwave) for 2 h, cooled to room temperature and extracted with a mixture of dichloromethane and water. The organic layers were dried over sodium sulphate and the solvent was evaporated. The crude product was purified by chromatography on silica gel (dichloromethane/ethyl acetate)

MS (M+1): 316

Characteristic 1H NMR (d6-DMSO, 300 MHz) signals: 9.0 ppm (s, 1H); 7.9 ppm (d, 1H); 7.8 ppm (d, 1H); 4.7 ppm (m, 1H), 1.2 ppm (d, 3H)

Step 2: 7-[4-(1-bromoethyl)phenyl]-6-phenylimidazo[1,2-a]pyrimidine (Racemic Mixture)

100 mg of the product of step 1 were dissolved in dichloromethane, cooled to 0° C. and 86 mg PBr$_3$ were added. The mixture was stirred at room temperature for 24 h. Ice was added, the mixture extracted with dichloromethane and water, the organic layer were dried over Na$_2$SO$_4$ and the solvent was evaporated. The crude product may be used without further purification.

MS (M+1): 378/380

Intermediate Example 44.0

2-(5-azetidin-3-yl-2H-[1,2,4]triazol-3-yl)-pyridine hydrochloride salt

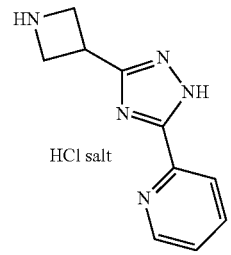 [SMILES: c1ccc(-c2nc(C3CNC3)n[nH]2)nc1]

Procedure A

Step 1: pyridine-2-carbohydrazonamide

A solution of pyridine-2-carbonitrile 20 g (192 mmol) and hydrazine hydrate (3 Eq.) in ethanol (50 mL) was stirred at room temperature for 18 hrs. The reaction mass was then diluted with water, extracted with ethyl acetate, and the organic portion dried (Na2SO4) and concentrated in vacuo to yield the desired compound.

MS (M+1): 137.07

$^1$H NMR (300 MHz, CDCl$_3$): δ 8.53 (d, 1H), 8.02 (d, 1H), 7.72 (t, 1H), 7.29 (t, 1H), 5.42 (bs, 2H), 4.60 (bs, 2H).

Step 2: 3-[1-amino-1-pyridin-2-yl-meth-(Z)-ylidene-hydrazinocarbonyl]-azetidine-1-carboxylic acid tert-butyl ester To a solution of 1-(tert-butoxycarbonyl) azetidine-3-carboxylic acid in dichloromethane (0.56 mL per mmol 1-(tert-butoxycarbonyl) azetidine-3-carboxylic acid) was added carbonyl diimidazole (1 Eq.) in small portions over a period of 30 min. Pyridine-2-carbohydrazonamide was then added to the reaction mixture and stirred at room temperature for 3 hrs. The mixture was concentrated in vacuo and the reaction mass was then stirred in water for 30 min. The precipitated solid was filtered and dried to afford the desired compound.

MS (M+1): 319.93

$^1$H NMR (300 MHz, CDCl3): δ 10.90 (s, 1H), 8.53 (d, 1H), 8.04 (d, 1H), 7.75-7.70 (m, 1H), 7.24 (d, 1H), 6.44 (s, 2H), 4.24-4.17 (m, 4H), 4.09-4.03 (m, 1H), 1.45 (s, 9H).

Step 3: 3-(5-pyridin-2-yl-1H-[1,2,4]triazol-3-yl)-azetidine-1-carboxylic acid tert-butyl ester The 3-[1-amino-1-pyridin-2-yl-meth-(Z)-ylidene-hydrazinocarbonyl]-azetidine-1-carboxylic acid tert-butyl ester obtained in step 2 was melted at 220° C. under nitrogen atmosphere for 1 hr. The reaction was then cooled until ethanol could be safely added to the still warm melt. Enough ethanol was added till the solid dissolved. The ethanol was evaporated to get the desired crude compound, which was used without further purification in the next step.

MS (M+1): 302.35

$^1$H NMR (300 MHz, CDCl3): δ 12.97 (bs, 1H), 8.76 (d, 1H), 8.24 (d, 1H), 7.89 (t, 1H), 7.45 (d, 1H), 4.3-4.27 (m, 4H), 4.03-4.0 (m, 1H), 1.46 (s, 9H).

Step 4: 2-(5-azetidin-3-yl-2H-[1,2,4]triazol-3-yl)-pyridine hydrochloride salt 3-(5-pyridin-2-yl-1H-[1,2,4]triazol-3-yl)-azetidine-1-carboxylic acid tert-butyl ester (3.13 g, 10.39 mmol) was suspended in a solution of HCl in dioxane (4M, 80 mL) and stirred at rt overnight. The reaction mixture was diluted with diethyl ether, filtered and the residue suspended in acetonitrile and stirred for 45 min at rt. The solid (hydroscopic) was isolated by filtration, partially dissolved in warm methanol and addition of diethyl ether resulted in precipitation of a yellow sticky solid which could not be filtered. The mixture was concentrated in vacuo and dried in a vacuum oven (40° C.) to obtain the desired compound as a light-yellow solid.

MS (M+1): 202.13

$^1$H NMR (300 MHz, d6-DMSO): δ 9.61 (bs, 1H), 9.25 (bs, 1H), 8.76 (d, 1H), 8.16 (m, 2H), 7.75 (d, 1H), 4.10-4.27 (m, 5H).

Procedure B

Step 1: 3-hydrazinocarbonyl-azetidine-1-carboxylic acid tert-butyl ester 1-(tert-butoxycarbonyl) azetidine-3-carboxylic acid (5 g, 24.8 mmol) was suspended in dichloromethane (15 mL) and 1,1'-carbonyldiimidazole (4.56 g, 28.1 mmol) was added in portions. The resulting mixture was stirred at rt for 30 minutes and then added dropwise to a solution of hydrazine hydrate (1.94 mL, 39.9 mmol) in dichloromethane (5 mL). After the addition was complete, the mixture was stirred for 30 min at rt. The reaction mixture was washed with saturated aqueous Na2CO3 solution (2×), brine, dried (Na2SO4) and concentrated under vacuum to give a white crystalline solid, which was triturated with diethyl ether overnight, filtered and air-dried for 5 h to give a white solid.

Step 2: 3-(5-pyridin-2-yl-1H-[1,2,4]triazol-3-yl)-azetidine-1-carboxylic acid tert-butyl ester 3-hydrazinocarbonyl-azetidine-1-carboxylic acid tert-butyl ester (2.74 g, 12.73 mmol) and 2-cyano-pyridine (1.45 g, 13.95 mmol) were dissolved in 2-ethoxyethanol (30 mL) and a 30 wt % solution of NaOMe in MeOH (1.19 mL, 6.38 mmol) was added. The resulting mixture was heated to 130° C. and stirred overnight. On cooling the mixture was neutralised by the addition of acetic acid and partitioned between EtOAc and saturated aqueous NaHCO3 solution. The organic phase was dried (Na2SO4) and concentrated in vacuo to give a yellow solid. Further purification was achieved by trituration with diethyl ether followed by recrystallisation from MeOH.

Step 3: 2-(5-azetidin-3-yl-2H-[1,2,4]triazol-3-yl)-pyridine hydrochloride salt

Prepared as described above for Procedure A Step 4.

Intermediate Example 44.1

2-[5-(azetidine-3-yl)-1H-1,2,4-triazole-3-yl]-6-methylpyridine dihydrochloride

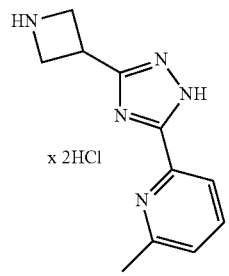 [SMILES: Cc1cccc(-c2nc(C3CNC3)n[nH]2)n1]

This intermediate has been prepared in analogy to example 44.0, procedure A.

Step 1: 6-methylpyridine-2-carbohydrazonamide 11.97 g (101.4 mmol) 6-methylpyridine-2-carbonitrile are dissolved in 25 mL ethanol. After addition of 36.3 mL (304.05 mmol) hydrazine hydrate (w=30%) the reaction mixture is stirred for 24 hours at room temperature. The precipitated product (K1=1.45 g) has been filtered off and the filtrate is evaporated to ⅓ of its volume. After dilution with water the reaction mixture is extracted three times with ethyl acetate. The combined organic extracts are washed with brine and dried (Na$_2$SO$_4$). The solvent has been removed yielding a K2 (11.11 g) of the desired product. The overall yield is 78.9%.

MS (ES+, M+1): 151

$^1$H-NMR (300 MHz, d6-DMSO): 7.65 (d, 1H), 7.90 (dd, 1H), 7.12 (d, 1H), 5.65 (br., 2H), 5.19 (br., 2H), 2.51 (s, 3H, under the signal of the solvent).

Step 2: tert-Butyl 3-({2-[amino(6-methylpyridine-2-yl)methylene]hydrazino}carbonyl)azetidine-1-carboxylate To a solution of 8.21 g (54.7 mmol) 1-(tert-butoxycarbonyl) azetidine-3-carboxylic acid in 80 mL dichloromethane are added 8.86 g (54.7 mmol) carbonyl diimidazole within 30 min. After stirring for five minutes 11 g (54.7 mmol) 6-methylpyridine-2-carbohydrazonamide are added and the reaction mixture is stirred at room temperature for 3 hours. The solvent has been evaporated and the residue is treated with water. The formed precipitate has been filtered off and dried yielding 16.47 g (81.3%) of the desired compound as a mixture of tautomers.

MS (CI, M+1): 334

$^1$H-NMR (300 MHz, d6-DMSO): 10.09, 9.87 (s, combined 1H), 7.64-7.89 (m, 2H), 7.22-7.31 (m, 1H), 6.59 (br., 2H), 3.80-4.10 (m, 4H), 3.25-3.45 (m, 1H, under the water signal of the solvent, 2.52 (s, 3H), 1.35 ("s", 9H).

Step 3: tert-Butyl 3-[3-(6-methylpyridine-2-yl)-1H-1,2,4-triazole-5-yl]azetidine-1-carboxylate 16.4 g (49.3 mmol) tert-Butyl 3-({2-[amino(6-methylpyridine-2-yl)methylene]hydrazino}carbonyl)azetidine-1-carboxylate are heated under a nitrogen atmosphere to the melting point (220° C.) and kept there for 90 minutes. Ethanol is cautiously added to the reaction mixture during the cooling down phase (at around 135° C.). The reaction mixture is stirred over night at room temperature and the ethanol is evaporated. Due to an incomplete reaction the residue is heated once more to 220° C. for one hour and the work up is repeated yielding 12.91 g (74.58%) of the desired crude product (the byproduct is the cyclised compound which has lost the Boc group).

$^1$H-NMR (300 MHz, d6-DMSO): 14.30 (br., 1H), 7.75-7.89 (m, 2H), 7.31 (d, 1H), 3.82-4.49 (m, 4H), 3.32-3.48 (m, 1H, partly under the water signal of the solvent), 2.52 (s, 3H), 1.39 (s, 9H).

Step 4: 2-[5-(Azetidine-3-yl)-1H-1,2,4-triazole-3-yl]-6-methylpyridine dihydrochloride 11.6 g (36.8 mmol) tert-Butyl 3-[3-(6-methylpyridine-2-yl)-1H-1,2,4-triazole-5-yl]azetidine-1-carboxylate are dissolved in 150 mL dioxane. 27.6 mL HCl in dioxane (4M) are added dropwise and the reaction mixture is stirred over night at room temperature. The reaction mixture is evaporated to dryness yielding 13.1 g (76.6%) of the desired salt which is 60% pure and is used without further purification.

Intermediate Example 45.0

2-(5-pyrrolidin-3-yl-2H-[1,2,4]triazol-3-yl)-pyridine hydrochloride salt

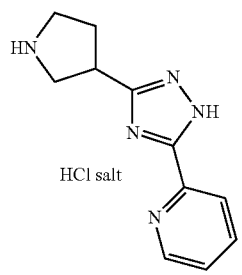 [SMILES: c1ccc(-c2nc(C3CCNC3)n[nH]2)nc1]

Prepared according to the procedures for 2-(5-azetidin-3-yl-2H-[1,2,4]triazol-3-yl)-pyridine hydrochloride salt.
MS (M+1): 216

Intermediate Example 46.0

5-fluoro-2-piperidin-4-yl-1H-benzoimidazole hydrochloride salt

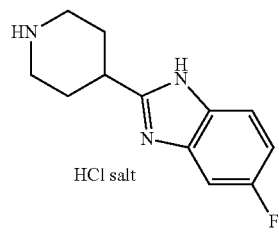 [SMILES: Fc1ccc2[nH]c(C3CCNCC3)nc2c1]

To a mixture of piperidine-4-carboxylic acid (18.33 g, 0.14 mol) and 4-fluoro-benzene-1,2-diamine (18.01 g, 0.14 mol) was added polyphosphoric acid (138.39 g) and the mixture heated at 180° C. (internal temperature) for 2 h 45 minutes. The reaction mixture was cooled, reheated to 80° C. and the reaction was quenched by cautious addition to water (300 mL). The mixture was made basic (pH 8) by the addition of concentrated aqueous NaOH. The aqueous phase was extracted sequentially with 3:7 isopropanol:CH2Cl2 (2×200 mL) and CH2Cl2 (150 mL) and the combined organic phase dried (Na2SO4) and concentrated. The aqueous phase was reextracted with n-butanol (2×200 mL), the organic layer dried (Na2SO4) and concentrated. The crude product was stirred in diethyl ether, filtered and dried to give crude 5-fluoro-2-piperidin-4-yl-1H-benzoimidazole. Further purification was achieved by preparing the hydrochloride salt.

Thus, 10 g of the crude 5-fluoro-2-piperidin-4-yl-1H-benzoimidazole was dissolved in MeOH (85 mL) and a solution of HCl in dioxane (20 mL) was added dropwise, and the title compound was obtained by filtration.
MS (M+1): 220.1
1H NMR (d6-DMSO+D$_2$O): δ 7.78 (m, 1H), 7.6 (m, 1H), 7.38 (m, 1H), 3.55 (m, 1H), 3.4 (m, 2H), 3.08 (m, 1H), 2.3 (m, 2H), 2.08 (m, 2H)

The following intermediates were prepared in analogy to 5-fluoro-2-piperidin-4-yl-1H-benzoimidazole dihydrochloride by replacing 4-fluoro-benzene-1,2-diamine with the appropriate diamine.

| Intermediate Example | Structure/Name | Analytical Data |
|---|---|---|
| 46.1 | 2-piperidin-4-yl-5-trifluoromethyl-1H-benzoimidazole hydrochloride salt | 1H NMR (d6-DMSO + D$_2$O): δ 8.1 (s, 1H), 7.9 (d, 1H), 7.78 (d, 1H), 3.56 (m, 1H), 3.4 (m, 2H), 3.1 (m, 2H), 2.32 (m, 2H), 2.1 (m, 2H) |

| Intermediate Example | Structure/Name | Analytical Data |
|---|---|---|
| 46.2 | 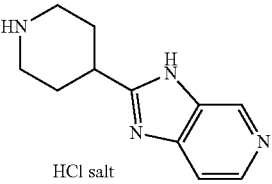<br>2-piperidin-4-yl-3H-imidazo[4,5-c]pyridine hydrochloride salt | MS (M + 1): 203.1<br>1H NMR (d6-DMSO + D$_2$O):<br>δ 9.28 (s, 1H), 8.5 (d, 1H),<br>8.1 (d, 1H), 3.42 (m, 1H),<br>3.27 (m, 2H), 2.28 (m, 2H),<br>2.04 (m, 2H) |
| 46.3 | 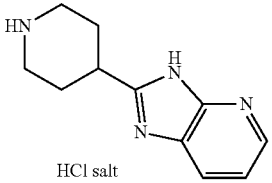<br>2-piperidin-4-yl-3H-imidazo[4,5-b]pyridine hydrochloride salt | MS (M + 1): 203.1<br>1H NMR (d6-DMSO + D$_2$O):<br>δ 8.58 (d, 1H), 8.4 (d, 1H),<br>7.6 (m, 1H), 3.36-3.5 (m,<br>3H), 3.08 (m, 2H), 2.28 (m,<br>2H), 2.04 (m, 2H) |

Intermediate Example 47.0

2-piperidin-4-yl-1H-benzoimidazole-5-carbonitrile hydrochloride salt

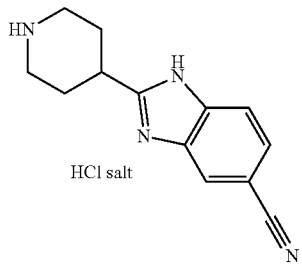 [SMILES: N#Cc1ccc2[nH]c(C3CCNCC3)nc2c1]

Step 1: 4-(2-amino-4-cyano-phenylcarbamoyl)-piperidine-1-carboxylic acid tert-butyl ester To a solution of piperidine-1,4-dicarboxylic acid mono-tert-butyl ester (14.1 g, 0.061 mol) in DMF (282 mL) was added HBTU (27.76 g, 0.073 mol), DMAP (10.2 g, 0.084 mol) and diisopropylethyl amine (24.2 mL). The reaction mixture was stirred for 30 minutes at rt before 3,4-diaminobenzonitrile (8 g, 0.059 mol) was added. The mixture was stirred overnight at rt before the reaction was quenched by pouring into water (2 L). The mixture was extracted with CH2Cl2 and the organic phase washed successively with 1M aq. HCl solution and 10% aq. Na2CO3 solution, dried (Na2SO4) and concentrated in vacuo. Purification by chromatography on silica gel afforded the title compound.

Step 2: 4-(5-cyano-1H-benzoimidazol-2-yl)-piperidine-1-carboxylic acid tert-butyl ester A solution of 4-(2-amino-4-cyano-phenylcarbamoyl)-piperidine-1-carboxylic acid tert-butyl ester (6 g) in EtOH (61 mL) and 2M aq. NaOH solution (61 mL) was heated at 75° C. (bath temperature) overnight. The heating was discontinued, the reaction was chilled (ice water bath) and quenched by pouring into saturated aq. citric acid solution (250 mL). The mixture was extracted with CH2Cl2 (5×) and the combined organic extract was dried (Na2SO4), filtered and concentrated in vacuo.

Purification by chromatography on silica gel afforded the title compound.

Step 3: 2-piperidin-4-yl-1H-benzoimidazole-5-carbonitrile hydrochloride salt To a solution of 4-(5-cyano-1H-benzoimidazol-2-yl)-piperidine-1-carboxylic acid tert-butyl ester (3.2 g, 10 mmol) in dioxane (13 mL) was added a solution of HCl in dioxane (25%, 14.3 mL). The resulting precipitate was filtered to give the title compound.

MS (M+1): 227.1

1H NMR (400 MHz, d6-DMSO+D$_2$O): δ 8.22 (s, 1H), 7.85 (d, 1H), 7.77 (d, 1H), 3.42-3.5 (m, 3H), 3.12 (m, 2H), 2.34 (m, 2H), 2.09 (m, 2H)

Intermediate Example 48.0

9-piperidin-4-yl-9H-purin-6-ylamine hydrochloride salt

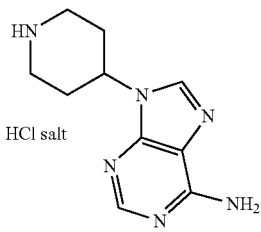 [SMILES: Nc1ncnc2c1ncn2C1CCNCC1]

Prepared according to procedures given in WO2006065601.
MS (M+1): 219.2

Intermediate Example 49.0

2-piperidin-4-yl-quinoxaline hydrochloride salt

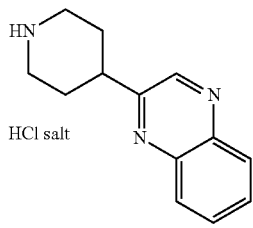 [SMILES: c1ccc2nc(C3CCNCC3)cnc2c1]

To a stirred solution of 4-quinoxalin-2-yl-piperidine-1-carboxylic acid tert-butyl ester (200 mg, 0.64 mmol, obtained commercially) in 0.5 mL dioxane/MeOH (2:3), at rt was added a solution of HCl in dioxane (1.6 mL, 10 Eq.). The mixture was stirred for 2 h before the solid was filtered, washed with CAN and dried to give the title compound.
MS (M+1): 214.2
1H NMR (300 MHz, d6-DMSO+D$_2$O): δ 9.45 (br s, 1H), 9.15 (br s, 1H), 8.95 (s, 1H), 8.08 (m, 2H), 7.85 (m, 2H), 3.35-3.45 (m, 3H), 3.06 (m, 2H), 2.1-2.2 (m, 4H)

Intermediate Example 50.0

2-(5-piperidin-4-yl-2H-[1,2,4]triazol-3-yl)-6-trifluoromethyl-pyridine hydrochloride salt

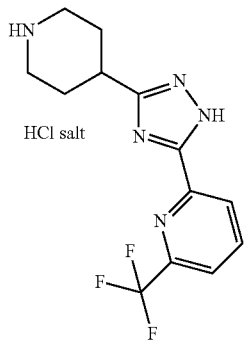 [SMILES: FC(F)(F)c1cccc(-c2nc(C3CCNCC3)n[nH]2)n1]

Step 1: 4-[5-(6-trifluoromethyl-pyridine-2-yl)-1H-[1,2,4]triazol-3-yl]-piperidine-1-carboxylic acid tert-butyl ester 4-Hydrazinocarbonyl-piperidine-1-carboxylic acid tert-butyl ester (2.36 g, 9.68 mmol, obtained commercially) and 6-trifluoromethyl-pyridine-2-carbonitrile (2 g, 11.6 mmol, obtained commercially) were dissolved in 2-ethoxyethanol (24 mL) and a 25 wt % solution of NaOMe in MeOH (1.11 mL, 4.84 mmol) was added. The resulting mixture was heated to 130° C. and stirred overnight. On cooling the mixture was neutralised by the addition of acetic acid and partitioned between EtOAc and saturated aqueous NaHCO$_3$ solution. The organic phase was washed with brine, dried (Na$_2$SO$_4$) and concentrated in vacuo to give the crude title compound as a yellow solid which was used without further purification in the next step.

Step 3: 2-(5-piperidin-4-yl-2H-[1,2,4]triazol-3-yl)-6-trifluoromethyl-pyridine hydrochloride salt A mixture of 4-[5-(6-trifluoromethyl-pyridine-2-yl)-1H-[1,2,4]triazol-3-yl]-piperidine-1-carboxylic acid tert-butyl ester (3.26 g) and 4M HCl in dioxane (47 mL) was stirred at rt until the reaction was complete. The reaction was diluted with Et$_2$O and stirred for 30 minutes. The solid was filtered, taken up in ACN and stirred for 15 minutes. The solid was filtered, dissolved in warm MeOH, cooled to 0° C. and triturated with Et$_2$O. The resulting solid was filtered and dried to give the title compound.
MS (M+1): 298
1H-NMR (300 MHz, d6-DMSO, characteristic signals): δ 9.16 (br s, 1H), 8.93 (br s, 1H), 8.28 (d, 1H), 8.19 (t, 1H), 7.93 (dd, 1H).

Intermediate Example 50.1

2-(5-piperidin-4-yl-2H-[1,2,4]triazol-3-yl)-4-trifluoromethyl-pyridine hydrochloride salt

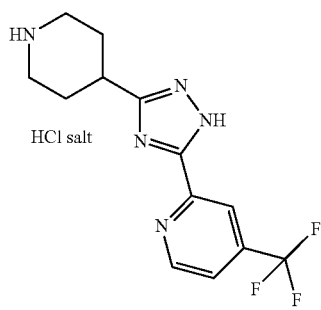 [SMILES: FC(F)(F)c1ccnc(-c2nc(C3CCNCC3)n[nH]2)c1]

This intermediate was prepared according to 2-(5-piperidin-4-yl-2H-[1,2,4]triazol-3-yl)-6-trifluoromethyl-pyridine hydrochloride salt (intermediate example 50.0).
$^1$H NMR (300 MHz, 400 MHz): δ9.22 (m, 1H), 9.0 (m, 1H), 8.93 (d, 1H), 8.21 (s, 1H), 7.86 (d, 1H), 3.29 (m, 2H), 3.15 (m, 1H), 3.02 (m, 2H), 2.13-2.17 (m, 2H), 1.91-2.01 (m, 2H)

117

Intermediate Example 51.0

2-methoxy-5-(5-piperidin-4-yl-2H-[1,2,4]triazol-3-yl)-pyridine

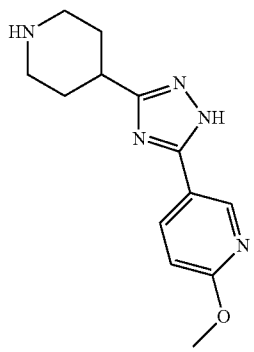 [SMILES: COc1ccc(-c2nc(C3CCNCC3)n[nH]2)cn1]

A mixture of 4-[5-(6-methoxy-pyridin-3-yl)-1H-[1,2,4]triazol-3-yl]-piperidine-1-carboxylic acid tert-butyl ester (1.23 g, prepared in analogy to intermediate example 44) in THF (15 mL) was treated with 4M HCl in dioxane (1.19 mL) and the reaction stirred at 50° C. for 1 hour. On cooling, the reaction was stirred overnight at rt. The volatiles were removed in vacuo and the residue was dissolved in water, made basic with 2M aqueous NaOH solution and extracted with EtOAc. The aqueous phase was extracted with $CH_2Cl_2$/MeOH, the organic phase was washed with brine and concentrated in vacuo to give the crude title compound which was used without further purification.

MS (M+1): 260.25

Compounds of General Formula (I) may typically be prepared according to the following General Procedures, or their preparation is illustrated by specific examples below. The preparation of further examples not listed here may be accomplished by analogy to, modification of, or adaptation to, these or known procedures.

General Procedure 1: Reductive Amination (Use of Amine Salt)

To a solution of 0.75 mmol of the aldehyde intermediate in THF (6 mL) is added triethylamine (2 Eq.). The reaction mixture is stirred for 5 minutes before the amine salt (1.5 Eq.) and acetic acid (2.5 Eq.) are added. The reaction mixture is stirred for 10 minutes before $NaBH(OAc)_3$ (6 Eq.) is added portionwise over 40 minutes. The reaction mixture is stirred overnight at room temperature, before quenching with methanol and concentration in vacuo. The residue is taken up in chloroform and washed with water, dried and concentrated in vacuo. Purification according to standard techniques affords the desired compound.

In the case that the free base of the amine is employed, the general procedures above may be modified by omitting the triethylamine.

General Procedure 2: Amination Via a Methanesulfonate Intermediate (Use of amine salt)

To the stirred solution of the benzyl alcohol intermediate (0.52 mmol) in 15 mL of dichloromethane is added methanesulfonyl chloride (1.1 eq) at 0° C. followed by triethylamine (1.5 eq). The reaction mixture is allowed to stir at room temperature for 3 h. The reaction is quenched with water and extracted with DCM. The organic layer is dried and concentrated. It is then taken up in the next reaction without further purification. The crude is dissolved in 5 mL of DMF. To this solution the amine hydrochloride salt (1 eq) and triethylamine (4 eq) is added. The reaction mixture is heated at 80° C. for 3 h. The reaction mixture is quenched with water and extracted with ethyl acetate. The organic layer is dried and concentrated. Purification by standard techniques obtains the desired compound.

In the case that the free base of the amine is employed, the general procedure above may be modified by reducing the number of equivalents of triethylamine from 4 to 2.

Example 1.0

6-phenyl-7-(4-{[3-(5-pyridin-2-yl-1,2,4-triazol-3-yl)azetidin-1-yl]methyl}phenyl)imidazo[1,2-a]pyrimidine

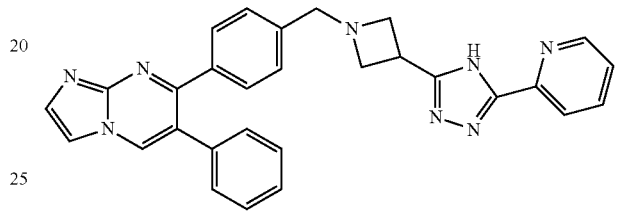

274 mg (1 mmol) 2-(5-azetidine-3-yl-[1,2,4]triazol-3-yl)-pyridine hydrochloride salt were dissolved in 5 mL methanol. After addition of 0.28 mL (2 mmol) triethylamine, 250 mg (0.84 mmol) 4-(6-phenylimidazo[1,2-a]pyrimidin-7-yl)benzaldehyde dissolved in 5 mL DMF, 0.13 mL (2.20 mmol) acetic acid and 356 mg (1.68 mmol) $NaBH(OAc)_3$, the reaction mixture was stirred at room temperature. Two additional portions of 2 equivalents $NaBH(OAc)_3$ each were added after 1.5 and 3 hours. After 4 hours the solvent was removed by evaporation. Evaporation was repeated after addition of toluene. The residue was purified by chromatography on silica gel (dichloromethane/methanol) to yield 291 mg of the desired product.

MS (M+1): 485

$^1$H-NMR (400 MHz, d6-DMSO): 9.02 (s, 1H), 8.65 (d, 1H), 8.03 (d, 1H), 7.90-8.00 (m, 2H), 7.79 (s, 1H), 7.48 (s, br, 1H), 7.29-7.40 (m, 5H), 7.19-7.29 (m, 4H), 3.70-3.83 (m, 1H), 3.56-3.70 (m, 4H), 3.30-3.40 (m, 2H).

Example 2.0

2-methyl-6-phenyl-5-(4-{[3-(5-pyridin-2-yl-1,2,4-triazol-3-yl)azetidin-1-yl]methyl}phenyl)[1,2,4]triazolo[1,5-a]pyrimidine

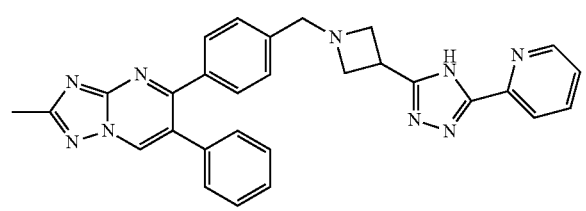 [SMILES: Cc1nc2nc(-c3ccc(CN4CC(c5nnc(-c6ccccn6)[nH]5)C4)cc3)c(-c3ccccc3)cn2n1]

77 mg (0.38 mmol) 2-(5-azetidine-3-yl-[1,2,4]triazol-3-yl)-pyridine hydrochloride salt was dissolved in 6 mL methanol and 0.1 mL triethylamine. After addition of 100 mg (0.31 mmol) 4-(2-methyl-6-phenyl[1,2,4]triazolo[1,5-a]pyrimidin-5-yl)benzaldehyde dissolved in 6 mL DMF, 0.06 mL acetic acid and 131 mg (0.76 mmol) NaBH(OAc)₃ the reaction mixture was stirred at room temperature. Three additional portions of 2 equivalents NaBH(OAc)₃ each were added after 2, 4 and 6 hours. The solvent was removed by evaporation and the residue was purified by chromatography on silica gel (dichloromethane/methanol) to yield 42 mg of the desired product.

MS (M+1): 500
¹H-NMR (400 MHz, d6-DMSO): 9.33 (s, 1H), 8.7 (s, 1H), 8.09 (d, 1H), 7.98 (s, br, 1H), 7.49 (s, br, 1H), 7.30-7.41 (m, 5H), 7.22-7.30 (m, 4H), 3.60-3.89 (m, 4H), 3.32-3.49 (m, 3H), 2.58 (s, 3H).

Example 3.0

2-cyclobutyl-6-phenyl-5-(4-{[3-(5-pyridin-2-yl-1,2,4-triazol-3-yl)azetidin-1-yl]methyl}phenyl)[1,2,4]triazolo[1,5-a]pyrimidine

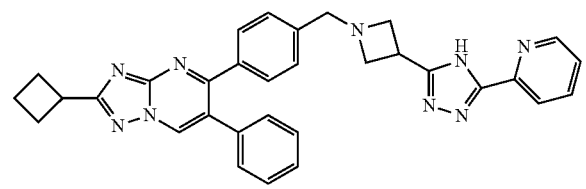 [SMILES: c1ccc(-c2cn3nc(C4CCC4)nc3nc2-c2ccc(CN3CC(c4nnc(-c5ccccn5)[nH]4)C3)cc2)cc1]

This compound was prepared in analogy to example 2.0 by using 4-(2-cyclobutyl-6-phenyl[1,2,4]triazolo[1,5-a]pyrimidin-5-yl)benzaldehyde instead of the 4-(2-methyl-6-phenyl[1,2,4]triazolo[1,5-a]pyrimidin-5-yl)benzaldehyde. 100 mg 4-(2-cyclobutyl-6-phenyl[1,2,4]triazolo[1,5-a]pyrimidin-5-yl)benzaldehyde gives 39 mg of the desired product after chromatography.

MS (M+1): 540
¹H-NMR (400 MHz, d6-DMSO): 9.33 (s, 1H), 8.69 (s, 1H), 8.08 (d, 1H), 7.98 (s, br, 1H), 7.49 (s, br, 1H), 7.31-7.41 (m, 5H), 7.22-7.31 (m, 4H), 3.60-3.89 (m, 6H), 3.42 (m, 2H), 2.38-2.48 (4H), 2.05-2.19 (m, 1H), 1.95-2.05 (1H).

Example 4.0

3-fluoro-6-phenyl-7-(4-{[3-(5-pyridin-2-yl-1,2,4-triazol-3-yl)azetidin-1-yl]methyl}phenyl)imidazo[1,2-a]pyrimidine

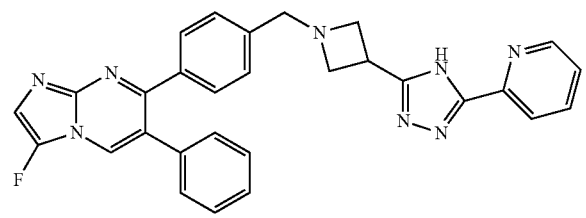 [SMILES: Fc1cnc2nc(-c3ccc(CN4CC(c5nnc(-c6ccccn6)[nH]5)C4)cc3)c(-c3ccccc3)cn12]

This compound was prepared in analogy by reacting 90 mg (0.28 mmol) 4-(3-fluoro-6-phenyl-imidazo[1,2-a]pyrimidin-7-yl)-benzaldehyde with 93 mg (0.34 mmol) 2-(5-azetidine-3-yl-[1,2,4]triazol-3-yl)-pyridine hydrochloride salt according to the procedure in example 1. After four and a half hours the reaction mixture was worked up and purified in the usual way as described in example 1. 81 mg of the desired product were obtained.

MS (M+1): 503
¹H-NMR (400 MHz, d6-DMSO): 8.80 (s, 1H), 8.65 (d, 1H), 8.05 (d, 1H), 7.95 (1H, br), 7.59 (s, br, 1H), 7.48 (s, br, 1H), 7.30-7.40 (m, 3H), 7.20-7.30 (m, 6H), 3.70-3.83 (m, 1H), 3.58-3.70 (m, 4H), 3.30-3.42 (m, 2H).

Example 5.0

3-Chloro-6-phenyl-7-(4-{[3-(5-pyridin-2-yl-1,2,4-triazol-3-yl)azetidin-1-yl]methyl}phenyl)imidazo[1,2-a]pyrimidine

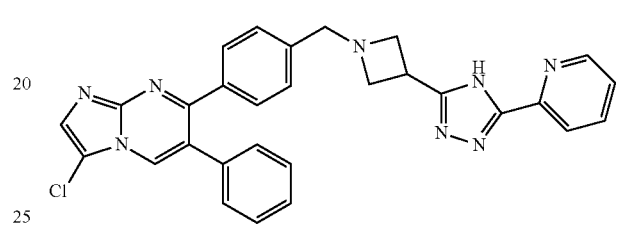

200 mg (0.6 mmol) 4-(3-chloro-6-phenyl-imidazo[1,2-a]pyrimidin-7-yl)benzaldehyde was reacted with 197 mg (0.72 mmol) 2-(5-azetidine-3-yl-[1,2,4]triazol-3-yl)-pyridine hydrochloride salt according to the procedure in example 1. After four and a half hours the reaction mixture was worked up and purified in the usual way as described in example 1. 162 mg of the desired product were obtained MS (M+1): 519
¹H-NMR (400 MHz, d6-DMSO): 8.72 (s, 1H), 8.68 (s, br, 1H), 8.08 (d, 1H), 7.90-8.00 (2H), 7.50 (s, br, 1H), 7.20-7.40 (m, 9H), 3.60-3.89 (m, 4H), 3.30-3.54 (m, 3H).

Example 6.0

2-{1-[4-(6-phenyl-imidazo[1,2-a]pyrimidin-7-yl)-benzyl]-piperidin-4-yl}-3H-imidazo[4,5-c]pyridine

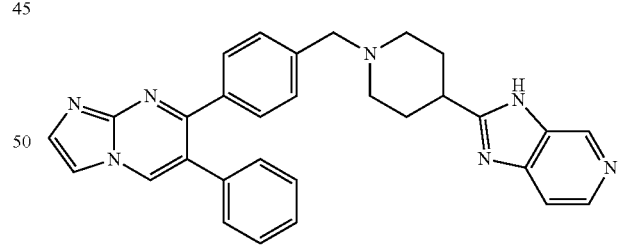

121 mg (0.6 mmol) 2-piperidine-4-yl-3H-imidazo[4,5-c]pyridine hydrochloride salt was dissolved in 3 mL methanol. 0.2 mL (1.2 mmol) Triethylamine in 3 mL DMF, 150 mg (0.5 mmol) 4-(6-phenylimidazo[1,2-a]pyrimidin-7-yl)benzaldehyde, 0.08 mL (1.3 mmol) acetic acid and 200 mg (1 mmol) NaBH(OAc)₃ were added. The reaction mixture was stirred at room temperature and after 1 and 2 hours two additional portions of 2 equivalents NaBH(OAc)₃ each were added. The solvent was removed by evaporation and the residue was purified by chromatography on silica gel (dichloromethane/methanol) to yield 126 mg of the desired product.

MS (M+1): 486

¹H-NMR (300 MHz, d6-DMSO): 9.05 (s, 1H), 8.80 (s, 1H), 8.24 (d, 1H), 7.95 (s, 1H), 7.79 (s, 1H), 7.48 (d, br, 1H), 7.29-7.40 (m, 5H), 7.19-7.29 (m, 4H), 3.5 (s, 2H), 2.78-2.98 (m, br, 3H), 1.95-2.18 (m, 4H), 1.73-1.95 (m, 2H).

Example 7.0

2-{1-[4-(6-phenyl-imidazo[1,2-a]pyrimidin-7-yl)-benzyl]-piperidin-4-yl}-3H-imidazo[4,5-b]pyridine

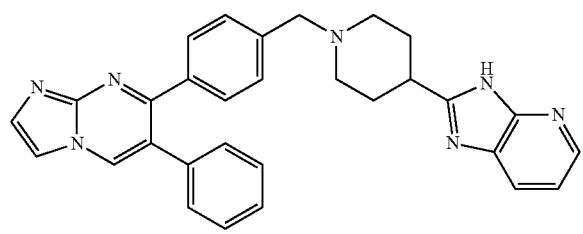 [SMILES: c1ccc(-c2cn3ccnc3nc2-c2ccc(CN3CCC(c4nc5cccnc5[nH]4)CC3)cc2)cc1]

By reacting 150 mg (0.5 mmol) 4-(6-phenylimidazo[1,2-a]pyrimidin-7-yl)benzaldehyde with 122 mg (0.6 mmol) 2-piperidine-4-yl-3H-imidazo[4,5-b]pyridine hydrochloride salt as described in example 6.0 the desired compound (166 mg) was obtained after purification on silicagel.

MS (M+1): 486

¹H-NMR (300 MHz, d6-DMSO): 9.03 (s, 1H), 8.25 (s, br, 1H), 7.82-7.95 (m, 2H), 7.80 (s, 1H), 7.20-7.40 (m, 9H), 7.15 (m, 1H), 3.53 (s, br, 2H), 2.80-2.98 (m, br, 3H), 1.70-2.28 (m, 6H).

Example 8.0

7-{4-[4-(6-fluoro-1H-benzimidazol-2-yl)-piperidin-1-ylmethyl]-phenyl}-6-phenylimidazo[1,2-a]pyrimidine

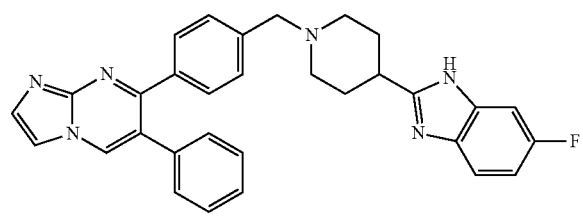 [SMILES: Fc1ccc2nc(C3CCN(Cc4ccc(-c5nc6nccn6cc5-c5ccccc5)cc4)CC3)[nH]c2c1]

150 mg (0.5 mmol) 4-(6-phenylimidazo[1,2-a]pyrimidin-7-yl)benzaldehyde were reacted with 132 mg (0.6 mmol) 6-fluoro-2-piperidine-4-yl-1H-benzimidazole hydrochloride salt in analogy as described in example 6.0. The desired compound (165 mg) was obtained after purification on silicagel.

MS (M+1): 503

¹H-NMR (400 MHz, d6-DMSO): 9.02 (s, 1H), 7.92 (s, 1H), 7.79 (s, 1H), 7.15-7.53 (m, 12H), 6.90-7.00 (m, 1H), 3.50 (s, br, 2H), 2.70-3.00 (m, br, 3H), 1.75-2.20 (m, 6H).

Example 9.0

2-{1-[4-(6-Phenyl-imidazo[1,2-a]pyrimidin-7-yl)-benzyl]-piperidin-4-yl}-3H-benzimidazole-5-carbonitrile

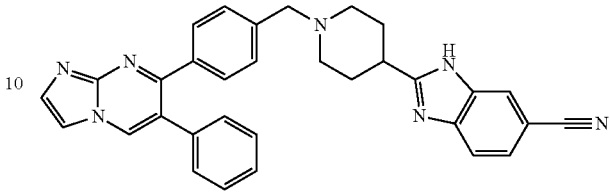

150 mg (0.5 mmol) 4-(6-phenylimidazo[1,2-a]pyrimidin-7-yl)benzaldehyde described in example 1 and 136 mg (0.6 mmol) 2-piperidine-4-yl-3H-benzimidazole-5-carbonitrile hydrochloride salt were reacted and purified as described in example 6.0. 199 mg of the desired compound were obtained.

MS (M+1): 510

¹H-NMR (400 MHz, d6-DMSO): 9.02 (s, 1H), 7.95 (s, 1H), 7.80 (s, 1H), 7.45-7.68 (m, 2H), 7.19-7.40 (m, 10H), 3.50 (s, br, 2H), 2.75-3.00 (m, br, 3H), 1.77-2.20 (m, 6H).

Example 10.0

2-{1-[4-(6-phenyl-imidazo[1,2-a]pyrimidin-7-yl)-benzyl]-piperidine-4-yl}-quinoxaline

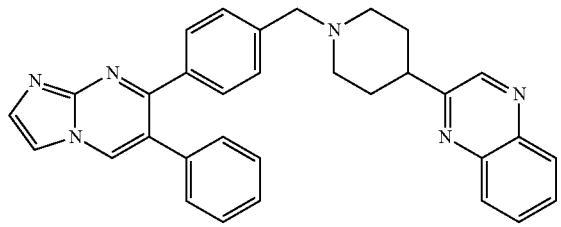 [SMILES: c1ccc(-c2cn3ccnc3nc2-c2ccc(CN3CCC(c4cnc5ccccc5n4)CC3)cc2)cc1]

160 mg (0.53 mmol) 4-(6-phenylimidazo[1,2-a]pyrimidin-7-yl)benzaldehyde and 182 mg (0.64 mmol) 2-piperidine-4-yl-quinoxaline were reacted for two days at room temperature and purified as described in example 6.0. 87.3 mg of the desired compound were obtained.

MS (M+1): 497

¹H-NMR (400 MHz, d6-DMSO): 9.03 (s, 1H), 8.9 (s, 1H), 7.99-8.10 (m, 2H), 7.93 (s, 1H), 7.75-7.80 (m, 3H), 7.30-7.39 (m, 5H), 7.21-7.39 (m, 4H), 3.51 (s, 2H), 2.90-3.02 (m, br, 3H), 2.05-2.20 (m, 2H), 1.85-2.00 (m, 4H).

Example 11.0

1-{1-[4-(6-phenyl-imidazo[1,2-a]pyrimidin-7-yl)-benzyl]-piperidin-4-yl}-1H-pyrazolo[3,4-d]pyrimidin-4-ylamine

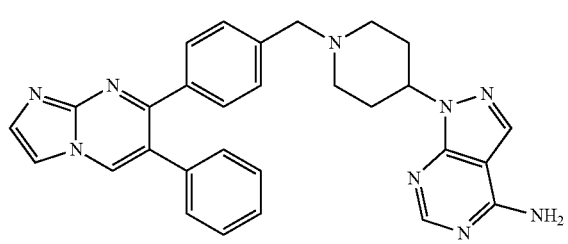 [SMILES: Nc1ncnc2c1cnn2C1CCN(Cc2ccc(-c3nc4nccn4cc3-c3ccccc3)cc2)CC1]

300 mg (1 mmol) 4-(6-phenylimidazo[1,2-a]pyrimidin-7-yl)benzaldehyde and 306 mg (1.20 mmol) 1-piperidine-4-yl-1H-pyrazolo[3,4-d]pyrimidin-4-ylamine were reacted for four days (additional NaBH(OAc)$_3$ has been added after four, six, eight, 24 and 28 hours (two equivalents each)) at room temperature and purified as previously described. 210 mg of the desired compound were obtained.

MS (M+1): 502

$^1$H-NMR (300 MHz, d6-DMSO): 9.02 (s, 1H), 8.16 (s, 1H), 8.09 (s, 1H), 7.92 (1H), 7.80 (s, 1H), 7.62 (s, br, 2H), 7.20-7.40 (m, 9H), 4.59 (m, br, 1H), 3.52 (s, 2H), 2.83-2.99 (m, br, 2H), 2.06-2.20 (m, 4H), 1.78-1.90 (m, 2H).

Example 12.0

2-{1-[4-(6-phenyl-pyrazolo[1,5-a]pyrimidin-5-yl)-benzyl]-piperidin-4-yl}-3H-benzimidazol-5-carbonitrile

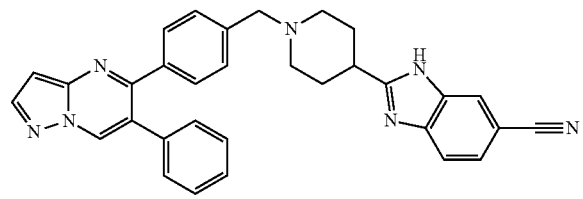 [SMILES: N#Cc1ccc2nc(C3CCN(Cc4ccc(-c5nc6ccnn6cc5-c5ccccc5)cc4)CC3)[nH]c2c1]

265 mg (1 mmol) 2-piperidine-4-yl-3H-benzimidazole-5-carbonitrile hydrochloride salt was dissolved in 5 mL methanol. 204 mg (2 mmol) triethylamine, 250 mg (0.84 mmol) 4-(6-phenylpyrazolo[1,5-a]pyrimidin-5-yl)benzaldehyde, 5 mL DMF, 12.5 mL dichloromethane and 131 mg (2.2 mmol) acetic acid were added and after 30 minutes stirring 355 mg (1.68 mmol) NaBH(OAc)$_3$ was added. Additional NaBH(OAc)$_3$ has been added after one, two, three and four hours (two equivalents each) and the reaction mixture has been stirred overnight at room temperature. Usual work-up and purification as described in previous experiments yields 138 mg of the desired material.

MS (M+1): 510

$^1$H-NMR (300 MHz, d6-DMSO): 9.12 (s, 1H), 8.28 (d, 1H), 7.48-7.62 (m, 2H), 7.15-7.39 (m, 10H), 6.79 (d, 1H), 3.50 (s, 2H), 2.78-2.95 (m, 3H), 1.92-2.18 (m, 4H), 1.73-1.93 (m, 2H).

Example 13.0

5-{4-[4-(6-fluoro-1H-benzoimidazol-2-yl)-piperidin-1-ylmethyl]-phenyl}-2-methyl-6-phenyl-[1,2,4]triazolo[1,5-a]pyrimidine

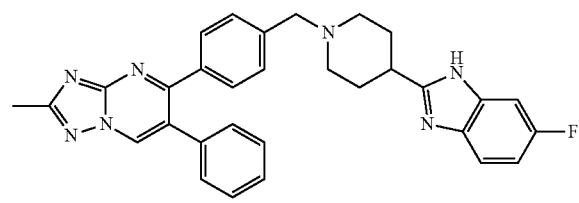 [SMILES: Cc1nc2nc(-c3ccc(CN4CCC(c5nc6ccc(F)cc6[nH]5)CC4)cc3)c(-c3ccccc3)cn2n1]

200 mg (0.64 mmol)-4-(2-methyl-6-phenyl[1,2,4]triazolo[1,5-a]pyrimidin-5-yl)benzaldehyde and 184 mg (0.76 mmol) 6-fluoro-2-piperidine-4-yl-1H-benzimidazole hydrochloride salt were treated as described in example 2.0. Additional NaBH(OAc)$_3$ has been added after 24 and 26 hours (two equivalents each). After stirring at room temperature for five days and the usual workup und purification 142 mg of the desired compound have been obtained.

MS (M+1): 518

$^1$H-NMR (300 MHz, d6-DMSO): 9.32 (s, 1H), 7.20-7.45 (m, 11H), 6.95 (m, 1H), 3.52 (s, 2H), 2.77-2.95 (m, 3H), 2.58 (s, 3H), 2.05-2.25 (m, 2H), 1.92-2.03 (m, 2H), 1.78-2.02 (m, 2H).

Example 14.0

5-{4-[4-(3H-imidazo[4,5-c]pyridin-2-yl)-piperidin-1-ylmethyl]-phenyl}-2-methyl-6-phenyl-[1,2,4]triazolo[1,5-a]pyrimidine

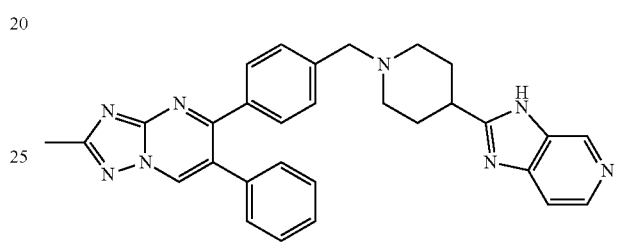

200 mg (0.64 mmol) 4-(2-methyl-6-phenyl[1,2,4]triazolo[1,5-a]pyrimidin-5-yl)benzaldehyde and 181 mg (0.76 mmol) 2-piperidine-4-yl-3H-imidazo[4,5-c]pyridine hydrochloride salt were treated as described in example 2.0. Additional NaBH(OAc)$_3$ has been added after one, two, three, four and a half, five and a half, and seven and a half hours (two equivalents each). The solvents were evaporated and the usual workup and purification yields 108 mg of the desired compound.

MS (M+1): 501

$^1$H-NMR (300 MHz, d6-DMSO): 9.33 (s, 1H), 8.80 (br, 1H), 8.22 (d, 1H), 7.20-7.45 (m, 10H), 3.52 (s, 2H), 2.79-2.98 (m, 3H), 2.55 (s, 3H), 2.05-2.20 (m, 2H), 1.94-2.05 (m, 2H), 1.78-1.93 (m, 2H).

Example 15.0

2-{1-[4-(6-phenyl-pyrazolo[1,5-a]pyrimidin-5-yl)-benzyl]-piperidin-4-yl}-3H-imidazo[4,5-c]pyridine

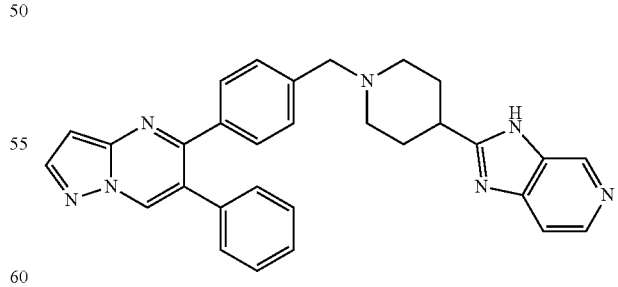

252 mg (1.06 mmol) 2-piperidine-4-yl-3H-imidazo[4,5-c]pyridine and 250 mg (0.84 mmol) 4-(6-phenylpyrazolo[1,5-a]pyrimidin-5-yl)benzaldehyde were reacted as described in example 12.0. Additional NaBH(OAc)$_3$ has been added after one, three and five hours (two equivalents each) and the reaction mixture has been stirred overnight at room temperature. Since the reaction has not been complete, 20 mL THF and 10 mL acetic acid were added. Another two equivalents of NaBH(OAc)$_3$ were added. Because after one hour stirring at room temperature the reaction has not changed additional 126 mg 2-piperidine-4-yl-3H-imidazo[4,5-c]pyridine and another two equivalents of NaBH(OAc)$_3$ were added. The reaction has been worked up after stirring at room temperature for 70 hours. After purification 28 mg of the desired material has been obtained.

MS (M+1): 486
$^1$H-NMR (300 MHz, d6-DMSO): 9.12 (s, 1H), 8.78 (br, 1H), 8.28 (s, 1H), 8.25 (s, 1H), 7.21-7.49 (m, 10H), 6.79 (d, 1H), 3.50 (s, 2H), 2.80-2.97 (m, 3H), 1.92-2.18 (m, 4H), 1.73-1.92 (m, 2H).

Example 16.0

2-{1-[4-(6-phenyl-pyrazolo[1,5-a]pyrimidin-5-yl)-benzyl]-piperidin-4-yl}-3H-imidazo[4,5-b]pyridine

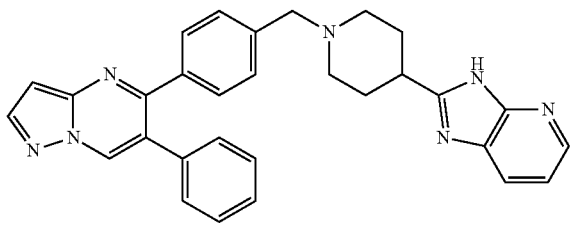 [SMILES: c1ccc(-c2cn3nccc3nc2-c2ccc(CN3CCC(c4nc5cccnc5[nH]4)CC3)cc2)cc1]

251.4 mg (0.84 mmol) 4-(6-phenylpyrazolo[1,5-a]pyrimidin-5-yl)benzaldehyde, a suspension in 10 mL DMF and 238 mg (1 mmol) 2-piperidine-4-yl-3H-imidazo[4,5-b]pyridine hydrochloride salt were stirred and treated as described in example 15.0. After stirring overnight at room temperature, the reaction mixture was worked up as described in example 15. After purification 90 mg of the desired product were obtained.

MS (M+1): 486
$^1$H-NMR (300 MHz, d6-DMSO): 9.12 (s, 1H), 8.30 (br, 1H), 8.20 (d, 1H), 7.19-7.39 (m, 10H), 7.10-7.20 (m, 1H), 6.80 (d, 1H), 3.50 (s, 2H), 2.79-2.95 (m, 3H), 1.75-2.20 (m, 6H).

Example 17.0

6-phenyl-5-{4-[4-(6-trifluoromethyl-1H-benzimidazol-2-yl)piperidin-1-ylmethyl]-phenyl}-pyrazolo[1,5-a]pyrimidine

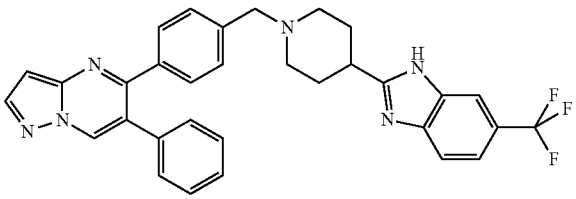 [SMILES: FC(F)(F)c1ccc2nc(C3CCN(Cc4ccc(-c5nc6ccnn6cc5-c5ccccc5)cc4)CC3)[nH]c2c1]

250 mg (0.84 mmol) 4-(6-phenylpyrazolo[1,5-a]pyrimidin-5-yl)benzaldehyde and 308 mg (1 mmol) 2-piperidine-4-yl-6-trifluoromethyl-1H-benzimidazole hydrochloride salt were treated as previously described. Additional NaBH (OAc)$_3$ has been added after one, two and three hours (two equivalents each). After a further hour stirring at room temperature additional 31 mg 2-piperidine-4-yl-6-trifluoromethyl-1H-benzimidazole hydrochloride salt and two equivalents NaBH(OAc)$_3$ were added. After stirring overnight and two further additions of NaBH(OAc)$_3$ the solvents were evaporated. Workup and purification yields 208 mg of the desired compound.

MS (M+1): 553
$^1$H-NMR (300 MHz, d6-DMSO): 9.12 (s, 1H), 8.29 (d, 1H), 7.71 (br, 1H), 7.48 (br, 1H), 7.20-7.40 (m, 10H), 6.79 (d, 1H), 3.51 (s, 2H), 2.79-2.98 (m, 3H), 1.93-2.18 (m, 4H), 1.75-1.93 (m, 2H).

Example 18.0

5-{4-[4-(6-fluoro-1H-benzimidazol-2-yl)-piperidin-1-ylmethyl]-phenyl}-6-phenyl-pyrazolo[1,5-a]pyrimidine

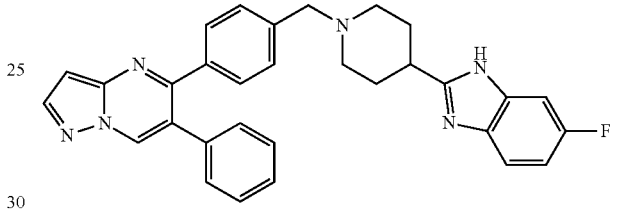

250 mg (0.84 mmol) 4-(6-phenylpyrazolo[1,5-a]pyrimidin-5-yl)benzaldehyde and 258 mg (1 mmol) 6-fluoro-2-piperidine-4-yl-1H-benzimidazole hydrochloride salt were treated as previously described. Additional NaBH(OAc)$_3$ has been added after one, two and three hours (two equivalents each). After a further hour stirring at room temperature additional 26 mg 6-fluoro-2-piperidine-4-yl-1H-benzimidazole hydrochloride salt and two equivalents NaBH(OAc)$_3$ were added. After stirring overnight and two further additions of NaBH(OAc)$_3$ the solvents were evaporated. Workup and purification yields 249 mg of the desired compound.

MS (M+1): 503
$^1$H-NMR (300 MHz, d6-DMSO): 9.12 (s, 1H), 8.29 (d, 1H), 7.12-7.45 (m, 11H), 6.95 (br, 1H), 6.79 (d, 1H), 3.50 (s, 2H), 2.75-3.00 (m, 3H), 1.75-2.15 (m, 6H).

Example 19.0

1-{1-[4-(6-phenyl-pyrazolo[1,5-a]pyrimidin-5-yl)-benzyl]-piperidin-4-yl}-1H-pyrazolo[3,4-d]pyrimidin-4-ylamine

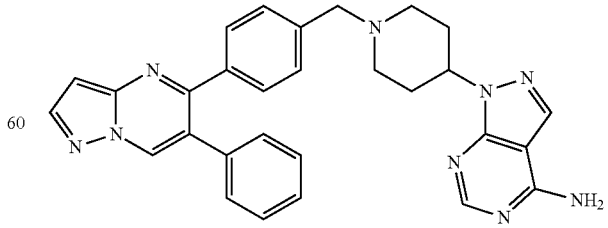

250 mg (0.84 mmol) 4-(6-phenylpyrazolo[1,5-a]pyrimidin-5-yl)benzaldehyde and 257 mg (1 mmol) 1-piperidine-4- yl-1H-pyrazolo[3,4-d]pyrimidin-4-ylamine were treated as previously described. Additional NaBH(OAc)₃ has been added after one, two and three hours (two equivalents each). After a further stirring at room temperature additional 26 mg 1-piperidine-4-yl-1H-pyrazolo[3,4-d]pyrimidin-4-ylamine and two equivalents NaBH(OAc)₃ were added. After stirring overnight and two further additions of NaBH(OAc)₃ the solvents were evaporated. Workup und purification yields 108 mg of the desired compound.

MS (M+1): 502

¹H-NMR (300 MHz, d6-DMSO): 9.12 (s, 1H), 8.28 (d, 1H), 8.15 (s, 1H), 8.08 (s, 1H), 7.65 (br, 2H), 7.20-7.36 (m, 10H), 6.79 (d, 1H), 4.56 (br, 1H), 3.52 (s, 2H), 2.84-2.96 (m, 2H), 2.07-2.23 (m, 4H), 1.79-1.92 (m, 2H).

Example 20.0

2-{1-[4-(2-methyl-6-phenyl-[1,2,4]triazolo[1,5-a]
pyrimidin-5-yl)benzyl]-piperidin-4-yl}-3H-benzimidazole-5-carbonitrile

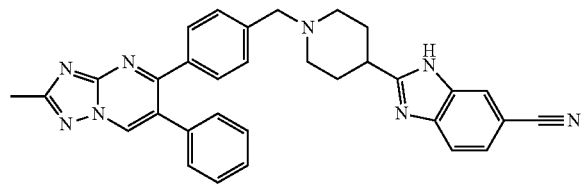 [SMILES: Cc1nc2nc(-c3ccc(CN4CCC(c5nc6ccc(C#N)cc6[nH]5)CC4)cc3)c(-c3ccccc3)cn2n1]

200 mg (0.64 mmol) 4-(2-methyl-6-phenyl[1,2,4]triazolo[1,5-a]pyrimidin-5-yl)benzaldehyde and 200 mg (0.64 mmol) 2-piperidine-4-yl-3H-benzimidazole-5-carbonitrile hydrochloride salt were treated as described in example 2.0. Additional NaBH(OAc)₃ has been added after 24 and 26 hours (two equivalents each). After five days stirring at room temperature the solvents have been evaporated and the residue was purified via chromatography. 121 mg of the desired compound were obtained.

MS (M+1): 525

¹H-NMR (300 MHz, d6-DMSO): 9.35 (s, 1H), 8.00 (s, 1H), 7.62 (d, 1H), 7.52 (d, 1H), 7.20-7.39 (m, 10H), 3.50 (s, 2H), 2.80-2.95 (m, 3H), 2.53 (s, 3H), 1.93-2.18 (m, 4H), 1.75-1.93 (m, 2H).

Example 21.0

2-methyl-6-phenyl-5-{4-[4-(6-trifluoromethyl-1H-benzimidazol-2-yl)-piperidin-1-ylmethyl]-phenyl}-[1,2,4]-triazolo[1,5-a]pyrimidine

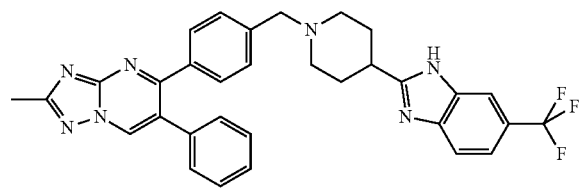 [SMILES: Cc1nc2nc(-c3ccc(CN4CCC(c5nc6ccc(C(F)(F)F)cc6[nH]5)CC4)cc3)c(-c3ccccc3)cn2n1]

200 mg (0.64 mmol) 4-(2-methyl-6-phenyl[1,2,4]triazolo[1,5-a]pyrimidin-5-yl)benzaldehyde and 232 mg (0.64 mmol) 2-piperidine-4-yl-6-trifluoromethyl-1H-benzimidazole hydrochloride salt were treated as described in example 2.0. Additional NaBH(OAc)₃ has been added after 24 and 26 hours (two equivalents each). After five days stirring at room temperature the solvents have been evaporated and the residue was purified via chromatography. 109 mg of the desired compound were obtained.

MS (M+1): 568

¹H-NMR (300 MHz, d6-DMSO): 9.38 (s, 1H), 7.99 (s, 1H), 7.72 (br, 1H), 7.60 (d, 1H), 7.45 (d, br, 1H), 7.22-7.40 (m, 9H), 3.51 (s, 2H), 2.80-2.95 (m, 3H), 2.57 (s, 3H), 1.93-2.18 (m, 4H), 1.78-1.93 (m, 2H).

Example 22.0

1-{1-[4-(2-methyl-6-phenyl-[1,2,4]-triazolo[1,5-a]
pyrimidin-5-yl)benzyl]-piperidin-4-yl}-1H-pyrazolo[3,4-d]pyrimidin-4-ylamine

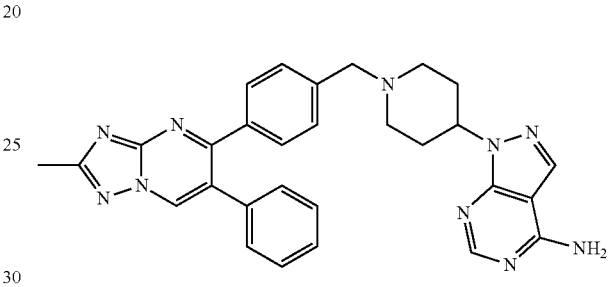

200 mg (0.64 mmol) 4-(2-methyl-6-phenyl[1,2,4]triazolo[1,5-a]pyrimidin-5-yl)benzaldehyde and 194 mg (0.64 mmol) 1-piperidine-4-yl-1H-pyrazolo[3,4-d]pyrimidin-4-ylamine were treated as described in example 2. Additional NaBH(OAc)₃ has been added after 24 and 26 hours (two equivalents each). After five days stirring at room temperature the solvents have been evaporated and the residue was purified via chromatography. 48 mg of the desired compound were obtained.

MS (M+1): 517

¹H-NMR (300 MHz, d6-DMSO): 9.35 (s, 1H), 8.15 (s, 1H), 8.09 (s, 1H), 7.63 (br, 2H), 7.20-7.40 (m, 9H), 4.59 (br, 1H), 3.55 (s, 2H), 2.91 (br, 2H), 2.58 (s, 3H), 2.08-2.23 (m, 4H), 1.79-1.91 (m, br, 2H).

Example 23.0

5-{4-[4-(3H-imidazo[4,5-b]pyridin-2-yl)-piperidin-1-ylmethyl]-phenyl}-2-methyl-6-phenyl-[1,2,4]triazolo[1,5-a]pyrimidine

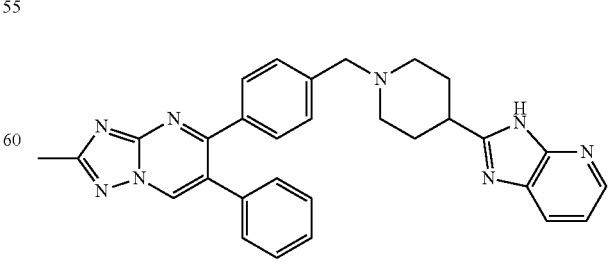

This compound is obtained in an analogous manner.

Example 24.0

(±)-2-methyl-6-phenyl-5-{4-[3-(5-pyridin-2-yl-1H-[1,2,4]triazol-3-yl)-pyrrolidin-1-ylmethyl]-phenyl}-[1,2,4]triazolo[1,5-a]pyrimidine

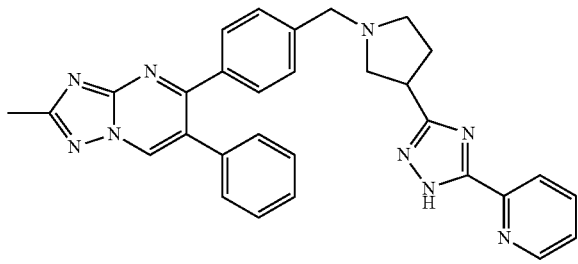 [SMILES: Cc1nc2nc(-c3ccc(CN4CCC(c5n[nH]c(-c6ccccn6)n5)C4)cc3)c(-c3ccccc3)cn2n1]

A mixture of 4-(2-methyl-6-phenyl[1,2,4]triazolo[1,5-a]pyrimidin-5-yl)benzaldehyde (300 mg, 0.95 mmol), 2-(5-pyrrolidin-3-yl-2H-[1,2,4]triazol-3-yl)-pyridine hydrochloride salt (358 mg), triethylamine (0.32 mL) and AcOH (0.098 mL) in NMP (8.1 mL) was stirred overnight at room temperature. Sodium triacetoxyborohydride (222 mg) was added and the mixture stirred for 4 h. The mixture was diluted with water, filtered and the filtrate concentrated in vacuo. The residue was co-distilled with toluene and to give the crude product which was purified by preparative HPLC to give the title compound (50 mg).

MS (M+1): 514

1H-NMR (300 MHz, d6-DMSO): δ 9.30 (s, 1H), 8.62 (m, 1H), 7.99 (d, 1H), 7.90 (m, 1H), 7.43 (m, 1H), 7.21-7.32 (m, 9H), 3.60 (s, partially obscured by solvent), 2.91-2.96 (m, 1H), 2.58-2.69 (m, 2H), 2.51 (s, 3H, plus further signals obscured by solvent), 2.05-2.24 (m, 2H) ppm The following example was prepared in analogy, by reductive amination with the appropriate aldehyde and amine intermediates:

Example 25.0

3-methyl-7-(4-{3-[5-(6-methylpyridine-2-yl)-1H-[1,2,4]triazole-3-yl]-azetidine-1-ylmethyl}-phenyl)-6-phenyl-imidazo[1,2-a]pyrimidine

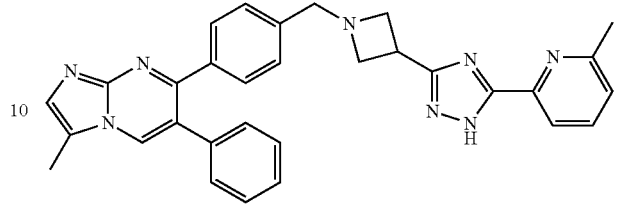

168 mg 2-(5-Azetidine-3-yl-[1,2,4]triazole-3-yl)-6-methylpyridine×2HCl (intermediate example 44.1; 60% pure) are dissolved in 2.8 ml NMP. After addition of 0.1 ml triethylamine the reaction mixture is stirred for one hour. 100 mg (0.32 mmol) 4-(3-Methyl-6-phenylimidazo[1,2-a]pyrimidin-7-yl)benzaldehyde (intermediate example 12.0) and 0.03 mL acetic acid are added and the reaction mixture is stirred overnight at room temperature. 74.4 mg (0.35 mmol) NaBH(OAc)$_3$, are added in portions and the reaction mixture is stirred at room temperature for 20 hours. The reaction mixture is treated with saturated NaHCO$_3$ and the precipitate filtered off, washed with water and dried. After chromatography of the precipitate on silica gel (dichloromethane/methanol) 36.6 mg (21%) of the desired product are obtained.

MS (ES+, M+1): 513

$^1$H-NMR (300 MHz, CDCl$_3$): 8.15 (s, 1H), 7.98 (d, 1H), 7.60-7.78 (m, 2H), 7.10-7.43 (m, 10H), 3.90-4.05 (m, 1H), 3.63-3.81 (m, 4H), 3.45-3.59 (m, 2H), 2.59 (s, 3H), 2.53 (s, 3H).

Example 26.0

3-bromo-2-methyl-6-phenyl-7-{4-[3-(5-pyridine-2-yl-1H-[1,2,4]triazole-3-yl]-azetidine-1-ylmethyl]-phenyl}-imidazo[1,2-a]pyrimidine

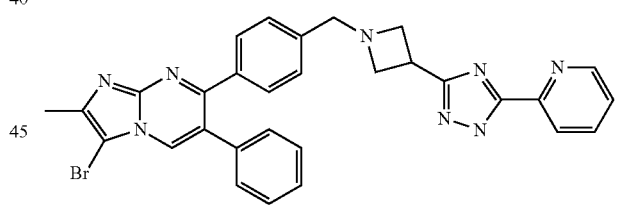

| Example | Structure/Name | Analytical Data |
|---|---|---|
| 24.1 | 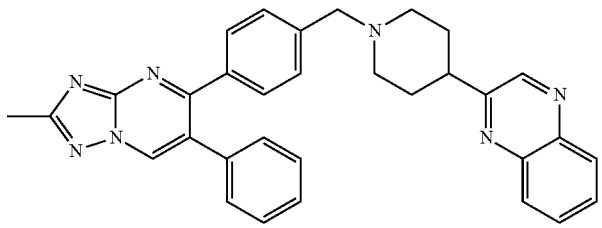

2-{1-[4-(2-methyl-6-phenyl-[1,2,4]-triazolo[1,5-a]pyrimidin-5-yl)-benzyl]-piperidin-4-yl}-quinoxaline | $^1$H-NMR (300 MHz, d6-DMSO + TFA): δ 9.40 (s, 1H), 8.89 (s, 1H), 8.02-8.05 (m, 1H), 7.95-7.97 (m, 1H), 7.74-7.81 (m, 2H), 7.42-7.48 (m, 4H), 7.22-7.33 (m, 5H), 4.36 (s, 2H), 3.10-3.48 (m, 5H), 2.53 (s, 3H), 2.04-2.20 (m, 4H) ppm |

147.6 mg 2-(5-Azetidine-3-yl-[1,2,4]triazole-3-yl)-pyridine×2HCl (intermediate example 44.0) are dissolved in 4.3 ml NMP. After addition of 0.16 ml triethylamine the reaction mixture is stirred for one hour. 192 mg (0.49 mmol) 4-(3-Bromo-2-methyl-6-phenylimidazo[1,2-a]pyrimidin-7-yl) benzaldehyde and 0.05 mL acetic acid are added and the reaction mixture is stirred for 23 hours at room temperature. 114.1 mg (0.54 mmol) NaBH(OAc)$_3$, are added in portions and the reaction mixture is stirred at room temperature for three days. The reaction mixture is treated with 30 mL saturated NaHCO$_3$ and stirred for 45 minutes. The precipitate is filtered off, washed with water and dried. After chromatography of the precipitate on silica gel (dichloromethane/methanol) 3.5 mg (1.2%) of the desired product are obtained.

MS (ES+, M+1): 579

$^1$H-NMR (300 MHz, CDCl$_3$): 8.69 (d, 1H), 8.10-8.25 (m, 2H), 7.78-7.91 (m, 1H), 7.09-7.52 (m, 10H), 3.91-4.08 (m, 1H), 3.65-3.85 (m, 4H), 3.40-3.61 (m, 2H), 2.53 (s, 3H).

Example 27.0

6-(2,6-difluorophenyl)-5-(4-{3-[5-(6-methylpyridine-2-yl)-1H-[1,2,4]triazole-3-yl]-azetidine-1-ylmethyl}-phenyl)-pyrazolo[1,5-a]pyrimidine-3-carboxylic acid methyl ester

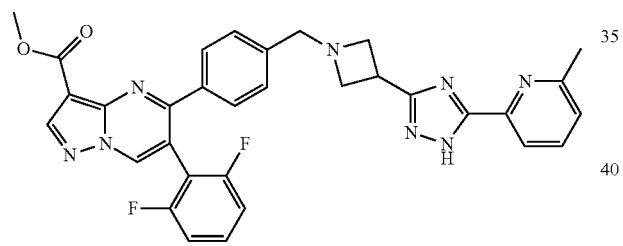

394.5 mg 2-(5-Azetidine-3-yl-[1,2,4]triazole-3-yl)-6-methylpyridine×2HCl (60% pure) are dissolved in 7 mL NMP. After addition of 0.3 mL triethylamine the reaction mixture is stirred for one hour. 350 mg (0.89 mmol) 6-(2,6-Difluorophenyl)-5-(4-formylphenyl)-pyrazolo[1,5-a]pyrimidine-3-carboxylic acid methyl ester and 0.09 mL acetic acid are added. The reaction mixture is stirred overnight at room temperature. 207.4 mg (0.98 mmol) NaBH(OAc)$_3$, are added in portions and the reaction mixture is stirred at room temperature for 5 hours. The reaction mixture is treated with saturated NaHCO$_3$. The precipitate is filtered off, washed with water and dried. After chromatography of the precipitate on silica gel (dichloromethane/methanol) 191.9 mg (34.6%) of the desired product are obtained.

MS (Cl, M+1): 593

$^1$H-NMR (300 MHz, d6-DMSO): 14.25 (s, br., 1H), 9.63 (s, 1H), 8.72 (s, 1H), 7.70-7.88 (m, 2H), 7.42-7.56 (m, 1H), 7.20-7.39 (m, 5H), 7.05-7.20 (m, 2H), 3.80 (s, 3H), 3.49-3.80 (m, 5H), 3.20-3.35 (m, 2H, under the water signal of the solvent), 2.50 (s, 3H).

Example 28.0

6-(2,6-difluorophenyl)-5-(4-{3-[5-(pyridine-2-yl)-1H-[1,2,4]triazole-3-yl]-azetidine-1-ylmethyl}-phenyl)-pyrazolo[1,5-a]pyrimidine-3-carboxylic acid methyl ester

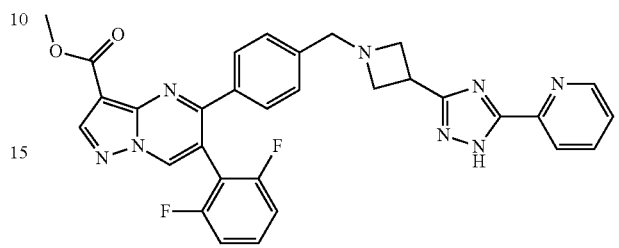

The compound is prepared in analogy to example 27.0. 348.5 mg 2-(5-Azetidine-3-yl-[1,2,4]triazole-3-yl)-pyridine×2HCl are reacted with 500 mg (1.27 mmol) 6-(2,6-difluorophenyl)-5-(4-formylphenyl)-pyrazolo[1,5-a]pyrimidine-3-carboxylic acid methyl ester. After the usual work-up and purification 254 mg (32.9%) of the title compound are obtained.

MS (Cl, M+1): 579

$^1$H-NMR (300 MHz, d6-DMSO): 14.40 (s, br., 1H), 9.64 (s, 1H), 8.70 (s, 1H), 8.65 (d, 1H), 7.83-8.06 (m, 2H), 7.39-7.57 (m, 1H), 7.20-7.34 (m, 4H), 7.07-7.20 (m, 3H), 3.80 (s, 3H), 3.49-3.80 (m, 5H), 3.20-3.35 (m, 2H, under the water signal of the solvent).

Example 29.0

2-isopropyl-6-phenyl-5-{4-[3-[5-pyridine-2-yl)-1H-[1,2,4]triazole-3-yl]-azetidine-1-ylmethyl}-phenyl}-[1,2,4]triazolo[1,5-a]pyrimidine

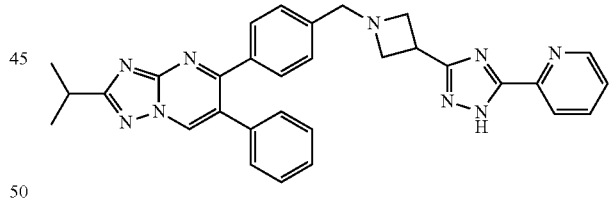

176.1 mg (0.64 mmol) 2-(5-Azetidine-3-yl-[1,2,4]triazole-3-yl)-pyridine×2HCl are dissolved in 5 mL NMP. After addition of 0.2 mL (1.4 mmol) triethylamine the reaction mixture is stirred for two and a half hours. 200 mg (0.58 mmol) 4-(2-isopropyl-6-phenyl[1,2,4]triazolo[1,5-a]pyrimidin-5-yl)benzaldehyde (intermediate example 20.0) and 0.06 mL acetic acid are added. The reaction mixture is stirred for three days at room temperature. 136 mg (0.64 mmol) NaBH (OAc)$_3$, are added in portions and the reaction mixture is stirred at room temperature for 18 hours. The reaction mixture is treated with saturated NaHCO$_3$ and stirred for two hours. The precipitate is filtered off, washed with water and dried. After chromatography of the precipitate on silica gel (dichloromethane/methanol) 215 mg (62.8%) of the desired product are obtained.

MS (Cl, M+1): 528

¹H-NMR (300 MHz, CDCl₃): 8.67-8.72 (m, 2H), 8.21 (d, 1H), 7.85 (t, 1H), 7.10-7.48 (m, 10H), 3.90-4.02 (m, 1H), 3.69-3.85 (m, 4H), 3.45-3.61 (m, 2H), 3.31 (h, 1H), 1.49 (d, 6H).

The following examples were prepared in analogy:

precipitate is filtered off, washed with water and dried. After chromatography of the precipitate on silica gel (dichloromethane/methanol) 23.4 mg (23%) of the desired product are obtained.

MS (ES+, M+1): 579

| Example | Structure/Name | Analytical Data |
|---|---|---|
| 30.0 | 2-{1-[4-(2-isopropyl-6-phenyl-[1,2,4]triazolo[1,5-a]pyrimidin-5-yl)benzyl]-piperidine-4-yl}-quinoxaline | MS (Cl, M + 1): 540<br>¹H-NMR (300 MHz, d6-DMSO): 9.30 (s, 1H), 8.89 (s, 1H), 7.92-8.03 (m, 2H), 7.69-7.80 (m, 2H), 7.19-7.35 (m, 9H), 3.49 (s, 2H), 3.20 (h, 1H), 2.86-3.01 (m, 3H), 2.00-2.17 (m, 2H), 1.90-1.98 (m, 4H), 1.39 (d, 6H). |
| 31.0 | 2-isopropyl-5-(4-{3-[5-(6-methyl-pyridine-2-yl)-1H-[1,2,4]triazolo-3-yl]-azetidine-1-ylmethyl}-phenyl)-6-phenyl-[1,2,4]triazolo[1,5-a]pyrimidine | MS (Cl, M + 1): 542<br>¹H-NMR (300 MHz, CDCl₃): 8.69 (s, 1H), 7.96 (d, 1H), 7.70 (t, 1H), 7.10-7.50 (m, 10 H), 3.85-4.02 (m, 1H), 3.64-3.82 (m, 4H), 3.43-3.59 (m, 2H), 3.31 (h, 1H), 2.59 (s, 3H), 1.49 (d, 6H). |

Example 32.0

6-(2,4-difluorophenyl)-5-(4-{3-[5-(pyridine-2-yl)-1H-[1,2,4]triazole-3-yl]-azetidine-1-ylmethyl}-phenyl)-pyrazolo[1,5-a]pyrimidine-3-carboxylic acid methyl ester

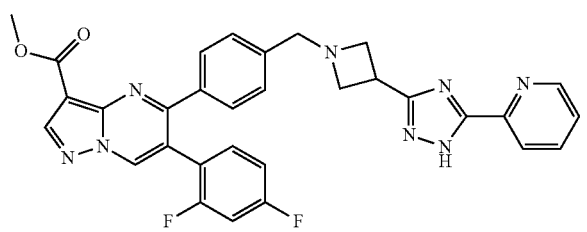 [SMILES: COC(=O)c1cnn2cc(-c3ccc(F)cc3F)c(-c3ccc(CN4CC(c5n[nH]c(-c6ccccn6)n5)C4)cc3)nc12]

49.8 mg (0.18 mmol) 2-(5-Azetidine-3-yl-[1,2,4]triazole-3-yl)-pyridine×2HCl are dissolved in 1.4 mL NMP. After addition of 0.06 mL triethylamine the reaction mixture is stirred for one hour. 65 mg (0.17 mmol) 6-(2,4-Difluorophenyl)-5-(4-formylphenyl)-pyrazolo[1,5-a]pyrimidine-3-carboxylic acid methyl ester in 1.5 mL NMP and 0.02 mL acetic acid are added. The reaction mixture is stirred overnight at room temperature. 38.5 mg (0.18 mmol) NaBH(OAc)₃, are added in portions and the reaction mixture is stirred at room temperature for 18 hours. The reaction mixture is treated with saturated NaHCO₃ and stirred vigorously for one hour. The ¹H-NMR (300 MHz, CDCl₃): 8.58-8.78 (m, 3H), 8.19 (d, 1H), 7.80-7.90 (m, 1H), 7.32-7.49 (m, 3H), 7.15-7.32 (m, 3H), 6.75-7.00 (m, 2H), 3.90-4.05 (m, 4H), 3.65-3.83 (m, 4H), 3.45-3.60 (m, 2H).

Example 33.0

6-(4-fluorophenyl)-7-{4-[3-(5-pyridine-2-yl-1H-[1,2,4]triazole-3-yl]-azetidine-1-ylmethyl]-phenyl}-imidazo[1,2-a]pyrimidine

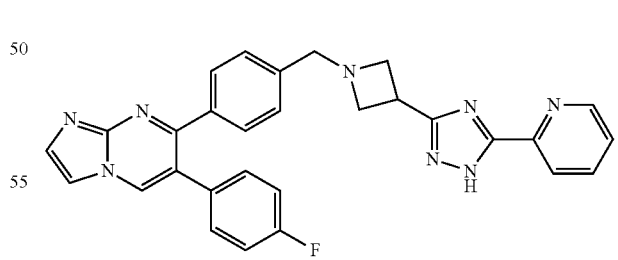

95 mg (0.35 mmol) 2-(5-Azetidine-3-yl-[1,2,4]triazole-3-yl)-pyridine×2HCl are dissolved in 2.7 mL NMP. After addition of 0.1 mL triethylamine the reaction mixture is stirred for one hour. 100 mg (0.32 mmol) 4-[6-(4-Fluorophenyl)imidazo[1,2-a]pyrimidin-7-yl]-benzaldehyde and 0.03 mL acetic acid are added. The reaction mixture is stirred for three days at room temperature. 73 mg (0.35 mmol) NaBH(OAc)₃, are added in portions and the reaction mixture is stirred at room temperature for 18 hours. The reaction mixture is treated with saturated NaHCO₃ and stirred vigorously for one hour. The precipitate is filtered off, washed with water and dried. After chromatography of the precipitate on silica gel (dichloromethane/methanol) 90 mg (54%) of the desired product are obtained.

MS (Cl, M+1): 503

¹H-NMR (300 MHz, CDCl₃): 8.70 (d, 1H), 8.39 (s, 1H), 8.20 (d, 1H), 7.78-7.91 (m, 2H), 7.56 (d, 1H), 7.30-7.41 (m, 3H), 6.92-7.28 (m, 6H), 3.95-4.09 (m, 1H), 3.69-3.82 (m, 4H), 3.48-3.61 (m, 2H).

Example 34.0

2-(1-{4-[6-(4-fluorophenyl)-imidazo[1,2-a]pyrimidin-7-yl]-benzyl}-piperidine-4-yl)-quinoxaline

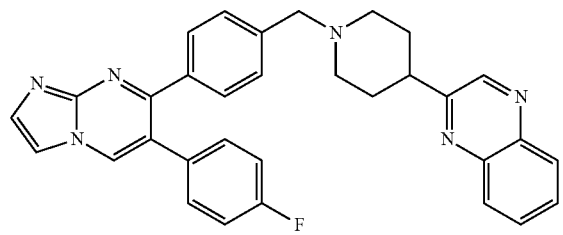 [SMILES: Fc1ccc(-c2cn3ccnc3nc2-c2ccc(CN3CCC(c4cnc5ccccc5n4)CC3)cc2)cc1]

The compound is prepared in analogy to example 33.0. 216 mg (0.756 mmol) 2-Piperidine-4-ylquinoxaline are reacted with 200 mg (0.63 mmol) 4-[6-(4-fluorophenyl)-imidazo[1,2-a]pyrimidin-7-yl]-benzaldehyde. After the usual work-up and purification 201 mg (58.9%) of the title compound are obtained.

MS (Cl, M+1): 515

¹H-NMR (400 MHz, CDCl₃): 8.81 (s, 1H), 8.40 (s, 1H), 8.00-8.13 (m, 2H), 7.89 (s, 1H), 7.69-7.90 (m, 2H), 7.58 (s, 1H), 7.38-7.47 (m, 2H), 7.23-7.35 (m, 2H), 7.12-7.22 (m, 2H), 6.98-7.10 (m, 2H), 3.59 (s, 2H), 2.90-3.12 (m, 3H), 1.92-2.29 (m, 6H).

Example 35.0

6-(2,4-difluorophenyl)-2-methyl-5-(4-{3-[5-(6-methyl-pyridine-2-yl)-1H-[1,2,4]triazole-3-yl]-azetidine-1-ylmethyl}-phenyl)-[1,2,4]triazolo[1,5-a]pyrimidine

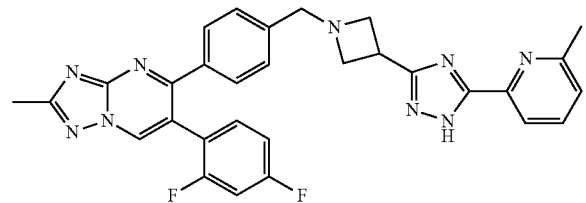

164.5 mg 2-(5-Azetidine-3-yl-[1,2,4]triazole-3-yl)-6-methylpyridine×2HCl (60% pure) are dissolved in 4.8 mL NMP. After addition of 0.2 mL triethylamine the reaction mixture is stirred for one hour. 200 mg (0.57 mmol) 4-[6-(2,4-Difluorophenyl)-2-methyl-[1,2,4]triazolo[1,5-a]pyrimidin-5-yl]-benzaldehyde and 0.06 mL acetic acid are added. The reaction mixture is stirred overnight at room temperature. 207.4 mg (0.98 mmol) NaBH(OAc)₃, are added in portions and the reaction mixture is stirred at room temperature for another night. The reaction mixture is poured on saturated NaHCO₃/ice water. The precipitate is filtered off, washed with water and dried. After chromatography of the precipitate on silica gel (dichloromethane/methanol) 92.2 mg (27.9%) of the desired product are obtained.

MS (Cl, M+1): 550

¹H-NMR (300 MHz, CDCl₃): 8.70 (s, 1H), 7.98 (d, 1H), 7.66-7.78 (m, 1H), 7.32-7.45 (m, 2H), 7.09-7.31 (m, 3H), 6.75-6.98 (m, 2H), 3.86-4.00 (m, 1H), 3.65-3.83 (m, 4H), 3.42-3.59 (m, 2H), 2.70 (s, 3H), 2.58 (s, 3H).

Example 36.0

2-{1-[4-(6-phenyl-imidazo[1,2-a]pyrimidin-7-yl)-benzyl]-piperidine-4-yl}-quinoxaline

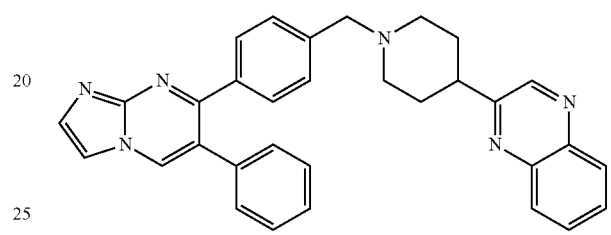 [SMILES: Cc1cn2cc(-c3ccccc3)c(-c3ccc(CN4CCC(c5cnc6ccccc6n5)CC4)cc3)nc2n1]

195 mg (0.6 mmol) 2-Piperidine-4-ylquinoxaline are dissolved in 4.9 mL NMP. After addition of 0.19 mL triethylamine the reaction mixture is stirred for one hour. 170 mg (0.57 mmol) 4-(6-Phenyl-imidazo[1,2-a]pyrimidin-7-yl)-benzaldehyde (intermediate example 1.0) and 0.06 mL acetic acid are added. The reaction mixture is stirred overnight at room temperature. 132 mg (0.63 mmol) NaBH(OAc)₃, are added in portions and the reaction mixture is stirred at room temperature for 18 hours. Additionally 75 mg NaBH(OAc)₃ and 0.03 mL acetic acid are added and the stirring is continued for 23 hours. The reaction mixture is treated with saturated NaHCO₃ and stirred vigorously for one hour. The precipitate is filtered off, washed with water and dried. After chromatography of the precipitate on silica gel (dichloromethane/methanol) 127.4 mg (45.2%) of the pure product are obtained. Another 66.1 mg (23.4%) of slightly contaminated product are obtained.

MS (Cl, M+1): 497

¹H-NMR (300 MHz, CDCl₃): 8.80 (s, 1H), 8.40 (s, 1H), 8.00-8.12 (m, 2H), 7.88 (s, 1H), 7.65-7.80 (m, 2H), 7.58 (s, 1H), 7.49-7.50 (m, 2H), 7.13-7.49 (m, 7H), 3.55 (s, 2H), 2.89-3.12 (m, 3H), 1.90-2.23 (m, 6H).

Example 37.0

2-{1-[4-(2-methyl-6-phenyl-imidazo[1,2-a]pyrimidin-7-yl)benzyl]-piperidine-4-yl}-quinoxaline

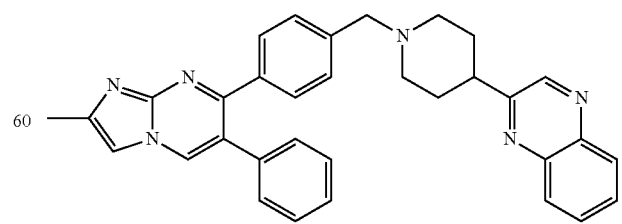

219.2 mg (0.76 mmol) 2-Piperidine-4-ylquinoxaline are dissolved in 5.5 mL NMP. After addition of 0.2 mL triethylamine the reaction mixture is stirred for one hour. 200 mg (0.64 mmol) 4-(2-Methyl-6-phenyl-imidazo[1,2-a]pyrimidin-7-yl)benzaldehyde and 0.06 mL acetic acid are added. The reaction mixture is stirred overnight at room temperature. 148 mg (0.7 mmol) NaBH(OAc)$_3$, are added in portions and the reaction mixture is stirred at room temperature for 18 hours. Additionally 75 mg NaBH(OAc)$_3$ and 0.03 mL acetic acid are added and the stirring is continued for four days. The reaction mixture is treated with saturated NaHCO$_3$ and vigorously stirred for one hour. The precipitate is filtered off, washed with water and dried. This solid is treated three times with each 20 mL dichloromethane. After filtration of the combined dichloromethane extracts the filtrate is evaporated and the residue purified by chromatography on silica gel (dichloromethane/methanol). After an additional purification by HPLC 84 mg (25.8%) of the pure product are obtained.

MS (Cl, M+1): 511
$^1$H-NMR (300 MHz, CDCl$_3$): 8.80 (s, 1H), 8.29 (s, 1H), 7.98-8.11 (m, 2H), 7.66-7.79 (m, 2H), 7.39-7.49 (2H), 7.13-7.39 (m, 8H), 3.54 (s, 2H), 2.89-3.10 (m, 3H), 2.53 (s, 3H), 1.90-2.25 (m, 6H).

Example 38.0

2-methyl-7-(4-{3-[5-(6-methylpyridine-2-yl)-1H-[1,2,4]triazole-3-yl]-azetidine-1-ylmethyl}-phenyl)-6-phenyl-imidazo[1,2-a]pyrimidine

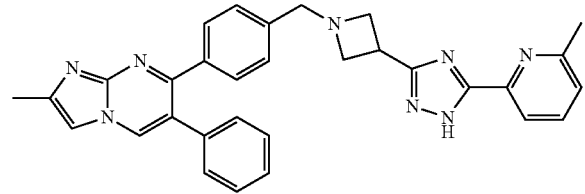

The compound is prepared in analogy to example 37.0. 306 mg 2-(5-Azetidine-3-yl-[1,2,4]triazole-3-yl)-6-methylpyridine×2HCl (60% pure) are reacted with 200 mg (0.64 mmol) 4-(2-methyl-6-phenyl-imidazo[1,2-a]pyrimidin-7-yl)-benzaldehyde. After the usual work-up and purification 146 mg (42.6%) of the title compound are obtained.

MS (Cl, M+1): 513
$^1$H-NMR (400 MHz, CDCl$_3$): 8.29 (s, 1H), 7.99 (d, 1H), 7.66-7.78 (m, 1H), 7.09-7.48 (m, 11H), 3.90-4.08 (m, 1H), 3.63-3.88 (m, 4H), 3.42-3.60 (m, 2H), 2.59 (s, 3H), 2.53 (s, 3H).

Example 39.0

2-cyclopropyl-6-(4-fluorophenyl)-5-(4-{3-[5-(6-methyl-pyridine-2-yl)-1H-[1,2,4]triazole-3-yl]-azetidine-1-ylmethyl}-phenyl)-[1,2,4]triazolo[1,5-a]pyrimidine 164.5 mg 2-(5-Azetidine-3-yl-[1,2,4]triazole-3-yl)-6-methylpyridine×2HCl (60% pure) are dissolved in 4.2 mL NMP. After addition of 0.16 mL triethylamine the reaction mixture is stirred for one hour. 350 mg 2-cyclopropyl-4-[6-(4-fluorophenyl)-[1,2,4]triazolo[1,5-a]pyrimidin-5-yl]-benzaldehyde (50% pure) and 0.05 mL acetic acid are added. The reaction mixture is stirred overnight at room temperature. 113.8 mg (0.54 mmol) NaBH(OAc)$_3$, are added in portions and the reaction mixture is stirred at room temperature for 18 hours. After the usual work-up and chromatography 167 mg (58.3%) of the desired product are obtained.

MS (Cl, M+1): 558
$^1$H-NMR (400 MHz, CDCl$_3$): 8.61 (s, 1H), 7.98 (d, 1H), 7.69-7.77 (m, 1H), 7.35-7.45 (m, 2H), 7.10-7.32 (m, 5H), 7.00-7.10 (m, 2H), 3.90-4.02 (m, 1H), 3.68-3.85 (m, 4H), 3.48-3.60 (m, 2H), 2.20-2.30 (m, 1H), 1.23-1.32 (m, 2H), 1.10-1.20 (2H).

Example 40.0

2-{1-[4-(2-cyclopropyl-6-phenyl-[1,2,4]triazolo[1,5-a]pyrimidin-5-yl)-benzyl]-piperidine-4-yl}-quinoxaline

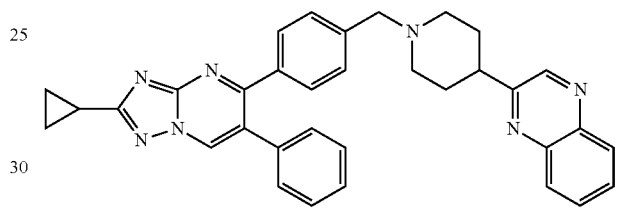

125.3 mg (0.59 mmol) 2-Piperidine-4-ylquinoxaline are dissolved in 5.2 mL NMP. After addition of 0.2 mL triethylamine the reaction mixture is stirred for one hour. 200 mg (0.59 mmol) 4-(2-cyclopropyl-6-phenyl-[1,2,4]triazolo[1,5-a]pyrimidin-5-yl)benzaldehyde (intermediate example 4.0) and 0.06 mL acetic acid are added. The reaction mixture is stirred overnight at room temperature. 137 mg (0.65 mmol) NaBH(OAc)$_3$, are added in portions and the reaction mixture is stirred at room temperature for four hours. Saturated NaHCO$_3$ is added to the reaction mixture, the precipitate is filtered off and purified by chromatography on silica gel (dichloromethane/methanol). 157.8 mg (47.5%) of the pure product are obtained.

MS (ES+, M+1): 538
$^1$H-NMR (400 MHz, CDCl$_3$): 8.80 (s, 1H), 8.68 (s, 1H), 8.00-8.10 (m, 2H), 7.68-7.80 (m, 2H), 18-7.50 (m, 9H), 3.58 (s, 2H), 2.90-3.10 (m, 3H), 1.93-2.29 (m, 7H), 1.20-1.32 (m, 2H), 1.09-1.20 (2H).

Example 41.0

2-cyclopropyl-5-(4-{3-[5-(6-methylpyridine-2-yl)-1H-[1,2,4]triazole-3-yl]-azetidine-1-ylmethyl}-phenyl)-6-phenyl-[1,2,4]triazolo[1,5-a]pyrimidine

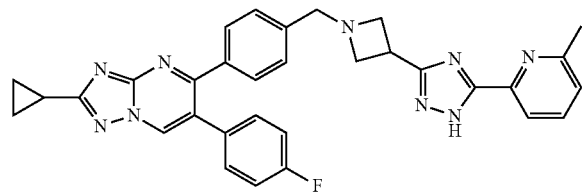 [SMILES: Cc1cccc(-c2nc(C3CN(Cc4ccc(-c5nc6nc(C7CC7)nn6cc5-c5ccc(F)cc5)cc4)C3)n[nH]2)n1]

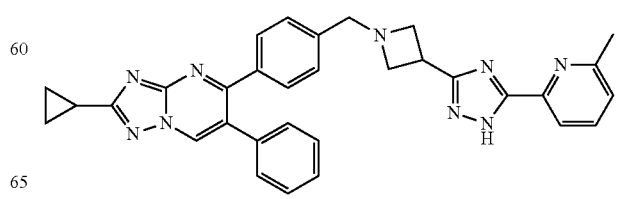

The compound is prepared in analogy to example 40.0. 211.6 mg 2-(5-Azetidine-3-yl-[1,2,4]triazole-3-yl)-6-methylpyridine×2HCl (60% pure) are reacted with 250 mg (0.73 mmol) 4-(2-cyclopropyl-6-phenyl-[1,2,4]triazolo[1,5-a]pyrimidin-5-yl)benzaldehyde (intermediate example 4.0) After the usual work-up and purification 97 mg (23.3%) of the desired compound are obtained.

MS (Cl, M+1): 540

$^1$H-NMR (300 MHz, CDCl$_3$): 8.62 (s, 1H), 7.98 (d, 1H), 7.66-7.78 (m, 1H), 7.10-7.48 (m, 10H), 3.85-4.01 (m, 1H), 3.65-3.84 (m, 4H), 3.43-3.59 (m, 2H), 2.18-2.30 (m, 1H), 1.20-1.32 (m, 2H), 1.09-1.20 (2H).

Example 42.0

3-ethyl-5-(4-{3-[5-(6-methyl-pyridin-2-yl)-1H-[1,2,4]triazol-3-yl]-azetidin-1-ylmethyl}-phenyl)-6-phenyl-pyrazolo[1,5-a]pyrimidine

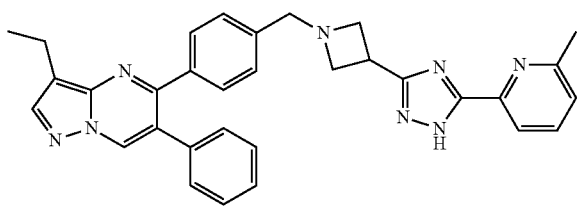 [SMILES: CCc1cnn2cc(-c3ccccc3)c(-c3ccc(CN4CC(c5n[nH]c(-c6cccc(C)n6)n5)C4)cc3)nc12]

A mixture of 142 mg (0.43 mmol) 4-(3-ethyl-6-phenyl-pyrazolo[1,5-a]pyrimidin-5-yl)-benzaldehyde and 314 mg (0.65 mmol, ca 60% pure) 2-(5-azetidin-3-yl-2H-[1,2,4]triazol-3-yl)-6-methyl-pyridine hydrochloride salt in 3.65 mL NMP was treated with 0.146 mL triethylamine and 0.045 mL acetic acid and stirred overnight at rt. The mixture was treated with 101 mg sodium triacetoxyborohydride and stirred overnight at rt. The reaction was partitioned between DCM and saturated sodium hydrogencarbonate solution, the organic phase dried and concentrated in vacuo and the residue purified by preparative reverse phase HPLC to give 49 mg of the title compound contaminated with formic acid.

$^1$H-NMR (400 MHz, d6-DMSO): δ 14.32 (br s), 9.00 (s, 1H), 8.12 (s, 1H), 7.78-7.83 (m, 2H), 7.18-7.30 (m, 10H), 3.71 (m, 1H), 3.55-3.58 (m, 4H), 2.77 (q, 2H), 2.52 (s, 3H), 1.27 (t, 3H) ppm [2H from azetidine obscured by solvent].

Example 42.1

2-{1-[4-(3-ethyl-6-phenyl-pyrazolo[1,5-a]pyrimidin-5-yl)benzyl]-piperidin-4-yl}-quinoxaline

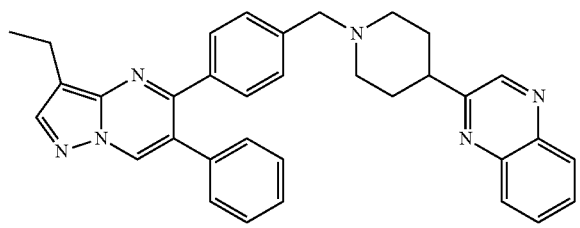 [SMILES: CCc1cnn2cc(-c3ccccc3)c(-c3ccc(CN4CCC(c5cnc6ccccc6n5)CC4)cc3)nc12]

The title compound was prepared in analogy to Example 42.0 by reductive amination with the appropriate amine intermediate.

$^1$H-NMR (300 MHz, d6-DMSO): δ 9.01 (s, 1H), 8.91 (s, 1H), 8.13 (s, 1H), 7.98-8.04 (m, 2H), 7.73-7.81 (m, 2H), 7.21-7.30 (m, 9H), 3.49 (s, 2H), 2.89-3.01 (m, 3H), 2.77 (q, 2H), 2.05-2.12 (m, 2H), 1.82-1.90 (m, 4H), 1.28 (t, 3H) ppm.

Example 43.0 methyl-(6-phenyl-5-{4-[3-(5-pyridin-2-yl-1H-[1,2,4]triazol-3-yl)azetidin-1-ylmethyl]-phenyl}-[1,2,4]triazolo[1,5-a]pyrimidin-2-yl)-amine

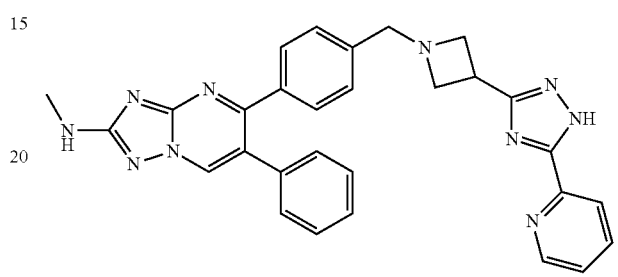

The title compound was prepared in analogy to Example 42.0 by reductive amination with the appropriate aldehyde and amine intermediate. Purification of the crude product by preparative HPLC yielded the title compound contaminated with formic acid.

UPLC-MS: RT=1.38 min; m/z=515.65;

$^1$H-NMR (400 MHz, d6-DMSO): δ 14.43 (br s, 1H), 9.02 (s, 1H), 8.63 (d, 1H), 8.02 (d, 1H), 7.92 (t, 1H), 7.45 (m, 1H), 7.17-7.30 (m, 9H), 6.90 (q, 1H), 3.75 (m, 1H), 3.60-3.67 (m, 4H), (2H obscured by solvent), 2.83 (d, 3H) ppm.

Example 43.1 isopropyl-(6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidin-2-yl)-amine

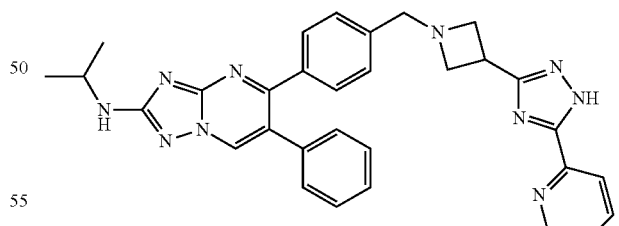

The title compound was prepared in analogy to Example 42.0 by reductive amination with the appropriate aldehyde and amine intermediate. Purification of the crude product by preparative HPLC yielded the title compound contaminated with formic acid.

UPLC-MS: RT=0.91 min; m/z=543.68;

$^1$H-NMR (300 MHz, d6-DMSO): δ 14.36 (br s), 9.00 (s, 1H), 8.63 (d, 1H), 8.02 (d, 1H), 7.91 (t, 1H), 7.44 (t, 1H), 7.17-7.29 (m, 9H), 6.89 (d, 1H), 3.79-3.90 (m, 1H), 3.67-3.77 (m, 1H), 3.55-3.59 (m, 4H), 3.30 (m, 2H partially obscured by solvent), 1.17 (d, 6H) ppm.

Example 44.0

2,7-dimethyl-6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidine

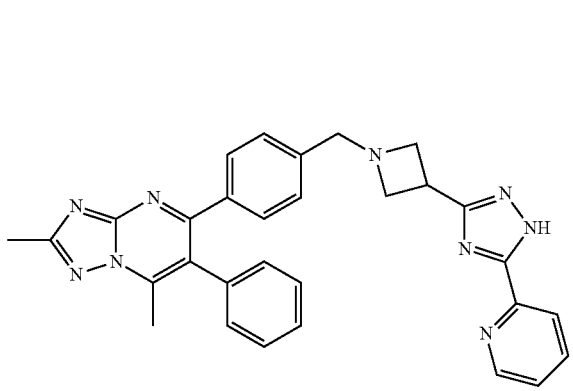 [SMILES: Cc1nc2nc(-c3ccc(CN4CC(c5n[nH]c(-c6ccccn6)n5)C4)cc3)c(-c3ccccc3)c(C)n2n1]

The title compound was prepared in analogy to Example 42.0 by reductive amination with the appropriate aldehyde and amine intermediate. Purification of the crude product by preparative HPLC yielded the title compound contaminated with formic acid.

UPLC-MS: RT=0.77 min; m/z=512.5 (ES−);
$^1$H-NMR (300 MHz, d6-DMSO): δ 14.31 (br s), 8.63 (d, 1H), 8.01 (d, 1H), 7.91 (t, 1H), 7.44 (m, 1H), 7.32-7.34 (m, 3H), 7.19-7.22 (m, 4H), 7.12 (d, 2H), 3.71 (m, 1H), 3.52-3.57 (m, 4H), 3.27 (m, 2H partially obscured by solvent), 2.53 (s, 3H), 2.52 (s, 3H) ppm.

The following Example was prepared in analogy to Example 44.0 by reductive amination with the appropriate aldehyde and amine intermediate.

Example 45.0 cyclobutyl-(2-methyl-6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidin-7-yl)-amine The title compound was prepared in analogy to Example 42.0 by reductive amination with the appropriate aldehyde and amine intermediate. Purification of the crude product by chromatography over a Biotage® Flash-NH2 column (gradient elution: 100% CH$_2$Cl$_2$-90% CH$_2$Cl$_2$/EtOH) yielded the title compound.

UPLC-MS: RT=0.99 min; m/z=567.67 (ES−);
$^1$H-NMR (400 MHz, d6-DMSO): δ 14.36 (br s), 8.63 (d, 1H), 8.02 (d, 1H), 7.91 (t, 1H), 7.45 (m, 1H), 7.25-7.29 (m, 4H), 7.18-7.20 (m, 2H), 7.05 (m, 4H), 3.61-3.71 (m, 2H), 3.50-3.53 (m, 4H), 3.24 (t, 2H), (s, 3H obscured by solvent), 1.93-2.03 (m, 2H), 1.67-1.74 (m, 2H), 1.39-1.46 (m, 1H), 1.06-1.16 (m, 1H) ppm.

The following Examples were prepared in analogy to Example 45.0 by reductive amination with the appropriate aldehyde and amine intermediate, except that Examples 45.1 and 45.3 were purified by preparative reverse phase HPLC.

| Example | Structure/Name | Analytical data |
|---|---|---|
| 44.1 | 2,7-Dimethyl-5-(4-{3-[5-(6-methyl-pyridin-2-yl)-1H-[1,2,4]triazol-3-yl]-azetidin-1-ylmethyl}-phenyl)-6-phenyl-[1,2,4]triazolo[1,5-a]pyrimidine | UPLC-MS: RT = 0.81 min; m/z = 526.6 (ES−); $^1$H-NMR (300 MHz, d6-DMSO): δ 14.20 (br s), 7.75-7.83 (m, 2H), 7.28-7.35 (m, 4H), 7.18-7.22 (m, 4H), 7.12 (d, 2H), 3.70 (m, 1H), 3.52-3.57 (m, 4H), 3.27 (m, 2H partially obscured by solvent), 2.53 (s, 3H), 2.52 (m, 6H) ppm. |

| Example | Structure/Name | Analytical data |
|---|---|---|
| 45.1 | 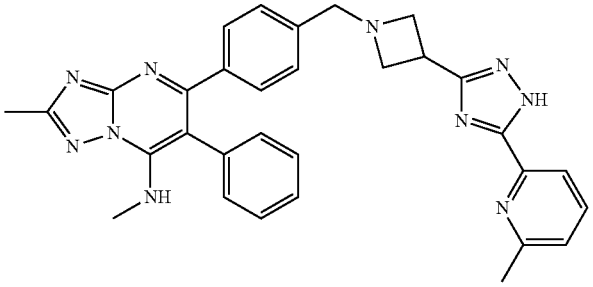<br>methyl-[2-methyl-5-(4-{3-[5-(6-methyl-pyridin-2-yl)-1H-[1,2,4]triazol-3-yl]-azetidin-1-ylmethyl}-phenyl)-6-phenyl-[1,2,4]triazolo[1,5-a]pyrimidin-7-yl]-amine | UPLC-MS: RT = 0.76 min; m/z = 541.2 (ES−); |
| 45.2 | 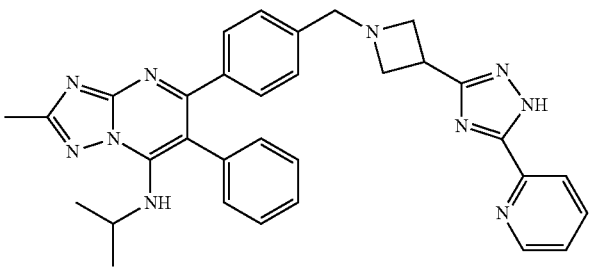<br>isopropyl-(2-methyl-6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidin-7-yl)-amine | Mp 176.8° C.;<br>UPLC-MS: RT = 0.95 min; m/z = 555.59 (ES−);<br>$^1$H-NMR (300 MHz, d6-DMSO): δ 14.38 (br s), 8.63 (d, 1H), 8.02 (d, 1H), 7.91 (m, 1H), 7.44 (m, 1H), 7.21-7.28 (m, 5H), 7.03-7.09 (m, 4H), 6.63 (d, 1H), 3.69 (m, 1H), 3.50-3.54 (m, 5H), 3.25 (m, 2H partially obscured by solvent), (s, 3H obscured by solvent), 0.95 (d, 6H) ppm. |
| 45.3 | 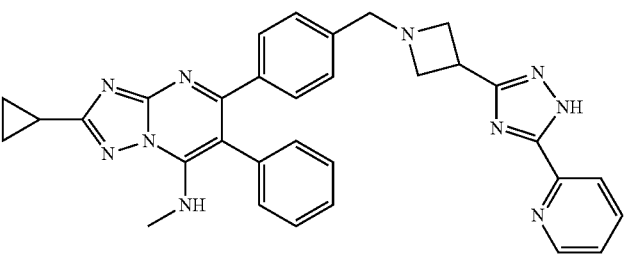<br>(2-cyclopropyl-6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidin-7-yl)-methyl-amine | UPLC-MS: RT = 0.81 min; m/z = 555.5;<br>$^1$H-NMR (300 MHz, d6-DMSO): δ 14.41 (br s), 8.63 (d, 1H), 8.01 (d, 1H), 7.91 (t, 1H), 7.56 (q, 1H), 7.44 (m, 1H), 7.19-7.24 (m, 5H), 7.02-7.08 (m, 4H), 3.69 (m, 1H), 3.50-3.54 (m, 4H), (d, 3H, obscured by solvent), (m, 2H partially obscured by solvent), 2.06-2.14 (m, 1H), 0.95-1.05 (m, 2H) ppm. |

Example 46.0

2-methyl-6-phenyl-5-(4-{4-[5-(6-trifluoromethyl-pyridin-2-yl)-1H-[1,2,4]triazol-3-yl]-piperidin-1-ylmethyl}-phenyl)-[1,2,4]triazolo[1,5-a]pyrimidine

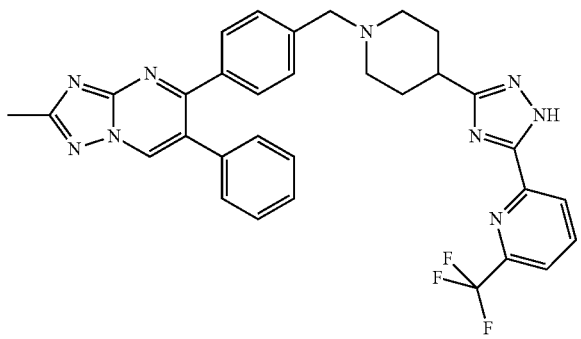 [SMILES: Cc1nc2nc(-c3ccc(CN4CCC(c5n[nH]c(-c6cccc(C(F)(F)F)n6)n5)CC4)cc3)c(-c3ccccc3)cn2n1]

A mixture of 4-(2-methyl-6-phenyl-[1,2,4]triazolo[1,5-a]pyrimidin-5-yl)benzaldehyde (300 mg, 0.95 mmol) and 2-(5-piperidin-4-yl-2H-[1,2,4]triazol-3-yl)-6-trifluoromethyl-pyridine hydrochloride salt (662 mg, 1.43 mmol) in NMP (8.1 mL) was treated with Et$_3$N (0.32 mL), followed by AcOH (98 µL) and the mixture was stirred overnight at rt. NaBH(OAc)$_3$ (222 mg) was added and the mixture stirred for 3 hours. The mixture was partitioned between CH$_2$Cl$_2$ and saturated aqueous NaHCO3 solution, the organic phase washed with brine and concentrated in vacuo. The crude product was purified by preparative HPLC to give the title compound.

MS (M+1): 596.41 (positive mode); 594.38 (negative mode)

UPLC-MS: RT=0.89 min; m/z=594.2 (ES−);

$^1$H-NMR (300 MHz, d6-DMSO): δ 14.09 (br s), 9.31 (s, 1H), 8.27 (d, 1H), 8.16 (t, 1H), 7.90 (d, 1H), 7.22-7.33 (m, 9H), 3.47 (s, 2H), 2.80-2.82 (m, 3H), 2.50 (s, 3H), 2.03-2.08 (m, 2H), 1.91 (m, 2H), 1.72-1.80 (m, 2H) ppm.

The following examples may be prepared in analogy to Example 46.0 by reacting the appropriate aldehyde intermediate with the appropriate amine intermediate.

| Example | Structure/Name | Analytical data |
|---|---|---|
| 46.1 | 2-methyl-6-phenyl-5-(4-{4-[5-(4-trifluoromethyl-pyridin-2-yl)-1H-[1,2,4]triazol-3-yl]-piperidin-1-ylmethyl}-phenyl)-[1,2,4]triazolo[1,5-a]pyrimidine | UPLC-MS: RT = 0.88 min; m/z = 594.3 (ES−); $^1$H-NMR (300 MHz, d6-DMSO): δ 9.31 (s, 1H), 8.91 (d, 1H), 8.18 (s, 1H), 7.80 (m, 1H), 7.21-7.33 (m, 9H), 3.47 (s, 2H), 2.79-2.82 (m, 3H), 2.51 (s, 3H), 2.03-2.10 (m, 2H), 1.91-1.95 (m, 2H), 1.73-1.81 (m, 2H) ppm. |
| 46.2 | 2,7-dimethyl-6-phenyl-5-(4-{4-[5-(4-trifluoromethyl-pyridin-2-yl)-1H-[1,2,4]triazol-3-yl]-piperidin-1-ylmethyl}-phenyl)-[1,2,4]triazolo[1,5-a]pyrimidine | UPLC-MS: RT = 0.93 min; m/z = 608.6 (ES−); $^1$H-NMR (300 MHz, d6-DMSO): δ 8.91 (d, 1H), 8.18 (s, 1H), 7.81 (br s, 1H), 7.32-7.34 (m, 3H), 7.20-7.22 (m, 4H), 7.15 (d, 2H), 3.43 (s, 2H), 2.76-2.79 (m, 3H), 2.54 (s, 3H), 2.53 (s, 3H), 2.01-2.06 (m, 2H), 1.90-1.93 (m, 2H), 1.70-1.78 (m, 2H) ppm. |

Example 47.0

5-(5-{1-[4-(2-methyl-6-phenyl-[1,2,4]triazolo[1,5-a]pyrimidin-5-yl)-benzyl]-piperidin-4-yl}-2H-[1,2,4]triazol-3-yl)-pyridin-2-ol

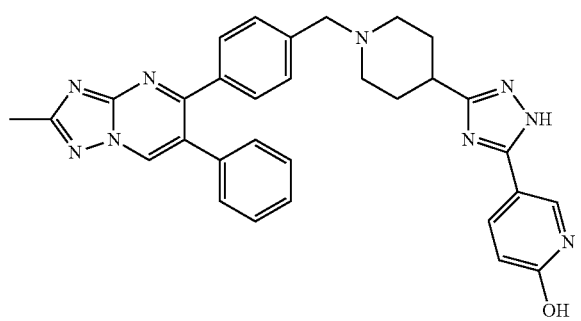 [SMILES: Cc1nc2nc(-c3ccc(CN4CCC(c5n[nH]c(-c6ccc(O)nc6)n5)CC4)cc3)c(-c3ccccc3)cn2n1]

A mixture of 4-(2-methyl-6-phenyl-[1,2,4]triazolo[1,5-a]pyrimidin-5-yl)benzaldehyde (293 mg, 1 mmol) and 2-methoxy-5-(5-piperidin-4-yl-2H-[1,2,4]triazol-3-yl)-pyridine (0.58 g) in CH$_2$Cl$_2$ (5 mL) and THF (23 mL) was treated with Ti(OiPr)$_4$ (0.82 mL) and stirred overnight at rt. The mixture was treated with NaBH(OAc)$_3$ (395 mg) and stirred for 2 hours at rt. The reaction was diluted with CH$_2$Cl$_2$ and water and filtered through Celite. The phases were separated and the organic phase was washed with brine. The Celite pad was washed with MeOH and the combined organic portions were concentrated in vacuo. Purification was achieved by preparative HPLC to give the title compound.

MS (M+1): 544 (positive mode); 542 (negative mode)

1H-NMR (400 MHz, d6-DMSO): δ 13.72 & 13.58 (br s, br s), 11.75 (br s), 9.35 (s, 1H), 7.85-7.95 (m, 2H), 7.25-7.36 (m, 9H), 6.41 (d, 1H), 3.49 (s, 2H), 2.67-2.84 (m, 3H), 2.06 (m, 2H), 1.89 (m, 2H), 1.75 (m, 2H).

Example 48.0

6-(2,6-difluorophenyl)-5-(4-{4-[5-(6-methylpyridine-2-yl)-1H-[1,2,4]triazole-3-yl]-piperidine-1-ylmethyl}-phenyl)-pyrazolo[1,5-a]pyrimidine-3-carboxylic acid methyl ester

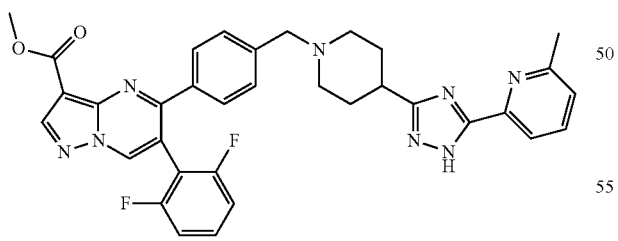

402 mg (1.27 mmol) 2-Methyl-6-(5-piperidine-4-yl-2H-[1,2,4]triazole-3-yl)-pyridine×2HCl are dissolved in 10 mL NMP. After addition of 0.43 mL triethylamine the reaction mixture is stirred for one hour. 500 mg (1.27 mmol) 6-(2,6-Difluorophenyl)-5-(4-formylphenyl)-pyrazolo[1,5-a]pyrimidine-3-carboxylic acid methyl ester and 0.13 mL acetic acid are added. The reaction mixture is stirred over night at room temperature. 296.3 mg (1.40 mmol) NaBH(OAc)$_3$ are added in portions and the reaction mixture is stirred at room temperature for 5 hours. After treatment of the reaction mixture with saturated NaHCO$_3$ the precipitate is filtered off, washed with water and dried. After chromatography of the precipitate on silica gel (dichloromethane/methanol) 368.6 mg (44.4%) of the desired product are obtained.

MS (Cl, M+1): 621

$^1$H-NMR (300 MHz, d6-DMSO): 13.65-14.20 (s, very br., 1H), 9.63 (s, 1H), 8.72 (s, 1H), 7.65-7.85 (m, 2H), 7.42-7.59 (m, 1H), 7.06-7.39 (m, 7H), 3.81 (s, 3H), 3.48 (s, 2H), 2.59-2.85 (m, 3H), 2.52 (s, 3H, partly under the signal of the solvent), 1.62-2.12 (m, 6H).

Example 48.1

6-(2,6-difluorophenyl)-5-(4-{4-[5-(pyridine-2-yl)-1H-[1,2,4]triazole-3-yl]-piperidine-1-ylmethyl}-phenyl)-pyrazolo[1,5-a]pyrimidine-3-carboxylic acid methyl ester

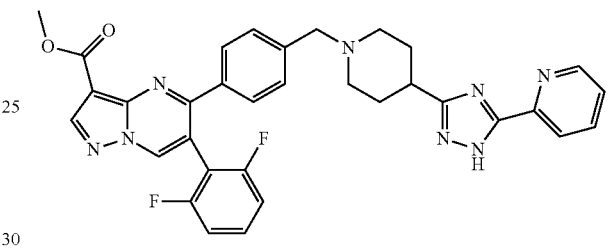

The title compound has been prepared in analogy to Example 48.0 by reductive amination with the appropriate amine intermediate.

MS (Cl, M+1): 607

$^1$H-NMR (400 MHz, d6-DMSO): 14.32 and 13.82 (br., 1H), 9.65 (s, 1H), 8.72 (s, 1H), 8.62 (br., 1H), 7.80-8.05 (m, 2H), 7.22-7.59 (m, 6H), 7.05-7.22 (m, 2H), 3.81 (s, 3H), 3.48 (s, 2H), 2.65-2.89 (m, 3H), 1.98-2.12 (m, 2H), 1.82-1.98 (m, 2H), 1.63-1.82 (m, 2H).

Example 49.0

6-(3-fluorophenyl)-2-methyl-5-(4-{4-[5-(6-methylpyridine-2-yl)-1H-[1,2,4]triazole-3-yl]-piperidine-1-ylmethyl}-phenyl)-[1,2,4]triazolo[1,5-a]pyrimidine

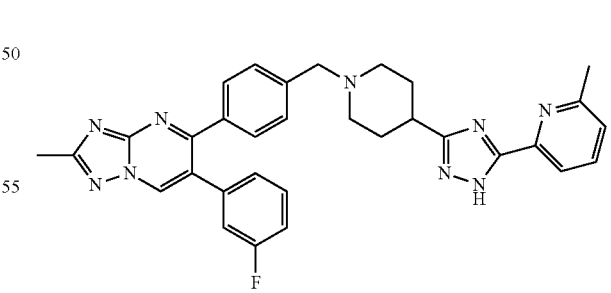

323 mg (1.02 mmol) 2-Methyl-6-(5-piperidine-4-yl-2H-[1,2,4]triazole-3-yl)-pyridine×2HCl are dissolved in 8.8 mL NMP. After addition of 0.34 mL triethylamine the reaction mixture is stirred for two hours. 340 mg (1.02 mmol) 4-[6-(3-Fluorophenyl)-2-methyl-[1,2,4]triazolo[1,5-a]pyrimidin-5-yl]-benzaldehyde and 0.1 mL acetic acid are added. The reaction mixture is stirred over night at room temperature.

251 mg (1.12 mmol) NaBH(OAc)₃, are added in portions and the reaction mixture is stirred at room temperature for 6 hours. The reaction mixture is treated with saturated NaHCO₃. The precipitate is filtered off, washed with water and dried. After purification by preparative HPLC 13.2 mg (2.3%) of the desired product are obtained.

¹H-NMR (400 MHz, d6-DMSO): 9.40 (s, 1H), 7.68-7.87 (m, 2H), 7.00-7.40 (m, 9H), 3.50 (s, 2H), 2.62-2.90 (m, 3H), 2.52 (s, 3H, under the signal of the solvent), 2.48 (s, 3H, under the signal of the solvent), 1.98-2.12 (m, 2H), 1.82-1.98 (m, 2H), 1.67-1.82 (m, 2H).

Example 49.1

6-(3-fluorophenyl)-2-methyl-5-{4-[4-(5-pyridine-2-yl)-1H-[1,2,4]triazole-3-yl)-piperidine-1-ylmethyl]-phenyl]-[1,2,4]triazolo[1,5-a]pyrimidine formiate

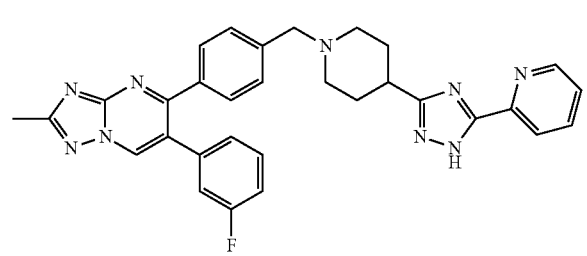 [SMILES: Cc1nc2nc(-c3ccc(CN4CCC(c5n[nH]c(-c6ccccn6)n5)CC4)cc3)c(-c3cccc(F)c3)cn2n1]

The title compound has been prepared in analogy to Example 49.0 by reductive amination with the appropriate amine intermediate.

¹H-NMR (400 MHz, d6-DMSO): 14.30 (br., 1H), 9.48 (s, 1H), 8.62 (d, 1H), 8.13 (formiate), 7.99 (d, 1H), 7.82-7.95 (m, 1H), 7.01-7.49 (m, 9H), 3.50 (s, 2H), 2.67-2.88 (m, 3H), 2.52 (s, 3H), 1.98-2.12 (m, 2H), 1.82-1.98 (m, 2H), 1.67-1.82 (m, 2H).

Example 50.0

5-(4-{4-[5-(4-chloropyridine-2-yl)-1H-[1,2,4]triazole-3-yl]-piperidine-1-ylmethyl}-phenyl) 6-(2,4-difluorophenyl)-2-methyl-[1,2,4]triazolo[1,5-a]pyrimidine

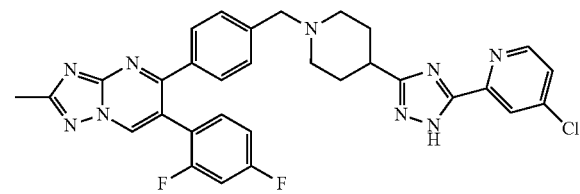 [SMILES: Cc1nc2nc(-c3ccc(CN4CCC(c5n[nH]c(-c6cc(Cl)ccn6)n5)CC4)cc3)c(-c3ccc(F)cc3F)cn2n1]

192 mg (0.57 mmol) 4-Chloro-2-(5-piperidine-4-yl-2H-[1,2,4]triazole-3-yl)-pyridine×2HCl are dissolved in 4.8 mL NMP. After addition of 0.19 mL triethylamine the reaction mixture is stirred for one hour. 200 mg (0.57 mmol) 4-[6-(2,4-Difluorophenyl)-2-methyl-[1,2,4]triazolo[1,5-a]pyrimidin-5-yl]-benzaldehyde and 0.06 mL acetic acid are added. The reaction mixture is stirred over night at room temperature. 133 mg (0.63 mmol) NaBH(OAc)₃, are added in portions and the reaction mixture is stirred at room temperature for 5 hours. The reaction mixture is treated with saturated NaHCO₃. The precipitate is filtered off, washed with water and dried. After chromatography of the precipitate on silica gel (dichloromethane/methanol) 99.1 mg (27.6%) of the desired product are obtained.

MS (Cl, M+1): 598

¹H-NMR (300 MHz, CDCl₃): 8.70 (s, 1H), 8.59 (d, 1H), 8.20 (d, 1H), 7.13-7.43 (m, 6H), 6.73-6.98 (m, 2H), 3.53 (s, 2H), 2.80-3.01 (m, 3H), 2.69 (s, 3H), 1.75-2.22 (m, 6H, partly under the water signal of the solvent).

Example 50.1

6-(2,4-difluorophenyl)-2-methyl-5-(4-{4-[5-(6-methylpyridine-2-yl)-1H-[1,2,4]triazole-3-yl]-piperidine-1-ylmethyl}-phenyl)-[1,2,4]triazolo[1,5-a]pyrimidine

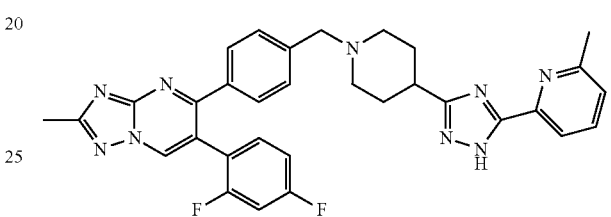

180 mg (0.57 mmol) 2-Methyl-6-(5-piperidine-4-yl-2H-[1,2,4]triazole-3-yl)-pyridine×2HCl are dissolved in 4.8 mL NMP. After addition of 0.19 mL triethylamine the reaction mixture is stirred for one hour. 200 mg (0.57 mmol) 4-[6-(2,4-Difluorophenyl)-2-methyl-[1,2,4]triazolo[1,5-a]pyrimidin-5-yl]-benzaldehyde and 0.06 mL acetic acid are added. The reaction mixture is stirred over night at room temperature. 133 mg (0.63 mmol) NaBH(OAc)₃, are added in portions and the reaction mixture is stirred at room temperature for 5 hours. The reaction mixture is treated with saturated NaHCO₃. The precipitate is filtered off, washed with water and dried. After chromatography of the precipitate on silica gel (dichloromethane/methanol) 99.7 mg (28.7%) of the desired product are obtained.

MS (Cl, M+1): 578

¹H-NMR (300 MHz, CDCl₃): 8.70 (s, 1H), 7.95 (d, 1H), 7.63-7.75 (m, 1H), 7.33-7.43 (m, 2H), 7.10-7.33 (m, 4H), 6.78-6.98 (m, 2H), 3.53 (s, 2H), 2.78-3.00 (m, 3H), 2.70 (s, 3H), 2.58 (s, 3H), 1.75-2.22 (m, 6H, partly under the water signal of the solvent).

Example 50.2

6-(2,4-difluorophenyl)-2-methyl-5-[4-{4-(5-pyrazine-2-yl-1H-[1,2,4]triazole-3-yl)-piperidine-1-ylmethyl]-phenyl}-[1,2,4]triazolo[1,5-a]pyrimidine

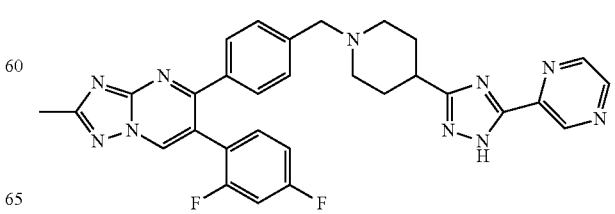

The title compound has been prepared in analogy to Example 50.0 by reductive amination with the appropriate amine intermediate.

MS (CI, M+1): 565

¹H-NMR (300 MHz, CDCl₃): 9.40 (s, 1H), 8.70 (s, 1H), 8.58-8.69 (m, 2H), 7.32-7.42 (m, 2H), 7.15-7.31 (m, 3H), 6.78-6.96 (m, 2H), 3.52 (s, 2H), 2.83-3.02 (m, 3H), 2.71 (s, 3H), 1.89-2.21 (m, 6H, partly under the water signal of the solvent).

Example 51.0

2-cyclopropyl-6-(4-fluorophenyl)-5-(4-{4-[5-(6-methylpyridine-2-yl)-1H-[1,2,4]triazole-3-yl]-piperidine-1-ylmethyl}-phenyl)-[1,2,4]triazolo[1,5-a]pyrimidine

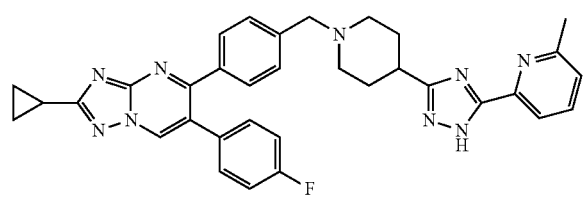 [SMILES: Cc1cccc(-c2nc(C3CCN(Cc4ccc(-c5nc6nc(C7CC7)nn6cc5-c5ccc(F)cc5)cc4)CC3)n[nH]2)n1]

154 mg (0.49 mmol) 2-Methyl-6-(5-piperidine-4-yl-2H-[1,2,4]triazole-3-yl)-pyridine×2HCl are dissolved in 4.2 mL NMP. After addition of 0.16 mL triethylamine the reaction mixture is stirred for one hour. 350 mg (50% pure) 2-Cyclopropyl-4-[6-(4-fluorophenyl)-[1,2,4]triazolo[1,5-a]pyrimidin-5-yl]-benzaldehyde and 0.05 mL acetic acid are added. The reaction mixture is stirred over night at room temperature. 113 mg (0.54 mmol) NaBH(OAc)₃, are added in portions and the reaction mixture is stirred at room temperature for 18 hours. The reaction mixture is treated with saturated NaHCO₃ and stirred for 20 minutes. The precipitate is filtered off, washed with water and dried. After chromatography of the precipitate on silica gel (dichloromethane/methanol) 192.2 mg (63.8%) of the desired product are obtained.

MS (CI, M+1): 586

¹H-NMR (400 MHz, CDCl₃): 8.63 (s, 1H), 7.97 (d, 1H), 7.68-7.75 (m, 1H), 7.38-7.46 (m, 2H), 7.12-7.32 (m, 5H), 6.98-7.10 (m, 2H), 3.55 (s, 2H), 2.80-3.02 (m, 3H), 2.61 (s, 3H), 1.80-2.30 (m, 7H, partly under the water signal of the solvent), 1.20-1.32 (m, 2H), 1.08-1.20 (m, 2H).

Example 51.1

2-cyclopropyl-6-(4-fluorophenyl)-5-{4-[4-(5-pyridine-2-yl-1H-[1,2,4]triazole-3-yl)-piperidine-1-ylmethyl]-phenyl}-[1,2,4]triazolo[1,5-a]pyrimidine

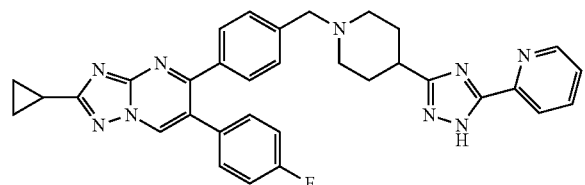

The title compound has been prepared in analogy to Example 51.0 by reductive amination with the appropriate amine intermediate.

MS (CI, M+1): 572

¹H-NMR (300 MHz, CDCl₃): 8.68 (d, 1H), 8.62 (s, 1H), 8.18 (d, 1H), 7.83 (dd, 1H), 7.31-7.48 (m, 3H), 7.21-7.31 (m, 2H), 7.10-7.21 (m, 2H), 6.96-7.10 (m, 2H), 3.53 (s, 2H), 2.80-3.05 (m, 3H), 1.85-2.30 (m, 7H, partly under the water signal of the solvent), 1.20-1.32 (m, 2H), 1.08-1.20 (m, 2H).

Example 51.2

5-(4-{4-[5-(4-chloropyridine-2-yl)-1H-[1,2,4]triazole-3-yl]-piperidine-1-ylmethyl}-phenyl)-2-cyclopropyl-6-(4-fluorophenyl)-[1,2,4]triazolo[1,5-a]pyrimidine

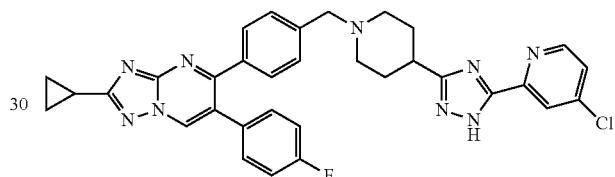

412 mg 4-Chloro-2-(5-piperidine-4-yl-2H-[1,2,4]triazole-3-yl)-pyridine×2HCl are dissolved in 7.2 mL NMP. After addition of 0.28 mL triethylamine the reaction mixture is stirred for one hour. 600 mg 2-Cyclopropyl-4-[6-(4-fluorophenyl)-[1,2,4]triazolo[1,5-a]pyrimidin-5-yl]-benzaldehyde (50% pure) and 0.09 mL acetic acid are added. The reaction mixture is stirred over night at room temperature. 191 mg (0.92 mmol) NaBH(OAc)₃, are added in portions and the reaction mixture is stirred at room temperature for three days. After treatment of the reaction mixture with saturated NaHCO₃ and stirring for one hour no solid precipitates. 200 mL tert.butyl-methylether are added and the mixture is stirred for one hour. After separation the organic phase is washed twice with water, dried and the solvent evaporated. Due to some remaining product in the aqueous phase this phase is extracted twice with tert.butyl-methylether (200 mL each). The combined organic phases are washed and dried. After removal of the solvent the residue is purified by chromatography on silica gel (dichloromethane/methanol). 134 mg (25.1%) of the pure product and additional 92.5 mg (18.2%) of the slightly contaminated product are obtained.

MS (CI, M+1): 606

¹H-NMR (400 MHz, CDCl₃): 8.63 (s, 1H), 8.58 (d, 1H), 8.20 (d, 1H), 7.30-7.43 (m, 3H), 7.21-7.32 (m, 2H), 7.13-7.21 (m, 2H), 6.99-7.10 (m, 2H), 3.53 (s, 2H), 2.82-3.01 (m, 3H), 1.80-2.30 (m, 7H, partly under the water signal of the solvent), 1.20-1.30 (m, 2H), 1.10-1.20 (m, 2H).

Example 52.0

6-(4-fluorophenyl)-7-(4-{4-[5-(6-methylpyridine-2-yl)-1H-[1,2,4]triazole-3-yl]-piperidine-1-ylmethyl}-phenyl)-imidazo[1,2-a]pyrimidine formiate

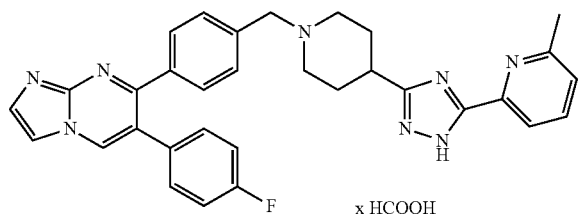 [SMILES: Cc1cccc(-c2nc(C3CCN(Cc4ccc(-c5nc6nccn6cc5-c5ccc(F)cc5)cc4)CC3)n[nH]2)n1]

x HCOOH 219 mg (0.69 mmol) 2-Methyl-6-(5-piperidine-4-yl-2H-[1,2,4]triazole-3-yl)-pyridine×2HCl are dissolved in 5.4 mL NMP. After addition of 0.2 mL triethylamine the reaction mixture is stirred for one hour. 200 mg (0.63 mmol) 4-[6-(4-Fluorophenyl)imidazo[1,2-a]pyrimidin-7-yl]-benzaldehyde and 0.06 mL acetic acid are added. The reaction mixture is stirred over night at room temperature. 147 mg (0.69 mmol) NaBH(OAc)$_3$, are added in portions and the reaction mixture is stirred at room temperature for 18 hours. The reaction mixture is treated with saturated NaHCO$_3$ and stirred for 20 minutes. The precipitate is filtered off, washed with water and dried. 233 mg (62.6%) of the desired product are obtained. 100 mg of this material are further purified by HPLC yielding 74.3 mg of the title compound as formiate.

MS (Cl, M+1): 545

$^1$H-NMR (300 MHz, d6-DMSO): 9.02 (s, 1H), 8.12 (s, 1H, formiate), 7.90 (d, 1H), 7.70-7.85 (m, 3H), 7.10-7.38 (m, 9H), 3.60 (s, 2H), 2.68-2.98 (m, 3H), 2.53 (s, 3H), 2.12-2.35 (m, 2H), 1.89-2.03 (m, 2H), 1.70-1.89 (m, 2H).

Example 52.1

6-(4-fluorophenyl)-7-{4-[4-(5-pyridine-2-yl)-1H-[1,2,4]triazole-3-yl)-piperidine-1-ylmethyl)-phenyl}-imidazo[1,2-a]pyrimidine formiate

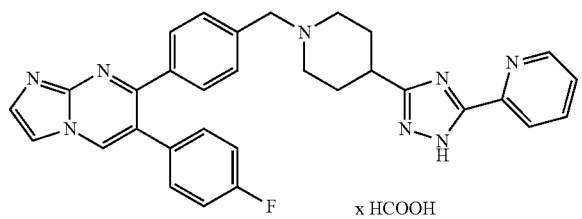 [SMILES: Fc1ccc(-c2cn3ccnc3nc2-c2ccc(CN3CCC(c4n[nH]c(-c5ccccn5)n4)CC3)cc2)cc1]

x HCOOH

The title compound has been prepared in analogy to Example 52.0 by reductive amination with the appropriate amine intermediate.

MS (Cl, M+1): 531

$^1$H-NMR (300 MHz, d6-DMSO): 9.02 (s, 1H), 8.62 (d, 1H), 8.10 (s, 1H, formiate), 8.01 (d, 1H), 7.85-7.96 (m, 2H), 7.79 (d, 1H), 7.43 (br., 1H), 7.10-7.35 (m, 8H), 3.58 (s, 2H), 2.69-2.93 (m, 3H), 2.09-2.29 (m, 2H), 1.89-2.03 (m, 2H), 1.70-1.89 (m, 2H).

Example 52.2

6-(4-fluorophenyl)-7-{4-[4-(5-pyrazine-2-yl-1H-[1,2,4]triazole-3-yl)-piperidine-1-ylmethyl]-phenyl}-imidazo[1,2-a]pyrimidine

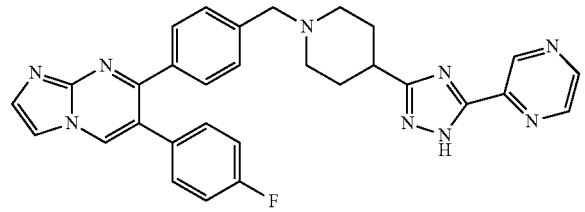 [SMILES: Fc1ccc(-c2cn3ccnc3nc2-c2ccc(CN3CCC(c4n[nH]c(-c5cnccn5)n4)CC3)cc2)cc1]

The title compound has been prepared in analogy to Example 52.0 by reductive amination with the appropriate amine intermediate.

MS (Cl, M+1): 532

$^1$H-NMR (300 MHz, d6-DMSO): 9.19 (d, 1H), 9.01 (s, 1H), 8.59-8.72 (m, 2H), 7.89 (d, 1H), 7.75 (d, 1H), 7.11-7.38 (m, 8H), 3.49 (s, 2H), 2.71-2.93 (m, 3H), 1.68-2.19 (m, 6H).

Example 53.0

3-bromo-6-(4-fluorophenyl)-7-(4-{4-[5-(6-methylpyridine-2-yl)-1H-[1,2,4]triazole-3-yl]-piperidine-1-ylmethyl}-phenyl)-imidazo[1,2-a]pyrimidine

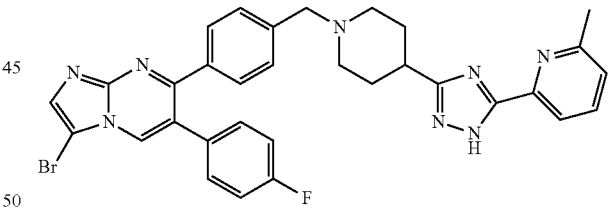

133 mg (0.24 mmol) 6-(4-fluorophenyl)-7-(4-{4-[5-(6-methylpyridine-2-yl)-1H-[1,2,4]triazole-3-yl]-piperidine-1-ylmethyl}-phenyl)-imidazo[1,2-a]pyrimidine are dissolved in 2.5 mL chloroform. After addition of 65.2 mg (0.37 mmol) N-bromosuccinimide the reaction mixture is heated for three hours at reflux. The solvent is evaporated and the residue purified by chromatography on silicagel (eluents: dichloromethane/methanol) yielding 97.5 mg (60.8%) of the desired product.

MS (ES+, M+1): 623/625

$^1$H-NMR (300 MHz, CDCl$_3$): 8.31 (s, 1H), 7.96 (d, 1H), 7.85 (s, 1H), 7.65-7.75 (m, 1H), 7.32-7.44 (m, 2H), 7.12-7.32 (m, 5H), 6.98-7.11 (m, 2H), 3.53 (s, 2H), 2.79-3.01 (m, 3H), 2.59 (s, 3H), 1.88-2.28 (m, 6H).

Example 53.1

3-chloro-6-(4-fluorophenyl)-7-{4-[4-(5-pyridine-2-yl-1H-[1,2,4]triazole-3-yl)-piperidine-1-ylmethyl]-phenyl}-imidazo[1,2-a]pyrimidine

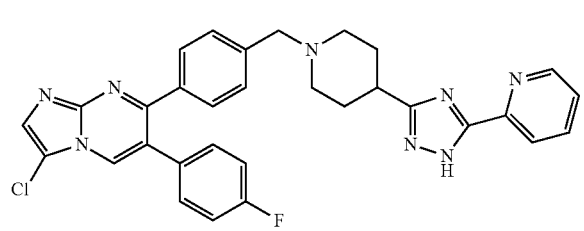 [SMILES: Fc1ccc(-c2cn3c(Cl)cnc3nc2-c2ccc(CN3CCC(c4n[nH]c(-c5ccccn5)n4)CC3)cc2)cc1]

The title compound has been prepared in analogy to Example 53.0 by reaction of the appropriate starting material with N-chlorosuccinimide.

MS (Cl, M+1): 565/567

$^1$H-NMR (300 MHz, CDCl$_3$): 8.68 (d, 1H), 8.30 (s, 1H), 8.15 (d, 1H), 7.72-7.90 (m, 2H), 6.90-7.49 (m, 9H), 3.68 (s, 2H), 2.80-3.11 (m, 3H), 1.91-2.40 (m, 6H).

Example 54.0

6-(2-fluorophenyl)-7-(4-{4-[5-(6-methylpyridine-2-yl)-1H-[1,2,4]triazole-3-yl]-piperidine-1-ylmethyl}-phenyl)-imidazo[1,2-a]pyrimidine

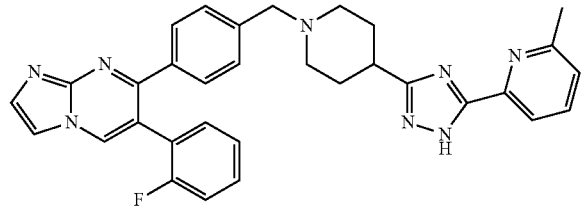 [SMILES: Cc1cccc(-c2nc(C3CCN(Cc4ccc(-c5nc6nccn6cc5-c5ccccc5F)cc4)CC3)n[nH]2)n1]

398.6 mg (1.26 mmol) 2-Methyl-6-(5-piperidine-4-yl-2H-[1,2,4]triazole-3-yl)pyridine×2HCl are dissolved in 10.9 mL NMP. After addition of 0.42 mL triethylamine the reaction mixture is stirred for one hour. 400 mg (1.26 mmol) 4-[6-(2-Fluorophenyl)-imidazo[1,2-a]pyrimidin-7-yl]-benzaldehyde and 0.13 mL acetic acid are added. The reaction mixture is stirred over night at room temperature. 293.9 mg (1.39 mmol) NaBH(OAc)$_3$, are added in portions and the reaction mixture is stirred at room temperature for 22 hours. The reaction mixture is treated with saturated NaHCO$_3$ and stirred for 60 minutes. The precipitate is filtered off, washed with water, dried and purified by HPLC yielding 139.1 mg (19.3%) of the title compound.

MS (Cl, M+1): 545

$^1$H-NMR (400 MHz, CDCl$_3$): 8.45 (s, 1H), 7.83-8.01 (m, 2H), 7.65-7.78 (m, 1H), 7.61 (s, 1H), 6.98-7.50 (m, 9H), 3.53 (s, 2H), 2.80-3.05 (m, 3H), 2.62 (s, 3H), 1.85-2.25, (m, 6H).

Example 55.0

3-bromo-6-phenyl-7-{4-{3-[5-(pyridine-2-yl)-1H-[1,2,4]triazole-3-yl]-azetidine-1-ylmethyl]-phenyl}-imidazo[1,2-a]pyrimidine

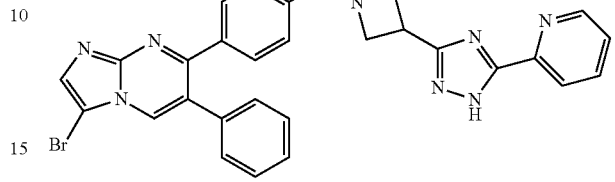

143 mg (0.3 mmol) 6-Phenyl-7-{4-{3-[5-(pyridine-2-yl)-1H-[1,2,4]triazole-3-yl)azetidine-1-ylmethyl]-phenyl}-imidazo[1,2-a]pyrimidine are dissolved in 11.8 mL chloroform. 57.8 mg (0.3 mmol) N-bromosuccinimide are added and the reaction mixture is heated for one hour at reflux. The solvent is evaporated and the residue is purified by chromatography (silicagel, eluents: dichloromethane/methanol). 19.1 mg (10%) pure compound and 75.8 mg (41%) slightly contaminated product are obtained.

MS (ES+, M+1): 563/565

$^1$H-NMR (400 MHz, CDCl$_3$): 8.69 (d, 1H), 8.36 (s, 1H), 8.19 (d, 1H), 7.80-7.92 (m, 2H), 7.12-7.49 (m, 9H), 3.92-4.08 (m, 1H), 3.70-3.91 (m, 4H), 3.52-3.65 (m, 2H).

Example 56.0

2-methyl-6-phenyl-7-{4-{3-[5-(pyridine-2-yl)-1H-[1,2,4]triazole-3-yl)-azetidine-1-ylmethyl]-phenyl}-imidazo[1,2-a]pyrimidine

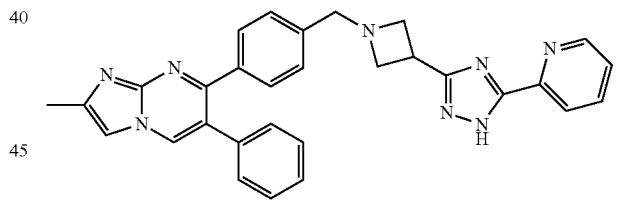

418.6 mg (1.53 mmol) 2-(5-Azetidine-3-yl-[1,2,4]triazole-3-yl)-pyridine×2HCl are dissolved in 12 mL NMP. After addition of 0.43 mL (3.05 mmol) triethylamine the reaction mixture is stirred for one hour. 435 mg (1.38 mmol) 4-(2-Methyl-6-phenyl-imidazo[1,2-a]pyrimidin-7-yl)-benzaldehyde and 0.19 mL acetic acid are added. The reaction mixture is stirred over night at room temperature. 706.1 mg (3.33 mmol) NaBH(OAc)$_3$, are added in portions and the reaction mixture is stirred at room temperature over the weekend. The reaction mixture is treated with saturated NaHCO$_3$ and stirred for two hours. The precipitate is filtered off, washed with water, dried and purified by chromatography (silicagel, eluents: dichloromethane/methanol) yielding 182.1 mg (24%) of the title compound.

MS (ES+, M+1): 499

$^1$H-NMR (400 MHz, d6-DMSO): 8.90 (s, 1H), 8.64 (d, 1H), 8.02 (d, 1H), 7.91 (br., 1H), 7.47 (br., 1H), 7.12-7.38 (m, 10H), 3.72 (br., 1H), 3.53-3.68 (m, 4H), 3.25-3.40 (m, 2H, under the water signal of the solvent), 2.39 (s, 3H).

Example 57.0

3-bromo-2-methyl-7-{4-{3-[5-(6-methylpyridine-2-yl)-1H-[1,2,4]triazole-3-yl)-azetidine-1-ylmethyl]-phenyl}-6-phenyl-imidazo[1,2-a]pyrimidine

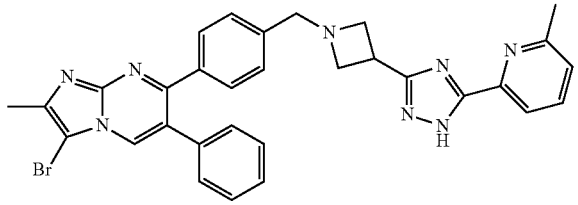 [SMILES: Cc1cccc(-c2nc(C3CN(Cc4ccc(-c5nc6nc(C)c(Br)n6cc5-c5ccccc5)cc4)C3)n[nH]2)n1]

50 mg (0.098 mmol) 2-Methyl-7-{4-{3-[5-(6-methylpyridine-2-yl)-1H-[1,2,4]triazole-3-yl)-azetidine-1-ylmethyl]-phenyl}-6-phenyl-imidazo[1,2-a]pyrimidine are dissolved in 3.9 mL chloroform. 19.1 mg (0.11 mmol) N-bromosuccinimide are added and the reaction mixture is heated for one hour at reflux. The solvent is evaporated and the residue is purified by chromatography (silicagel, eluents: dichloromethane/methanol). 19.1 mg (31.5%) of the desired compound are obtained.

MS (ES+, M+1): 591/593

$^1$H-NMR (400 MHz, d6-DMSO): 8.49 (s, 1H), 7.74-7.88 (br., 2H), 7.18-7.38 (m, 10H), 3.50-3.80 (m, 5H), 3.23-3.90 (m, 2H, under the water signal of the solvent), 2.52 (s, 3H), 2.40 (s, 3H).

Example 58.0 methyl-(6-phenyl-7-{4-{3-[5-(pyridine-2-yl)-1H-[1,2,4]triazole-3-yl)-azetidine-1-ylmethyl]-phenyl}-imidazo[1,2-a]pyrimidin-5-yl)-amine

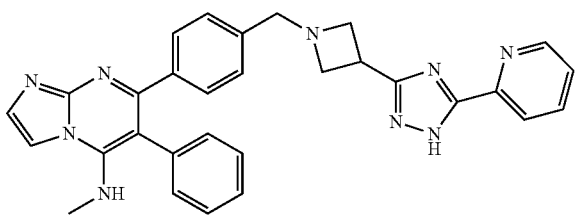 [SMILES: CNc1c(-c2ccccc2)c(-c2ccc(CN3CC(c4n[nH]c(-c5ccccn5)n4)C3)cc2)nc2nccn12]

257 mg (0.94 mmol) 2-(5-Azetidine-3-yl-[1,2,4]triazole-3-yl)-pyridine×2HCl are dissolved in 7.3 mL NMP. After addition of 0.26 mL (1.88 mmol) triethylamine the reaction mixture is stirred for one hour. 280 mg (0.85 mmol) 4-(5-Methylamino-6-phenyl-imidazo[1,2-a]pyrimidin-7-yl)-benzaldehyde and 0.12 mL (2.05 mmol) acetic acid are added. The reaction mixture is stirred for 24 hours at room temperature. 469.9 mg (2.2 mmol) NaBH(OAc)$_3$, are added in portions and the reaction mixture is stirred at room temperature over night. The reaction mixture is treated with saturated NaHCO$_3$. The precipitate is filtered off, washed with water, dried and purified by chromatography (silicagel, eluents: dichloromethane/methanol) yielding 163 mg (33.5%) of the desired title compound.

MS (ES+, M+1): 514

$^1$H-NMR (400 MHz, d6-DMSO): 14.45 (br., 1H), 8.63 (br., 1H), 8.02 (d, 1H), 7.85-8.00 (br. with d, 2H), 7.60 (d, 1H), 7.48 (br., 1H), 7.13-7.22 (m, 5H), 6.99-7.13 (m, 4H), 3.69 (br., 1H), 3.45-3.60 (m, 4H), 3.20-3.35 (m, 2H, under the water signal of the solvent), 2.32 (d, 3H).

Example 59.0

(3-bromo-6-phenyl-7-{4-{3-[5-(pyridine-2-yl)-1H-[1,2,4]triazole-3-yl)-azetidine-1-ylmethyl]-phenyl}-imidazo[1,2-a]pyrimidin-5-yl)-methylamine

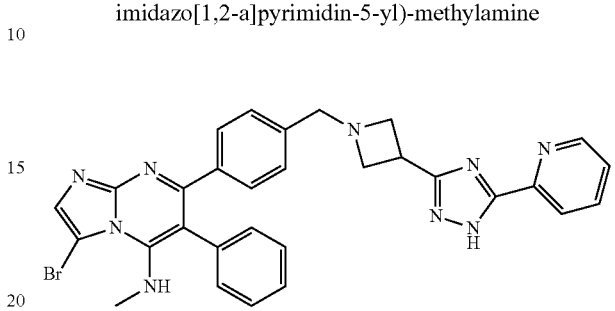

50 mg (0.097 mmol) Methyl-(6-phenyl-7-{4-{3-[5-(pyridine-2-yl)-1H-[1,2,4]triazole-3-yl)-azetidine-1-ylmethyl]-phenyl}-imidazo[1,2-a]pyrimidin-5-yl)-amine are dissolved in 3.9 mL chloroform. 19.1 mg (0.11 mmol) N-bromosuccinimide are added and the reaction mixture is heated for one hour at reflux. The solvent is evaporated and the residue purified by chromatography (silicagel, eluents: dichloromethane/methanol). 15 mg (24.7%) of the desired compound are obtained.

MS (ES-): 590/592

$^1$H-NMR (400 MHz, CD$_3$OD): 8.65 (d, 1H), 8.10 (d, 1H), 7.92 (m, 1H), 7.68 (s, 1H), 7.42-7.49 (m, 1H), 7.12-7.28 (m, 9H), 3.82-3.91 (m, 1H), 3.65-3.78 (m, 4H), 3.50-3.60 (m, 2H), 2.42 (s, 3H).

Example 60.0 methyl-(2-methyl-6-phenyl-7-{4-{3-[5-(pyridine-2-yl)-1H-[1,2,4]triazole-3-yl)-azetidine-1-ylmethyl]-phenyl}-imidazo[1,2-a]pyrimidin-5-yl)-amine

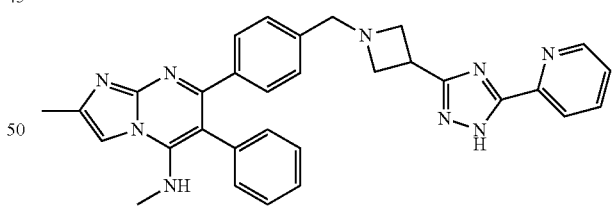

237.8 mg (0.87 mmol) 2-(5-Azetidine-3-yl-[1,2,4]triazole-3-yl)-pyridine×2HCl are dissolved in 6.8 mL NMP. 0.24 mL (1.74 mmol) triethylamine are added and the reaction mixture is stirred for one hour. 270 mg (0.79 mmol) 4-(2-Methyl-5-methylamino-6-phenyl-imidazo[1,2-a]pyrimidin-7-yl)-benzaldehyde and 0.11 mL (1.89 mmol) acetic acid are added. The reaction mixture is stirred for two days at room temperature. 401.1 mg (1.89 mmol) NaBH(OAc)$_3$, are added in portions and the reaction mixture is stirred at room temperature for 9 days. After the usual work-up and purification by HPLC 29.6 mg (7.1%) of the desired title compound are obtained.

MS (ES+, M+1): 528

$^1$H-NMR (300 MHz, CD$_3$OD): 8.68 (d, 1H), 8.10 (d, 1H), 7.89-7.98 (m, 1H), 7.58 (s, 1H), 7.40-7.50 (m, 1H), 7.13-7.30 (m, 9H), 3.82-4.05 (m, 5H), 3.70-3.82 (m, 2H), 2.53 (s, 3H), 2.45 (s, 3H).

Example 61.0 methyl-(2-methyl-7-{4-{3-[5-(6-methylpyridine-2-yl)-1H-[1,2,4]triazole-3-yl]-azetidine-1-ylmethyl]-phenyl}-6-phenyl-imidazo[1,2-a]pyrimidin-5-yl)-amine

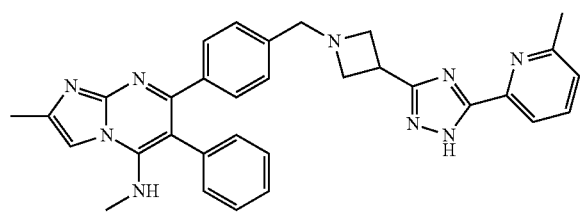 [SMILES: CNc1c(-c2ccccc2)c(-c2ccc(CN3CC(c4n[nH]c(-c5cccc(C)n5)n4)C3)cc2)nc2nc(C)cn12]

The compound is prepared in analogy to example 60. 416 mg 2-(5-Azetidine-3-yl-[1,2,4]triazole-3-yl)-6-methylpyridine×2HCl (60% pure) are reacted with 270 mg (0.79 mmol) 4-(2-methyl-5-methylamino-6-phenyl-imidazo[1,2-a]pyrimidin-7-yl)benzaldehyde to yield finally after HPLC purification 88.3 mg (20.7%) of the expected compound.

MS (ES+, M+1): 542

$^1$H-NMR (300 MHz, CD$_3$OD): 7.89 (d, 1H), 7.80 (dd, 1H), 7.59 (s, 1H), 7.32 (d, 1H), 7.15-7.29 (m, 9H), 3.88-4.01 (m, 5H), 3.75-3.86 (m, 2H), 2.61 (s, 3H), 2.52 (s, 3H), 2.42 (s, 3H).

Examples 62.0 and 63.0

(6-(2,6-difluorophenyl)-5-{4-[3-[5-pyridine-2-yl-1H-[1,2,4]triazole-3-yl)-azetidine-1-ylmethyl]-phenyl}-pyrazolo[1,5-a]pyrimidin-3-yl)-methanol and (6-(2,6-difluorophenyl)-2-methoxy-5-{4-[3-[5-pyridine-2-yl-1H-[1,2,4]triazole-3-yl)-azetidine-1-ylmethyl]-phenyl}-pyrazolo[1,5-a]pyrimidin-3-yl)-methanol

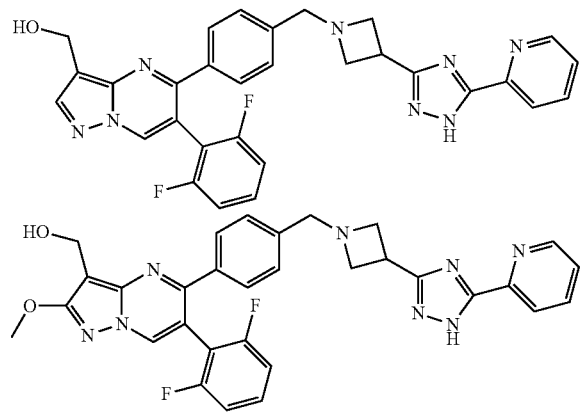

240 mg (0.42 mmol) 6-(2,6-difluorophenyl)-5-(4-{3-[5-(pyridine-2-yl)-1H-[1,2,4]triazole-3-yl]-azetidine-1-ylmethyl}-phenyl)-pyrazolo[1,5-a]pyrimidin-3-carboxylic acid methyl ester (example 28) are dissolved in 8.3 mL diethylether/tetrahydrofuran. 15.7 mg (0.42 mmol) LiAlH$_4$ are added and the reaction mixture is stirred at room temperature over night. Additional 10 mg LiAlH$_4$ are added and stirring is continued for 5 hours. The reaction mixture is treated with saturated NaHCO$_3$ and extracted three times with methyl-tert. butylether. The combined organic extracts are washed with brine, dried and after evaporation of the solvent purified by HPLC. 1 mg (0.4%) of the methanol- and 53.8 mg (21.2%) of the 2-methoxy-methanol derivative are obtained.

Methanol Derivative:

$^1$H-NMR (400 MHz, CD$_3$OD): 9.01 (s, 1H), 8.69 (d, 1H), 8.29 (s, 1H), 8.09 (d, 1H), 7.89-7.98 (m, 1H), 7.35-7.50 (m, 4H), 7.28-7.34 (m, 2H), 6.92-7.05 (m, 2H), 4.92 (s, 2H), 3.85-3.99 (m, 1H), 3.69-3.83 (m, 4H), 3.52-3.66 (m, 2H).

Methoxy-Methanol Derivative:

MS (ES+, M+1): 581

$^1$H-NMR (300 MHz, d6-DMSO): 14.40 (br., 1H), 8.65 (d, 1H), 8.53 (s, 1H), 8.03 (d, 1H), 7.85-7.98 (m, 1H), 7.78 (s, 1H), 7.39-7.50 (m, 1H), 7.20-7.35 (m, 1H), 7.05-7.20 (m, 4H), 6.89-7.01 (m, 2H), 4.90 (s, 2H), 3.62-3.78 (m with s, 4H), 3.50-3.62 (m, 4H), 3.20-3.40 (m, 2H, water signal of the solvent influences the integration).

Example 63.1

[6-(2,6-difluorophenyl)-2-methoxy-5-(4-{3-[5-(6-methylpyridine-2-yl)-1H-[1,2,4]triazole-3-yl]-azetidine-1-ylmethyl}-phenyl)-pyrazolo[1,5-a]pyrimidin-3-yl)-methanol

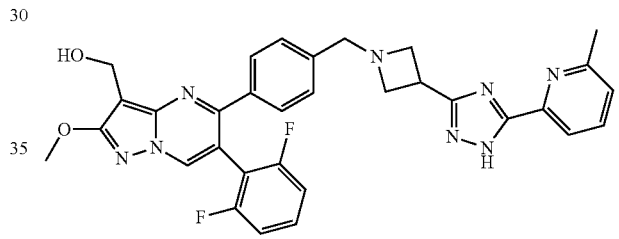

The title compound has been prepared in analogy to Example 63.0 by reductive amination with the appropriate amine intermediate.

MS (ES+, M+1): 595

$^1$H-NMR (400 MHz, d6-DMSO): 14.30 (br., 1H), 8.55 (s, 1H), 7.71-7.87 (m, 3H), 7.22-7.38 (m, 2H), 7.04-7.21 (m, 4H), 6.90-7.01 (m, 2H), 4.90 (s, 2H), 3.62-3.78 (m, 4H), 3.49-3.60 (m, 4H), 3.20-3.40 (m, 2H, water signal of the solvent influences the integration), 2.52 (s, 3H).

Example 63.2

[6-(2,6-difluorophenyl)-2-methoxy-5-(4-{4-[5-(6-methylpyridine-2-yl)-1H-[1,2,4]triazole-3-yl]-piperidine-1-ylmethyl}-phenyl)-pyrazolo[1,5-a]pyrimidin-3-yl)-methanol

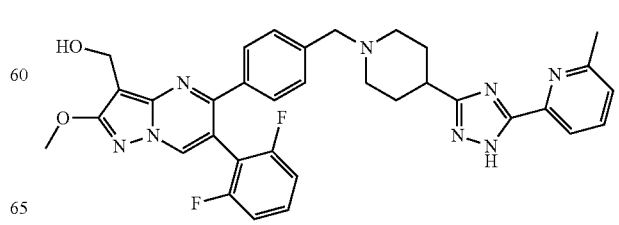

The title compound has been prepared in analogy to Example 63.0 by reductive amination with the appropriate amine intermediate.

¹H-NMR (400 MHz, d6-DMSO): 14.18 (br., 1H), 8.59 (s, 1H), 7.73-7.83 (m, 3H), 7.22-7.34 (m, 2H), 7.10-7.21 (m, 4H), 6.90-7.00 (m, 2H), 4.92 (s, 2H), 3.70 (s, 3H), 3.40 (s, 2H), 2.68-2.82 (m, 3H), 2.52 (s, 3H, under the signal of the solvent), 1.95-2.08 (m, 2H), 1.83-1.95 (m, 2H), 1.63-1.82 (m, 2H).

Example 63.3

(6-(2,6-difluorophenyl)-2-methoxy-5-{4-[4-(5-pyridine-2-yl-1H-[1,2,4]triazole-3-yl)-piperidine-1-ylmethyl]-phenyl}-pyrazolo[1,5-a]pyrimidin-3-yl)-methanol

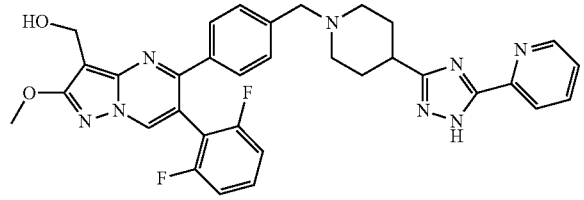 [SMILES: COc1nn2cc(-c3c(F)cccc3F)c(-c3ccc(CN4CCC(c5n[nH]c(-c6ccccn6)n5)CC4)cc3)nc2c1CO]

The title compound has been prepared in analogy to Example 63.0 by reductive amination with the appropriate amine intermediate.

MS (ES+, M+1): 609

¹H-NMR (400 MHz, d6-DMSO): 14.33 and 13.82 (br., 1H), 8.55-8.70 (m, 2H), 7.73-8.03 (m, 3H), 7.35-7.52 (m, 1H), 7.21-7.35 (m, 1H), 7.05-7.23 (m, 4H), 6.89-7.01 (m, 2H), 4.92 (s, 2H), 3.69 (s, 3H), 3.42 (s, 2H), 2.68-2.82 (m, 3H), 1.95-2.11 (m, 2H), 1.82-1.95 (m, 2H), 1.64-1.80 (m, 2H).

Example 64.0 isopropyl-(2-methyl-6-phenyl-7-{4-{3-[5-(pyridine-2-yl)-1H-[1,2,4]triazole-3-yl)-azetidine-1-ylmethyl]-phenyl}-imidazo[1,2-a]pyrimidin-5-yl)-amine

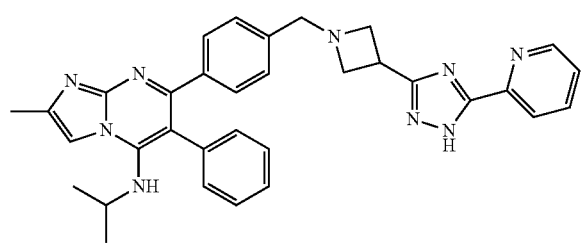 [SMILES: Cc1cn2c(NC(C)C)c(-c3ccccc3)c(-c3ccc(CN4CC(c5n[nH]c(-c6ccccn6)n5)C4)cc3)nc2n1]

227.9 mg (0.83 mmol) 2-(5-Azetidine-3-yl-[1,2,4]triazole-3-yl)-pyridine×2HCl are dissolved in 6.5 mL NMP. 0.25 mL (1.8 mmol) triethylamine are added and the reaction mixture is stirred for one hour. 280 mg (0.76 mmol) 4-(2-Methyl-5-isopropylamino-6-phenyl-imidazo[1,2-a]pyrimidin-7-yl)-benzaldehyde and 0.08 mL (1.36 mmol) acetic acid are added. The reaction mixture is stirred for three days at room temperature. 176.2 mg (0.83 mmol) NaBH(OAc)₃, are added in portions and the reaction mixture is stirred at room temperature for 18 hours. Additional 88 mg NaBH(OAc)₃ are added and stirring is continued for 26 hours. After the usual work-up and purification by column chromatography and by HPLC 4.9 mg (1.1%) of the desired title compound are obtained.

MS (ES+): 556

¹H-NMR (300 MHz, CD₃OD): 8.66 (d, 1H), 8.09 (d, 1H), 7.89-7.98 (m, 1H), 7.72 (s, 1H), 7.40-7.50 (m, 1H), 7.12-7.34 (m, 9H), 3.86-3.99 (m, 1H), 3.71-3.86 (m, 4H), 3.57-3.70 (m, 2H), 3.40 (sep., 1H), 2.43 (s, 3H), 1.00 (d, 6H).

Example 65.0 isopropyl-(2-methyl-6-phenyl-7-{4-{3-[5-(6-methylpyridine-2-yl)-1H-[1,2,4]triazole-3-yl)-azetidine-1-ylmethyl]-phenyl}-imidazo[1,2-a]pyrimidin-5-yl)-amine

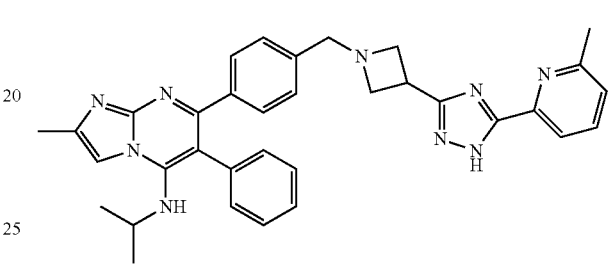

The compound is prepared in analogy to example 64. 399.3 mg 2-(5-Azetidine-3-yl-[1,2,4]triazole-3-yl)-6-methylpyridine×2HCl (60% pure) are reacted with 280 mg (0.76 mmol) 4-(2-methyl-5-isopropylamino-6-phenyl-imidazo[1,2-a]pyrimidin-7-yl)-benzaldehyde to yield finally after HPLC purification 10.4 mg (2.34%) of the desired compound.

MS (ES+, M+1): 570

¹H-NMR (300 MHz, CDCl₃): 7.96 (d, 1H), 7.71 (dd, 1H), 7.03-7.42 (m, 11H), 4.25 (1H), 3.70-4.10 (m, 6H), 3.53-3.70 (m, 2H), 2.59 (s, 3H), 2.52 (s, 3H), 1.03 (d, 6H).

Example 66.0 isopropyl-(6-phenyl-7-{4-{3-[5-(pyridine-2-yl)-1H-[1,2,4]triazole-3-yl)-azetidine-1-ylmethyl]-phenyl}-imidazo[1,2-a]pyrimidin-5-yl)-amine

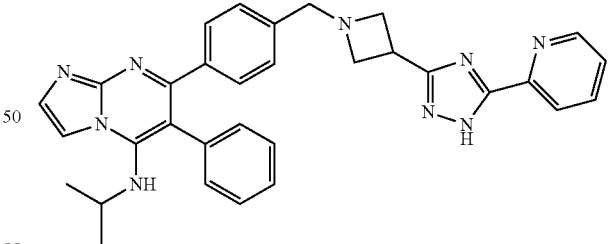

253.8 mg (0.93 mmol) 2-(5-Azetidine-3-yl-[1,2,4]triazole-3-yl)-pyridine×2HCl are dissolved in 7.2 mL NMP. 0.26 mL (1.85 mmol) triethylamine are added and the reaction mixture is stirred for one hour. 300 mg (0.84 mmol) 4-(5-Isopropylamino-6-phenyl-imidazo[1,2-a]pyrimidin-7-yl)-benzaldehyde and 0.12 mL (2.02 mmol) acetic acid are added. The reaction mixture is stirred for 24 hours at room temperature. 463.8 mg (2.2 mmol) NaBH(OAc)₃, are added in portions and the reaction mixture is stirred at room temperature over night. After the usual work-up and purification by column chromatography (silicagel, eluents: dichloromethane/methanol) 132 mg (27.5%) of the pure title compound and 42 mg (9.2%) of the slightly contaminated title compound are obtained.

$^1$H-NMR (400 MHz, d6-DMSO): 8.65 (br., 1H), 8.16 (d, 1H), 8.02 (d, 1H), 7.91 (br., 1H), 7.62 (s, 1H), 7.45 (br., 1H), 7.12-7.30 (m, 5H), 6.97-7.10 (m, 4H), 6.16 (d, 1H), 3.70 (br., 1H), 3.48-3.51 (m, 4H), 3.22-3.38 (m, 2H, under the water signal of the solvent), 3.03 (sep., 1H), 0.90 (d, 6H).

Example 67.0 methyl-(6-phenyl-2-pyridine-2-yl-5-{4-[3-[5-pyridine-2-yl)-1H-[1,2,4]triazole-3-yl)-azetidine-1-ylmethyl]-phenyl}-[1,2,4]triazolo[1,5-a]pyrimidin-7-yl)-amine

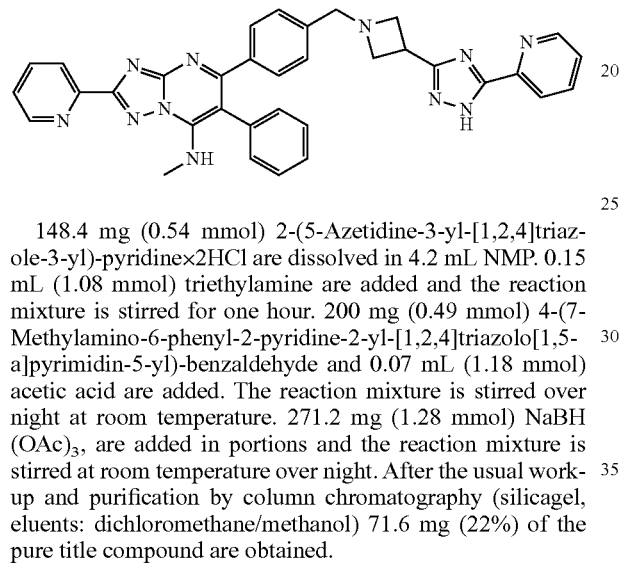

148.4 mg (0.54 mmol) 2-(5-Azetidine-3-yl-[1,2,4]triazole-3-yl)-pyridine×2HCl are dissolved in 4.2 mL NMP. 0.15 mL (1.08 mmol) triethylamine are added and the reaction mixture is stirred for one hour. 200 mg (0.49 mmol) 4-(7-Methylamino-6-phenyl-2-pyridine-2-yl-[1,2,4]triazolo[1,5-a]pyrimidin-5-yl)-benzaldehyde and 0.07 mL (1.18 mmol) acetic acid are added. The reaction mixture is stirred over night at room temperature. 271.2 mg (1.28 mmol) NaBH(OAc)$_3$, are added in portions and the reaction mixture is stirred at room temperature over night. After the usual work-up and purification by column chromatography (silicagel, eluents: dichloromethane/methanol) 71.6 mg (22%) of the pure title compound are obtained.

MS (Cl, M+1): 592
$^1$H-NMR (300 MHz, CDCl$_3$): 8.80 (d, 1H), 8.69 (d, 1H), 8.50 (d, 1H), 8.20 (d, 1H), 7.78-7.95 (m, 2H), 7.05-7.50 (m, 11H), 6.70 (q, 1H), 3.90-4.10 (m, 1H), 3.63-3.85 (m, 4H), 3.45-3.60 (m, 2H), 2.59 (d, 3H).

Example 68.0 isopropyl-(6-phenyl-2-pyridine-2-yl-5-{4-[3-[5-pyridine-2-yl)-1H-[1,2,4]triazole-3-yl)-azetidine-1-ylmethyl]-phenyl}-[1,2,4]triazolo[1,5-a]pyrimidin-7-yl)-amine

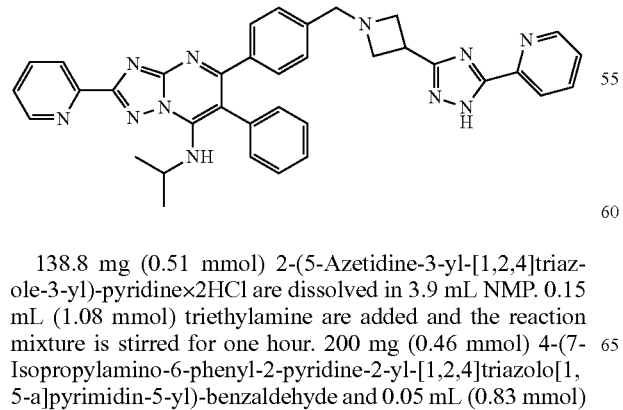

138.8 mg (0.51 mmol) 2-(5-Azetidine-3-yl-[1,2,4]triazole-3-yl)-pyridine×2HCl are dissolved in 3.9 mL NMP. 0.15 mL (1.08 mmol) triethylamine are added and the reaction mixture is stirred for one hour. 200 mg (0.46 mmol) 4-(7-Isopropylamino-6-phenyl-2-pyridine-2-yl-[1,2,4]triazolo[1,5-a]pyrimidin-5-yl)-benzaldehyde and 0.05 mL (0.83 mmol) acetic acid are added. The reaction mixture is stirred over night at room temperature. 107 mg (0.51 mmol) NaBH(OAc)$_3$, are added in portions and the reaction mixture is stirred at room temperature over night. After the usual work-up and purification by column chromatography (silicagel, eluents: dichloromethane/methanol) 87.2 mg (30.6%) of the pure title compound are obtained.

MS (ES+, M+1): 620
$^1$H-NMR (300 MHz, CD$_3$OD): 8.75 (d, 1H), 8.69 (d, 1H), 8.40 (d, 1H), 8.10 (d, 1H), 8.05 (dd, 1H), 7.95 (dd, 1H), 7.50-7.61 (m, 1H), 7.40-7.50 (m, 1H), 7.12-7.38 (m, 9H), 3.94 (hep, 1H), 3.54-3.82 (m, 7H), 1.09 (d, 6H).

Example 69.0 isopropyl-(6-phenyl-2-pyridine-2-yl-5-{4-[3-[5-(6-methylpyridine-2-yl)-1H-[1,2,4]triazole-3-yl)-azetidine-1-ylmethyl]-phenyl}-[1,2,4]triazolo[1,5-a]pyrimidin-7-yl)-amine

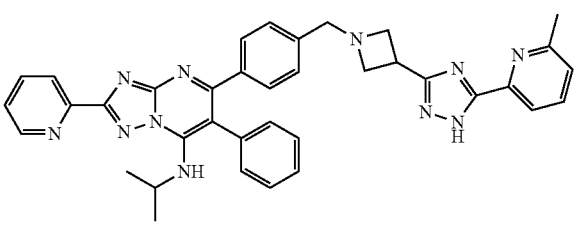 [SMILES: Cc1cccc(-c2nc(C3CN(Cc4ccc(-c5nc6nc(-c7ccccn7)nn6c(NC(C)C)c5-c5ccccc5)cc4)C3)n[nH]2)n1]

138.8 mg (0.51 mmol) 2-(5-Azetidine-3-yl-[1,2,4]triazole-3-yl)-6-methylpyridine×2HCl (60% pure) are dissolved in 3.9 mL NMP. 0.15 mL (1.08 mmol) triethylamine are added and the reaction mixture is stirred for one hour. 200 mg (0.46 mmol) 4-(7-Isopropylamino-6-phenyl-2-pyridine-2-yl-[1,2,4]triazolo[1,5-a]pyrimidin-5-yl)benzaldehyde and 0.05 mL (0.83 mmol) acetic acid are added. The reaction mixture is stirred over night at room temperature. 107 mg (0.51 mmol) NaBH(OAc)$_3$, are added in portions and the reaction mixture is stirred at room temperature over night. The reaction mixture is treated with NaHCO$_3$ and the formed precipitate has been filtered off. The filtrate is extracted with methyl-tert.butylether. The organic phase is washed with water, dried (Na$_2$SO$_4$) and the solvent removed. This residue and the precipitate are combined and purified by column chromatography (silicagel, eluents: dichloromethane/methanol) and additionally by HPLC yielding 7.4 mg (2.54%) of the desired compound.

MS (ES+, M+1): 634
$^1$H-NMR (400 MHz, CD$_3$OD): 8.75 (d, 1H), 8.39 (d, 1H), 8.03 (dd, 1H), 7.90 (d, 1H), 7.81 (dd, 1H), 7.51-7.59 (m, 1H), 7.14-7.39 (m, 10H), 3.89 (hep, 1H), 3.60-3.78 (m, 5H), 3.49-3.59 (m, 2H), 2.60 (s, 3H), 1.09 (d, 6H).

Example 70.0

2-cyclopropyl-6-phenyl-5-{4-[3-(5-pyridine-2-yl)-1H-[1,2,4]triazole-3-yl)-azetidine-1-ylmethyl]-phenyl}-[1,2,4]triazolo[1,5-a]pyrimidine

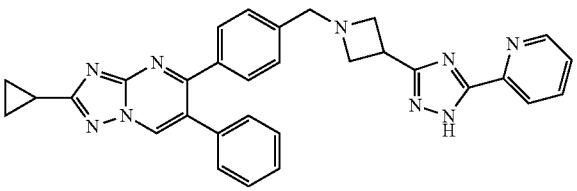 [SMILES: c1ccc(-c2cn3nc(C4CC4)nc3nc2-c2ccc(CN3CC(c4n[nH]c(-c5ccccn5)n4)C3)cc2)cc1]

221.5 mg (0.81 mmol) 2-(5-Azetidine-3-yl-[1,2,4]triazole-3-yl)-pyridine×2HCl are dissolved in 6.3 mL NMP. 0.23 mL (1.62 mmol) triethylamine are added and the reaction mixture is stirred for one hour. 250 mg (0.73 mmol) 4-(2-Cyclopropyl-6-phenyl-[1,2,4-a]triazolo[1,5-a]pyrimidin-5-yl)-benzaldehyde and 0.1 mL (1.76 mmol) acetic acid are added. The reaction mixture is stirred over night at room temperature. 404 mg (1.91 mmol) NaBH(OAc)$_3$, are added in portions and the reaction mixture is stirred at room temperature for four hours. The reaction mixture is treated with saturated NaHCO$_3$ solution and the precipitated crude product has been filtered off and purified by column chromatography (silicagel, eluents: dichloromethane/methanol) yielding 229.4 mg (59.4%) of the pure title compound.

MS (ES+, M+1): 526
$^1$H-NMR (400 MHz, d6-DMSO): 14.45 (br., 1H), 9.29 (s, 1H), 8.65 (d, 1H), 8.03 (d, 1H), 7.93 (br., 1H), 7.48 (br., 1H), 7.18-7.38 (m, 9H), 3.72 (br., 1H), 3.50-3.65 (m, 4H), 3.24-3.40 (m, 2H, under the water signal of the solvent), 2.12-2.22 (m, 1H), 0.93-1.13 (m, 4H).

Example 71.0

5-(4-{3-[5-(6-methyl-pyridin-2-yl)-1H-[1,2,4]triazol-3-yl]-azetidin-1-ylmethyl}-phenyl)-2-methylsulfanyl-6-phenyl-[1,2,4]triazolo[1,5-a]pyrimidine

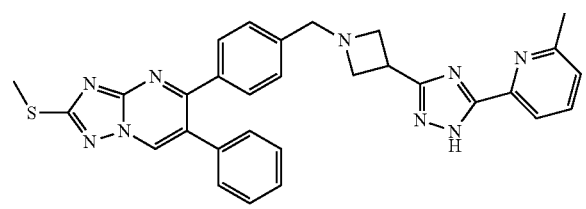 [SMILES: CSc1nc2nc(-c3ccc(CN4CC(c5n[nH]c(-c6cccc(C)n6)n5)C4)cc3)c(-c3ccccc3)cn2n1]

A mixture of 4-(2-methylsulfanyl-6-phenyl-[1,2,4]triazolo[1,5-a]pyrimidin-5-yl)benzaldehyde (200 mg, 0.548 mmol), 2-(5-Azetidine-3-yl-[1,2,4]triazole-3-yl)-6-methylpyridine×2HCl (174 mg, 60% pure), triethylamine (0.168 mL), AcOH (0.075 mL) and NMP (4.6 mL) were stirred overnight at room temperature. Sodium triacetoxyborohydride (279 mg) and the mixture stirred for 3 h. The reaction was partitioned between CH$_2$Cl$_2$ and water, the organic phase separated, dried and concentrated in vacuo. The residue was purified by preparative HPLC to give the title compound (78 mg) as a white solid.

UPLC-MS: RT=0.96 min; m/z=546.55;
$^1$H-NMR (300 MHz, d6-DMSO): δ=14.15 (br s), 9.33 (s, 1H), 7.75-7.83 (m, 2H), 7.19-7.33 (m, 10H), 3.66-3.74 (m, 1H), 3.54-3.59 (m, 4H), [2H obscured by solvent], 2.65 (s, 3H), 2.52 (s, 3H) ppm.

Example 72.0

2-methylsulfanyl-6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidine

The title compound was prepared from the respective aldehyde (200 mg) and amine hydrochloride (165 mg) in analogy to Example 71. Purification by preparative HPLC gave the title compound (120 mg) slightly contaminated with formic acid UPLC-MS: RT=0.90 min; m/z=530.1 (ES-);
$^1$H-NMR (300 MHz, d6-DMSO): δ=14.46 (br s), 9.33 (s, 1H), 8.64 (m, 1H), 8.02 (d, 1H), 8.92 (br s, 1H), 7.46 (br s, 1H), 7.20-7.33 (m, 9H), 3.72 (m, 1H), 3.57-3.61 (m, 4H), [2H obscured by solvent], 2.65 (s, 3H) ppm.

The following examples were prepared in analogy to Example 72.0 by using the appropriate amine hydrochloride.

| Example | Structure/Name | Analytical Data |
|---|---|---|
| 72.1 | 2-methylsulfanyl-6-phenyl-5-{4-[4-(5-pyridin-2-yl-1H-[1,2,4]triazol-3-yl)-piperidin-1-ylmethyl]-phenyl}-[1,2,4]triazolo[1,5-a]pyrimidine | UPLC-MS: RT = 0.80 min; m/z = 558.1 (ES-); $^1$H-NMR (400 MHz, d6-DMSO): δ 14.33 & 13.82 (2 × br s, 1H), 9.33 (s, 1H), 8.62 (br s, 1H), 7.99 (d, 1H), 7.90 (br s, 1H), 7.44 (br s, 1H), 7.22-7.33 (m, 9H), 3.46 (s, 2H), 2.63-2.81 (m, 6H), 2.02-2.08 (m, 2H), 1.90-1.92 (m, 2H), 1.69-1.77 ppm |

| Example | Structure/Name | Analytical Data |
|---|---|---|
| 72.2 | 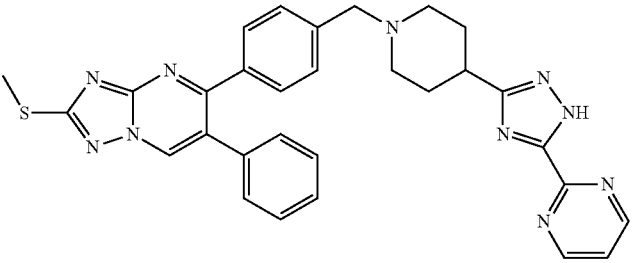<br>2-methylsulfanyl-6-phenyl-5-{4-[4-(5-pyrimidin-2-yl-1H-[1,2,4]triazol-3-yl)-piperidin-1-ylmethyl]-phenyl}-[1,2,4]triazolo[1,5-a]pyrimidine | UPLC-MS: RT = 0.85 min; m/z = 561.68; $^1$H-NMR (300 MHz, d6-DMSO): δ 9.33 (s, 1H), 8.88 (d, 2H), 7.51 (t, 1H), 7.21-7.33 (m, 9H), 3.46 (s, 2H), 2.66-2.81 (m, 6H), 2.02-2.09 (m, 2H), 1.90-1.94 (m, 2H), 1.67-1.78 (m, 2H) ppm |
| 72.3 | 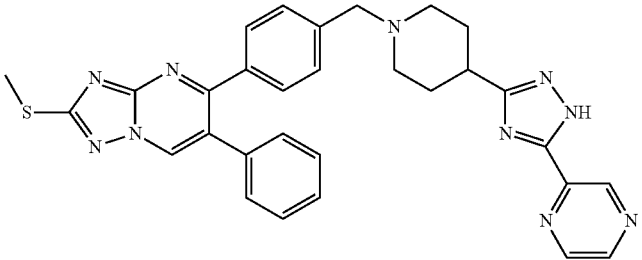<br>2-methylsulfanyl-6-phenyl-5-{4-[4-(5-pyrazin-2-yl-1H-[1,2,4]triazol-3-yl)-piperidin-1-ylmethyl]-phenyl}-[1,2,4]triazolo[1,5-a]pyrimidine | UPLC-MS: RT = 0.87 min; m/z = 561.58; $^1$H-NMR (400 MHz, d6-DMSO): δ 14.20 (br s), 9.34 (s, 1H), 9.20 (s, 1H), 8.67-8.71 (m, 2H), 7.24-7.35 (m, 9H), 3.49 (s, 2H), 2.79-2.84 (m, 3H), 2.68 (s, 3H), 2.06-2.11 (m, 2H), 1.94-1.97 (m, 2H), 1.74-1.82 (m, 2H) ppm |
| 72.4 | 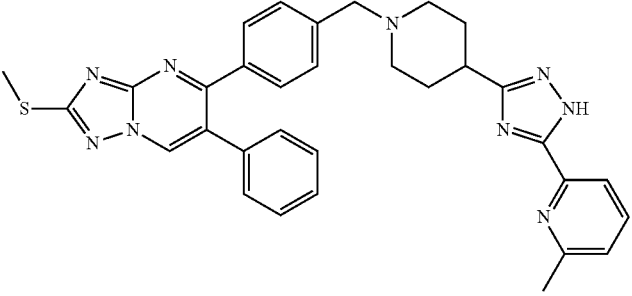<br>5-(4-{4-[5-(6-methyl-pyridin-2-yl)-1H-[1,2,4]triazol-3-yl]-piperidin-1-ylmethyl}-phenyl)-2-methylsulfanyl-6-phenyl-[1,2,4]triazolo[1,5-a]pyrimidine | UPLC-MS: RT = 0.93 min; m/z = 572.62 (ES−); $^1$H-NMR (300 MHz, d6-DMSO): δ 14.14, 13.80 (2 × br s), 9.33 (s, 1H), 7.78 (m, 2H), 7.21-7.33 (m, 10H), 3.46 (s, 2H), 2.65-2.81 (m, 6H), 2.00-2.07 (m, 2H), 1.88-1.92 (m, 2H), 1.67-1.78 (m, 2H) ppm |

Example 73.0

2-methanesulfonyl-6-phenyl-5-{4-[3-(5-pyridin-2-yl-1H-[1,2,4]triazol-3-yl)-azetidin-1-ylmethyl]-phenyl}-[1,2,4]triazolo[1,5-a]pyrimidine

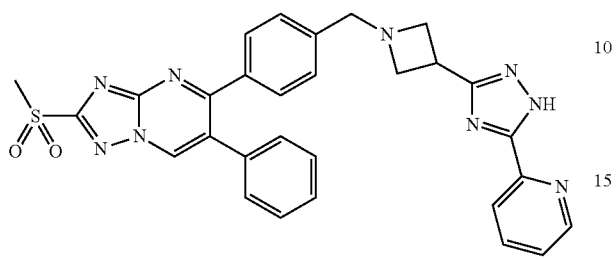

Step 1: [4-(2-Methylsulfanyl-6-phenyl-[1,2,4]triazolo[1,5-a]pyrimidin-5-yl)-phenyl]-methanol A mixture of 5-chloro-2-methylsulfanyl-6-phenyl-[1,2,4]triazolo[1,5-a]pyrimidine (310 mg, 1.12 mmol), [4-(hydroxymethyl)phenyl]boronic acid (187 mg, 1.23 mmol), 2.32 mL $Na_2CO_3$ solution (10%), 56 mg 1,1'-bis(diphenylphosphino)ferrocenedichloropalladium(II) and 3.6 mL DME was heated at 100° C. for 50 min under microwave irradiation. In parallel, a second reaction was performed with a 100 mg portion of 5-chloro-2-methylsulfanyl-6-phenyl-[1,2,4]triazolo[1,5-a]pyrimidine. On cooling, both mixtures were combined, diluted with water and extracted with $CH_2Cl_2$. The combined organic extract was washed with brine, dried and concentrated in vacuo to give the crude title compound which was used without further purification in the next step.

UPLC-MS: RT=1.08 min; m/z=349.51;

Step 2: [4-(2-Methylsulfanyl-6-phenyl-[1,2,4]triazolo[1,5-a]pyrimidin-5-yl)-phenyl]-methanol Meta-chloro-perbenzoic acid (0.517 g, 70% pure), was added to the crude product from Step 1 and CH2Cl2 was added till the mixture dissolved (15.8 mL). The mixture was stirred overnight at room temperature. The reaction was concentrated in vacuo, taken up in a small amount of CH2Cl2 and filtered. The filtrate was concentrated in vacuo and the residue purified by chromatography on silica gel (gradient elution: 1:1 hexane:EtOAc to EtOAc) to give the title compound (180 mg) as a white foam.

UPLC-MS: RT=0.93 min; m/z=381.44;

Step 3: 2-methanesulfonyl-6-phenyl-5-{4-[3-(5-pyridin-2-yl-1H-[1,2,4]triazol-3-yl)azetidin-1-ylmethyl]-phenyl}-[1,2,4]triazolo[1,5-a]pyrimidine The alcohol from Step 2 (180 mg, 0.47 mmol) was dissolved in $CH_2Cl_2$ (14 mL) and triethylamine (0.098 mL) added before the mixture was cooled to 0° C. Methanesulfonyl chloride (0.040 mL) was added dropwise and the mixture allowed to warm to rt overnight. The reaction was quenched with water, extracted with CH2Cl2 and the combined organic phase washed with brine, dried and concentrated in vacuo.

The crude mesylate was immediately taken up in DMF (4.5 mL) and 2-(5-azetidine-3-yl-[1,2,4]triazole-3-yl)-pyridine×2HCl (130 mg), followed by triethylamine (0.264 mL) were added. The mixture was heated at 80° C. for 3 hours. On cooling the reaction was quenched with water and the precipitated solid was filtered to give the crude product. Purification by chromatography followed by preparative HPLC gave the title compound;

UPLC-MS: RT=0.80 min; m/z=564.51.

Example 73.1

2-methanesulfonyl-6-phenyl-5-{4-[4-(5-pyridin-2-yl-1H-[1,2,4]triazol-3-yl)-piperidin-1-ylmethyl]-phenyl}-[1,2,4]triazolo[1,5-a]pyrimidine

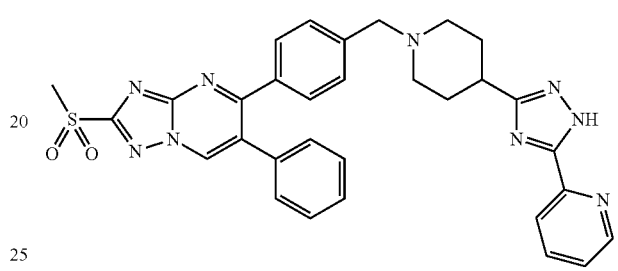

The title compound was prepared in analogy to Example 73.0 by using the appropriate amine hydrochloride salt in Step 3.

UPLC-MS: RT=0.77 min; m/z=590.32 (ES−);

$^1$H-NMR (300 MHz, d6-DMSO): δ=14.13 (br s), 9.63 (s, 1H), 8.62 (d, 1H), 7.99 (d, 1H), 7.89 (t, 1H), 7.24-7.44 (m, 10H), 3.47-3.49 (m, 5H), 2.77-2.81 (m, 2H), [1H obscured by solvent], 2.01-2.09 (m, 2H), 1.89-1.94 (m, 2H), 1.68-1.79 (m, 2H) ppm.

Example 74.0

7-(4-{3-[5-(6-methylpyridine-2-yl)-1H-[1,2,4]triazole-3-yl]-azetidine-1-ylmethyl}-phenyl)-6-phenyl-imidazo[1,2-a]pyrimidine-2-carboxylic acid methyl ester

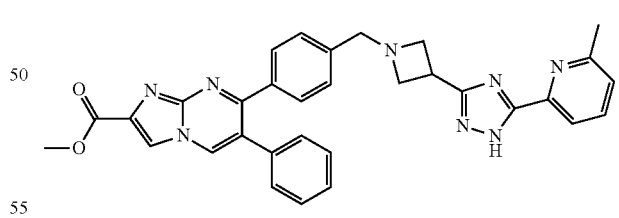

The title compound has been prepared in analogy to the aforementioned descriptions by reacting 500 mg (1.4 mmol) 7-(4-formylphenyl)-6-phenyl-imidazo[1,2-a]pyrimidine-2-carboxylic acid methyl ester with 671.9 mg (1.4 mmol) 2-(5-azetidine-3-yl-[1,2,4]triazole-3-yl)-6-methylpyridine×2HCl (60% pure), yielding 75.6 mg (9.2%) of the desired product after purification.

MS (ES+, M+1): 557

$^1$H-NMR (300 MHz, d6-DMSO): 14.23 (very br., 1H), 9.00 (s, 1H), 8.45 (s, 1H), 7.72-7.88 (m, 2H), 7.15-7.40 (m, 10H), 3.88 (s, 3H), 3.50-3.80 (m, 5H), 3.22-3.39 (m, 2H, under the water signal of the solvent), 2.51 (s, 3H).

Example 74.1

6-phenyl-7-{4-[3-[5-pyridine-2-yl-1H-[1,2,4]triazole-3-yl)azetidine-1-ylmethyl]-phenyl}-imidazo[1,2-a]pyrimidine-2-carboxylic acid methyl ester

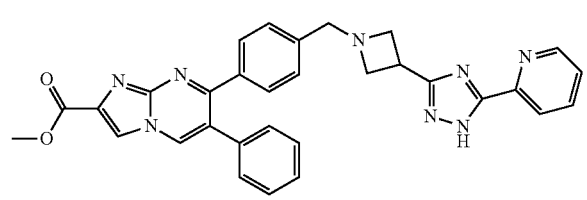 [SMILES: COC(=O)c1cn2cc(-c3ccccc3)c(-c3ccc(CN4CC(c5n[nH]c(-c6ccccn6)n5)C4)cc3)nc2n1]

The title compound has been prepared in analogy to the aforementioned descriptions by reacting 500 mg (1.4 mmol) 7-(4-formylphenyl)-6-phenyl-imidazo[1,2-a]pyrimidine-2-carboxylic acid methyl ester with 383.6 mg (1.4 mmol) 2-(5-azetidine-3-yl-[1,2,4]triazole-3-yl)-pyridine×2HCl, yielding 132.6 mg (15.7%) of the desired product after purification.

MS (ES+, M+1): 543

$^1$H-NMR (300 MHz, d6-DMSO): 14.42 (very br., 1H), 9.00 (s, 1H), 8.63 (d, 1H), 8.44 (s, 1H), 8.03 (d, 1H), 7.94 (br., 1H), 7.12-7.52 (m, 10H), 3.89 (s, 3H), 3.50-3.82 (m, 5H), 3.22-3.39 (m, 2H, under the water signal of the solvent).

Example 75.0

6-phenyl-7-{4-[3-[5-pyridine-2-yl-1H-[1,2,4]triazole-3-yl)azetidine-1-ylmethyl]-phenyl}-imidazo[1,2-a]pyrimidin-2-yl)-methanol

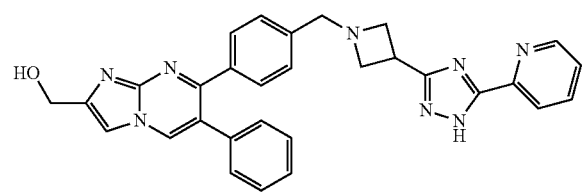 [SMILES: OCc1cn2cc(-c3ccccc3)c(-c3ccc(CN4CC(c5n[nH]c(-c6ccccn6)n5)C4)cc3)nc2n1]

To a solution of 61.4 mg (0.11 mmol) 6-phenyl-7-{4-[3-[5-pyridine-2-yl-1H-[1,2,4]triazole-3-yl)-azetidine-1-ylmethyl]-phenyl}-imidazo[1,2-a]pyrimidine-2-carboxylic acid methyl ester (described in example 74.1) in 3 mL THF are given 4.3 mg (0.11 mmol) LiAlH$_4$. After heating at reflux for 5 hours the reaction mixture is poured on saturated NaHCO$_3$ and extracted three times with tert. butyl-methylether. The solvent is removed and the residue is purified by HPLC chromatography. 2.6 mg (4%) of the desired product are obtained.

$^1$H-NMR (400 MHz, CDCl$_3$): 8.68 (d, 1H), 8.35 (s, 1H), 8.19 (d, 1H), 7.79-7.89 (m, 1H), 7.52 (s, 1H), 7.08-7.50 (10H), 4.90 (s, 2H), 3.95-4.12 (m, 1H), 3.62-3.90 (m, 4H), 3.48-3.63 (m, 2H).

Example 76.0

6-(2,5-difluorophenyl)-2-methyl-5-{4-[4-(5-pyridine-2-yl-1H-[1,2,4]triazole-3-yl)-piperidine-1-ylmethyl]-phenyl}-[1,2,4]triazolo[1,5-a]pyrimidine

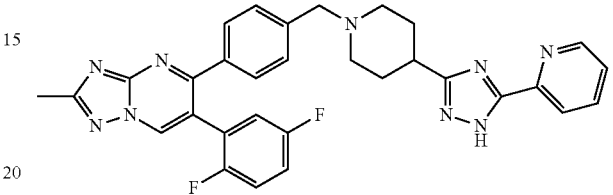

The title compound has been prepared in analogy to the aforementioned descriptions by reacting 276 mg 4-[6-(2,5-difluorophenyl)-2-methyl-[1,2,4]triazolo[1,5-a]pyrimidin-5-yl]-benzaldehyde which is only 30% pure, with 71.4 mg 2-(5-piperidine-4-yl-2H-[1,2,4]triazole-3-yl)-pyridine× 2HCl, yielding 42.4 mg (30.2%) of the desired product after chromatography.

MS (CI, M+1): 564

$^1$H-NMR (300 MHz, CDCl$_3$): 8.72 (s, 1H), 8.65 (d, 1H), 8.18 (d, 1H), 7.78-7.89 (m, 1H), 7.18-7.84 (m, 5H), 6.98-7.12 (m, 2H), 6.86-6.98 (m, 1H), 3.52 (s, 2H), 2.78-3.01 (m, 3H), 1.83-2.25 (m, 6H).

Biological Investigations

The following assays can be used to illustrate the commercial utility of the compounds according to the present invention.

Biological Assay 1.0: Akt1 Kinase Assay

Akt1 inhibitory activity of compounds of the present invention may be quantified employing the Akt1 TR-FRET assay as described in the following paragraphs. His-tagged human recombinant kinase full-length Akt1 expressed in insect cells was purchased form Invitrogen (part number PV 3599). As substrate for the kinase reaction the biotinylated peptide biotin-Ahx-KKLNRTLSFAEPG (C-terminus in amide form) was used which can be purchased e.g. from the company Biosynthan GmbH (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 μl of a solution of Akt1 in assay buffer [50 mM TRIS/HCl pH 7.5, 5 mM MgCl$_2$, 1 mM dithiothreitol, 0.02% (v/v) Triton X-100 (Sigma)] were added and the mixture was incubated for 15 min at 22° C. to allow prebinding of the test compounds to the enzyme before the start of the kinase reaction. Then the kinase reaction was started by the addition of 3 μl of a solution of adenosine-tri-phosphate (ATP, 16.7 μM=>final conc. in the 5 μl assay volume is 10 μM) and substrate (1.67 μM=>final conc. in the 5 μl assay volume is 1 μM) in assay buffer and the resulting mixture was incubated for a reaction time of 60 min at 22° C. The concentration of Akt1 in the assay was adjusted depending of the activity of the enzyme lot and was chosen appropriate to have the assay in the linear range, typical enzyme concentrations were in the range of about 0.05 ng/μl (final conc. in the 5 μl assay volume).

The reaction was stopped by the addition of 5 µl of a solution of HTRF detection reagents (200 nM streptavidine-XL665 [Cisbio] and 1.5 nM anti-phosho-Serine antibody [Millipore, cat. #35-001] and 0.75 nM LANCE Eu-W 1024 labeled anti-mouse IgG antibody [Perkin Elmer]) in an aqueous EDTA-solution (100 mM EDTA, 0.1% (w/v) bovine serum albumin in 50 mM HEPES/NaOH pH 7.5).

The resulting mixture was incubated 1 h at 22° C. to allow the binding of the biotinylated phosphorylated peptide to the streptavidine-XL665 and the antibodies. Subsequently the amount of phosphorylated substrate was evaluated by measurement of the resonance energy transfer from the anti-mouse-IgG-Eu-Chelate to the streptavidine-XL665. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an inhouse software.

Biological Assay 2.0: Akt2 Kinase Assay

Akt2 inhibitory activity of compounds of the present invention was quantified employing the Akt2 TR-FRET assay as described in the following paragraphs.

His-tagged human recombinant kinase full-length Akt2 expressed in insect cells and activated by PDK1 was purchased form Invitrogen (part number PV 3975). As substrate for the kinase reaction the biotinylated peptide biotin-Ahx-KKLNRTLSFAEPG (C-terminus in amide form) was used which can be purchased e.g. from the company Biosynthan GmbH (Berlin-Buch, Germany).

For the assay 50 nl of a 100 fold concentrated solution of the test compound in DMSO was pipetted into a black low volume 384 well microtiter plate (Greiner Bio-One, Frickenhausen, Germany), 2 µl of a solution of Akt2 in assay buffer [50 mM TRIS/HCl pH 7.5, 5 mM $MgCl_2$, 1 mM dithiothreitol, 0.02% (v/v) Triton X-100 (Sigma)] were added and the mixture was incubated for 15 min at 22° C. to allow prebinding of the test compounds to the enzyme before the start of the kinase reaction. Then the kinase reaction was started by the addition of 3 µl of a solution of adenosine-tri-phosphate (ATP, 16.7 µM=>final conc. in the 5 µl assay volume is 10 µM) and substrate (1.67 µM=>final conc. in the 5 µl assay volume is 1 µM) in assay buffer and the resulting mixture was incubated for a reaction time of 60 min at 22° C. The concentration of Akt2 in the assay was adjusted depending of the activity of the enzyme lot and was chosen appropriate to have the assay in the linear range, typical enzyme concentrations were in the range of about 0.2 ng/µl (final conc. in the 5 µl assay volume).

The reaction was stopped by the addition of 5 µl of a solution of HTRF detection reagents (200 nM streptavidine-XL665 [Cisbio] and 1.5 nM anti-phosho-Serine antibody [Millipore, cat. #35-001] and 0.75 nM LANCE Eu-W 1024 labeled anti-mouse IgG antibody [Perkin Elmer]) in an aqueous EDTA-solution (100 mM EDTA, 0.1% (w/v) bovine serum albumin in 50 mM HEPES/NaOH pH 7.5).

The resulting mixture was incubated 1 h at 22° C. to allow the binding of the biotinylated phosphorylated peptide to the streptavidine-XL665 and the antibodies. Subsequently the amount of phosphorylated substrate was evaluated by measurement of the resonance energy transfer from the anti-mouse-IgG-Eu-Chelate to the streptavidine-XL665. Therefore, the fluorescence emissions at 620 nm and 665 nm after excitation at 350 nm was measured in a TR-FRET reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition). Normally test compound were tested on the same microtiter plate at 10 different concentrations in the range of 20 µM to 1 nM (20 µM, 6.7 µM, 2.2 µM, 0.74 µM, 0.25 µM, 82 nM, 27 nM, 9.2 nM, 3.1 nM and 1 nM, dilution series prepared before the assay at the level of the 100 fold conc. stock solutions by serial 1:3 dilutions) in duplicate values for each concentration and $IC_{50}$ values were calculated by a 4 parameter fit using an inhouse software.

Preferred compounds of the present invention show in either the Akt1 or Akt2 kinase assay: $IC_{50}<5$ µM, more preferably, $IC_{50}<0.5$ µM, even more preferably, $IC_{50}<0.05$ µM.

Cellular Assays: p-PRAS40 and p-AKT Assay

The assessment of cellular AKT activities was conducted with HEK293-AKT and HEK293-PRAS40 cell lines. The cell lines express AKT or PRAS40 as fusions with green fluorescent protein (GFP, a suitable TR-FRET acceptor for the excited-state Tb fluorophore) respectively. The effects of AKT inhibitors on the phosphorylation state of the GFP-PRAS40 or the GFP-AKT fusion proteins were detected in cell lysates using LanthaScreen™ Tb-anti-AKT(S473) and Tb-anti-pPRAS40 [pThr246] antibodies.

Biological Assay 3.1: p-PRAS40 Assay

HEK293-PRAS40 cells (PerkinElmer #6007688) were plated at 20000 cells/well in 384 well MTP. Following overnight incubation at 37° C., testing compounds diluted into growth medium were added to the cells. After 1 hour treatment, cells were stimulated with insulin (Insulin #12585-014 Invitrogen) with a final concentration of 500 µM for 40 min. Thereafter, cells were lysed with a buffer containing 20 mM Tris, pH 7.4, 5 mM EDTA, 150 mM NaCl, 1% NP-40, phosphatase/protease inhibitors, and 5 nM of Tb-anti-AKT. After 2 hours incubation at room temperature, the TR-FRET value was detected using a PHERAstar plate reader (BMG LABTECH) and 520/490 nm emission ratio is used for $IC_{50}$ calculation.

Biological Assay 3.2: p-AKT Assay

The phospho-AKT assay was conducted in analogy to the p-PRAS40 protocol, except that the cell line is HEK293-AKT, and the stimulation is 5 ng/mL IGF-1.

Preferred compounds of the present invention show, in either the p-PRAS40 or p-AKT assay: $IC_{50}<10$ µM, more preferably, $IC_{50}<1$ µM.

Biological Assay 4.0: Tumor Cell Proliferation Assays

Compounds were tested in a cell-based assay that measures the capacity of the compounds to inhibit tumor cell proliferation following a 72 h drug exposure. Cell viability is determined using the Cell Titer-Glo luminescent cell viability kit from Promega (Cat. #G7573). Cells were plated at 1000-5000 cells/well (depending on cell lines) in 100 mL growth medium on black/clear bottom plates (Fisher #07-200-565). For each cell line assayed, cells were plated onto a separate plate for determination of luminescence at the t=0 hours and t=72 hour time points. Following overnight incubation at 37° C., luminescence values for the t=0 samples were determined by adding 100 µL of Cell Titer-Glo solution per well, transferring the plates to an orbital shaker for 10 minutes at room temperature, and then reading the plates on a Wallac Victor2 1420 Multi-label HTS Counter using the luminometry window (maximum light detection is measured at 428 nM). Dose plates for t=72 hour time points were treated with compounds diluted into growth medium in a final volume of 50 µL. Cells were then incubated for 72 hours at 37° C. Luminescence values for the t=72 hour samples were determined by adding 150 µL of Promega CellTiter-Glo solution, placing the cells on a shaker for 10 minutes at room temperature, and then reading the luminescence using a Victor luminometer. Data were processed using a template specific for the luciferase assay. Briefly, t=0 values were subtracted from those determined for the t=72 hour time points, for both the treated and untreated samples. Percent differences in luminescence between drug treated and controls were used to determine the percent inhibition of growth.

The following further cellular assays can be used to further illustrate the commercial utility of the compounds according to the present invention.

Biological Assay 5.0: Cellular PI3K/Akt Pathway Assay

In order to study the cellular activity of the compounds according to the present invention, an Enzyme Linked Immunosorbent Assay (ELISA)-based assay may be used to investigate the inhibitory effect on Akt phosphorylation. The assay is based on a Sandwich ELISA kit (PathScan™ Phospho-Akt1 (Ser473); Cell Signaling, USA; #7160).

The ELISA Kit detects endogenous levels of phosphorylated Akt protein. A phospho-Akt (Ser473) antibody (Cell Signaling, USA; #9271) has been coated onto the microwells. After incubation with cell lysates, the coated antibody captures the phosphorylated Akt protein. Following extensive washing, Akt1 monoclonal anti-body (Cell Signaling, USA; #2967) is added to detect the captured phospho-Akt1 protein. HRP-linked anti-mouse antibody (HRP: horseradish peroxidase; Cell Signaling, USA; #7076) is then used to recognize the bound detection antibody. HRP substrate (=3,3',5,5'-tetramethylbenzidine (TMB); Cell Signaling, USA; #7160) is added to develop colour. The magnitude of optical density for this developed color is proportional to the quantity of phosphorylated Akt protein. MCF7 cells (ATCC HTB-22) are seeded into 96 well fate bottom plates at a density of 10000 cells/well. 24 hours after seeding, the cells are serum starved using low-serum medium (IMEM media including 0.1% charcoal treated FCS (FCS: fetal calf serum)). After 24 hours 1 µl each of the compound dilutions (test compounds were dissolved as 10 mM solutions in dimethylsulfoxide (DMSO) and subsequently diluted) are added into each well of the 96 well plates and incubated for 48 h at 37° C. in a humidified athmosphere containing 5% $CO_2$. To stimulate Akt phosphorylation, β-Heregulin (20 ng/mL β-HRG) is added in parallel to the compounds. Wells containing unstimulated control cells (no β-Heregulin stimulation) are incubated with or without the diluted compound. Wells containing untreated control cells (no compound) are filled with medium containing 0.5% v:v DMSO and are or are not stimulated with β-Heregulin.

Cells are harvested and lysed with brief sonification in 1× cell lysis buffer (20 mM Tris (pH7.5), 150 mM NaCl, 1 mM ethylene diaminetetraacetate (EDTA), 1 mM ethylene glycol-bis(2-aminoethyl)-N,N,N',N'-tetraacetic acid (EGTA), 1 vol % Triton X-100, 2.5 mM sodium pyrophosphate, 1 mM β-glycerolphosphate, 1 mM $Na_3VO_4$, 1 µg/mL leupeptin). The lysate is centrifuged for 10 min. at 4° C. and the supernatant is transferred to a new tube. 100 µl of sample diluent (0.1 vol % Tween-20, 0.1 vol % sodium azide in phosphate buffered saline (PBS)) are added to a microcentrifuge tube and 100 µl of cell lysate are transferred into the tube and vortexed. 100 µl of each diluted cell lysate are added to the appropriate ELISA well, and incubated overnight at 4° C. The plates are washed 4 times with 1× wash buffer (1 vol % tween-20, 0.33 vol % thymol, in PBS). Next 100 µl of detection antibody (Akt1 (2H10) monoclonal detection antibody; Cell Signaling, USA; #2967) are added to each well and incubation continued for 1 h at 37° C. The washing procedure is repeated between each step. 100 µl of secondary antibody (anti-mouse IgG HRP-linked antibody; Cell Signaling, USA; #7076) are added to each well and incubated for 30 min. at 37° C. Than, 100 µl of TMB substrate (0.05% 3,3',5,5' tetramethylbenzidine, 0.1% hydrogen peroxide, complex polypeptides in a buffered solution; Cell Signaling, USA; #7160) are added to each well and incubated for 30 min. at 25° C. Finally 100 µC of STOP solution (0.05 vol % α and β unsaturated carbonyl compound) are added to each well and the plate are shaked gently. The absorbance is measured at λ=450 nm (Wallac Victor2; Perkin Elmer, USA) within 30 min. after adding the STOP solution. The analysis of the data is performed using a statistical program (Excel; Microsoft, USA).

Biological Assay 6.0: Cellular pGSK3 Assay:

In order to study the cellular activity of the compounds according to the present invention, an ELISA-based assay may be used for the phosphorylated protein glycogen synthetase kinase 3 (GSK3). The assay is based on a solid phase sandwich ELISA that detects endogenous levels of phosphorylated GSK3 using a phospho-GSK3 (Ser9) specific antibody (BioSource International, Inc.; Catalog #KH00461). After incubation with cell lysates, the coated antibody captures the phosphorylated GSK3 protein. Following extensive washing, GSK3 polyclonal antibody is added to detect the captured phospho-GSK3 protein. Secondary antibody (anti-rabbit IgG-HRP) is then used to recognize the bound detection antibody. After the second incubation and washing to remove all the excess anti-rabbit IgG-HRP, a substrate solution is added, which is acted upon by the bound enzyme to produce color. The intensity of this colored product is directly proportional to the concentration of GSK-3β [pS9] present in the original specimen.

MCF7 cells (ATCC HTB-22) were seeded into 96 well fate bottom plates at a density of 10000 cells/well. After 24 h 1 µl each of the compound dilutions (test compounds were dissolved as 10 mM solutions in dimethylsulfoxide (DMSO) and subsequently diluted) were added into each well of the 96 well plates and incubated for 48 h at 37° C. in a humidified athmosphere containing 5% $CO_2$.

Cells were harvested and lysed in cell extraction buffer (10 mM Tris, pH 7.4, 100 mM NaCl, 1 mM EDTA, 1 mM EGTA, 1 mM NaF, 20 mM $Na_4P_2O_7$, 2 mM $Na_3VO_4$, 1% Triton X-100, 10 vol % glycerol, 0.1 vol % SDS, 0.5 vol % deoxycholate, 1 mM phenylmethylsulfonylfluorid (PMSF)). The lysate were centrifuged for 10 min. at 4° C. and the supernatant were transferred to a new tube. 50 µl of sample diluent (standard diluent buffer, Biosource) were added and 100 µl of cell lysate transferred into the tube and vortexed. 100 µl of each diluted cell lysate were added to the appropriate ELISA well plate and incubated for 3 h at room temperature. The plates were washed 4 times with 1× wash buffer (Biosource). 50 µl of detection antibody (GSK3 (Ser9) detection antibody; BioSource) were added to each well and incubated for 30 min. at room temperature. The washing procedure was repeated between each step. 100 µl of HRP-linked secondary antibody (anti-mouse IgG HRP-linked antibody) were added to each well and incubated for 30 min. at room temperature. 100 µl of TMB substrate (0.05 vol % 3,3',5,5' tetramethylbenzidine, 0.1 vol % hydrogen peroxide, complex polypeptides in a buffered solution; Biosource) were added to each well and incubated for 30 min. at room temperature. Finally 100 µl of Stop solution (0.05 vol % α and β unsaturated carbonyl compound) were added to each well and the plate were shaked gently for a few seconds. The absorbance was measured at λ=450 nm (Wallac Victor2; Perkin Elmer, USA) within 30 min. after adding the stop solution.

The analysis of the data was performed using a statistical program (Excel; Microsoft, USA) and the $IC_{50}$ of pGSK3 inhibition was determined.

Biological Assay 7.0: Cellular Proliferation/Cytotoxicity Assay:

The anti-proliferative activity of the compounds as described herein, may be evaluated using the OvCAR3, HCT116 and A549 cell lines and the Alamar Blue (Resazurin) cell viability assay (O'Brien et al. Eur J Biochem 267, 5421-5426, 2000). Resazurin is reduced to the fluorescent resorufin by cellular dehydrogenase activity, correlating with viable, proliferating cells. Test compounds are dissolved as 10 mM solutions in DMSO and subsequently diluted. Cells like HCT116 or A549 cells were seeded into 96 well flat bottom plates at a density of 10000 cells/well (OvCAR3 cells), 1000 cells/well (HCT116 cells) or 2000 cells/well (A549 cells) in a volume of 200 µl/well. 24 hours after seeding, 1 µl each of the compound dilutions are added into each well of the 96 well plates. Each compound dilution is tested as at least as duplicates. Wells containing untreated control cells were filled with 200 µl DMEM (Dulbecco's Modified Eagle Medium) containing 0.5 vol % v:v DMSO. The cells are then incubated with the substances for 72 h at 37° C. in a humidified atmosphere containing 5 vol % CO2. To determine the viability of the cells, 20 µl of a Resazurin solution (90 mg/l) are added. After 4 h incubation at 37° C., the fluorescence is measured by extinction at λ=544 nm and an emission of λ=590 nm (Wallac Victor2; Perkin Elmer, USA). For the calculation of the cell viability, the emission value from untreated cells is set as 100% viability and the fluorescence intensity of treated cells are set in relation to the values of untreated cells. Viabilities are expressed as % values. The corresponding IC50 values of the compounds for cytotoxic activity are determined from the concentration-effect curves by means of non-linear regression. The analysis of the data is performed using a biostatistical program (GraphPad Prism, USA).

Biological Assay 8.0: Chemosensitization Assay

The herein disclosed compounds may be evaluated for the ability to sensitize cancer cells towards apoptotic stimuli. Inhibitors of Akt are tested alone and in combination with chemotherapeutic and targeted cancer therapeutics to determine the effect on apoptosis induction.

Cancer cells are seeded in 96 well plates at concentrations ranging from $2 \times 10^3$ to $1 \times 10^4$ cells per well in their respective growth media. 48-72 hours later, the apoptosis assay are set up as follows:

For combination assays with a chemotherapeutic agent especially preferred topoisomerase inhibitors (such as doxorubicin, etoposide, camptothecin or mitoxantrone) or antimitotic agents/tubulin inhibitors (such as vincristine), compounds are added at respective concentrations indicated and plates incubated at 37° C. in a $CO_2$ incubator for 18 hours. For standard combination assays utilizing treatment with chemotherapeutic agent are added at the same time at the respective concentrations indicated.

For combinations assays involving addition of targeted pro-apoptotic agents like the death receptor ligand TRAIL/Apo2L (Research Diagnostics) compounds are added for 1.5 hours prior to addition of TRAIL and plates incubated an additional 3 to 4 hours post TRAIL addition. In the case of the time course, plates are incubated for 2, 3, 4 and 6 hours with TRAIL ligand before ending the assay.

For both procedures, total final volumes do not exceed 250 µl. At the end of the incubation time, the cells are pelleted by centrifugation (200×g; 10 min. at rt) and the supernatant is discarded. The cells are resuspended and incubated using lysis buffer for 30 min. at rt (Cell Death Detection ELISA$^{P}$-$_{LUS}$, Roche, Cat. No. 11774425001). After the centrifugation is repeated (200×g; 10 min. at rt) an aliquot of the supernatant is transferred to a streptavidin-coated well of a microplate. Followed by the incubation (2 h, rt) and binding of nucleosomes in the supernatant with, anti-histone antibody (biotin-labeled) and anti-DNA antibody (peroxidase-conjugated; Cell Death Detection ELISA$^{PLUS}$, Roche, Cat. No. 11774425001). The antibody-nucleosome complexes are bound to the microplate. The immobilized antibody-histone complexes are washed three times at rt to remove cell components that are not immunoreactive. The substrate solution (2,2'-AZINO-bis [3-ethylbenziazoline-6-sulfonic acid (ABTS); Cell Death Detection ELISA$^{PLUS}$, Roche, Cat. No. 11 774 425 001) is added and the samples were incubated for 15 min., rt. The amount of colored product is determined spectrophotometrically (absorbance at o=405 nm). Data are expressed as percent activity of control with cisplatin used as a positive control. Apoptosis induction by 50 M cisplatin is arbitrarily defined as 100 cisplatin units (100 CPU).

The following Table gives selected data for selected Examples of the present invention.

| Example | $IC_{50}$ Akt1 (Biological Assay 1.0), µM | $IC_{50}$ Akt2 (Biological Assay 2.0), µM |
|---|---|---|
| 1.0 | <0.050 | <0.5 |
| 2.0 | 0.023 | 0.065 |
| 4.0 | <0.050 | <0.050 |
| 5.0 | 0.006 | 0.011 |
| 6.0 | 0.157 | 1.22 |
| 7.0 | 0.056 | 0.607 |
| 9.0 | 0.083 | 0.426 |
| 10.0 | 0.004 | 0.009 |
| 12.0 | 0.039 | 0.316 |
| 13.0 | 0.112 | 0.228 |
| 14.0 | 3.0 | 5.84 |
| 16.0 | 0.042 | 1.08 |
| 17.0 | 0.338 | >20 |
| 18.0 | 0.042 | 1.09 |
| 19.0 | 0.025 | 0.332 |
| 20.0 | 0.525 | 1.01 |
| 21.0 | 1.45 | 2.5 |
| 22.0 | 0.288 | 0.417 |
| 23.0 | 0.315 | 0.759 |
| 24.0 | 0.044 | 0.435 |
| 24.1 | 4.37 | 9.88 |
| 25.0 | 0.007 | 0.018 |
| 26.0 | 0.004 | 0.004 |
| 27.0 | 0.012 | 0.115 |
| 28.0 | 0.014 | 0.761 |
| 29.0 | 0.084 | 0.035 |
| 30.0 | 6.7 | 0.509 |
| 31.0 | 0.070 | 0.014 |
| 32.0 | 0.007 | 0.214 |
| 33.0 | 0.026 | 0.253 |
| 34.0 | 0.365 | 2.29 |
| 35.0 | 0.029 | 0.042 |
| 36.0 | 0.070 | 0.589 |
| 37.0 | 0.077 | 0.256 |
| 38.0 | 0.013 | 0.016 |
| 39.0 | 0.029 | 0.027 |
| 40.0 | 0.247 | 0.273 |
| 41.0 | 0.010 | 0.010 |
| 42.0 | 0.005 | 0.019 |
| 43.0 | 0.063 | |
| 43.1 | 0.022 | 0.011 |

-continued

| Example | IC$_{50}$ Akt1 (Biological Assay 1.0), μM | IC$_{50}$ Akt2 (Biological Assay 2.0), μM |
| --- | --- | --- |
| 44.0 | 0.007 | 0.017 |
| 44.1 | 0.010 | 0.008 |
| 44.2 | 0.021 | 0.078 |
| 45.0 | 0.032 | 0.374 |
| 45.1 | 0.011 | 0.021 |
| 45.2 | 0.015 | 0.031 |
| 45.2 | 0.009 | 0.020 |
| 48.0 | 0.007 | 0.082 |
| 48.1 | 0.005 | 0.203 |
| 49.0 | 0.013 | 0.037 |
| 49.1 | 0.028 | 0.129 |
| 50.0 | 0.022 | 0.097 |
| 50.1 | 0.062 | 0.108 |
| 50.2 | 0.355 | 1.1 |
| 51.0 | 0.041 | 0.046 |
| 51.1 | 0.032 | 0.069 |
| 51.2 | 0.056 | 0.165 |
| 52.0 | 0.009 | 0.017 |
| 52.1 | 0.008 | 0.032 |
| 52.2 | 0.186 | 1.44 |
| 53.0 | 0.011 | 0.007 |
| 53.1 | 0.025 | 0.033 |
| 54.0 | 0.003 | 0.017 |
| 55.0 | 0.006 | 0.014 |
| 56.0 | 0.010 | 0.047 |
| 57.0 | 0.006 | 0.003 |
| 58.0 | 0.030 | 0.476 |
| 59.0 | 0.042 | 0.128 |
| 60.0 | 0.016 | 0.055 |
| 61.0 | 0.011 | 0.019 |
| 62.0 | 0.055 | 0.801 |
| 63.0 | 0.014 | 0.118 |
| 63.1 | 0.008 | 0.034 |
| 63.2 | 0.018 | 0.108 |
| 63.3 | 0.010 | 0.097 |
| 64.0 | 0.030 | 0.039 |
| 65.0 | 0.033 | 0.036 |
| 66.0 | 0.025 | 0.053 |
| 67.0 | 0.029 | 0.145 |
| 68.0 | 0.024 | 0.088 |
| 69.0 | 0.014 | 0.016 |
| 70.0 | 0.007 | 0.005 |
| 71.0 | 0.005 | 0.004 |
| 72.0 | 0.005 | 0.10 |
| 72.1 | 0.007 | 0.012 |
| 72.2 | 0.077 | 0.222 |
| 72.3 | 0.026 | 0.080 |
| 72.4 | 0.005 | 0.004 |
| 73.1 | 0.054 | 0.102 |
| 74.0 | 0.012 | 0.014 |
| 74.1 | 0.010 | 0.017 |
| 75.0 | 0.072 | 0.124 |
| 76.0 | 0.060 | 0.154 |

The invention claimed is:

1. A compound of formula (I)

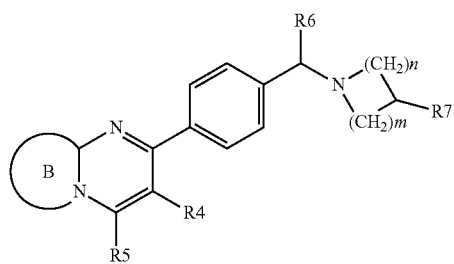

wherein ring B and the pyrimidine to which it is fused form a ring system selected from

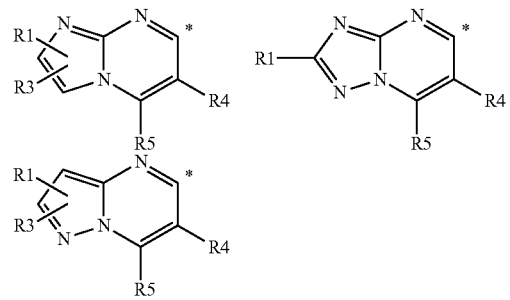

* marks the point of the attachment,

R1 is hydrogen, 1-4C-alkyl optionally substituted by halogen, hydroxy, amino, mono- or di-1-4C-alkylamino, halogen, amino, —SR2, —SO—R2, SO$_2$—R2, trifluoromethyl, cyano, 3-7C-cycloalkyl, 2-4C-alkenyl, 2-4C-alkynyl, 1-4C-alkoxy optionally substituted by halogen, 3-7C-cycloalkoxy, NR10R11, —C(O)NR12R13, —C(NH)NH2, —C(O)OR2, or a monocyclic 5- or 6-membered heteroarylene comprising 1 nitrogen atom and optionally 1,2 or 3 further heteroatoms independently selected from oxygen, nitrogen and sulphur, R2 is hydrogen, 1-4C-alkyl optionally substituted by halogen, hydroxy, amino, mono- or di-1-4C-alkylamino, or 3-7C-cycloalkyl, R3 is hydrogen, 1-4C-alkyl or halogen, 1-4-Calkoxy R4 is phenyl, thienyl, pyridinyl, thiazolyl or oxazolyl and wherein R4 is optionally independently substituted one or two times by R5A, R5A is 1-4C-alkyl, halogen or 1-4C-alkoxy or NR10R11, R5 is hydrogen, 1-4C-alkyl, halogen, 1-4C-alkoxy, NR10R11 or 3-7C-cycloalkyl, R6 is hydrogen or 1-4C-alkyl, R7 is —W—Y, W is a monocyclic 5- or 6-membered heteroarylene comprising 1 nitrogen atom and optionally 1,2 or 3 further heteroatoms independently selected from oxygen, nitrogen and sulphur or a bicyclic heteroarylene comprising 1 nitrogen atom and optionally 1,2 or 3 further heteroatoms independently selected from oxygen, nitrogen and sulphur and wherein the monocyclic 5- or 6-membered heteroarylene and the bicyclic heteroarylene are optionally substituted by R8, R8 is hydrogen, 1-4C-alkyl, 3-7C-cycloalkyl, 1-4C-haloalkyl, NR10R11, 4C-alkoxy, cyano, halogen or hydroxy, Y is hydrogen, aryl or a monocyclic 5- or 6-membered heteroaryl comprising 1 nitrogen atom and optionally 1,2 or 3 further heteroatoms independently selected from oxygen, nitrogen, sulphur and wherein the aryl or heteroaryl is optionally substituted independently one or more times by R9 and optionally further substituted by R9A R9 is 1-4C-alkyl, 1-4C-alkoxy, halogen, hydroxy, 1-4C-haloalkyl, NR10R11, cyano, or —C(O)NH2

R9A is 1-4C-alkyl or halogen n is 1 or 2, m is 1 or 2, with the proviso that
when
n is 2 and m is 2,
and
W is a monocyclic 5-membered heteroarylene and
R4 is phenyl or thienyl
then
A:
R1 must be SR2, SOR2 or SO2R2, or
B:
R4 must be substituted by R5A, or
C:
R5 must be halogen or
D:
R9 must be hydroxy, 1-4C-haloalkyl, NR10R11, cyano, or —C(O)NH2
R10, R11 which can be same or different, is hydrogen, 1-4C-alkyl optionally substituted by halogen, hydroxy, amino, mono- or di-1-4C-alkylamino, or 3-7C-cycloalkyl,
R12, R13 which can be same or different, is hydrogen, 1-4C-alkyl optionally substituted by halogen, hydroxy, amino, mono- or di-1-4C-alkylamino, or 3-7C-cycloalkyl,
or an N-oxide, a salt, a tautomer or a stereoisomer of said compound, or a salt of said N-oxide, tautomer or stereoisomer.

2. A compound of formula (I) according to claim 1 wherein
R1 is hydrogen, 1-4C-alkyl optionally substituted by halogen, hydroxy, amino, mono- or di-1-4C-alkylamino, halogen, amino, —SR2, —SO—R2, —SO2R2, trifluoromethyl, cyano, 3-7C-cycloalkyl, 1-4C-alkoxy, NR10R11, —C(O)NR12R13, —C(NH)NH2, —C(O)OR2, or a monocyclic 5- or 6-membered heteroarylene comprising 1 nitrogen atom and optionally 1,2 or 3 further heteroatoms independently selected from oxygen, nitrogen and sulphur,
R2 is hydrogen, 1-4C-alkyl optionally substituted by halogen, hydroxy, amino, mono- or di-1-4C-alkylamino, or 3-7C-cycloalkyl,
R3 is hydrogen, 1-4C-alkyl or halogen, 1-4C-alkoxy
R4 is phenyl, and wherein R4 is optionally independently substituted one or two times by R5A,
R5A halogen,
R5 is hydrogen, 1-4C-alkyl, NR10R11
R6 is hydrogen
R7 is —W—Y,
W is a monocyclic 5- or 6-membered heteroarylene comprising 1 nitrogen atom and optionally 1,2 or 3 further heteroatoms independently selected from oxygen, nitrogen and sulphur or a bicyclic heteroarylene comprising 1 nitrogen atom and optionally 1,2 or 3 further heteroatoms independently selected from oxygen, nitrogen and sulphur
and wherein the bicyclic heteroarylene are optionally substituted by R8,
R8 is hydrogen, 1-4C-alkyl, 3-7C-cycloalkyl, 1-4C-haloalkyl, NR10R11, 1-4C-alkoxy, cyano, halogen or hydroxy,
Y is hydrogen, aryl or a monocyclic 5- or 6-membered heteroaryl comprising 1 nitrogen atom and optionally 1,2 or 3 further heteroatoms independently selected from oxygen, nitrogen, sulphur and wherein the aryl or heteroaryl is optionally substituted by R9 and optionally further substituted by R9A
R9 is 1-4C-alkyl, or halogen,
n is 1 or 2,
m is 1 or 2,
with the proviso that
when
n is 2 and m is 2, and
W is a monocyclic 5-membered heteroarylene
and
R4 is phenyl or thienyl
then
A:
R1 must be SR2, SOR2 or SO2R2, or
B:
R4 must be substituted by R5A, or
C:
R5 must be halogen or
D:
R9 must be hydroxy, 1-4C-haloalkyl, NR10R11, cyano, or —C(0)NH2
R10, R11 which can be same or different, is hydrogen, 1-4C-alkyl or 3-7C-cycloalkyl,
R12, R13 which can be same or different, is hydrogen, 1-4C-alkyl optionally substituted by halogen, hydroxy, amino, mono- or di-1-4C-alkylamino, or 3-7C-cycloalkyl,
or an N-oxide, a salt, a tautomer or a stereoisomer of said compound, or a salt of said N-oxide, tautomer or stereoisomer.

3. A compound of formula (I) according to claim 1, wherein
R1 is hydrogen, 1-4C-alkyl optionally substituted by halogen, hydroxy, amino, mono- or di-1-4C-alkylamino, halogen, amino, —SR2, trifluoromethyl, cyano, 3-7C-cycloalkyl, 2-4C-alkenyl, 2-4C-alkynyl, 1-4C-alkoxy optionally substituted by halogen, 3-7C-cycloalkoxy, NR10R11, —C(C)NR12R13, —C(NH)NH2, —C(O)0R2, or a monocyclic 5- or 6-membered heteroarylene comprising 1 nitrogen atom and optionally 1,2 or 3 further heteroatoms independently selected from oxygen, nitrogen and sulphur,
R2 is hydrogen, 1-4C-alkyl optionally substituted by halogen, hydroxy, amino, mono- or di-1-4C-alkylamino, or 3-7C-cycloalkyl,
R3 is hydrogen, 1-4C-alkyl or halogen,
R4 is phenyl, thienyl, pyridinyl, thiazolyl or oxazolyl and wherein R4 is optionally substituted by R5A,
R5A is 1-4C-alkyl, halogen or 1-4C-alkoxy or NR10R11,
R5 is hydrogen, 1-4C-alkyl, halogen, 1-4C-alkoxy, NR10R11 or 3-7C-cycloalkyl,
R6 is hydrogen or 1-4C-alkyl,
R7 is —W—Y,
W is a monocyclic 5- or 6-membered heteroarylene comprising 1 nitrogen atom and optionally 1,2 or 3 further heteroatoms independently selected from oxygen, nitrogen and sulphur or a bicyclic heteroarylene comprising 1 nitrogen atom and optionally 1,2 or 3 further heteroatoms independently selected from oxygen, nitrogen and sulphur
and wherein the bicyclic heteroarylene is optionally substituted by R8,
R8 is hydrogen, 1-4C-alkyl, 3-7C-cycloalkyl, 1-4C-haloalkyl, NR10R11, 4C-alkoxy, cyano, halogen or hydroxy,
Y is hydrogen, aryl or a monocyclic 5- or 6-membered heteroaryl comprising 1 nitrogen atom and optionally 1,2 or 3 further heteroatoms independently selected from oxygen, nitrogen, sulphur and wherein the aryl or heteroaryl is optionally substituted by R9,
R9 is 1-4C-alkyl, 1-4C-alkoxy, halogen, hydroxy, 1-4C-haloalkyl, NR10R11, cyano, or —C(O)NH2
n is 1 or 2, m is 1 or 2, with the proviso that when n is 2 and m is 2, W is not a monocyclic 5- or 6-membered heteroarylene, R10, R11 which can be same or different, is hydrogen, 1-4C-alkyl optionally substituted by halogen, hydroxy, amino, mono- or di-1-4C-alkylamino, or 3-7C-cycloalkyl, R12, R13 which can be same or different, is hydrogen, 1-4C-alkyl optionally substituted by halogen, hydroxy, amino, mono- or di-1-4C-alkylamino, or 3-7C-cycloalkyl, or an N-oxide, a salt, a tautomer or a stereoisomer of said compound, or a salt of said N-oxide, tautomer or stereoisomer.

4. A compound according to claim 1

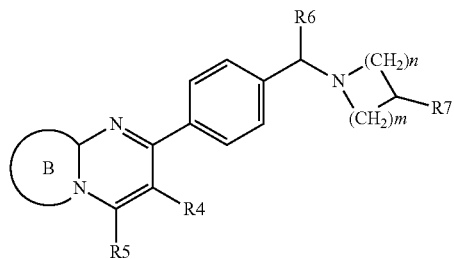
(I)

wherein ring B and the pyrimidine to which it is fused form a ring system selected from

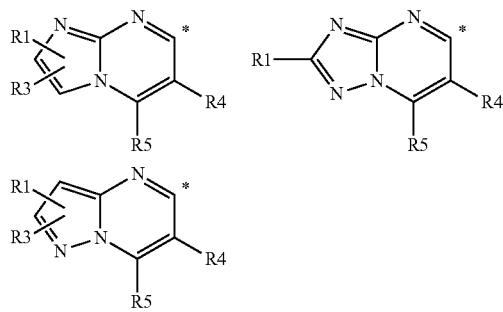

wherein

R1 is hydrogen, halogen, 1-4C-alkyl optionally substituted by hydroxyl, NR10R11, —SR2, 3-7C-cycloalkyl, COOR2, or a monocyclic 6-membered heteroarylene comprising 1 nitrogen atom, 1-4C-alkoxy, R2 is 1-4-Calkyl R3 is hydrogen, 1-4C-alkoxy, or halogen R4 is phenyl and wherein R4 is optionally substituted one or two times by R5A, R5A is halogen, R5 is hydrogen, NR10R11, or 1-4C-alkyl, R6 is hydrogen

R7 W—Y

W is 1,2,4-triazolylene, 2-pyridinylen or a fused ring system selected from

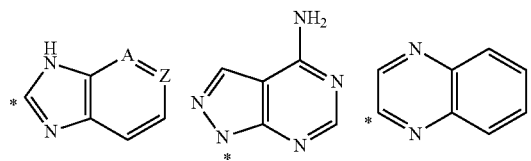

whereby A is —N= or —CH=, and Z is —N= or —CR8=, each of which is optionally substituted by R8

R8 is cyano, halogen, trifluoromethyl, amino, or 1-4C-alkyl

Y is hydrogen, 2-pyridinyl, 3-pyridinyl, 2-pyrazine, or 2-pyrimidine,

R9 is 1-4C alkyl, or halogen n is 1 or 2, m is 1 or 2, with the proviso that when n is 2 and m is 2, and W is a monocyclic 5-membered heteroarylene and R4 is phenyl or thienyl then A:
R1 must be SR2, SOR2 or SO2R2, or B:
R4 must be substituted by R5A, or C:
R5 must be halogen or D:
R9 must be hydroxy, 1-4C-haloalkyl, NR10R11, cyano, or —C(O)NH2

R10/R11 are independently hydrogen, 1-4C-alkyl, 3-7C-cycloalkyl , or an N-oxide, a salt, a tautomer or a stereoisomer of said compound, or a salt of said N-oxide, tautomer or stereoisomer.

5. Process for the manufacture of compounds of general formula (I), characterized in that a aldehyde or ketone of formula (III) can be reacted with an amine (II) or a salt thereof, to yield compounds of formula (I),

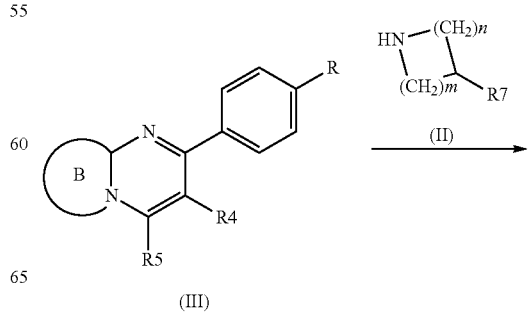
(III)

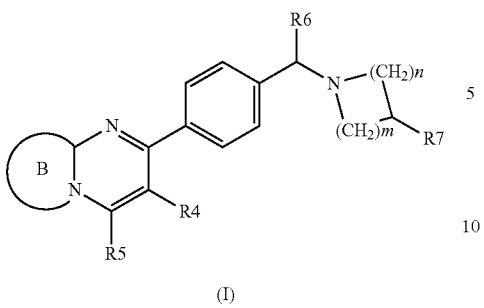

(I)

wherein B, R4, R5, R6, R7, m and n have the meanings that are indicated in claim 1 and R has the meaning —C(O)R6.

6. Process for the manufacture of a compound according to claim 1 comprising reacting a compound of formula (IIIa) with an amine (II) or a salt thereof, to yield a compound of formula (I),

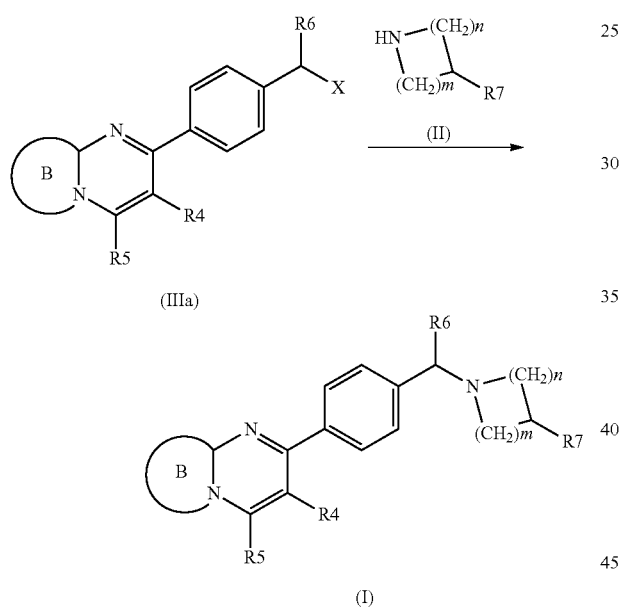

wherein B, R4, R5, R6, R7, m and n have the meanings that are indicated in claim 1 and X is a suitable leaving group.

7. Process for the manufacture of intermediates of general formula (III), characterized in that a compound of formula (V) can be reacted with a compound of formula (IV) to yield compounds of formula (III),

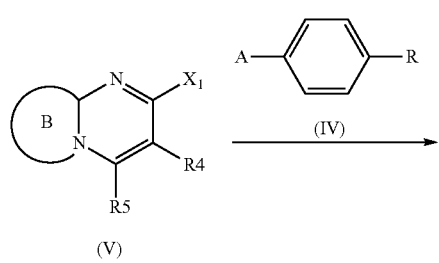

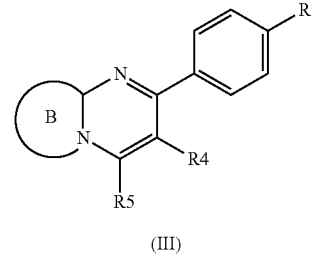

(III)

wherein B, R4, R5 and R6 have the meanings that are indicated in claim 1 and R has the meanings —C(O)O(1-4C-alkyl), —C(O)R6, —CH(R6)OH or —CH2R6 and $X_1$ is a suitable leaving group.

8. Compounds of general formula (III) and (IIIa),

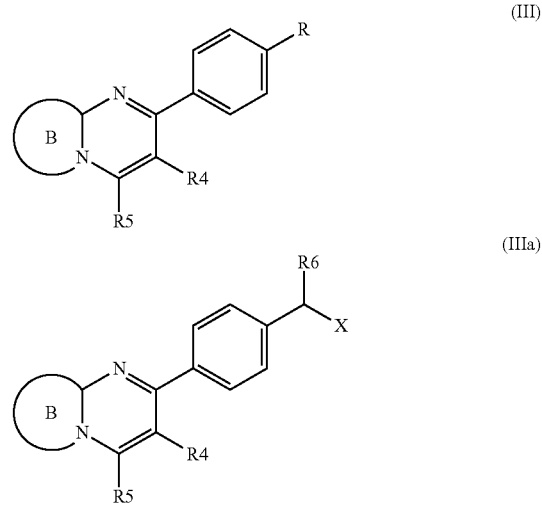

wherein B, R4, R5 and R6 have the meanings that are indicated in claim 1, R has the meanings —C(O)O(1-4C-alkyl), —C(O)R6, —CH(R6)OH or —CH2R6 and X is a suitable leaving group.

9. A compound of formula (IIa)

wherein R7 is defined as in claim 1 and salts thereof.

10. A method for the treatment of a hyperproliferative disease disorder responsive to inhibition of the Pi3K/Akt pathway comprising administering to a mammal in need thereof an effective amount of a compound according to claim 1.

11. A method for the treatment of a a tumor of the breast, bladder, bone, brain, central or peripheral nervous system, colon, endocrine glands, esophagus, endometrium, germ cells, head or neck, kidney, liver, lung, larynx or hypopharynx, mesothelioma, ovary, pancreas, prostate, rectum, renal, small intestine, soft tissue, testis, stomach, skin, ureter, vagina, vulva, or metastases thereof; non-Hodgkins disease, chronic or acute myeloid leukemia (CML / AML), acute lymphoblastic leukemia (ALL), Hodgkins disease, multiple myeloma or T-cell lymphoma; or myelodysplastic syndrome, plasma cell neoplasia, or paraneoplastic syndrome comprising administering to a mammal in need thereof an effective amount of a compound according to claim 1.

12. A pharmaceutical composition comprising at least one compound of according to claim 1, together with at least one pharmaceutically acceptable auxiliary.

13. A combination comprising one or more first active ingredients selected from a compound of general formula (I) according to claim 1, and one or more second active ingredients selected from chemotherapeutic anti-cancer agents and target-specific anti-cancer agents.

* * * * *